US012734170B2

(12) United States Patent
Alexander et al.

(10) Patent No.: US 12,734,170 B2
(45) Date of Patent: Sep. 15, 2026

(54) CEREBLON BINDING COMPOUNDS, COMPOSITIONS THEREOF, AND METHODS OF TREATMENT THEREWITH

(71) Applicant: CELGENE CORPORATION, Summit, NJ (US)

(72) Inventors: Matthew D. Alexander, San Diego, CA (US); Matthew D. Correa, San Diego, CA (US); Deepak Dalvie, San Diego, CA (US); Virginia Heather Sharron Grant, San Diego, CA (US); Joshua Hansen, La Jolla, CA (US); Roy L. Harris, III, San Diego, CA (US); Evan J. Horn, San Diego, CA (US); Dehua Huang, San Diego, CA (US); Christopher Mayne, Boulder, CO (US); Stephen Norris, San Diego, CA (US); Veronique Plantevin-Krenitsky, San Francisco, CA (US); John J. Sapienza, Chula Vista, CA (US); Lida Tehrani, San Diego, CA (US); Brandon W. Whitefield, San Diego, CA (US)

(73) Assignee: Celgene Corporation, Summit, NJ (US)

( * ) Notice: Subject to any disclaimer, the term of this patent is extended or adjusted under 35 U.S.C. 154(b) by 420 days.

(21) Appl. No.: 18/573,752

(22) PCT Filed: Jun. 24, 2022

(86) PCT No.: PCT/US2022/034902
§ 371 (c)(1),
(2) Date: Dec. 22, 2023

(87) PCT Pub. No.: WO2022/272061
PCT Pub. Date: Dec. 29, 2022

(65) Prior Publication Data

US 2024/0374591 A1 Nov. 14, 2024

Related U.S. Application Data

(60) Provisional application No. 63/215,294, filed on Jun. 25, 2021.

(51) Int. Cl.

| | |
|---|---|
| ***A61K 31/506*** | (2006.01) |
| ***A61K 31/4545*** | (2006.01) |
| ***A61K 31/496*** | (2006.01) |
| ***A61P 35/00*** | (2006.01) |
| ***C07D 401/14*** | (2006.01) |

(52) U.S. Cl.
CPC ........ *A61K 31/506* (2013.01); *A61K 31/4545* (2013.01); *A61K 31/496* (2013.01); *A61P 35/00* (2018.01); *C07D 401/14* (2013.01)

(58) Field of Classification Search
CPC .... A61K 31/506; A61K 31/4545; A61P 35/00
See application file for complete search history.

(56) References Cited

U.S. PATENT DOCUMENTS

| | | | | |
|---|---|---|---|---|
| 11,149,007 | B2 | 10/2021 | Ammirante et al. | |
| 11,325,889 | B2 | 5/2022 | Ammirante et al. | |
| 11,560,371 | B2 | 1/2023 | Alexander et al. | |
| 11,634,407 | B2 | 4/2023 | Alexander et al. | |
| 11,739,075 | B2 | 8/2023 | Alexander et al. | |
| 11,883,389 | B2 | 1/2024 | Hui et al. | |
| 2016/0214972 | A1* | 7/2016 | Jin | C07D 417/14 |
| 2018/0215731 | A1 | 8/2018 | Crew et al. | |
| 2018/0224435 | A1 | 8/2018 | Chamberlain et al. | |
| 2019/0240304 | A1 | 8/2019 | Xu | |
| 2020/0199073 | A1 | 6/2020 | Ammirante et al. | |
| 2023/0242509 | A1 | 8/2023 | Alexander et al. | |
| 2023/0348431 | A1 | 11/2023 | Alexander et al. | |
| 2024/0368083 | A1 | 11/2024 | Ammirante et al. | |

FOREIGN PATENT DOCUMENTS

| | | |
|---|---|---|
| WO | WO 2019/140387 A1 | 7/2019 |
| WO | WO 2020/006264 A1 | 1/2020 |
| WO | WO 2021/113557 | 6/2021 |
| WO | WO 2022/272053 | 12/2022 |
| WO | WO 2022/272061 | 12/2022 |
| WO | WO 2022/272074 | 12/2022 |

OTHER PUBLICATIONS

Pubchem, Substance Record for SID 145140517, Modify Date: May 31, 2019 [retrieved on Aug. 17, 2022]. Retrieved from the Internet: <URL: https://pubchem.ncbi.nlm.nih.gov/substance/145140517>.
Pubchem, Substance Record for SID 435776705, Modify Date: 321 Nov. 2020 [retrieved on Oct. 3, 2022]. Retrieved from the Internet: <URL: https://pubchem.ncbi.nlm.nih.gov/substance/435776705>.
Chen et al., 2009, "Antiandrogens and androgen depleting therapies in prostate cancer: novel agents for an established target," Lancet Oncol, 10:981-91.

(Continued)

*Primary Examiner* — Samantha L Shterengarts
*Assistant Examiner* — Ernesto Valle
(74) *Attorney, Agent, or Firm* — Jones Day

(57) ABSTRACT

Provided herein are piperidine dione compounds having the following structure: (I) wherein Y, $R^1$, $R^2$, $R^3$, $R^4$, $R^N$, L, V, X, a, m, and n are as defined herein, compositions comprising an effective amount of a piperidine dione compound, and methods for treating or preventing an androgen receptor mediated disease.

I

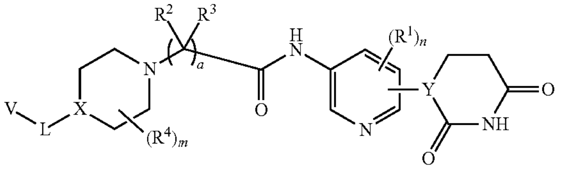

20 Claims, No Drawings

(56) References Cited

OTHER PUBLICATIONS

Mills, 2014, "Maintaining and reprogramming genomic androgen receptor activity in prostate cancer," Nat Rev Cancer, 14:187-98.
Taplin, 2007, "Drug Insight: role of the androgen receptor in the development and progression of prostate cancer," Nat Clin Pract Oncol, 4:236-44.
Wirth et al., 2007, "Antiandrogens in the Treatment of Prostate Cancer," Eur Urol, 51(2):306-13.
Brinkmann et al., 1999, "Mechanisms of androgen receptor activation and function," J Steroid Biochem Mol Biol, 69:307-13.
Tran et al., 2009, "Development of a Second-Generation Antiandrogen for Treatment of Advanced Prostate Cancer," Science, 324:787-90.
Murtha et al., 1993, "Androgen Induction of a Human Prostate-Specific Kallikrein, hKLK2: Characterization of an Androgen Response Element in the 5' Promoter Region of the Gene," Biochemistry (Mosc.), 32:6459-64.
Wilen, et al., 1977, "Strategies in Optical Resolutions," Tetrahedron 33:2725.
International Search Report and Written Opinion, dated Aug. 23, 2022, for International Patent Application No. PCT/US2022/034902 (7 pages).
Supplementary European Search Report dated May 7, 2025, for European Patent Application No. EP 22 82 9384 (8 pages).

* cited by examiner

CEREBLON BINDING COMPOUNDS, COMPOSITIONS THEREOF, AND METHODS OF TREATMENT THEREWITH

RELATED APPLICATIONS

This application is a U.S. National Stage filing under 35 U.S.C. § 371 of International Application No. PCT/US2022/034902, filed Jun. 24, 2022, which claims the benefit of U.S. Provisional Application No. 63/215,294, filed Jun. 25, 2021, the disclosure of each of which is incorporated herein by reference in its entirety.

FIELD

Provided herein are compounds, compositions comprising an effective amount of such compounds, and methods for treating or preventing androgen receptor mediated diseases, comprising administering an effective amount of such compounds to a subject in need thereof. Also provided herein are the compounds and compositions for use in these methods.

BACKGROUND

Androgen receptor signaling is known to play a crucial role in the pathogenesis of prostate cancer and is involved in the development of other androgen receptor positive cancers (Chen Y et al., *Lancet Oncol,* 2009, 10:981-91; Mills I G, *Nat Rev Cancer,* 2014, 14:187-98; Taplin M E, *Nat Clin Pract Oncol,* 2007, 4:236-44; Wirth M P et al., *Eur Urol,* 2007, 51(2):306-13). The inhibition of androgen receptor signaling with anti-androgens that antagonize the androgen receptor has been used or proposed for the treatment of prostate cancer.

The androgen receptor normally resides in the cytoplasm bound to chaperones such as HSP90 (Brinkmann A O et al., *J Steroid Biochem Mol Biol,* 1999, 69:307-13). Upon binding of dihydrotestosterone (DHT) the androgen receptor changes its conformation and translocates to the nucleus, where it binds androgen responsive elements (AREs) driving the transcription of canonical targets such as KLK3 (also known as prostate specific antigen PSA), TMPRSS2 and KLK2 (Tran C et al., *Science,* 2009, 324:787-90; Murtha P et al., *Biochemistry* (Mosc.), 1993, 32:6459-64).

Prostate cancer (PCa) is one of the most frequently diagnosed non-cutaneous cancers among men in the US and is the second most common cause of cancer deaths with more than 200,000 new cases and over 30,000 deaths each year in the United States.

Androgen-deprivation therapy (ADT) is the standard of treatment for advanced PCa. Patients with advanced PCa undergo ADT, either by luteinizing hormone releasing hormone (LHRH) agonists, LHRH antagonists or by bilateral orchiectomy. Despite initial response to ADT, disease progression is inevitable and the cancer emerges as castration-resistant prostate cancer (CRPC). Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

There remains a significant need for safe and effective methods of treating, preventing and managing AR mediated diseases, particularly for AR mediated diseases that are refractory to standard treatments, such as surgery, radiation therapy, chemotherapy and hormonal therapy, while reducing or avoiding the toxicities and/or side effects associated with conventional therapies.

Citation or identification of any reference in this section of this application is not to be construed as an admission that the reference is prior art to the present application.

SUMMARY

Provided herein are compounds having the following formula I.

I

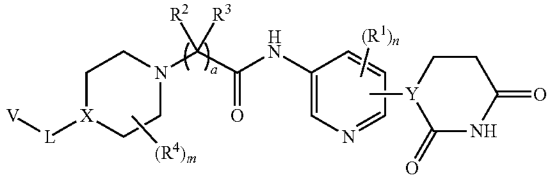

or a pharmaceutically acceptable salt, tautomer, isotopolog, or stereoisomer thereof, wherein $R^1$, $R^2$, $R^3$, $R^4$, X, Y, L, V, a, m and n are as defined herein.

A compound of formula I or a pharmaceutically acceptable salt, tautomer, isotopolog, or stereoisomer thereof is useful for treating or preventing androgen receptor mediated diseases in a subject.

In one aspect, provided herein are compounds as described in the instant disclosure, such as, for example, in Table 1.

In one aspect, provided herein are pharmaceutical compositions comprising an effective amount of a compound as described herein, and a pharmaceutically acceptable carrier, excipient or vehicle. In one aspect, provided herein are pharmaceutical compositions comprising an effective amount of a compound as described herein, and a pharmaceutically acceptable carrier, excipient or vehicle. In some embodiments the pharmaceutical composition is suitable for oral, parenteral, mucosal, transdermal or topical administration.

In one aspect, provided herein are methods for treating or preventing androgen receptor mediated diseases in a subject, comprising administering to a subject in need thereof an effective amount of a compound as described herein; and a pharmaceutically acceptable carrier, excipient or vehicle. In one aspect, provided herein are methods for treating or preventing androgen receptor mediated diseases in a subject, comprising administering to a subject in need thereof an effective amount of a compound as described herein; and a pharmaceutically acceptable carrier, excipient or vehicle. In another aspect, provided herein are compounds for use in methods of treatment of androgen receptor mediated diseases. In another aspect, provided herein are compounds for use in methods of treatment of androgen receptor mediated diseases.

In another aspect provided herein are methods for preparing compounds as described herein. In another aspect provided herein are methods for preparing compounds as described herein.

The present embodiments can be understood more fully by reference to the detailed description and examples, which are intended to exemplify non-limiting embodiments.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 carbon atoms. In some embodiments, the alkyl group is a saturated alkyl group. Representative saturated alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. In some embodiments, the alkyl group is an unsaturated alkyl group, also termed an alkenyl or alkynyl group. An "alkenyl" group is an alkyl group that contains one or more carbon-carbon double bonds. An "alkynyl" group is an alkyl group that contains one or more carbon-carbon triple bonds. Examples of unsaturated alkyl groups include, but are not limited to, vinyl, allyl, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, $-C{\equiv}CH$, $-C{\equiv}C(CH_3)$, $-C{\equiv}C(CH_2CH_3)$, $-CH_2C{\equiv}CH$, $-CH_2C{\equiv}C(CH_3)$ and $-CH_2C{\equiv}C(CH_2CH_3)$, among others. An alkyl group can be substituted or unsubstituted. When the alkyl groups described herein are said to be "substituted," they may be substituted with any substituent or substituents as those found in the exemplary compounds and embodiments disclosed herein, as well as halogen; hydroxy; alkoxy; cycloalkyloxy, aryloxy, heterocyclyloxy, heteroaryloxy, heterocycloalkyloxy, cycloalkylalkyloxy, aralkyloxy, heterocyclylalkyloxy, heteroarylalkyloxy, heterocycloalkylalkyloxy; oxo (=O); amino, alkylamino, cycloalkylamino, arylamino, heterocyclylamino, heteroarylamino, heterocycloalkylamino, cycloalkylalkylamino, aralkylamino, heterocyclylalkylamino, heteroaralkylamino, heterocycloalkylalkylamino; imino; imido; amidino; guanidino; enamino; acylamino; sulfonylamino; urea, nitrourea; oxime; hydroxylamino; alkoxyamino; aralkoxyamino; hydrazino; hydrazido; hydrazono; azido; nitro; thio (—SH), alkylthio; =S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or $-B(OH)_2$. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; $B(OH)_2$, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted. In some embodiments, the cycloalkyl group has 3 to 8 ring members, whereas in other embodiments the number of ring carbon atoms ranges from 3 to 5, 3 to 6, or 3 to 7. In some embodiments, the cycloalkyl groups are saturated cycloalkyl groups. Such saturated cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. In other embodiments, the cycloalkyl groups are unsaturated cycloalkyl groups. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups. A heteroaryl group can be substituted or unsubstituted.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

As used herein and unless otherwise specified, a "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopropylmethyl, cyclobutylmethyl, cyclopentylmethyl, cyclohexylmethyl, cyclopropylethyl, cyclobutylethyl, cyclopentylethyl, cyclohexylethyl, cyclopentylpropyl, cyclohexylpropyl and the like.

As used herein and unless otherwise specified, an "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and aralkyl groups wherein the aryl group is fused to a cycloalkyl group such as indan-4-yl ethyl.

As used herein and unless otherwise specified, a "heterocyclylalkyl" group is a radical of the formula: -alkyl-heterocyclyl, wherein alkyl and heterocyclyl are defined above. A "heteroarylalkyl" group is a radical of the formula: -alkyl-heteroaryl, wherein alkyl and heteroaryl are defined above. A "heterocycloalkylalkyl" group is a radical of the formula: -alkyl-heterocycloalkyl, wherein alkyl and heterocycloalkyl are defined above. Substituted heterocyclylalkyl groups may be substituted at the alkyl, the heterocyclyl, or both the alkyl and the heterocyclyl portions of the group. Representative heterocylylalkyl groups include but are not limited to morpholin-4-yl ethyl, morpholin-4-yl propyl, furan-2-yl methyl, furan-3-yl methyl, pyridin-3-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: $—NH_2$, $—NH(R^{\#})$, or $—N(R^{\#})_2$, wherein each $R^{\#}$ is independently an alkyl, cycloalkyl, cycloalkylalkyl, aryl, aralkyl, heterocyclyl (e.g., heteroaryl or heterocycloalkyl), or heterocyclylalkyl (e.g., heteroarylalkyl or heterocycloalkylalkyl) group defined above, each of which is independently substituted or unsubstituted.

In one embodiment, an "amino" group is an "alkylamino" group, which is a radical of the formula: —NH-alkyl or $—N(alkyl)_2$, wherein each alkyl is independently defined above. The term "cycloalkylamino", "arylamino", "heterocyclylamino", "heteroarylamino", "heterocycloalkylamino", or the like, mirrors the above description for "alkylamino" where the term "alkyl" is replaced with "cycloalkyl", "aryl", "heterocyclyl", "heteroaryl", "heterocycloalkyl", or the like, respectively.

A "carboxy" group is a radical of the formula: —C(O)OH.

As used herein and unless otherwise specified, an "acyl" group is a radical of the formula: —C(O)($R^{\#}$) or —C(O)H, wherein $R^{\#}$ is defined above. A "formyl" group is a radical of the formula: —C(O)H.

As used herein and unless otherwise specified, an "amido" group is a radical of the formula: —C(O)—$NH_2$, —C(O)—NH($R^{\#}$), —C(O)—N($R^{\#}$)$_2$, —NH—C(O)H, —NH—C(O)—($R^{\#}$), —N($R^{\#}$)—C(O)H, or —N($R^{\#}$)—C(O)—($R^{\#}$), wherein each $R^{\#}$ is independently defined above.

In one embodiment, an "amido" group is an "aminocarbonyl" group, which is a radical of the formula: —C(O)—$NH_2$, —C(O)—NH($R^{\#}$), —C(O)—N($R^{\#}$)$_2$, wherein each $R^{\#}$ is independently defined above.

In one embodiment, an "amido" group is an "acylamino" group, which is a radical of the formula: —NH—C(O)H, —NH—C(O)—($R^{\#}$), —N($R^{\#}$)—C(O)H, or —N($R^{\#}$)—C(O)—($R^{\#}$), wherein each $R^{\#}$ is independently defined above.

A "sulfonylamino" group is a radical of the formula: —$NHSO_2$($R^{\#}$) or —N(alkyl)$SO_2$($R^{\#}$), wherein each alkyl and $R^{\#}$ are defined above.

A "urea" group is a radical of the formula: —N(alkyl)C(O)N($R^{\#}$)$_2$, —N(alkyl)C(O)NH($R^{\#}$), —N(alkyl)C(O)$NH_2$, —NHC(O)N($R^{\#}$)$_2$, —NHC(O)NH($R^{\#}$), or —NH(CO)$NH_2$, wherein each alkyl and $R^{\#}$ are independently as defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (═O); $B(OH)_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula I include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride formic, and mesylate salts. Others are well known in the art, see for example, *Remington's Pharmaceutical Sciences,* $18^{th}$ eds., Mack Publishing, Easton PA (1990) or *Remington: The Science and Practice of Pharmacy,* $19^{th}$ eds., Mack Publishing, Easton PA (1995).

As used herein and unless otherwise indicated, the term "stereoisomer" or "stereoisomerically pure" means one stereoisomer of a compound provided herein that is substantially free of other stereoisomers of that compound. For example, a stereoisomerically pure compound having one chiral center will be substantially free of the opposite enantiomer of the compound. A stereoisomerically pure compound having two chiral centers will be substantially free of other diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds can have chiral centers and can occur as racemates, individual enantiomers or diastereomers, and mixtures thereof. All such isomeric forms are included within the embodiments disclosed herein, including mixtures thereof.

The use of stereoisomerically pure forms of such compounds, as well as the use of mixtures of those forms, are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. *L., Stereochemistry of Carbon Compounds* (McGraw-Hill, NY, 1962); Wilen, S. H., *Tables of Resolving Agents and Optical Resolutions* p. 268 (E. L. Eliel, Ed., Univ. of Notre Dame Press, Notre Dame, IN, 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuja, S., *Chiral Separation Methods for Pharmaceutical and Biotechnological Products* (John Wiley & Sons, 2011).

It should also be noted the compounds can include E and Z isomers, or a mixture thereof, and cis and trans isomers or a mixture thereof. In certain embodiments, the compounds are isolated as either the E or Z isomer. In other embodiments, the compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

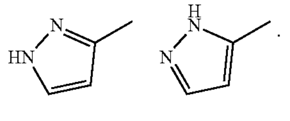

As readily understood by one skilled in the art, a wide variety of functional groups and other structures may exhibit tautomerism and all tautomers of compounds of formula I are within the scope of the present invention.

It should also be noted the compounds provided herein can contain unnatural proportions of atomic isotopes at one or more of the atoms. For example, the compounds may be radiolabeled with radioactive isotopes, such as for example tritium (H), iodine-125 ($^{125}I$), sulfur-35 ($^{35}S$), or carbon-14 ($^{14}C$), or may be isotopically enriched, such as with deuterium (2H), carbon-13 ($^{13}C$), or nitrogen-15 ($^{5}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds, for example, the isotopologues are deuterium, carbon-13, and/or nitrogen-15 enriched compounds. As used herein, "deuterated", means a compound wherein at least one hydrogen (H) has been replaced by deuterium (indicated by D or $^{2}H$), that is, the compound is enriched in deuterium in at least one position.

It is understood that, independently of stereoisomerical or isotopic composition, each compound referred to herein can be provided in the form of any of the pharmaceutically acceptable salts discussed herein. Equally, it is understood that the isotopic composition may vary independently from the stereoisomerical composition of each compound referred to herein. Further, the isotopic composition, while being restricted to those elements present in the respective compound or salt thereof, may otherwise vary independently from the selection of the pharmaceutically acceptable salt of the respective compound.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is an androgen receptor mediated disease, as described herein, or a symptom thereof.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is an androgen receptor mediated disease, as described herein, or symptoms thereof.

The term "effective amount" in connection with a compound means an amount capable of treating or preventing a disorder, disease or condition, or symptoms thereof, disclosed herein.

The terms "subject" and "patient" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having an androgen receptor mediated disease, or a symptom thereof.

The term "androgen receptor" or "AR" or "NR3C4" as used herein refers to a nuclear hormone receptor activated by binding of the androgenic hormones, including testosterone or dihydrotestosterone. The term "androgen receptor" may refer to the nucleotide sequence or protein sequence of human androgen receptor (e.g., Entrez 367, Uniprot P10275, RefSeq NM_000044, or RefSeq NP_000035).

The term "AR-full length" (AR-FL) as used herein refers to AR protein that contains all four functional domains, including the N-terminal transactivation domain (NTD, exon 1), the DNA-binding domain (DBD, exons 2-3), the hinge domain (exon 4), and the C-terminal ligand binding domain (LBD, exons 4-8).

The term "castration resistant prostate cancer" (CRPC) refers to advanced prostate cancer that is worsening or progressing while the patient remains on androgen deprivation therapy or other therapies to reduce testosterone, or prostate cancer which is considered hormone refractory, hormone naive, androgen independent or chemical or surgical castration resistant. Castration resistant prostate cancer (CRPC) is an advanced prostate cancer that developed despite ongoing ADT and/or surgical castration. Castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix or abarelix), antiandrogens (e.g., bicalutamide, flutamide, enzalutamide, ketoconazole, aminoglutethamide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa®), cabozantinib (Cometriq®, also known as XL184)) or other prostate cancer therapies (e.g., vaccines (sipuleucel-T (Provenge®), GVAX, etc.), herbal (PC-SPES) and lyase inhibitor (abiraterone)) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition.

Compounds

In certain embodiments, provided herein are compounds of formula I

I

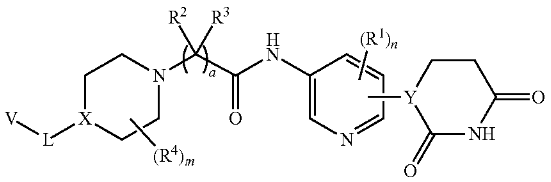

or pharmaceutically acceptable salts, tautomers, isotopologs, or stereoisomers thereof, wherein Y is CH or N;

n is 0-3;

each $R^1$ is independently selected from halogen, CN, and $C_{1-3}$ alkyl;

a is 1 or 2;

$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;

m is 0-8;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;

X is N or $CR^X$;

$R^X$ is hydrogen, halogen, —O($C_{1-6}$ alkyl) or —($C_{1-9}$ alkyl);

L is substituted or unsubstituted —O($C_{1-6}$ alkyl)-, —($C_{1-6}$ alkyl)O—, —O($C_{1-6}$ alkyl)O—, or —($C_{1-9}$ alkyl)-;

V is

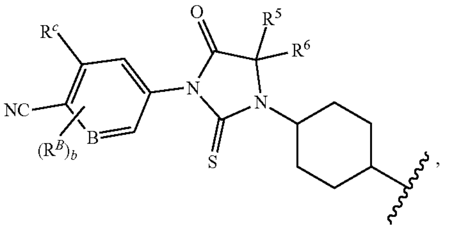

wherein

B is N, CH, or $CR^B$;

each $R^B$ is independently selected from halogen, and substituted or unsubstituted $C_{1-6}$ alkyl;

$R^C$ is halogen, $CF_3$ or $SF_5$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl; and b is 0-2.

In certain embodiments, provided herein are compounds of formula I

I

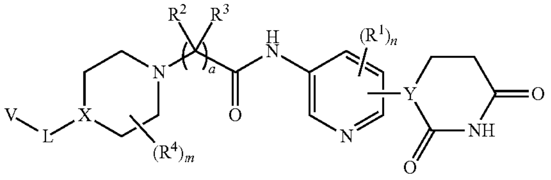

or pharmaceutically acceptable salts, tautomers, isotopologs, or stereoisomers thereof, wherein Y is CH or N;

n is 0-3;

each $R^1$ is independently selected from halogen, CN, and $C_{1-3}$ alkyl;

a is 1 or 2;

$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;

m is 0-8;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;

X is N or $CR^X$;

$R^X$ is hydrogen, halogen, —O($C_{1-6}$ alkyl) or —($C_{1-9}$ alkyl);

L is substituted or unsubstituted —O($C_{1-6}$ alkyl)-, —($C_{1-6}$ alkyl)O—, or —($C_{1-9}$ alkyl)-;

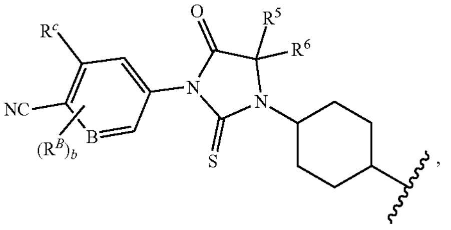

wherein

B is N, CH, or $CR^B$;

each $R^B$ is independently selected from halogen, and substituted or unsubstituted $C_{1-6}$ alkyl;

$R^C$ is halogen, $CF_3$ or $SF_5$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl; and b is 0-2.

In some embodiments of compounds of formula I, n is 0. In some embodiments of compounds of formula I, a is 1, and $R^2$ and $R^3$ are both H. In some embodiments of compounds of formula I, each $R^4$ is substituted or unsubstituted methyl. In some embodiments of compounds of formula I, each $R^4$ is independently selected from methyl and $CF_3$.

In some embodiments of compounds of formula I, m is 0, 1, 2, 3 or 4. In some embodiments of compounds of formula I, m is 1 or 2.

In some embodiments of compounds of formula I, X is N. In some embodiments of compounds of formula I, X is $CR^X$; and $R^X$ is hydrogen, halogen, —O($C_{1-6}$ alkyl) or —($C_{1-9}$ alkyl).

In some embodiments of compounds of formula I, Y is N. In some embodiments of compounds of formula I, Y is CH.

In some embodiments of compounds of formula I, L is substituted or unsubstituted $—O(CH_2)_p—$, $—O(CH_2)_pO—$ or $—(CH_2)_p—$, and p is 1-4.

In some embodiments of compounds of formula I, L is substituted or unsubstituted $—O(CH_2)_p—$ or $—(CH_2)_p—$, and p is 1-4.

In some embodiments of compounds of formula I, L is substituted or unsubstituted $—O(CH_2)_p—$, and p is 2 or 3.

In some embodiments of compounds of formula I, L is substituted or unsubstituted $—O(CH_2)_pO—$, and p is 2 or 3.

In some embodiments of compounds of formula I, L is substituted or unsubstituted $—(CH_2)_p—$, and p is 3 or 4.

In some embodiments of compounds of formula I, L is $—O(CH_2)(CH_2)—$, $—O(CH_2)(CH_2)(CH_2)—$, $—O(CH_2)(CH_2)O—$, $—O(CH_2)(CH_2)(CH_2)O—$, $—(CH_2)(CH_2)—$, $—(CH_2)(CH_2)(CH_2)—$, or $—(CH_2)(CH_2)(CH_2)(CH_2)—$. In some embodiments of compounds of formula I, L is $—O(CH_2)(CH_2)—$ or $—(CH_2)(CH_2)(CH_2)—$.

In some embodiments of compounds of formula I, L is $—O(CH_2)(CH_2)—$, $—O(CH_2)(CH_2)(CH_2)—$, $—(CH_2)(CH_2)—$, $—(CH_2)(CH_2)(CH_2)—$, or $—(CH_2)(CH_2)(CH_2)(CH_2)—$. In some embodiments of compounds of formula I, L is $—O(CH_2)(CH_2)—$ or $—(CH_2)(CH_2)(CH_2)—$.

In some embodiments of compounds of formula I, B is CH. In some embodiments of compounds of formula I, B is N.

In some embodiments of compounds of formula I, b is 0. In some embodiments of compounds of formula I, $R^C$ is $CF_3$, Cl or $SF_5$. In some embodiments of compounds of formula I, $R^C$ is $CF_3$. In some embodiments of compounds of formula I, $R^5$ and $R^6$ are methyl.

In some embodiments of compounds of formula I, the compound is

II

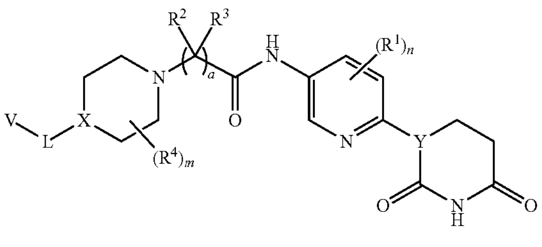

or a pharmaceutically acceptable salt, tautomer, isotopolog, or stereoisomer thereof.

In some embodiments of compounds of formula I, the compo

III

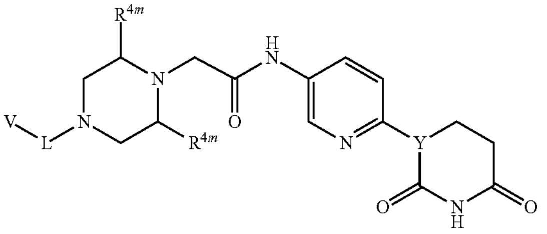

or a pharmaceutically acceptable salt, tautomer, isotopolog, or stereoisomer thereof, wherein each $R^{4m}$ is independently hydrogen or substituted or unsubstituted methyl, wherein the substituents, when present are selected from 1 to 5 halo;

Y is CH or N;

L is substituted or unsubstituted —O($C_{1-3}$ alkyl)-, —O($C_{1-3}$ alkyl)O— or —($C_{1-4}$ alkyl)-;

V is

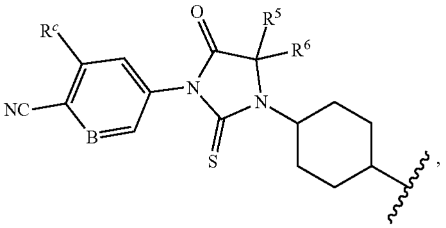

B is N or CH;

$R^C$ is halogen, $CF_3$ or $SF_5$; and $R^5$ and $R^6$ are $C_{1-3}$ alkyl.

In some embodiments of compounds of formula I, the compound is

IV

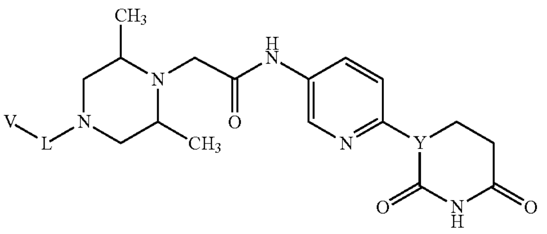

or a pharmaceutically acceptable salt, tautomer, isotopolog, or stereoisomer thereof, wherein Y is CH or N;

L is substituted or unsubstituted —O($C_{1-3}$ alkyl)-, —O($C_{1-3}$ alkyl)O— or —($C_{1-4}$ alkyl)-;

V is

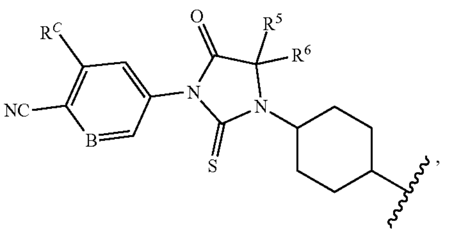

B is N or CH;

$R^C$ is halogen, $CF_3$ or $SF_5$; and $R^5$ and $R^6$ are $C_{1-3}$ alkyl.

In some embodiments of compounds of formula I, the compound is

V

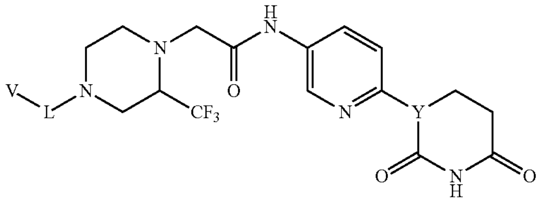

or a pharmaceutically acceptable salt, tautomer, isotopolog, or stereoisomer thereof, wherein wherein Y is CH or N;

L is substituted or unsubstituted —O($C_{1-3}$ alkyl)-, —O($C_{1-3}$ alkyl)O— or —($C_{1-4}$ alkyl)-;

V is

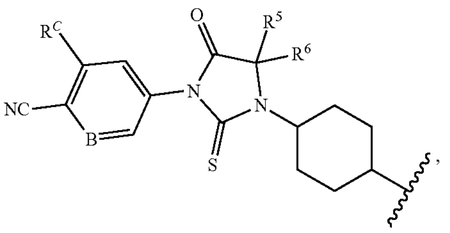

B is N or CH;

$R^C$ is halogen, $CF_3$ or $SF_5$; and $R^5$ and $R^6$ are $C_{1-3}$ alkyl.

In some embodiments of compounds of formula I, II, III, IV and V, Y is CH; X is N or $CR^X$, $R^X$ is hydrogen, halogen, —O($C_{1-6}$ alkyl) or —($C_{1-9}$ alkyl); L is substituted or unsubstituted —O$(CH_2)_p$—, —O$(CH_2)_p$O— or —$(CH_2)_p$—, p is 1-4; B is CH or N; b is 0; $R^C$ is $CF_3$, Cl or $SF_5$; $R^C$ is $CF_3$; and $R^5$ and $R^6$ are methyl.

In some embodiments of compounds of formula I, II, III, IV and V, Y is CH; X is N or $CR^X$, $R^X$ is hydrogen, halogen, —O($C_{1-6}$ alkyl) or —($C_{1-9}$ alkyl); L is substituted or unsubstituted —O$(CH_2)_p$— or —$(CH_2)_p$—, p is 1-4; B is CH or N; b is 0; $R^C$ is $CF_3$, Cl or $SF_5$; $R^C$ is $CF_3$; and $R^5$ and $R^6$ are methyl.

In some embodiments of compounds of formula I, II, III, IV and V, n is 0; Y is CN; X is N or $CR^X$, $R^X$ is hydrogen, halogen, —O($C_{1-6}$ alkyl) or —($C_{1-9}$ alkyl); L is substituted or unsubstituted —O$(CH_2)_p$—, —O$(CH_2)_p$O— or —$(CH_2)_p$—, p is 1-4; B is CH or N; b is 0; $R^C$ is $CF_3$, Cl or $SF_5$; $R^C$ is $CF_3$; and $R^5$ and $R^6$ are methyl.

In some embodiments of compounds of formula I, II, III, IV and V, n is 0; Y is CN; X is N or $CR^X$, $R^X$ is hydrogen, halogen, —O($C_{1-6}$ alkyl) or —($C_{1-9}$ alkyl); L is substituted or unsubstituted —O$(CH_2)_p$— or —$(CH_2)_p$—, p is 1-4; B is CH or N; b is 0; $R^C$ is $CF_3$, Cl or $SF_5$; $R^C$ is $CF_3$; and $R^5$ and $R^6$ are methyl.

In some embodiments of compounds of formula I, II, III, IV and V, L is —O$(CH_2)(CH_2)$—, —O$(CH_2)(CH_2)(CH_2)$—, —O$(CH_2)(CH_2)$O—, —O$(CH_2)(CH_2)(CH_2)$O—, —$(CH_2)(CH_2)$—, —$(CH_2)(CH_2)(CH_2)$—, or —$(CH_2)(CH_2)(CH_2)(CH_2)$—.

In some embodiments of compounds of formula I, II, III, IV and V, L is —O$(CH_2)(CH_2)$—, —O$(CH_2)(CH_2)(CH_2)$—, —$(CH_2)(CH_2)$—, —$(CH_2)(CH_2)(CH_2)$—, or —$(CH_2)(CH_2)(CH_2)(CH_2)$—.

Further embodiments provided herein include any combination of one or more of the particular embodiments set forth above.

In some embodiments of compounds of formula I, the compound is a compound from Table 1.

The compounds set forth in Table 1 were tested in the AR mediated assays described herein and were found to have activity therein. In one embodiment, the compounds described herein, at a concentration of 1 μM, leads to degradation of AR protein, by at least about 50% or more.

Methods for Making Piperidine Dione Compounds

The compounds described herein can be made using conventional organic syntheses and commercially available starting materials, or the methods provided herein. By way of example and not limitation, compounds of formula I, wherein Y, $R^1$, $R^2$, $R^3$, $R^4$, $R^5$, $R^6$, $R^B$, $R^C$, L, V, X, n, m, a and b are as defined herein, can be prepared as outlined in the schemes shown below, as well as in the examples set forth herein. It should be noted that one skilled in the art would know how to modify the procedures set forth in the illustrative schemes and examples to arrive at the desired products.

Scheme 1

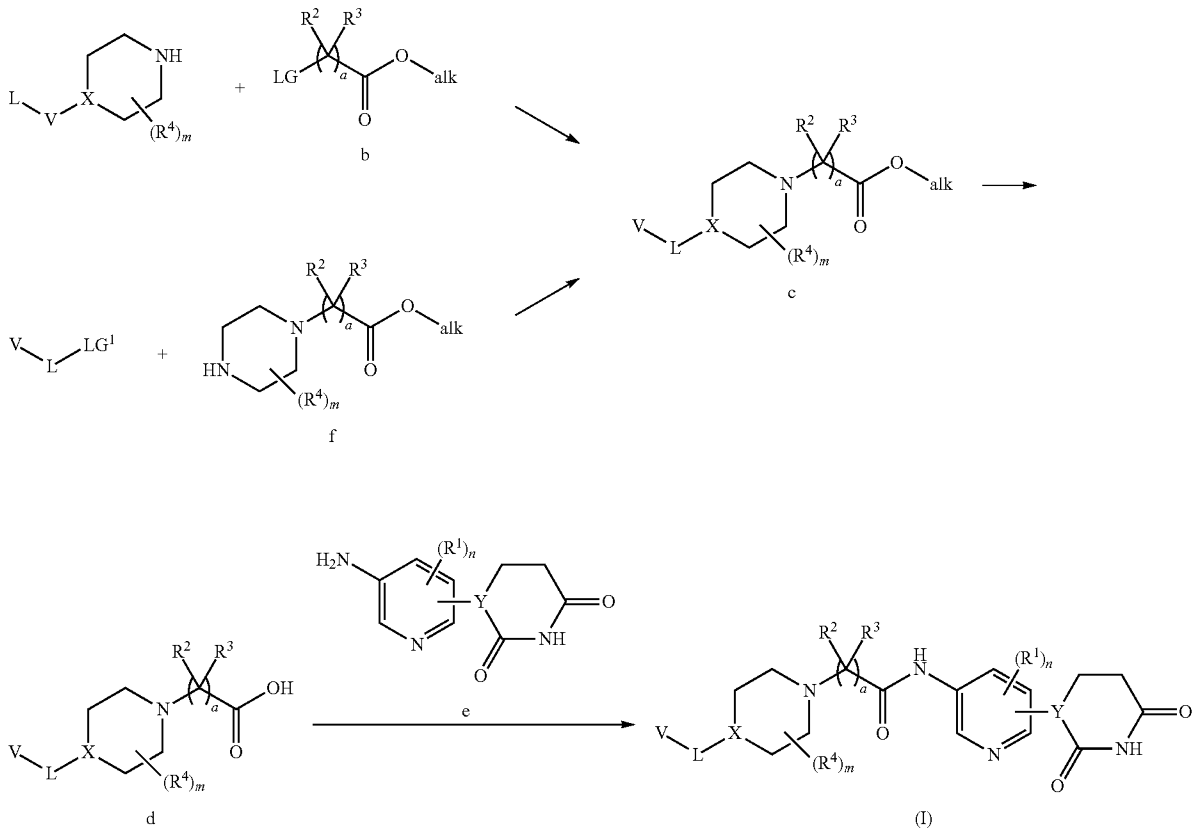

b c f d e (I)

As shown in Scheme 1, compounds of formula (I), wherein X is N or $CR^X$ and L is —O($C_{1-3}$ alkyl)-, —($C_{1-3}$ alkyl)O—, or —($C_{1-4}$ alkyl)- can be prepared starting by reacting the piperidine derivative a with ester intermediate b (where LG is a leaving group such as Cl, Br, I triflate or alkyl sulfonate, and alk is an alkyl group such as Me, Et, Bn, or tert-Bu) in the presence of a base, in a solvent (for example, N,N-diisopropylethylamine in DMF, or $K_2CO_3$ in acetonitrile) at elevated temperature (for example, between about 40° C. and about 100° C.) to provide intermediate c. In some cases, an iodide salt is used to facilitate this transformation (such as sodium iodide or potassium iodide). Removal of the ester protecting group from intermediate c (for example when alk=Me, Et or other alkyl, by treatment with a hydroxide base in a solvent, for example LiOH in THE and water, or when alk=tert-butyl, by treatment with an acid in a solvent such as trifluoroacetic acid in dichloromethane or hydrochloric acid in 1,4-dioxane), provides intermediate d. Coupling of intermediate d with a piperidine dione intermediate e in the presence of a coupling agent (for example HATU, HBTU, or EDC or TCFH, optionally in combination with HOBt), and a base (for example N,N-diisopropylethylamine, triethylamine, or N-methylimidazole), in a solvent, for example, DCM, DMF, NMP or mixtures thereof) at a temperature between 0° C. to about 70° C. provides compounds of formula (I), wherein X is N or $CR^X$ and L is —O($C_{1-3}$ alkyl)-, —($C_{1-3}$ alkyl)O—, or —($C_{1-4}$ alkyl)-. Alternatively, for intermediate c wherein X is N and L is —O($C_{1-3}$ alkyl)- or —($C_{1-4}$ alkyl)- can be prepared starting by reacting the derivative V-L-LG (LG is an appropriate leaving group such as Cl, Br, I, triflate or alkyl sulfonate) with an appropriately derivatized piperidyl ester derivative f (for example, wherein alk is an alkyl group such as Me, Et, Bn, or tert-Bu) in the presence of a base, in a solvent (for example, N,N-diisopropylethylamine in DMF, or $K_2CO_3$ in acetonitrile), at elevated temperature (for example, between about 40° C. and about 80° C.) to provide intermediate c.

Scheme 2

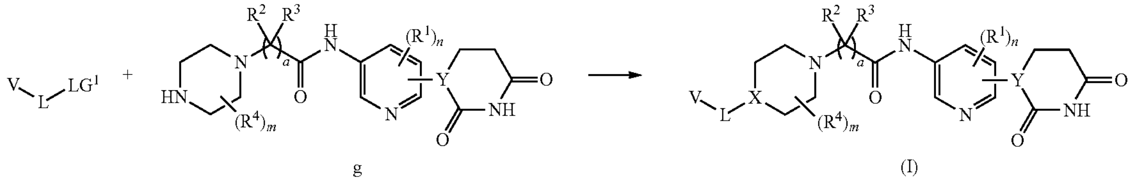

g (I)

-continued

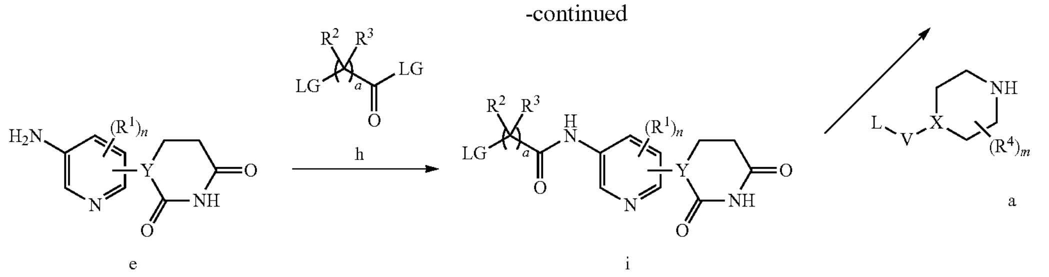

Compounds of formula (I) wherein X is N and L is —O($C_{1-3}$ alkyl)- or —($C_{1-4}$ alkyl)- can also be prepared according to an alternative sequence shown in Scheme 2 by reacting the derivative V-L-LG (LG is an appropriate leaving group such as Cl, Br, I, triflate or alkyl sulfonate) with an appropriately derivatized piperidyl derivative g in the presence of a base, in a solvent (for example, N,N-diisopropylethylamine in DMF, or $K_2CO_3$ in acetonitrile) at elevated temperature (for example, between about 40° C. and about 100° C.). In some cases, an iodide salt is used to facilitate this transformation (such as sodium iodide or potassium iodide). Alternatively, compounds of formula (I) wherein X is N or $CR^X$ and L is —O($C_{1-3}$ alkyl)-, —($C_{1-3}$ alkyl)O—, or —($C_{1-4}$ alkyl)- can be prepared starting by reacting compound e with an appropriately functionalized carbonyl intermediate h (where LG is a leaving group such as Cl, Br, I triflate or alkyl sulfonate) in the presence of a base, in a solvent (for example, N,N-diisopropylethylamine in DCM, or triethylamine in pyridine) at a temperature between 0° c. to about 60° C. to provide intermediate i. Reacting i (where LG is a leaving group such as Cl, Br, I triflate or alkyl sulfonate) with amine intermediate a in the presence of a base, in a solvent (for example, N,N-diisopropylethylamine in DMF, or $K_2CO_3$ in acetonitrile), at elevated temperature (for example, between about 40° C. and about 80° C.) provides compound of formula (I) wherein X is N or $CR^X$ and L is —O($C_{1-3}$ alkyl)-, —($C_{1-3}$ alkyl)O—, or —($C_{1-4}$ alkyl)-.

Scheme 3

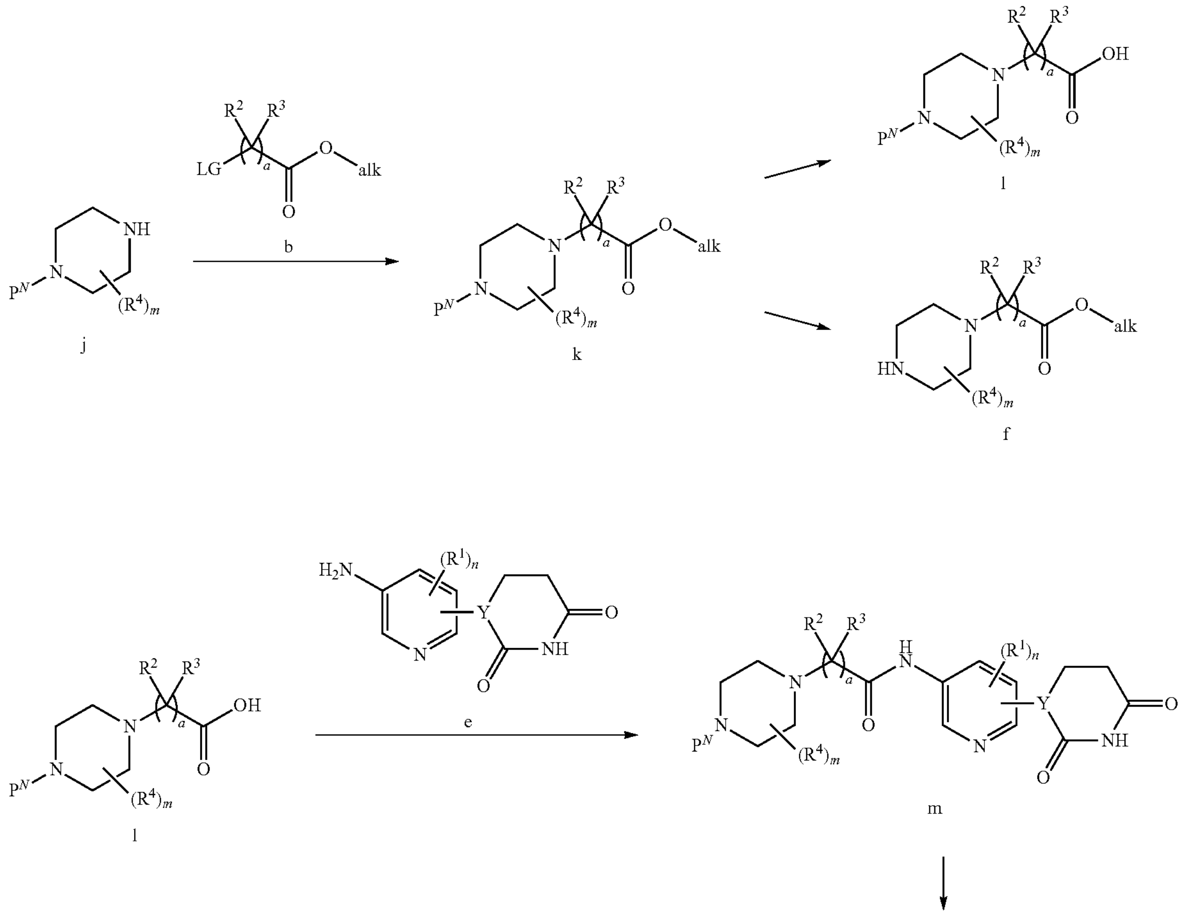

-continued

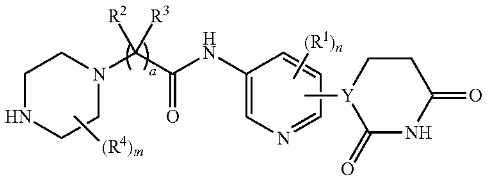

g

Intermediates such as amine g can be prepared according to Scheme 3. Starting by reacting an appropriately functionalized piperazine j with ester intermediate b (where LG is a leaving group such as Cl, Br, I triflate or alkyl sulfonate, and alk is an alkyl group such as Me, Et, Bn, or tert-Bu) in the presence of a base, in a solvent (for example, N,N-diisopropylethylamine in DMF, or $K_2CO_3$ in acetonitrile) at elevated temperature (for example, between about 40° C. and about 100° C.) to provide intermediate k. In some cases, an iodide salt is used to facilitate this transformation (such as sodium iodide or potassium iodide). Removal of the ester protecting group from intermediate k (for example when alk=Me, Et or other alkyl, by treatment with a hydroxide base in a solvent, for example LiOH in THE and water, or when alk=tert-butyl, by treatment with an acid in a solvent such as trifluoroacetic acid in dichloromethane or hydrochloric acid in 1,4-dioxane), provides intermediate 1. Coupling of intermediate 1 with a piperidine dione intermediate e in the presence of a coupling agent (for example HATU, HBTU, or EDC or TCFH, optionally in combination with HOBt), and a base (for example N,N-diisopropylethylamine, triethylamine, or N-methylimidazole), in a solvent, for example, DCM, DMF, NMP or mixtures thereof) at a temperature between 0° C. to about 70° C. provides amine intermediate g. Intermediates such as amine f can be prepared by removal of the N-protecting group $P^N$ from intermediate k, (for example, when $P^N$ is Boc, by treatment with an acid in a solvent, for example, HCl in dioxane or EtOAc, at room temperature, or with TFA in DCM, at room temperature or when $P^N$ is Bn or Cbz by hydrogenation with a metal catalyst, in a solvent such as palladium on carbon in methanol).

Scheme 4

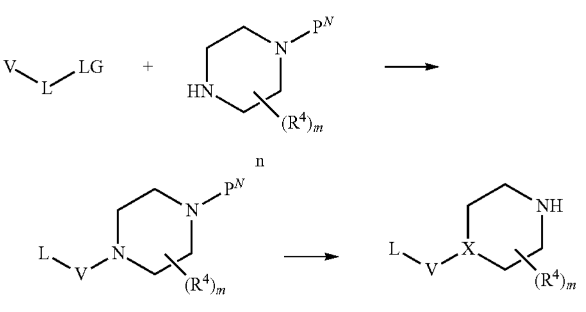

n o a

Intermediates such as a wherein X is N and L is —O($C_{1-3}$ alkyl)- or —($C_{1-4}$ alkyl)- can be prepared according to Scheme 4. Treating V-L-LG (where L is —O($C_{1-3}$ alkyl)- or —($C_{1-4}$ alkyl)- and LG is a leaving group such as Cl, Br, I triflate or alkyl sulfonate) with amine n in the presence of a base, in a solvent (for example, N,N-diisopropylethylamine in DMF, or $K_2CO_3$ in acetonitrile) at elevated temperature (for example, between about 40° C. and about 100° C.) to provide intermediate o. In some cases, an iodide salt is used to facilitate this transformation (such as sodium iodide or potassium iodide). Removal of the N-protecting group $P^N$ from intermediate o, (for example, when $P^N$ is Boc, by treatment with an acid in a solvent, for example, HCl in dioxane or EtOAc, at room temperature, or with TFA in DCM, at room temperature or when $P^N$ is Bn or Cbz by hydrogenation with a metal catalyst, in a solvent such as palladium on carbon in methanol) provides intermediate a wherein X is N and L is —O($C_{1-3}$ alkyl)- or —($C_{1-4}$alkyl)-.

Scheme 5

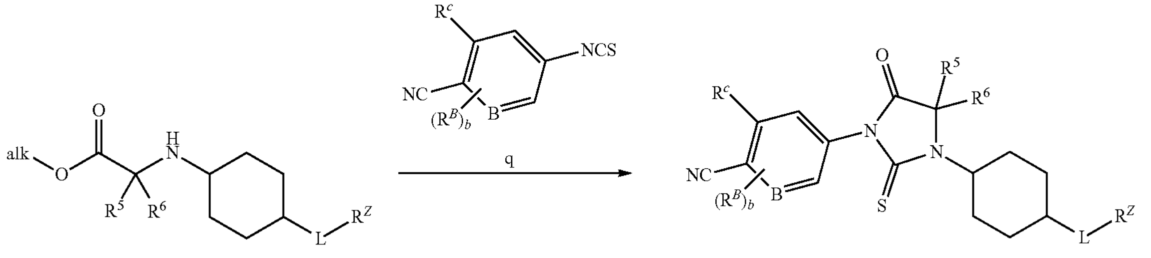

p r

-continued

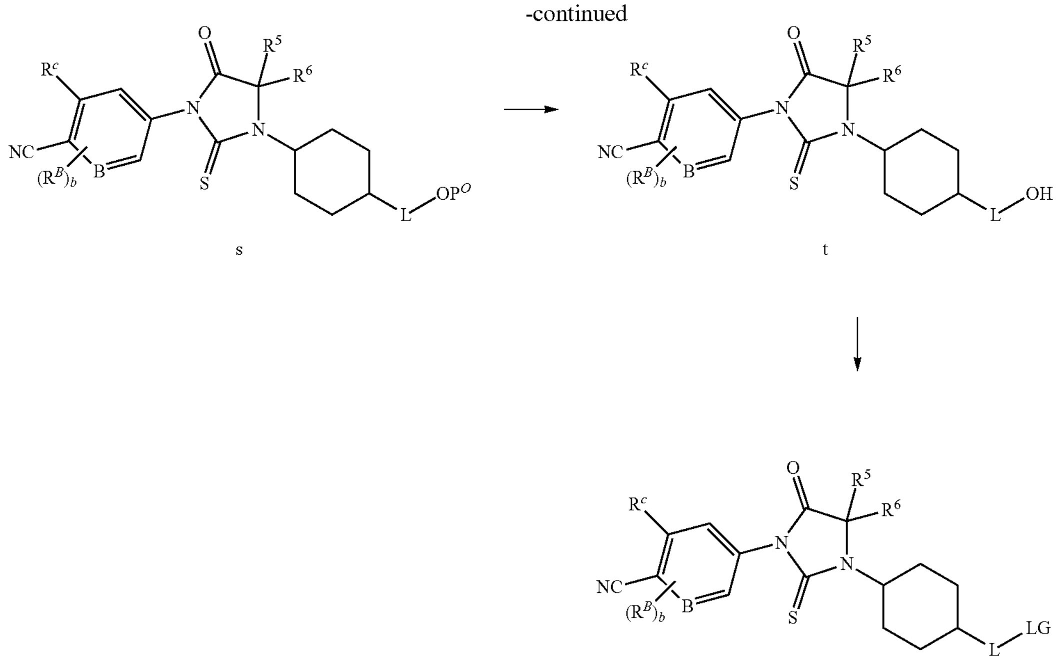

s t u

Intermediates such as V-L-$R^Z$ (for example, intermediate r) where $R^Z$ is an alcohol, protected alcohol, leaving group or heterocycle (such as a substituted piperidine or piperazine) can be prepared according to Scheme 5. Treatment of ester intermediate p (where alk is an alkyl group such as Me, Et, Bn, or tert-Bu) with an appropriately derivatized 4-isothiocyanatobenzonitrile or 5-isothiocyanatopicolinonitrile q, in the presence of a base, such as triethylamine, in a solvent, such as EtOAc, at elevated temperature, for example, between about 70° C. and about 90° C. provides intermediate r. Intermediates such as u wherein LG is a leaving group (such as Cl, Br, I triflate or alkyl sulfonate), and L is —O($C_{1-3}$ alkyl)- or —($C_{1-4}$ alkyl)- can be prepared from intermediate s (where $P^O$ is an alcohol protecting group such as THP, TBS, acetate or benzyl). Removal of the protecting group $P^O$ (for example, when $P^O$ is THP by treatment with catalytic acid in a solvent, for example HCl in dioxane) in s provides alcohol intermediate t. Activation of the alcohol functional group in t to a leaving group (for example when LG is Br by treatment of t with thionyl bromide in dichloromethane) provides intermediate u wherein LG is a leaving group (such as Cl, Br, I triflate or alkyl sulfonate), and L is —O($C_{1-3}$ alkyl)- or —($C_{1-4}$ alkyl)-, which can be further reacted to provide compounds of formula (I).

Scheme 6

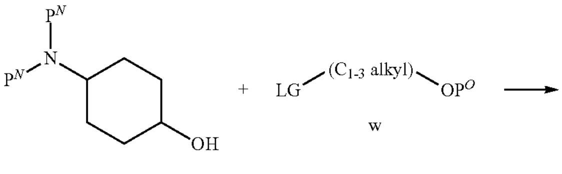

v w

-continued

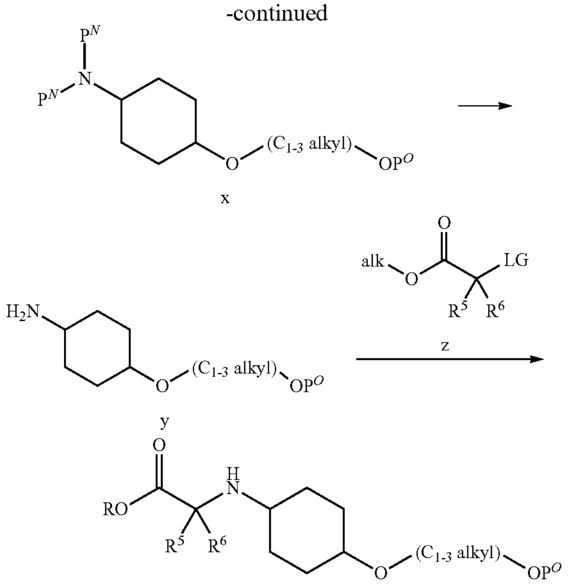

x y aa

Intermediates p, wherein L is —O($C_{1-3}$ alkyl)- and $R^Z$ is a protected alcohol $OP^O$ (for example a THP ether or TBS ether), for example aa, can be prepared according to Scheme 6. Starting from alcohol intermediate v (where $P^N$ is an amine protecting group such as Bn or Boc), reacting with electrophile w (where LG is a leaving group such as Cl, Br, I triflate or alkyl sulfonate, and $P^O$ is an oxygen protecting group such as THP or TBS) in the presence of a base, optionally with a catalyst, in a solvent (for example KOH and tetrabutylammonium bromide in xylene) at elevated temperature, for example between 70° C. and 130° C.

provides intermediate x. Removal of the protecting group $P^N$ in x (for example, when $P^N$ is Bn by hydrogenation with palladium on carbon in methanol, or when $P^N$ is Boc by treatment with HCL in dioxane) provides amine intermediate y. Reacting amine y with ester z (where alk is an alkyl group such as Me, Et, Bn, or tert-Bu, and LG is a leaving group such as Cl, Br, I triflate or alkyl sulfonate) in the presence of a base, possibly with an iodide salt, in a solvent (for example, potassium carbonate and potassium iodide in acetonitrile), at an elevated temperature (for example between about 70° C. and 130° C.) provides intermediate aa, which can be further reacted to provide compounds of formula (I) where in L=—O($C_{1-3}$ alkyl)-.

palladium on carbon in methanol, or when $P^N$ is Boc by treatment with HCL in dioxane) provides amine intermediate gg. Reacting amine gg with ester z (where alk is an alkyl group such as Me, Et, Bn, or tert-Bu, and LG is a leaving group such as Cl, Br, I triflate or alkyl sulfonate) in the presence of a base, optionally with an iodide salt, in a solvent (for example, potassium carbonate and potassium iodide in acetonitrile), at an elevated temperature (for example between about 70° C. and 130° C.) provides intermediate hh, where $R^Y$ is H or an alcohol protecting group (for example THP, TBS or Tr) which can be further reacted to provide compounds of formula (I) where in L —($C_{1-3}$ alkyl)-.

Scheme 7

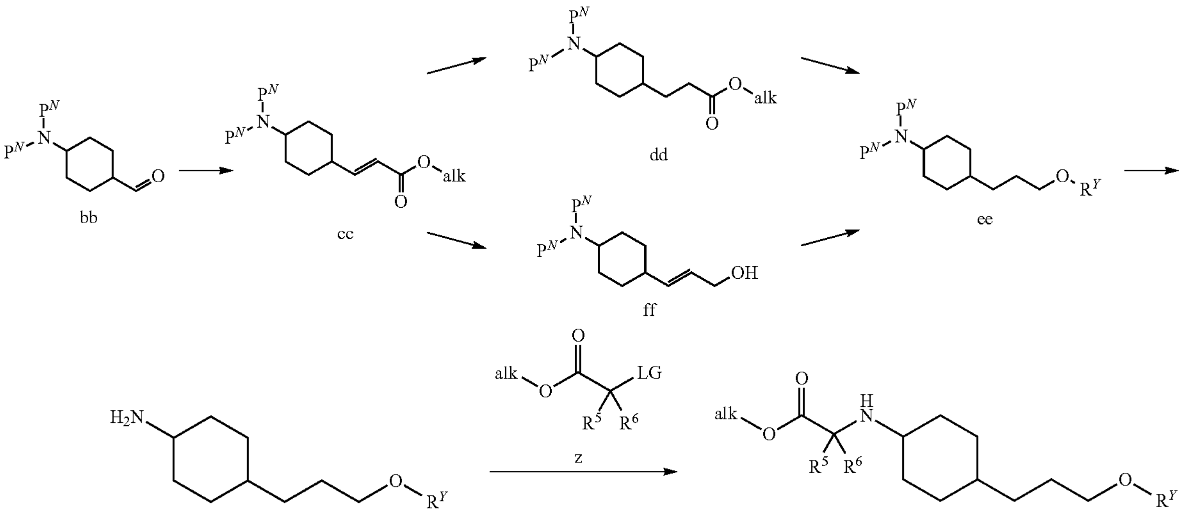
bb cc dd ee ff z gg hh

Intermediates p, wherein L is —($C_{1-3}$ alkyl)- and $R^Z$ is an alcohol or a protected alcohol (for example a THP ether or TBS ether), for example hh, can be prepared according to Scheme 6. Starting from aldehyde intermediate bb (where $P^N$ is an amine protecting group such as Bn or Boc), reacting with an olefination reagent, in the presence of a base, in a solvent (for example, ethyl 2-(diethoxyphosphoryl)acetate and sodium hydride in THF) at a temperature between 0° C. and 60° C. provides olefin intermediate cc. Reduction of cc by hydrogenation, in the presence of a catalyst, in a solvent (for example, palladium on carbon in methanol under a hydrogen atmosphere), at elevated pressure (for example between 10 and 100 psi) provides intermediate dd. Reduction of the ester functional group can be accomplished by treatment with a reducing agent, in a solvent (for example, diisobutylaluminum hydride in DCM) at a temperature between −78° C. and 25° C. provides intermediate ee, wherein $R^Y$ is H. Alternatively, intermediate ee can be prepared by treatment of intermediate cc with a reducing agent, in a solvent (for example, diisobutylaluminum hydride in DCM) at a temperature between −78° C. and 25° C. to provide intermediate ff. Hydrogenation of ff, in the presence of a catalyst, in a solvent (for example, palladium on carbon, in methanol, under a hydrogen atmosphere), at elevated pressure (for example between 10 and 100 psi) provides intermediate ee. Removal of the protecting group $P^N$ in ee (for example, when $P^N$ is Bn, by hydrogenation with Scheme 8

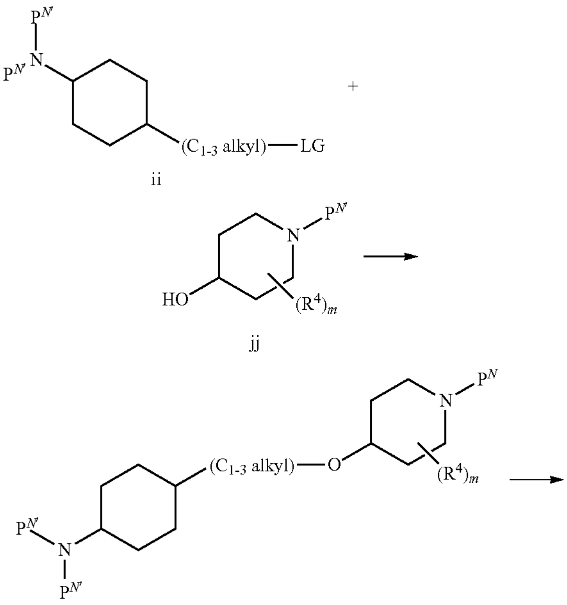
ii + jj kk

-continued

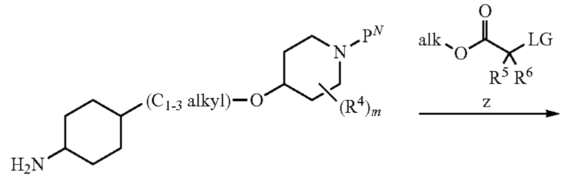

ll

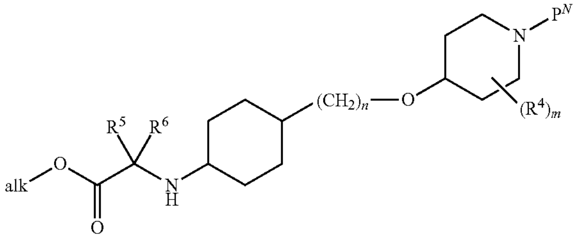

mm

Intermediates p wherein L is —($C_{1-3}$ alkyl)O— and $R^Z$ is a heterocycle or cycloalkyl group, for example mm, can be prepared according to Scheme 8. Starting from intermediate ii (where $P^{N'}$ is an amine protecting group for example Bn or Boc), and LG is a leaving group, for example Cl, Br, I triflate or alkyl sulfonate), reacting with alcohol jj (where $P^N$ is an amine protecting group for example Bn or Boc), in the presence of a base, optionally with a catalyst, in a solvent (for example KOH and tetrabutylammonium bromide in xylene) at elevated temperature (for example between 70° C. and 130° C.), provides ether intermediate kk. Removal of the protecting group $P^{N'}$ in kk (for example, when $P^{N'}$ is Bn, by hydrogenation with palladium on carbon in methanol, or when $P^N$ is Boc by treatment with HCl in dioxane) provides amine intermediate ll.

Reacting amine ll with ester z (where alk is an alkyl group such as Me, Et, Bn, or tert-Bu, and LG is a leaving group such as Cl, Br, I triflate or alkyl sulfonate) in the presence of a base, optionally with an iodide salt, in a solvent (for example, potassium carbonate and potassium iodide in acetonitrile), at an elevated temperature (for example between about 70° C. and 130° C.) provides intermediate mm, which can be further reacted to provide compounds of formula (I) wherein L is —($C_{1-3}$ alkyl)O—.

Scheme 9

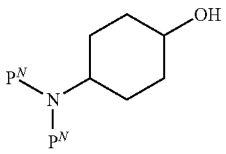

v

+

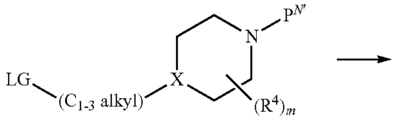

nn

-continued

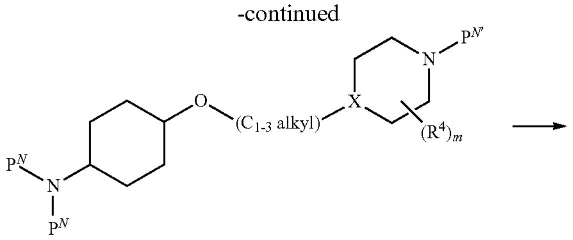

oo

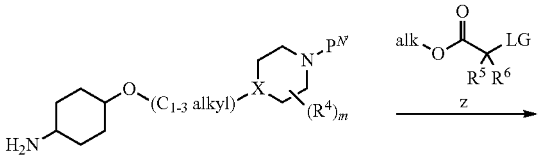

pp

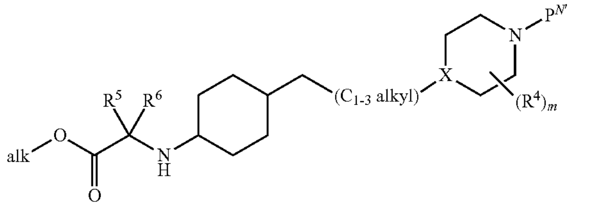

qq

For certain intermediates p wherein L is —O($C_{1-3}$ alkyl)- and $R^Z$ is a protected heterocycle or cycloalkyl group, for example qq, a modified sequence can be used, shown in Scheme 9. Starting from alcohol v (wherein $P^N$ is an amine protecting group such as Bn or Boc), reactiong with electrophile intermediate nn (where LG is a leaving group, for example Cl, Br, I, triflate or alkyl sulfonate, and $P^{N'}$ is an amine protecting group such as Bn or Boc) in the presence of a base, optionally with a catalyst, in a solvent (for example KOH and tetrabutylammonium bromide in xylene) at elevated temperature (for example between 70° C. and 130° C.), provides ether intermediate oo. Removal of the protecting group $P^N$ in oo (for example, when $P^{N'}$ is Bn, by hydrogenation with palladium on carbon in methanol, or when $P^N$ is Boc by treatment with HCl in dioxane) provides amine intermediate pp. Reacting amine pp with ester z (where alk is an alkyl group such as Me, Et, Bn, or tert-Bu, and LG is a leaving group such as Cl, Br, I triflate or alkyl sulfonate) in the presence of a base, optionally with an iodide salt, in a solvent (for example, potassium carbonate and potassium iodide in acetonitrile), at an elevated temperature (for example between about 70° C. and 130° C.) provides intermediate qq, which can be further reacted to provide compounds of formula (I) wherein L is —O($C_{1-3}$ alkyl)-.

Scheme 10

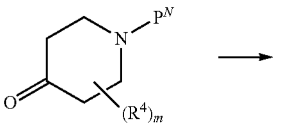

rr

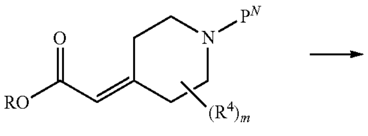

ss

-continued

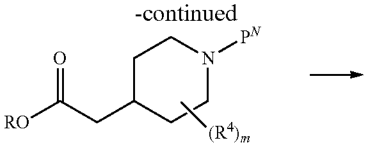

tt

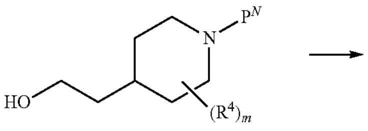

uu

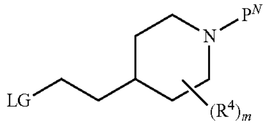

vv

Certain examples of intermediates nn wherein X is $CR^Z$, for example vv, were prepared according to Scheme 10. Olefination of ketone intermediate rr, wherein $P^N$ is an amine protecting group (for example Bn, Boc, or Cbz) with an olefination reagent and a base, in a solvent (for example, ethyl 2-(diethoxyphosphoryl)acetate and sodium hydride in THF) at a temperature between 0° C. and 60° C. provides olefin intermediate ss. Hydrogenation of ss, in the presence of a catalyst, in a solvent (for example, palladium on carbon in methanol under a hydrogen atmosphere), at elevated pressure (for example between 10 and 100 psi) provides intermediate tt. Reduction of the ester functional group in tt is accomplished by treatment with a reducing agent, in a solvent (for example, diisobutylaluminum hydride in DCM) at a temperature between −78° C. and 25° C. provides intermediate uu. Activation of the alcohol uu to a leaving group LG (for example, if LG is Br, by treatment with thionyl bromide in dichloromethane and DMF, or if LG is triflate, by treatment with triflic anhydride in dichloromethane) provides intermediate vv, which can be further reacted to provide compounds of formula (I) wherein L is —O($C_{1-3}$ alkyl)- and X is $CR^X$.

Scheme 11

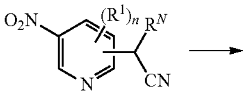

ww

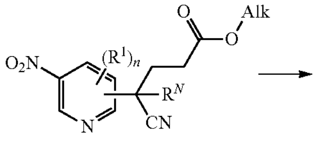

xx

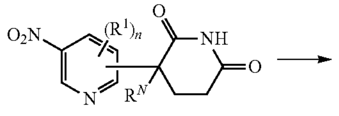

yy

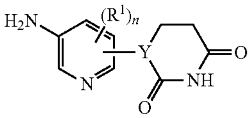

e

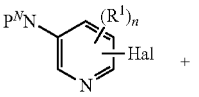

zz

+

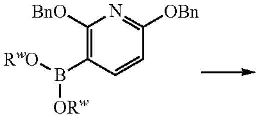

aaa

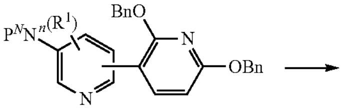

bbb

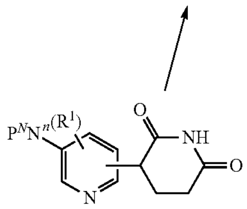

ccc

Appropriately derivatized piperidine diones e, wherein Y is $CR^N$ (for example, CH or C-Me) can be prepared from $R^1$-derivatized (nitro)phenylacetonitrile derivatives ww, by treatment with an acrylate ester (for example, tert-butyl acrylate) in the presence of a base, optionally with a catalyst, in a solvent (for example, potassium carbonate and benzyltriethylammonium chloride in toluene) at elevated temperature (for example between 50° C. to about 120° C.), to provide intermediate xx. Treatment of xx with an acid, in a solvent (for example concentrated sulfuric acid in acetic acid) at elevated temperature (for example, 50° C. to about 140° C.) provides cyclized intermediate yy. Reduction of the nitro group in yy (for example, by treatment with a reducing agent, for example $H_2$, in the presence of a catalyst, such as Pd/C, in a solvent, such as EtOH or MeOH; or Fe and $NH_4Cl$, in a solvent such as EtOH and $H_2O$) provides intermediate e, wherein Y is $CR^N$ (for example, CH or C-Me). Alternatively, intermediates such as e wherein Y is $CR^N$ (for example, CH or C-Me) can be prepared by reacting a protected aniline such as zz, wherein $P^N$ is an amine protecting group (for example, Boc, SEM, or Cbz) and Hal is a halogen or pseudohalogen (for example, Cl, Br, I, or triflate), with an arylboronic acid derivative aaa, wherein $R^W$ is a proton or alkyl group, in the presence of a palladium catalyst and a base, in a solvent (for example, [1,1'-bis(diphenylphosphino)ferrocene]dichloropalladium(II) and sodium bicarbonate in dioxane and water or XPhos Pd G3 and cesium carbonate in THF and water) to give intermediate bbb. Hydrogenation of bbb, with a catalyst, in a solvent (for example, palladium on activated carbon in methanols) at elevated pressure of hydrogen (for example, between 5 and 100 psi provides intermediate ccc, which following removal of the protecting group $P^N$ (for example, when $P^N$ is Boc, by treatment with an acid, in a solvent such as HCl in dioxane or trifluoroacetic acid in dichioromethane) to give intermediate e, which can be further reacted to provide compounds of formula (I) wherein Y is $CR^N$ (for example, CH or C-Me).

tions (for example, concentrated aqueous hydrochloric acid) induces cyclization to provide intermediate jjj, which under reductive conditions for example, by treatment with a reducing agent, for example $H_2$, in the presence of a catalyst, such as Pd/C, in a solvent, such as EtOH or MeOH; or Fe and $NH_4Cl$, in a solvent such as EtOH and $H_2O$) provides intermediate e, which can be further reacted to provide compounds of formula (I) wherein Y is N.

Methods of Use

In one embodiment, the compounds described herein have utility as pharmaceuticals to treat, prevent or improve conditions in animals or humans. The compounds described herein have utility as pharmaceuticals to treat, prevent or improve conditions in animals or humans. Accordingly, provided herein are many uses of compounds, including the treatment or prevention of those diseases set forth below. In one embodiment, the methods provided herein comprise the administration of an effective amount of a compound to a subject in need thereof.

Scheme 12

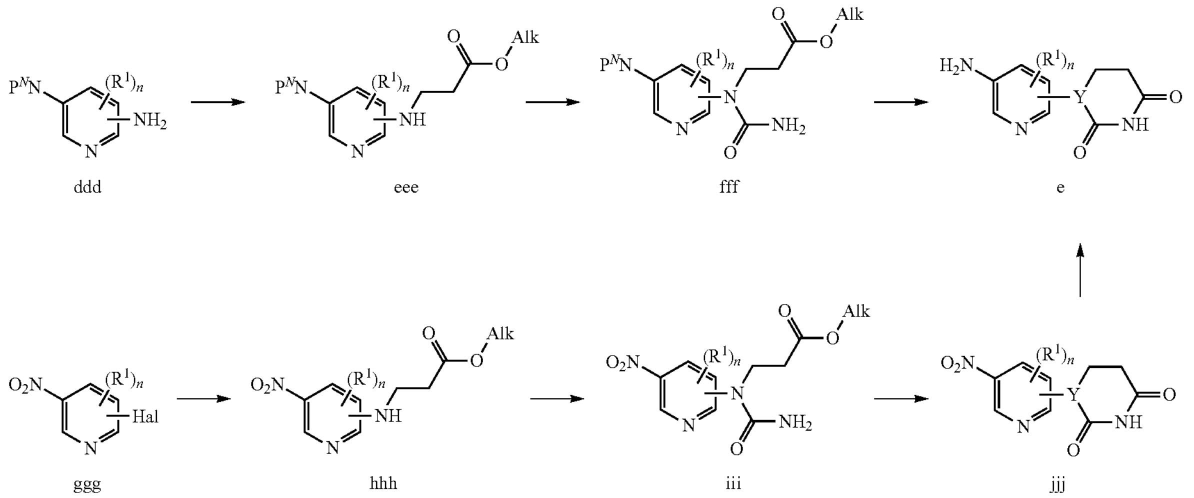

Intermediates such as e wherein Y is N are prepared according to Scheme 12. Starting from an appropriately $R^1$ functionalized protected dianiline ddd wherein $P^N$ is an amine protecting group (for example, Boc, Bn, or Cbz), treatment with a 3-bromopropionate ester (for example, methyl 3-bromopropionate or tert-butyl 3-bromopropionate), in the presence of a base, optionally with a phase transfer catalyst, in a solvent (for example, potassium carbonate and benzyltriethylammonium chloride in toluene) at elevated temperature (for example, between 50° and 120° C.) provides intermediate eee. Treating eee with an isocyanate salt (for example, potassium isocyanate or sodium isocyanate), in a solvent (for example, potassium isocyanate in acetic acid) provides urea intermediate fff. Exposing fff to acidic conditions (for example, concentrated aqueous hydrochloric acid) induces cyclization to provide intermediate e, which can be further reacted to provide compounds of formula (I) wherein Y is N. Alternatively, intermediates such as e, wherein Y is N can be prepared starting from an appropriately functionalized nitroarene ggg, where Hal is a halogen or pseudo halogen (for example, fluoro, chloro, bromo or trifluoromethanesulfonate), treating with a 3-aminopropionate ester (for example methyl 3-aminopropionate or tert-butyl 3-aminopropionate), in the presence of a base, in a solvent (for example potassium carbonate in DMF, or cesium carbonate in NMP) at elevated temperature (for example between 50° C. and about 150° C.) to provide intermediate hhh. Treating hhh with an isocyanate salt (for example, potassium isocyanate or sodium isocyanate), in a solvent (for example, potassium isocyanate in acetic acid) provides urea intermediate iii. Exposing iii to acidic condi- The methods provided herein comprise the administration of an effective amount of one or more compound(s) to a subject in need thereof.

Provided herein are methods for treating or preventing an androgen receptor (AR) mediated disease in a subject, the method comprising administering to a subject in need thereof an effective amount of a compound as described herein.

Provided herein are methods for treating or preventing an AR mediated disease in a subject, the method comprising administering to a subject in need thereof an effective amount of a compound as described herein.

In another aspect, provided herein are compounds for use in the treatment or prevention of an AR mediated disease in a subject, comprising administering to a subject in need thereof an effective amount of a compound as described herein. In some embodiments, provided herein are compounds for use in the treatment of an AR mediated disease in a subject, comprising administering to a subject in need thereof an effective amount of a compound as described herein. In some embodiments, provided herein are compounds for use in the prevention of an AR mediated disease in a subject, comprising administering to a subject in need thereof an effective amount of a compound as described herein.

In some embodiments, the compound used in the methods herein is a compound as described herein. In some embodiments, the compound is a compound of formula I. In some embodiments, the compound is a compound of formula II. In some embodiments, the compound is a compound of formula III. In some embodiments, the compound is a compound of formula IV. In some embodiments, the compound is a compound of formula V. In some embodiments, the compound is a compound from Table 1.

In some embodiments, the AR mediated disease is AR wild-type mediated disease. In other embodiments, the AR mediated disease is the result of AR amplification.

In certain embodiments, the AR mediated disease is prostate cancer. In some such embodiments, the prostate cancer is castration resistant prostate cancer (CRPC). In some such embodiments, the prostate cancer is metastatic castration resistant prostate cancer (mCRPC). In still another embodiment, the prostate cancer is non-metastatic CRPC (nmCRPC). In some embodiments, the prostate cancer is hormone refractory. In some embodiments, the prostate cancer is resistant to treatment with an AR antagonist. For example, the prostate cancer is resistant to treatment with enzalutamide, bicalutamide, abiraterone, ARN-509, ODM-201, EPI-001, EPI-506, AZD-3514, galeterone, ASC-J9, flutamide, hydroxyflutamide, nilutamide, cyproterone acetate, ketoconazole, or spironolactone.

Provided herein are methods of reducing AR levels, the method comprising administering to a subject an effective amount of a compound. Also provided herein are compounds for use in methods of reducing AR levels in a cell in vivo, ex vivo or in vitro, comprising contacting the cell with an effective amount of a compound. In one embodiment, the cell is in a patient. In one embodiment, the cell is not in a patient. In one embodiment, provided herein are methods of reducing levels of wild-type AR within a tumor, the method comprising administering a therapeutically effective amount of a compound, to reduce the level of wild-type AR within the tumor. In one embodiment, provided herein are methods of reducing levels of AR-full length (AR-FL) within a tumor, the method comprising administering a therapeutically effective amount of a compound, to reduce the level of AR-full length (AR-FL) within the tumor. In some embodiments, the AR levels are reduced compared to the AR levels prior to compound administration. In some embodiments, the AR levels are reduced by 20%, 30%, 40%, 50%, 60%, 70%, 80%, 90%, 95%, or 99% compared to the AR levels prior to compound administration.

Also provided herein are methods for regulating protein activity of AR in a patient in need thereof, comprising administering to said patient an amount of a compound. In some such embodiments, provided herein are methods for decreasing protein activity of AR in a patient in need thereof, comprising administering to said patient an amount of a compound. In some embodiments, the protein activity of AR is reduced compared to the protein activity of AR prior to compound administration. In some embodiments, the protein activity of AR is reduced by 20%, 30%, 40%, 50%, 60%, 70%, 80%, 90%, 95%, or 99% compared to the protein activity of AR prior to compound administration.

In some embodiments of the methods described herein, the methods additionally comprise administering one or more second agents selected from an AR antagonist (such as cyproterone acetate, spironolactone, bicalutamide, and enzalutamide), a 5a-reductase inhibitor (such as finasteride and dutasteride), a CYP17A1 inhibitor (such as abiraterone acetate), a gonadotropin-releasing hormone (GnRH) analog (such as leuprorelin and cetrorelix), and an anti-gonadotropin (such as megestrol acetate and medroxyprogesterone acetate).

In some embodiments, the compounds provided herein may be used in any of the above-mentioned methods.

In some embodiments, the compound provided herein may be used in any of the above-mentioned methods.

Pharmaceutical Compositions and Routes of Administration

The compounds provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions.

The compounds can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the compounds in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a compound to be administered to a subject is rather widely variable and can be subject to the judgment of a health-care practitioner. In general, the compounds can be administered one to four times a day in a dose of about 0.001 mg/kg of a subject's body weight to about 10 mg/kg of a subject's body weight, but the above dosage may be properly varied depending on the age, body weight and medical condition of the subject and the type of administration. In one embodiment, the dose is about 0.001 mg/kg of a subject's body weight to about 5 mg/kg of a subject's body weight, about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the compound administered will depend on such factors as the solubility of the active component, the formulation used and the route of administration.

In another embodiment, provided herein are methods for the treatment or prevention of a disease or disorder comprising the administration of about 0.01 mg/day to about 750 mg/day, about 0.1 mg/day to about 375 mg/day, about 0.1 mg/day to about 150 mg/day, about 0.1 mg/day to about 75 mg/day, about 0.1 mg/day to about 50 mg/day, about 0.1 mg/day to about 25 mg/day, or about 0.1 mg/day to about 10 mg/day of a compound to a subject in need thereof.

In another embodiment, provided herein are unit dosage formulations that comprise between about 0.1 mg and 500 mg, about 1 mg and 250 mg, about 1 mg and about 100 mg, about 1 mg and about 50 mg, about 1 mg and about 25 mg, or between about 1 mg and about 10 mg of a compound.

In a particular embodiment, provided herein are unit dosage formulations comprising about 0.1 mg or 100 mg of a compound.

In another embodiment, provided herein are unit dosage formulations that comprise 0.5 mg, 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a compound.

An compound can be administered once, twice, three, four or more times daily. In a particular embodiment, doses of 100 mg or less are administered as a once daily dose and doses of more than 100 mg are administered twice daily in an amount equal to one half of the total daily dose.

An compound can be administered orally for reasons of convenience. In one embodiment, when administered orally, a compound is administered with a meal and water. In another embodiment, the compound is dispersed in water or juice (e.g., apple juice or orange juice) or any other liquid and administered orally as a solution or a suspension.

The compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a compound without an additional carrier, excipient or vehicle.

In another embodiment, provided herein are compositions comprising an effective amount of a compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the compound can be delayed or prolonged by proper formulation. For example, a slowly soluble pellet of the compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound in oily or emulsified vehicles that allow it to disperse slowly in the serum.

EXAMPLES

The following Examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Salts of the compounds described herein can be prepared by standard methods, such as inclusion of an acid (for example TFA, formic acid, or HCl) in the mobile phases during chromatography purification, or stirring of the products after chromatography purification, with a solution of an acid (for example, aqueous HCl).

Abbreviations Used

DCM Dichloromethane
DIEA N,N-Diisopropylethylamine
DMA N,N-Dimethylacetamide
DMF N,N-Dimethylformamide
DMSO Dimethylsulfoxide
ESI Electrospray ionization
HATU 1-[Bis(dimethylamino)methylene]-1H-1,2,3-triazolo[4,5-b]pyridinium 3-oxide hexafluorophosphate
HPLC High performance liquid chromatography
IBX 1-Hydroxy-19?,2-benziodoxole-1,3-dione
LCMS Liquid chromatography mass spectrometry
MeOH Methanol
MS Mass spectrometry
MTBE Methyl tert-butyl ether
NMP N-Methylpyrrolidone
NMR Nuclear magnetic resonance
OMs Mesylate
OTs Tosylate
PPh3 Triphenylphosphine
TFA Trifluoracetic acid
TfzO Triflic anhydride
THF Tetrahydrofuran
THP Tetrahydropyrane
TLC Thin layer chromatography
TMSCl Trimethylsilyl chloride
TMSCN Trimethylsilyl cyanide
TMSOTf Trimethylsilyl trifluoromethanesulfonate Example 1: 2-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1(2H)-yl)pyridin-3-yl)acetamide

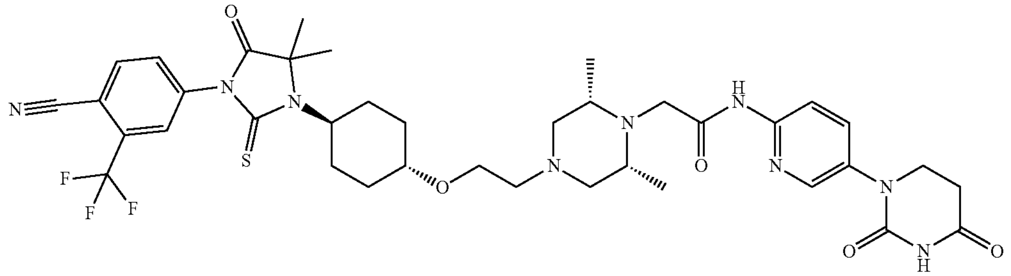 [SMILES: C[C@@H]1CN(CCO[C@H]2CC[C@H](N3C(=S)N(c4ccc(C#N)c(C(F)(F)F)c4)C(=O)C3(C)C)CC2)C[C@H](C)N1CC(=O)Nc1ccc(N2CCC(=O)NC2=O)cn1]

trans-4-(Dibenzylamino)cyclohexan-1-ol. To a mixture of trans-4-aminocyclohexane-1-ol (40 g, 347 mmol, 1.0 equiv.) and cesium carbonate (339 g, 1.04 mol, 3 equiv.) in acetonitrile (900 mL) was added drop wise benzyl bromide (119 g, 698 mmol, 2.01 equiv.). The reaction solution was stirred at room temperature. After 48 h the reaction mixture was filtered and concentrated. The resulting residue was diluted with DCM (300 mL), washed with water (100 mL×3), dried over anhydrous sodium sulfate and concentrated. To provide trans-4-(dibenzylamino)cyclohexan-1-ol (77 g, 261 mmol, 75% yield) as a light red solid. The crude product was carried forward without further purification. MS (ESI) m/z 116.3 $[M+1]^+$; $^1$H NMR400 MHz DMSO-$d_6$ δ7.27-7.34 (m, 8H), 7.19-7.21 (m, 2H), 4.42 (d, J=4.8 Hz, 1H), 3.55 (s, 4H), 2.33-2.36 (m, 1H), 1.74-1.84 (m, 4H), 1.40 (dd, J=12.4 Hz, 2.0 Hz, 2H), 0.98 (d, J=13.2 Hz, 2H).

trans-N,N-Dibenzyl-4-(2-((tetrahydro-2H-pyran-2-yl)oxy)ethoxy)cyclohexan-1-amine. To a mixture of trans-4-(dibenzylamino)cyclohexan-1-ol(60 g, 203 mmol, 1.0 equiv.) and tetrabutylammonium hydrogensulfate (13.8 g, 40.6 mmol, 0.2 equiv.) in THE (400 mL) and water (200 mL) was added 2-(2-bromoethoxy)tetrahydro-2H-pyran (84.9 g, 406 mmol, 61.5 mL, 2.0 equiv.) and sodium hydroxide (200 g, 5.00 mol, 24.6 equiv.) at 0° C. The reaction solution was heated to 65° C. After 12 h the reaction solution was poured into ice-water (1.0 L) and the aqueous phase was extracted with ethyl acetate (300 mL×2). The combined organic layers were washed with brine (300 mL), dried with anhydrous sodium sulfate, filtered and concentrated. The resulting crude material was purified by column chromatography ($SiO_2$, 2-50% ethyl acetate in petroleum ether) to give trans-N,N-dibenzyl-4-(2-((tetrahydro-2H-pyran-2-yl)oxy)ethoxy)cyclohexan-1-amine (60 g, 142 mmol, 70% yield) as a colorless oil. $^1$H NMR 400 MHz $CDCl_3$δ 7.37-7.39 (m, 4H), 7.28-7.32 (m, 4H), 7.22 (m, 2H), 4.63-4.67 (m, 1H), 3.57-3.89 (m, 9H), 3.23-3.25 (m, 1H), 2.55 (m, 1H), 2.08-2.11 (m, 2H), 1.92-1.95 (m, 5H), 1.58-1.64 (m, 6H), 1.54-1.56 (m, 2H), 1.20-1.39 (m, 2H).

trans-4-(2-((Tetrahydro-2H-pyran-2-yl)oxy)ethoxy)cyclohexan-1-amine. To a mixture of trans-N,N-dibenzyl-4-(2-((tetrahydro-2H-pyran-2-yl)oxy)ethoxy)cyclohexan-1-amine (65 g, 153 mmol, 1.0 equiv.) in methanol (500 mL) was added 10% palladium on carbon (6.5 g) under $N_2$. The suspension was degassed under vacuum and purged with hydrogen gas three times. The reaction solution was stirred under an atmosphere of hydrogen gas (15 psi) at room temperature. After 1 h the reaction solution was filtered and the filtrate was concentrated to give trans-4-(2-((tetrahydro-2H-pyran-2-yl)oxy)ethoxy)cyclohexan-1-amine (46 g) as an off-white oil. The crude material was carried forward without further purification. $^1$H NMR400 MHz $CDCl_3$δ 7.34-7.36 (m, 1H), 4.63-4.65 (m, 1H), 3.82-3.91 (m, 3H), 3.52-3.66 (m, 5H), 3.28 (m, 1H), 2.70-2.71 (m, 1H), 2.01-2.04 (m, 2H), 1.85-1.89 (m, 3H), 1.58-1.59 (m, 1H), 1.45-1.56 (m, 8H), 1.29-1.32 (m, 2H), 1.11-1.14 (m, 2H).

Methyl 2-methyl-2-((trans-4-(2-((tetrahydro-2H-pyran-2-yl)oxy)ethoxy)cyclohexyl)amino)propanoate. To a mixture of trans-4-(2-((tetrahydro-2H-pyran-2-yl)oxy)ethoxy)cyclohexan-1-amine (25 g, 103 mmol, 1.0 equiv.) in acetonitrile (175 mL) was added methyl 2-bromo-2-methylpropanoate (37.2 g, 205 mmol, 26.6 mL, 2.0 equiv.), potassium carbonate (28.4 g, 205 mmol, 2.0 equiv.) and potassium iodide (1.71 g, 10.3 mmol, 0.1 equiv.). The reaction solution was heated to 110° C. After 16 h the reaction solution was diluted with water (100 mL) and extracted with ethyl acetate (2×75 mL). The combined organic layers were washed with brine (50 mL), dried over anhydrous sodium sulfate concentrated. The resulting crude material was purified by column chromatography ($SiO_2$, 0-50% ethyl acetate in petroleum ether) to afford methyl 2-methyl-2-((trans-4-(2-((tetrahydro-2H-pyran-2-yl)oxy)ethoxy)cyclohexyl)amino)propanoate (18.6 g, 54 mmol, 53% yield) as a yellow oil. MS (ESI) m/z 344.4 $[M+1]^+$; $^1H$ NMR (400 MHz $CDCl_3$) δ 4.63 (t, J=3.2 Hz, 1H), 3.82-3.87 (m, 2H), 3.70 (s, 3H), 3.61-3.63 (m, 4H), 3.51-3.60 (m, 2H), 3.22-3.24 (m, 1H), 2.36 (m, 1H), 1.99 (m, 2H), 1.83-1.86 (m, 3H), 1.62 (m, 1H), 1.53-1.60 (m, 6H), 1.30 (m, 6H), 1.12-1.14 (m, 2H).

4-(4,4-Dimethyl-5-oxo-3-(trans-4-(2-((tetrahydro-2H-pyran-2-yl)oxy)ethoxy)cyclohexyl)-2-thioxoimidazolidin-1-yl)-2-(trifluoromethyl)benzonitrile. To a solution of methyl 2-methyl-2-((trans-4-(2-((tetrahydro-2H-pyran-2-yl)oxy)ethoxy)cyclohexyl)amino)propanoate (18.6 g, 54.2 mmol, 1.0 equiv.) in ethyl acetate (130 mL) was added 4-isothiocyanato-2-(trifluoromethyl)benzonitrile (24.7 g, 108 mmol, 2.0 equiv.) and N,N-diisopropylethylamine (14.0 g, 108 mmol, 2.0 equiv.). The reaction solution was heated to 90° C. with stirring. After 12 h the reaction solution was concentrated and the resulting crude material was purified by silica gel column chromatography (0-50% ethyl acetate in petroleum ether) to give 4-(4,4-dimethyl-5-oxo-3-(trans-4-(2-((tetrahydro-2H-pyran-2-yl)oxy)ethoxy)cyclohexyl)-2-thioxoimidazolidin-1-yl)-2-(trifluoromethyl)benzonitrile (25 g, 46.3 mmol, 86% yield) as a yellow oil.

4-(3-(trans-4-(2-Hydroxyethoxy)cyclohexyl)-4,4-dimethyl-5-oxo-2-thioxoimidazolidin-1-yl)-2-(trifluoromethyl)benzonitrile. To a solution of 4-(4,4-dimethyl-5-oxo-3-(trans-4-(2-((tetrahydro-2H-pyran-2-yl)oxy)ethoxy)cyclohexyl)-2-thioxoimidazolidin-1-yl)-2-(trifluoromethyl)benzonitrile (42.5 g, 78.8 mmol, 1.0 equiv.) in dichloromethane (300 mL) was added 4 M hydrochloric acid in 1,4-dioxane (400 mL) drop-wise. The reaction solution was stirred at room temperature. After 1 h the reaction solution was concentrated and purified by silica gel column chromatography (1-20% THE in dichloromethane) to give 4-(3-(trans-4-(2-hydroxyethoxy)cyclohexyl)-4,4-dimethyl-5-oxo-2-thioxoimidazolidin-1-yl)-2-(trifluoromethyl)benzonitrile (21 g, 46.1 mmol, 59% yield) as a yellow glassy oil. MS (ESI) m/z 456.4 $[M+1]^+$; $^1H$ NMR (400 MHz $CDCl_3$) δ 7.95 (d, J=8.0 Hz, 1H), 7.85 (m, 1H), 7.72 (dd, J=10.0 Hz, 1.6 Hz, 1H), 3.73-3.77 (m, 4H), 3.60-3.62 (m, 2H), 3.37-3.39 (m, 1H), 2.88-2.91 (m, 2H), 2.21-2.24 (m, 2H), 1.97 (m, 1H), 1.83-1.88 (m, 3H), 1.61 (s, 6H), 1.33-1.41 (m, 2H).

4-(3-(trans-4-(2-Bromoethoxy)cyclohexyl)-4,4-dimethyl-5-oxo-2-thioxoimidazolidin-1-yl)-2-(trifluoromethyl)benzonitrile. To a mixture of 4-(3-(trans-4-(2-hydroxyethoxy)cyclohexyl)-4,4-dimethyl-5-oxo-2-thioxoimidazolidin-1-yl)-2-(trifluoromethyl)benzonitrile (3.500 g, 7.72 mmol, 1.0 equiv.) in dichloromethane (80 mL) was added N,N-dimethylformamide (8 mL) and thionyl bromide(3.201 g, 15.43 mmol, 2.0 equiv.) at 0° C. After 12 h the reaction solution was poured into aqueous saturated sodium bicarbonate solution (100 mL) and extracted with dichloromethane (3×50 mL). The combined organic layers were dried over sodium sulfate, filtered and concentrated under reduced pressure. The crude material was purified by column chromatography (9-20% ethyl acetate in petroleum ether) to give 4-(3-(trans-4-(2-bromoethoxy)cyclohexyl)-4,4-dimethyl-5-oxo-2-thioxoimidazolidin-1-yl)-2-(trifluoromethyl)benzonitrile (4.200 g, 8.13 mmol, crude) as a yellow solid. MS (ESI) m/z 518.1 $[M+1]^+$.

tert-Butyl (3R,5S)-4-(2-methoxy-2-oxoethyl)-3,5-dimethylpiperazine-1-carboxylate. A solution of tert-butyl (3S,5R)-3,5-dimethylpiperazine-1-carboxylate (5. g, 23.33 mmol, 1 equiv.), methyl bromoacetate (3.57 g, 23.33 mmol, 1 equiv.) and triethylamine (10.2 mL, 70 mmol, 3 equiv.) in THE (100 mL, 0.23 M) was stirred at 50° C. After 18 h the reaction solution was diluted with saturated aqueous sodium bicarbonate (50 mL) and extracted with ethyl acetate (3×100 mL). the combined organic layers were washed with brine (50 mL), dried over anhydrous sodium sulfate and concentrated. The resulting crude material was purified by silica gel column chromatography (10-100% ethyl acetate in hexanes) to give tert-butyl (3R,5S)-4-(2-methoxy-2-oxoethyl)-3,5-dimethylpiperazine-1-carboxylate (6.2 g, 21.6 mmol, 92% yield) as a yellow oil. MS (ESI) m/z 287.2 $[M+1]^+$.

Methyl 2-((2R,6S)-2,6-dimethylpiperazin-1-yl)acetate. To a solution of tert-butyl (3R,5S)-4-(2-methoxy-2-oxoethyl)-3,5-dimethylpiperazine-1-carboxylate (1 g, 3.49 mmol, 1 equiv.) in dichloromethane (3 mL) was added 4 M HCl in 1,4-dioxane (8.7 mL, 34.9 mmol, 10 equiv.) and the reaction solution was stirred at room temperature. After 2 h the reaction solution was concentrated neutralized with aqueous sodium bicarbonate, and extracted with ethyl acetate (5×50 mL). The combined organic layers were dried over anhydrous magnesium sulfate and concentrated to provide methyl 2-((2R,6S)-2,6-dimethylpiperazin-1-yl)acetate (510 mg, 2.72 mmol, 78% yield) as a yellow oil. MS (ESI) m/z 187.5 $[M+1]^+$.

Methyl 2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl) acetate. To a solution of 4-(3-(trans-4-(2-bromoethoxy)cyclohexyl)-4,4-dimethyl-5-oxo-2-thioxoimidazolidin-1-yl)-2-(trifluoromethyl)benzonitrile (208 mg, 0.400 mmol, 1 equiv.), methyl 2-((2R,6S)-2,6-dimethylpiperazin-1-yl)acetate hydrochloride (116 mg, 0.520 mmol, 1.3 equiv.) and sodium iodide (79 mg, 0.5200 mmol, 1.3 equiv.) was added N,N-dimethylformamide (3.2 mL, 0.13 M) and N,N-diisopropylethylamine (0.17 mL, 0.960 mmol, 2.4 equiv.). The reaction was stirred at 60° C. After 48 h the reaction solution was concentrated and the crude material was purified by silica gel column chromatography (0-100% ethyl acetate in hexanes) to give methyl 2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)acetate (250 mg, 0.40 mmol, 97% yield) as a yellow solid. MS (ESI) m/z 624.0 $[M+1]^+$.

2-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)acetic acid. To a solution of methyl 2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)acetate (250 mg, 0.400 mmol, 1 equiv.) in 3:1 water/THF (5 mL) was added lithium hydroxide (100 mg, 4.17 mmol, 10 equiv.) and the reaction solution was stirred at room temperature. After 1 h the reaction solution was diluted with water and adjusted to pH~4 by addition of 1 M hydrochlorid acid. The solution was extracted with ethyl acetate (4×50 mL), and the combined organic layers were dried over anhydrous sodium sulfate and concentrated to give 2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)acetic acid (218 mg, 0.358 mmol, 90% yield) as a pale orange solid. MS (ESI) m/z 610.0 $[M+1]^+$.

Methyl 3-((5-nitropyridin-2-yl)amino)propanoate. A stirred mixture 2-chloro-5-nitropyridine (5.000 g, 31.54 mmol, 1.00 equiv.), methyl 3-aminopropanoate hydrochloride (5.720 g, 41.00 mmol, 1.30 equiv.) and potassium carbonate (13.08 g, 94.61 mmol, 3.00 equiv.) in N,N-dimethylformamide (50 mL) was heated to 100° C. After 12 h the reaction solution was diluted with water (600 mL) and extracted with ethyl acetate (3×200 mL). The combined organic layers were washed with brine (100 mL), dried over anhydrous sodium sulfate and concentrated. The resulting crude material was purified by silica gel column chromatography (10-60% ethyl acetate in petroleum ether) to give methyl 3-((5-nitropyridin-2-yl)amino)propanoate (4.700 g, 18.66 mmol, 59% yield) as a yellow-green solid. MS (ESI) m/z 226.0 $[M+1]^+$.

Methyl 3-(1-(5-nitropyridin-2-yl)ureido)propanoate. To a solution of methyl 3-((5-nitropyridin-2-yl)amino)propanoate (4.000 g, 17.76 mmol, 1.00 equiv.) in tetrahydrofuran (80 mL) was added sulfurisocyanatidic chloride (3.270 g, 23.09 mmol, 2.00 mL, 1.30 equiv.) in one portion at 0° C. under nitrogen. After stirring at 0° C. for 90 min the reaction solution was diluted with water (5 mL) and extracted with ethyl acetate (4×40 mL). The combined organic layers were washed with brine (50 mL), dried over anhydrous sodium sulfate and concentrated to give crude methyl 3-(1-(5-nitropyridin-2-yl)ureido)propanoate(4.800 g, crude) as a yellow-green solid which was carried forward without further purification. $^1$H NMR (400 MHz, DMSO-$d_6$) δ 9.18-9.10 (m, 1H), 8.45 (dd, J=2.9, 9.4 Hz, 1H), 7.69 (d, J=9.4 Hz, 1H), 7.53 (br s, 2H), 4.24-4.15 (m, 2H), 3.60-3.54 (m, 3H), 2.70-2.64 (m, 2H).

1-(5-Nitropyridin-2-yl)dihydropyrimidine-2,4(1H,3H)-dione. To methyl 3-(1-(5-nitropyridin-2-yl)ureido)propanoate (4.800 g, 17.90 mmol, 1.00 equiv.) was added concentrated aqueous hydrochloric acid (25 mL, 16.76 equiv.) in one portion and reaction solution was stirred at room temperature. After 12 h the reaction solution was adjusted top pH 7 by addition of saturated aqueous sodium bicarbonate and extracted with dichloromethane (6×100 mL). the combined organic layers were washed with brine (300 mL), dried over anhydrous sodium sulfate and concentrated. The resulting solids were washed with ethyl acetate (3×50 ml) and dichloromethane 3×50 mL) to give 1-(5-nitropyridin-2-yl)dihydropyrimidine-2,4(1H,3H)-dione (2.000 g, 8.470 mmol, 47% yield) as a white solid. MS (ESI) m/z 237.2 $[M+1]^+$; $^1$H NMR (400 MHz, DMSO-$d_6$) δ 10.80 (s, 1H), 9.23 (d, J=2.7 Hz, 1H), 8.58 (dd, J=2.9, 9.4 Hz, 1H), 8.09 (d, J=9.3 Hz, 1H), 4.21 (t, J=6.5 Hz, 2H), 2.72 (t, J=6.5 Hz, 2H).

1-(5-Aminopyridin-2-yl)dihydropyrimidine-2,4(1H,3H)-dione. To a solution of 1-(5-nitropyridin-2-yl)dihydropyrimidine-2,4(1H,3H)-dione (2.000 g, 8.470 mmol, 1.00 equiv.) in tetrahydrofuran (40 mL) and N,N-dimethylacetamide (10 mL) was added palladium on alumina (0.100 g, 10% purity) under nitrogen. The suspension was degassed under vacuum and purged with hydrogen three times. The mixture was stirred under hydrogen (15 psi) at 25° C. for 12 h. The reaction mixture was filtered and the filter cake was washed by N,N-dimethylacetamide (20 mL×5). The combined filtrates were concentrate and the resulting solids were washed with ethyl acetate (30 mL×3) and dichloromethane (30 mL×3) to give 1-(5-aminopyridin-2-yl)dihydropyrimidine-2,4(1H,3H)-dione (1.600 g, 7.760 mmol, 91% yield) as a brown solid. MS (ESI) m/z 207.2 $[M+1]^+$; $^1$H NMR (400 MHz, DMSO-$d_6$) δ10.31 (s, 1H), 7.74 (d, J=2.5 Hz, 1H), 7.26 (d, J=8.6 Hz, 1H), 6.98 (dd, J=2.9, 8.8 Hz, 1H), 5.25 (s, 2H), 3.84 (t, J=6.7 Hz, 2H), 2.64 (t, J=6.7 Hz, 2H).

2-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1(2H)-yl)pyridin-3-yl) acetamide hydrochloride. 2-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)acetic acid (95.6 mg, 0.15 mmol, 1.0 equiv.) was combined with 1-(5-aminopyridin-2-yl)dihydropyrimidine-2,4(1H,3H)-dione hydrochloride (86.2 mg, 0.36 mmol, 2.4 equiv.), 1-methylimidazole (0.06 mL, 0.75 mmol, 5.1 equiv.), N-(chloro(dimethylamino)methylene)-N-methylmethanaminium hexafluorophosphate (91.3 mg, 0.33 mmol, 2.2 equiv.), and acetonitrile (1.93 mL), and the reaction was stirred at room temperature. After 2 h the reaction solution was diluted with water (40 mL) and extracted with ethyl acetate (3×40 mL). the combined organic layers were washed with brine (20 mL), dried over anhydrous sodium sulfate and concentrated. The crude material was purified by standard methods to give 2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1(2H)-yl)pyridin-3-yl)acetamide hydrochloride (19.9 mg, 0.03 mmol, 16% yield) as a white solid. MS (ESI) m/z 798.0 $[M+1]^+$; $^1$H NMR (DMSO-$d_6$, 400 MHz) δ 10.51 (s, 1H), 10.4-11.1 (m, 1H), 8.68 (d, 1H, J=2.0 Hz), 8.34 (d, 1H, J=8.2 Hz), 8.19 (s, 1H), 8.04 (dd, 1H, J=2.2, 8.9 Hz), 7.97 (br d, 1H, J=8.2 Hz), 7.72 (d, 1H, J=8.9 Hz), 4.01 (br t, 2H, J=6.5 Hz), 3.8-3.9 (m, 3H), 3.7-3.7 (m, 1H), 3.4-3.5 (m, 4H), 3.3-3.4 (m, 2H), 3.27 (br s, 2H), 3.06 (br s, 2H), 2.86 (q, 2H, J=11.3 Hz), 2.69 (t, 2H, J=6.5 Hz), 2.11 (br d, 2H, J=10.3 Hz), 1.73 (br d, 2H, J=11.5 Hz), 1.55 (s, 6H), 1.37 (q, 2H, J=11.6 Hz), 1.23 (br s, 6H).

Example 2: 2-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,6-dioxopiperidin-3-yl)pyridin-3-yl)acetamide hydrochloride

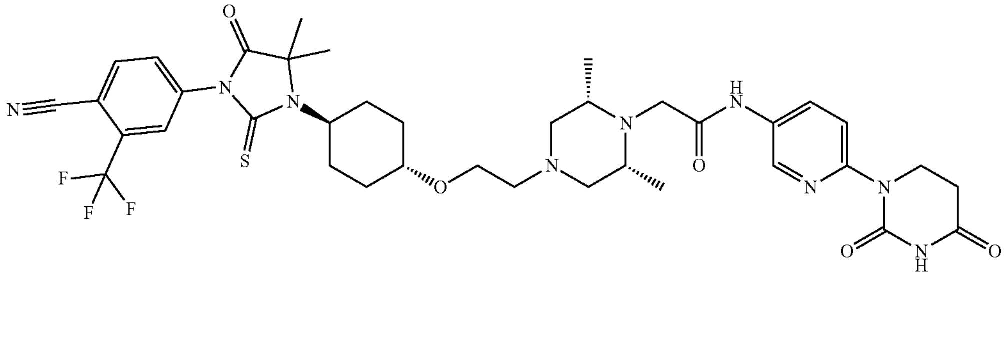 [SMILES: C[C@@H]1CN(CCO[C@H]2CC[C@H](N3C(=S)N(c4ccc(C#N)c(C(F)(F)F)c4)C(=O)C3(C)C)CC2)C[C@H](C)N1CC(=O)Nc1ccc(N2CCC(=O)NC2=O)nc1]

2,6-Bis(benzyloxy)-3-bromopyridine. To a solution of benzyl alcohol (167 g, 1.55 mol, 3 equiv.) and 3-bromo-2,6-difluoro-pyridine (100 g, 515 mmol) in acetonitrile (1 L) was added cesium carbonate (369 g, 1.13 mol, 2.2 equiv.). The mixture was stirred at 100° C. After 16 h the reaction solution was cooled to 20° C., filtered and concentrated. To the residue was added petroleum ether (2 L×3) with stirring at 0° C. for 2 hrs. A precipitate was formed and the mixture was filtered and filter cake was dried under vacuum to provide 2,6-bis(benzyloxy)-3-bromopyridine (300 g, 405 mmol, 78% yield) as a white solid. $^1$H NMR (400 MHz, DMSO-$d_6$) δ 7.89 (d, J=8.0 Hz, 1H), 7.42-7.32 (m, 10H), 6.44 (d, J=8.4 Hz, 1H), 5.37 (d, J=34.0 Hz, 4H).

2,6-Bis(benzyloxy)-3-(4,4,5,5-tetramethyl-1,3,2-dioxaborolan-2-yl)pyridine. To a solution of 2,6-bis(benzyloxy)-3-bromopyridine (90 g, 243 mmol) and 4,4,4',4',5,5,5',5'-octamethyl-2,2'-bi(1,3,2-dioxaborolane) (185 g, 729 mmol, 3 equiv.) in DMSO (900 mL, 0.27 M) was added potassium acetate (71.6 g, 729 mmol, 3 equiv.) followed by [1,1-bis(diphenylphosphino)ferrocene]dichloropalladium(II) (17.8 g, 24.3 mmol, 0.1 equiv.) under $N_2$. The reaction solution was stirred at 100° C. under $N_2$. After 16 h the reaction solution was filtered and concentrated. The resulting crude material was purified by silica gel column chromatography (5-100% ethyl acetate in petroleum ether) to give 2,6-bis(benzyloxy)-3-(4,4,5,5-tetramethyl-1,3,2-dioxaborolan-2-yl)pyridine (80 g, 192 mmol, 79% yield) as a yellow solid. $_1$H NMR (400 MHz, DMSO-$d_6$) δ 7.85 (d, J=7.6 Hz, 1H), 7.54-7.52 (m, 2H), 7.43-7.29 (m, 8H), 6.42 (d, J=8.0 Hz, 1H), 5.38 (d, J=6.0 Hz, 4H), 1.28 (s, 12H).

tert-Butyl (2',6'-bis(benzyloxy)-[2,3'-bipyridin]-5-yl)carbamate. To a solution of tert-butyl (6-bromopyridin-3-yl) carbamate (3.0 g, 11.0 mmol, 1 eq) and 2,6-dibenzyloxy-3-(4,4,5,5-tetramethyl-1,3,2-dioxaborolan-2-yl)pyridine (5.0 g, 12.1 mmol, 1.1 eq) in dioxane (50 mL) and water (5 mL) was added [1,1'-bis(diphenylphosphino)ferrocene]dichloropalladium(II) (0.800 g, 1.100 mmol, 0.1 eq) and sodium bicarbonate (1.384 g, 16.48 mmol, 1.5 eq). The mixture was stirred at 90° C. nitrogen. After 12 h the reaction solution was diluted with water (100 mL) and extracted with ethyl acetate (100 mL×3). The combined organic layers were washed with brine, dried over sodium sulfate and concentrated. The crude product was purified by flash silica gel column chromatography (15% ethyl acetate in petroleum ether) to afford tert-butyl (2',6'-bis(benzyloxy)-[2,3'-bipyridin]-5-yl)carbamate (4.7 g, 9.7 mmol, 88% yield) as a yellow solid. $^1$H NMR (400 MHz, DMSO-$d_6$) δ 9.60 (s, 1H), 8.66 (d, J=2.4 Hz, 1H), 8.25 (d, J=8.4 Hz, 1H), 7.95-7.90 (m, 1H), 7.85-7.83 (m, 1H), 7.47-7.41 (m, 4H), 7.40-7.30 (m, 6H), 6.57 (d, J=8.4 Hz, 1H), 5.48 (s, 2H), 5.39 (s, 2H), 1.48 (s, 9H).

tert-Butyl (6-(2,6-dioxopiperidin-3-yl)pyridin-3-yl)carbamate. To a solution of tert-butyl (2',6'-bis(benzyloxy)-[2,3'-bipyridin]-5-yl)carbamate (4.700 g, 9.720 mmol) in methanol (30 mL) and THE (120 mL) was added 10% palladium hydroxide on carbon (0.500 g, 9.720 mmol) under nitrogen atmosphere. The suspension was degassed under vacuum and purged with hydrogen 3 times. The mixture was stirred at room temperature under hydrogen atmosphere (50 psi). After 12 h the reaction mixture was filtered through a pad of celite and the filtrate was concentrated. The crude material was purified by flash silica gel column chromatography (3% methanol in dichloromethane) to give tert-butyl (6-(2,6-dioxopiperidin-3-yl)pyridin-3-yl)carbamate (2.100 g, 6.878 mmol, 71% yield) as a yellow solid. $^1$H NMR (400 MHz, DMSO-$d_6$) δ 10.77 (s, 1H), 9.50 (s, 1H), 8.51 (d, J=2.4 Hz, 1H), 7.85 (dd, J=8.4, 2.4 Hz, 1H), 7.25 (d, J=8.4 Hz, 1H), 3.93 (dd, J=9.2, 5.2 Hz, 1H), 2.64-2.52 (m, 2H), 2.26-2.15 (m, 1H), 2.14-2.05 (m, 1H), 1.48 (s, 9H).

3-(5-Aminopyridin-2-yl)piperidine-2,6-dione. A solution of tert-butyl (6-(2,6-dioxopiperidin-3-yl)pyridin-3-yl)carbamate (2.10 g, 6.88 mmol) in 2 M hydrogen chloride (20 mL, 6.88 mmol) was stirred at 25° C. After 12 h the reaction solution was frozen and lyophilized to give 3-(5-aminopyridin-2-yl)piperidine-2,6-dione hydrochloride (1.650 g, 8.040 mmol, 99% yield) as a yellow solid which was carried forward without further purification. $^1$H NMR (400 MHz, DMSO-$d_6$) δ 11.09 (s, 1H), 8.02 (d, J=2.4 Hz, 1H), 7.67-7.58 (m, 2H), 4.32 (d, J=8.4 Hz, 1H), 2.80-2.68 (m, 1H), 2.63-2.55 (m, 1H), 2.48-2.39 (m, 1H), 2.14-2.07 (m, 1H).

2-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,6-dioxopiperidin-3-yl)pyridin-3-yl)acetamide hydrochloride. 2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)acetic acid (95.6 mg, 0.15 mmol, 1.0 equiv.) was combined with 3-(5-aminopyridin-2-yl)piperidine-2,6-dione (85.8 mg, 0.36 mmol, 2.4 equiv.), 1-methylimidazole (0.06 mL, 0.75 mmol, 5.1 equiv.), N-(chloro(dimethylamino)methylene)-N-methylmethanaminium hexafluorophosphate (91.3 mg, 0.33 mmol, 2.2 equiv.), and acetonitrile (1.93 mL). The reaction solution was stirred at room temperature. After 30 min the reaction solution was diluted with water (50 mL) and extracted with ethyl acetate (3×50 mL). The combined organic layers were dried over sodium sulfate, concentrated and purified by standard methods to give 2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,6-dioxopiperidin-3-yl)pyridin-3-yl)acetamide hydrochloride (27.1 mg, 0.033 mmol, 22% yield) as a white solid. MS (ESI) m/z 797.0 $[M+1]^+$; $^1$H NMR (400 MHz, $CD_3CN$) δ 11.69 (br s, 1H), 9.46 (br s, 1H), 9.13 (br s, 1H), 8.62 (br s, 1H), 8.08 (br d, 1H, J=8.6 Hz), 7.97 (s, 1H), 7.82 (br d, 2H, J=7.9 Hz), 4.51 (br s, 2H), 4.30 (br s, 2H), 3.94 (br s, 2H), 3.79 (br s, 1H), 3.66 (br s, 4H), 3.42 (br s, 2H), 3.29 (br d, 2H, J=13.9 Hz), 2.87 (br s, 3H), 2.74 (br s, 2H), 2.6-2.7 (m, 1H), 2.11 (td, 1H, J=2.5, 4.9 Hz), 1.7-1.8 (m, 3H), 1.55 (s, 6H), 1.46 (br s, 6H), 1.3-1.4 (m, 2H).

Example 3: 2-((2R,6S)-4-(3-(trans-4-(3-(4-Cyano-3-(trifluoromethyl)phenyl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide

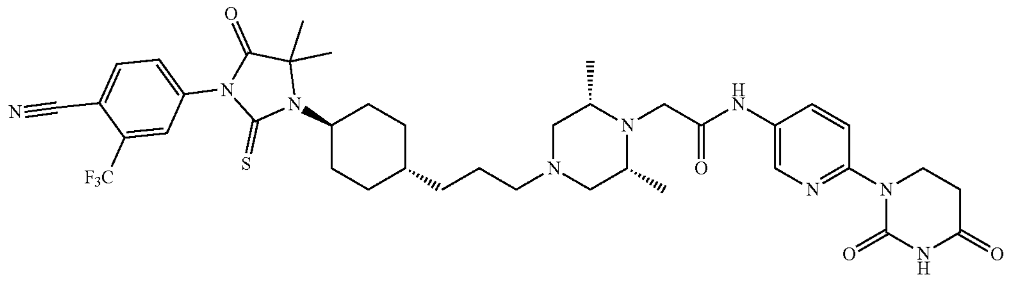 [SMILES: C[C@@H]1CN(CCC[C@H]2CC[C@H](N3C(=S)N(c4ccc(C#N)c(C(F)(F)F)c4)C(=O)C3(C)C)CC2)C[C@H](C)N1CC(=O)Nc1ccc(N2CCC(=O)NC2=O)nc1]

tert-butyl (trans-4-formylcyclohexyl)carbamate. To a mixture of tert-butyl (trans-4-(hydroxymethyl)cyclohexyl) carbamate (240 g, 1.05 mol, 1 equiv.) in acetonitrile (1.60 L) was added IBX (352 g, 1.26 mol, 1.2 equiv.) at 15° C. The reaction was stirred at 65° C. for 1 h. The two batches were combined for work up and purification. The reaction mixture was filtered and the filter was concentrated in vacuum to give tert-butyl (trans-4-formylcyclohexyl)carbamate (470 g, crude) as a white solid. The crude was used for next step directly without further purification. $^1$H NMR (400 MHz $CDCl_3$) δ 9.62 (s, 1H), 4.43 (s, 1H), 4.41 (s, 1H), 2.10-2.14 (m, 3H), 2.01-2.05 (m, 2H), 1.45 (s, 9H), 1.38-1.41 (m, 2H), 1.14-1.18 (m, 2H).

Ethyl (E)-3-(trans-4-((tert-butoxycarbonyl)amino)cyclohexyl)acrylate. To a mixture of sodium hydride (49.6 g, 1.24 mol, 60% purity, 1.2 equiv.) in THF (900 mL) at 0° C. was added ethyl 2-(diethoxyphosphoryl)acetate (255 g, 1.14 mol, 1.1 equiv.) drop-wise. The reaction was stirred at 0° C. for 1 h. A solution of tert-butyl (trans-4-formylcyclohexyl) carbamate (235 g, 1.03 mol, 1 equiv.) in THE (500 mL) was added drop-wise at 0° C. The reaction was stirred at 25° C. for 2 h. The reaction solution was poured into ice water (3.0 L) and stirred for 20 min. The aqueous phase was extracted with ethyl acetate (800 mL, 500 mL). The combined organic phase was washed with brine (500 mL), dried over anhydrous sodium sulfate and concentrated to give ethyl (E)-3-(trans-4-((tert-butoxycarbonyl)amino)cyclohexyl)acrylate (560 g, crude) as a light yellow solid. The material was carried forward without further purification without further purification. $^1$H NMR (400 MHz $CDCl_3$) δ 6.88 (dd, J=15.6 Hz, 6.8 Hz 1H), 5.75-5.79 (m, 1H), 4.40 (s, 1H), 4.12-4.23 (m, 3H), 3.39 (s, 1H), 2.04-2.08 (m, 3H), 1.81-1.85 (m, 2H), 1.44 (s, 9H), 1.33-1.35 (m, 1H), 1.26-1.30 (m, 6H), 1.10-1.16 (m, 3H).

tert-Butyl ((trans-4-((E)-3-hydroxyprop-1-en-1-yl)cyclohexyl)carbamate. Reaction set up as two reactions in parallel. To a solution of compound ethyl (E)-3-(trans-4-((tert-butoxycarbonyl)amino)cyclohexyl)acrylate (280 g, 942 mmol, 1 equiv.) in dichloromethane (1.12 L) under argon atmosphere at −78° C. was added diisobutylaluminum hydride (1 M, 1.88 L, 2 equiv.). The reaction was stirred at −78° C. for 1 h. The reaction was quenched by MeOH (280 mL) at −60° C. Two reaction mixtures were combined and poured into sat. citric acid (1.0 kg citric acid in 4.0 L $H_2O$) below 10° C. The mixture was extracted with ethyl acetate (2.0 L, 1.5 L). The combined organic layers were washed with aqeous sodium bicarbonate (2.0 L), brine (2.0 L), dried over anhydrous sodium sulfate and concentrated. The crude material was purified by column chromatography ($SiO_2$, petroleum ether/ethyl acetate=50/1 to 0/1) to provide tert-butyl ((trans-4-((E)-3-hydroxyprop-1-en-1-yl)cyclohexyl) carbamate (420 g, 1.645 mol, 87% yield) as a light yellow solid. $^1$H NMR (400 MHz $CDCl_3$) δ 5.58-5.60 (m, 2H), 4.39 (s, 1H), 4.06-4.07 (m, 2H), 3.35 (s, 1H), 1.80-2.00 (m, 3H), 1.74-1.78 (m, 2H), 1.42 (s, 9H), 1.08-1.20 (m, 4H).

tert-Butyl ((trans-4-(3-hydroxypropyl)cyclohexyl)carbamate. Four batches of this reaction were run in parallel. A mixture of tert-butyl ((trans-4-((E)-3-hydroxyprop-1-en-1-yl)cyclohexyl)carbamate(105 g, 411 mmol, 1 equiv.) and palladium on carbon (10.5 g, 10% purity) in MeOH (600 mL) was degassed and purged with $H_2$ for 3 times, and then the mixture was stirred at 25° C. for 12 h under $H_2$ (15 psi). The four batches were combined for work up and purification. The reaction solutions were filtered and concentrated under reduced pressure. The crude material was purified by column chromatography ($SiO_2$, Petroleum ether/Ethyl acetate=20/1 to 0/1). tert-butyl (trans-4-(3-hydroxypropyl) cyclohexyl)carbamate (82 g, 19% yield) and tert-butyl (trans-4-(3-oxopropyl)cyclohexyl)carbamate (200 g, 48% yield) as white solids. $^1$H NMR (400 MHz $CDCl_3$) δ 4.38 (s, 1H), 3.63 (t, J=6.4 Hz, 2H), 3.37 (s, 1H), 1.98-2.01 (m, 2H), 1.60-1.79 (m, 2H), 1.55-1.59 (m, 2H), 1.44 (s, 9H), 1.22-1.28 (m, 3H), 0.95-1.05 (m, 4H).

3-(trans-4-Aminocyclohexyl)propan-1-ol hydrochloride. Two reactions were carried out in parallel. To a solution of tert-butyl (trans-4-(3-hydroxypropyl)cyclohexyl)carbamate (115 g, 447 mmol, 1 equiv.) in methanol (200 mL) was added 4 M hydrochloric acid in methanol (500 mL). The reaction was stirred at 15° C. for 6 h. The two batches were combined for work up and purification. The reaction solution was filtered and concentrated to give 3-(trans-4-aminocyclohexyl)propan-1-ol hydrochloride(160 g, 92% yield) as a light yellow solid. The material was carried forward without further purification. $^1$H NMR (400 MHz DMSO-$d_6$) δ 8.09 (s, 4H), 4.62 (s, 2H), 3.35 (t, J=6.8 Hz, 2H), 2.87 (d, J=4.4 Hz, 1H), 1.93 (d, J=10.8 Hz, 2H), 1.73 (d, J=12.8 Hz, 2H), 1.38-1.42 (m, 2H), 1.29-1.31 (m, 3H), 1.13-1.17 (m, 3H), 0.89-0.92 (m, 2H).

Methyl 2-((trans-4-(3-hydroxypropyl)cyclohexyl)amino)-2-methylpropanoate. To a mixture of 3-(trans-4-aminocyclohexyl)propan-1-ol hydrochloride (120 g, 619 mmol, 1 equiv.) in acetonitrile (750 mL) was added potassium carbonate (428 g, 3.10 mol, 5 equiv.) and methyl 2-bromo-2-methylpropanoate (449 g, 2.48 mol, 4 equiv.). The mixture was stirred at 110° C. for 12 h. The reaction solution was filtered and concentrated. The crude material was purified by silica gel column chromatography (5-100% ethyl acetate in petroleum ether) to give methyl 2-((trans-4-(3-hydroxypropyl)cyclohexyl)amino)-2-methylpropanoate (54 g, 210 mmol, 34% yield) as a yellow oil. MS (ESI) m/z 258.2 [M+1]$^+$.

4-(3-(trans-4-(3-Hydroxypropyl)cyclohexyl)-4,4-dimethyl-5-oxo-2-thioxoimidazolidin-1-yl)-2-(trifluoromethyl)benzonitrile. To a solution of methyl 2-((trans-4-(3-hydroxypropyl)cyclohexyl)amino)-2-methylpropanoate (54 g, 210 mmol, 1 equiv.) and 4-isothiocyanato-2-(trifluoromethyl)benzonitrile (62.2 g, 273 mmol, 1.3 equiv.) in ethylacetate (350 mL) was added N,N-diisopropylethylamine (54.2 g, 420 mmol, 2 equiv.). The mixture was stirred at 80° C. for 12 h. The reaction mixture was concentrated under reduced pressure and purified by column chromatography ($SiO_2$, Petroleum ether/Ethyl acetate=15/1 to 0/1) to give 4-(3-(trans-4-(3-hydroxypropyl)cyclohexyl)-4,4-dimethyl-5-oxo-2-thioxoimidazolidin-1-yl)-2-(trifluoromethyl)benzonitrile (63 g, 139 mmol, 66% yield) as a yellow solid. $^1$H NMR (400 MHz $CDCl_3$) δ7.94-7.96 (m, 1H), 7.85 (m, 1H), 7.72-7.75 (m, 1H), 3.64-3.67 (m, 2H), 2.69 (s, 2H), 1.95 (d, J=12.8 Hz, 2H), 1.84 (d, J=11.2 Hz, 2H), 1.61 (s, 7H), 1.29-1.37 (m, 5H), 1.05-1.08 (m, 2H).

4-(3-(trans-4-(3-Bromopropyl)cyclohexyl)-4,4-dimethyl-5-oxo-2-thioxoimidazolidin-1-yl)-2-(trifluoromethyl)benzonitrile. To a solution of 4-(3-(trans-4-(3-hydroxypropyl)cyclohexyl)-4,4-dimethyl-5-oxo-2-thioxoimidazolidin-1-yl)-2-(trifluoromethyl)benzonitrile (0.820 g, 1.81 mmol, 1 equiv.) in N,N-dimethylformamide (0.800 mL) and dichloromethane (8 mL) was added thionyl bromide (0.752 g, 3.620 mmol, 2 equiv.) slowly at 0° C. After 2 h stirring at 0° C., the reaction solution was concentrated and purified by silica gel column chromatography (15-25% ethyl acetate in petroleum ether) to give 4-(3-(trans-4-(3-bromopropyl)cyclohexyl)-4,4-dimethyl-5-oxo-2-thioxoimidazolidin-1-yl)-2-(trifluoromethyl)benzonitrile (0.650 g, 1.259 mmol, 70% yield) as a brown solid. MS (ESI) m/z 516.1 [M+1]$^+$.

Methyl 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetate. To a solution of 4-(3-(trans-4-(3-bromopropyl)cyclohexyl)-4,4-dimethyl-5-oxo-2-thioxoimidazolidin-1-yl)-2-(trifluoromethyl)benzonitrile (500 mg, 0.968 mmol, 1 equiv.) and methyl 2-((2R,6S)-2,6-dimethylpiperazin-1-yl)acetate (270 mg, 1.45 mmol, 1.5 equiv.) in N,N-dimethylformamide (4.8 mL, 0.2 M) was added N,N-diisoproplyethylamine (0.46 mL, 4.84 mmol, 5 equiv.) and the reaction solution was stirred at 50° C. After 18 h the reaction solution was diluted with ethyl acetate (100 mL) and washed with saturated aqueous sodium bicarbonate (2×100 mL) and brine (100 mL). The organic layer was dried over anhydrous magnesium sulfate and concentrated. The crude material was purified by silica gel column chromatography (1-10% methanol in dichloromethane) to give methyl 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetate (487 mg, 0.784 mmol, 81% yield) as a pale yellow oil. MS (ESI) m/z 622.3 [M+1]$^+$.

2-((2R,6S)-4-(3-(trans-4-(3-(4-Cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetic acid. To a solution of methyl 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetate (500 mg, 0.82 mmol, 1 equiv.), in 5:1 THF/water (4 mL, 0.2 M) was added lithium hydroxide (59 mg, 2.46 mmol, 3 equiv.). The reaction solution was stirred at room temperature. After 12 h the reaction solution was diluted with water (10 mL), adjusted to pH 5 by addition of 2 M HCl and extracted with ethyl acetate (4×50 mL). The combined organic layers were dried over anhydrous sodium sulfate and concentrated to give 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetic acid (364 mg, 0.599 mmol, 73% yield) as an off-white solid. MS (ESI) m/z 608.4 [M+1]$^+$; $^1$H NMR (400 MHz $CDCl_3$) δ 8.33 (d, J=8.0 Hz, 1H), 8.19 (s, 1H), 7.97 (d, J=8.4 Hz, 1H), 3.83 (s, 1H), 3.37 (s, 2H), 3.14 (s, 2H), 2.89 (s, 2H), 2.73 (s, 2H), 2.40 (s, 2H), 2.00 (s, 2H), 1.81 (d, J=12.0 Hz, 2H), 1.72 (d, J=10.4 Hz, 2H), 1.44-1.54 (m, 8H), 1.15-1.19 (m, 3H), 1.05-1.08 (m, 2H), 1.01 (d, J=6.4 Hz, 6H).

2-((2R,6S)-4-(3-(trans-4-(3-(4-Cyano-3-(trifluoromethyl)phenyl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide. To a 2 dram vial containing 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)acetic acid (75. mg, 0.12 mmol, 1 equiv.) and 3-(5-amino-2-pyridyl)piperidine-2,6-dione hydrochloride (38.77 mg, 0.16 mmol, 1.3 equiv.), added N,N-dimethylformamide (0.54 mL, 0.23 M) and stirred until all solids were dissolved. 1-Methylimidazole (0.1 mL, 1.23 mmol, 10 equiv.) was added, followed by N-(chloro(dimethylamino)methylene)-N-methylmethanaminium hexafluorophosphate(V) (51.94 mg, 0.19 mmol, 1.5 equiv.) and the reaction was stirred at room temperature. After 20 min the reaction solution was diluted with DMSO to a total volume of 4 ml, filtered, and purified by standard methods to provide 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide (51 mg, 0.063 mmol, 51% yield) as an off white solid. MS (ESI) m/z 795.4 [M+1]$^+$; $^1$H NMR (500 MHz, DMSO-$d_6$) δ 1.11 (br d, J=5.99 Hz, 6H) 1.18-1.32 (m, 3H) 1.56 (s, 6H) 1.61-1.79 (m, 4H) 1.81-1.89 (m, 2H) 2.08 (s, 1H) 2.10-2.16 (m, 1H) 2.19-2.30 (m, 1H) 2.56-2.82 (m, 6H) 2.96-3.07 (m, 2H) 3.40-3.46 (m, 2H) 3.54 (br s, 2H) 3.78-3.89 (m, 1H) 3.99 (dd, J=9.62, 5.20 Hz, 1H) 7.34 (d, J=8.20 Hz, 1H) 7.98 (dd, J=8.20, 1.58 Hz, 1H) 8.01 (dd, J=8.51, 2.21 Hz, 1H) 8.20 (d, J=1.58 Hz, 1H) 8.35 (d, J=8.20 Hz, 1H) 8.70 (d, J=2.84 Hz, 1H) 9.32-9.45 (m, 1H) 10.01 (br s, 1H) 10.81 (s, 1H).

Example 4: 2-((2R,6S)-4-(3-((trans-4-(3-(6-Cyano-5-(trifluoromethyl)pyridin-3-yl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide hydrochloride

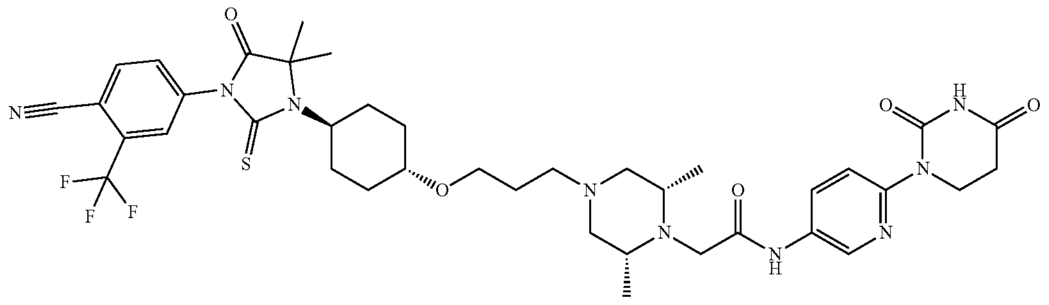 [SMILES: C[C@@H]1CN(CCCO[C@H]2CC[C@H](N3C(=S)N(c4ccc(C#N)c(C(F)(F)F)c4)C(=O)C3(C)C)CC2)C[C@H](C)N1CC(=O)Nc1ccc(N2CCC(=O)NC2=O)nc1]

trans-N,N-Dibenzyl-4-(3-((tetrahydro-2H-pyran-2-yl)oxy)propoxy)cyclohexan-1-amine. To a solution of trans-4-(dibenzylamino)cyclohexanol (60.00 g, 203.1 mmol, 1 equiv.) in xylenes (450 mL, 0.45 M) was added 2-(2-bromoethoxy)tetrahydro-2H-pyran (113.28 g, 507.75 mmol, 2.5 equiv.), tetra-N-butylammonium bromide (13.09 g, 40.62 mmol, 0.2 equiv.) and potassium hydroxide (52.42 g, 934.26 mmol, 4.6 equiv.) and the reaction solution was stirred at room temperature. After 24 h the reaction solution was diluted with ethyl acetate (500 mL) and washed with water (200 mL), brine (200 mL), dried over anhydrous sodium sulfate and concentrated. The crude material was purified by silica gel column chromatography (100% petroleum ether) to give trans-N,N-dibenzyl-4-(3-((tetrahydro-2H-pyran-2-yl)oxy)propoxy)cyclohexan-1-amine (40.0 g, 91.4 mmol, 45% yield) as a light yellow oil. MS (ESI) m/z 438.4 $[M+1]^+$; $^1H$ NMR (400 MHz, $CDCl_3$) δ 7.38-7.32 (m, 4H), 7.31-7.28 (m, 4H), 7.24-7.22 (m, 2H), 4.61-4.57 (m, 1H), 3.88-3.84 (m, 2H), 3.63 (s, 4H), 3.55-3.52 (m, 4H), 3.51-3.16 (m, 1H), 2.54-2.09 (m, 1H), 2.08-2.07 (m, 2H), 1.92-1.90 (m, 2H), 1.61-1.60 (m, 2H), 1.59-1.57 (m, 6H), 1.55-1.53 (m, 2H), 1.38-1.16 (m, 2H)

trans-4-(3-((Tetrahydro-2H-pyran-2-yl)oxy)propoxy)cyclohexan-1-amine. To a solution of trans-N,N-dibenzyl-4-(3-((tetrahydro-2H-pyran-2-yl)oxy)propoxy)cyclohexan-1-amine (20.0 g, 45.7 mmol, 1 equiv.) in methanol (100 mL) was added 10% palladium on carbon (10.0 g, 9.39 mmol). The reaction flask was evacuated and purged with hydrogen gas three times and then stirred under hydrogen atmostphere (15 psi) at room temperature. After 12 h the reaction solution was filtered and the filtrate concentrated to provide trans-4-(3-((tetrahydro-2H-pyran-2-yl)oxy)propoxy)cyclohexan-1-amine (11.00 g, 42.74 mmol, 94% yield) as a light yellow oil. The material was carried forward without further purification. $^1H$ NMR (400 MHz, DMSO-$d_6$) δ 4.52 (m, 1H), 3.79-3.61 (m, 2H), 3.50-3.30 (m, 4H), 3.18-3.05 (m, 1H), 1.94-1.83 (m, 2H), 1.77-1.65 (m, 6H), 1.64-1.55 (m, 1H), 1.53-1.38 (m, 4H), 1.20-0.91 (m, 4H).

Methyl 2-methyl-2-((trans-4-(3-((tetrahydro-2H-pyran-2-yl)oxy)propoxy)cyclohexyl)amino)propanoate. To a solution of trans-4-(3-((tetrahydro-2H-pyran-2-yl)oxy)propoxy)cyclohexan-1-amine (7.00 g, 27.2 mmol, 1 equiv.) and methyl 2-bromo-2-methyl-propanoate (12.5 mL, 108.79 mmol, 4 equiv.) in acetonitrile (10 mL) was added potassium iodide (0.451 g, 2.72 mmol, 0.1 equiv.) and potassium carbonate (7.518 g, 54.4 mmol, 2 equiv.). The reaction vessel was sealed and heated to 110° C. with stirring. After 12 h the reaction solution was filtered and concentrated. The crude material was purified by silica gel column chromatography (10-80% ethyl acetate in petroleum ether) to give methyl 2-methyl-2-((trans-4-(3-((tetrahydro-2H-pyran-2-yl)oxy)propoxy)cyclohexyl)amino)propanoate (8.00 g, 22.4 mmol, 82% yield) as a light yellow oil. MS (ESI) m/z 358.4 $[M+1]^+$.

5-(4,4-Dimethyl-5-oxo-3-(trans-4-(3-((tetrahydro-2H-pyran-2-yl)oxy)propoxy)cyclohexyl)-2-thioxoimidazolidin-1-yl)-3-(trifluoromethyl)picolinonitrile. To a solution of methyl 2-methyl-2-((trans-4-(3-((tetrahydro-2H-pyran-2-yl)oxy)propoxy)cyclohexyl)amino)propanoate (5.00 g, 14.0 mmol, 1 equiv.) and 5-isothiocyanato-3-(trifluoromethyl)pyridine-2-carbonitrile (6.41 g, 28.0 mmol, 2 equiv.) in ethyl acetate (50 mL, 0.28 M) was added N,N-diisopropylethylamine (4.62 mL, 28.0 mmol, 2 equiv.) and the reaction solution was stirred at 90° C. After 12 h the reaction solution was concentrated and purified by silica gel column chromatography (10-50% ethyl acetate in petroleum ether) to give 5-(4,4-dimethyl-5-oxo-3-(trans-4-(3-((tetrahydro-2H-pyran-2-yl)oxy)propoxy)cyclohexyl)-2-thioxoimidazolidin-1-yl)-3-(trifluoromethyl)picolinonitrile (7.00 g, 12.6 mmol, 90% yield) as a brown oil. $^1H$ NMR (400 MHz, $CDCl_3$) δ 8.95 (s, 1H), 8.23 (s, 1H), 4.55-4.51 (m, 1H), 3.81-3.78 (m, 2H), 3.70-3.68 (m, 1H), 3.57-3.54 (m, 2H), 3.48-3.45 (m, 2H), 3.29-2.87 (m, 1H), 2.85 (d, J=10.8 Hz, 2H), 1.85-1.80 (m, 8H), 1.60 (s, 6H), 1.56-1.52 (m, 4H), 1.32-1.29 (m, 2H).

5-(3-(trans-4-(3-Hydroxypropoxy)cyclohexyl)-4,4-dimethyl-5-oxo-2-thioxoimidazolidin-1-yl)-3-(trifluoromethyl)picolinonitrile. To a solution of 5-(4,4-dimethyl-5-oxo-3-(trans-4-(3-((tetrahydro-2H-pyran-2-yl)oxy)propoxy)cyclohexyl)-2-thioxoimidazolidin-1-yl)-3-(trifluoromethyl)picolinonitrile (7.00 g, 12.6 mmol, 1 equiv.) in methanol (50 mL) was added 1 M hydrogen chloride (5.0 mL, 5 mmol) and the reaction solution was stirred at room temperature. After 2 h the reaction solution was diluted with saturated aqueous sodium bicarbonate (20 mL) and extracted with ethyl acetate (2×50 mL). The combined organic layers were washed with brine (50 mL), dried over anhydrous sodium sulfate and concentrated to give 5-(3-(trans-4-(3-hydroxypropoxy)cyclohexyl)-4,4-dimethyl-5-oxo-2-thioxoimidazolidin-1-yl)-3-(trifluoromethyl)picolinonitrile (5.00 g, 10.6 mmol, 84% yield) as a brown oil. MS (ESI) m/z 471.2 $[M+1]^+$.

5-(3-(trans-4-(3-Bromopropoxy)cyclohexyl)-4,4-dimethyl-5-oxo-2-thioxoimidazolidin-1-yl)-3-(trifluoromethyl)picolinonitrile. To a solution of 5-(3-(trans-4-(3-hydroxypropoxy)cyclohexyl)-4,4-dimethyl-5-oxo-2-thioxoimidazolidin-1-yl)-3-(trifluoromethyl)picolinonitrile (5.00 g, 10.6 mmol, 1 equiv.) in dichloromethane (50 mL)

and DMF (5 mL) was added thionyl bromide (1.7 mL, 21.3 mmol, 2 equiv.) at 0° C. After stirring for 12 h the reaction solution was diluted with saturated aqueous sodium bicarbonate (20 mL) and extracted with dichloromethane (2×50 mL). the combined organic layers were washed with brine (30 mL), dried over anhydrous sodium sulfate and concentrated. The resulting crude material was purified by silica gel column chromatography (10-20% ethyl acetate in petroleum ether) to give 5-(3-(trans-4-(3-bromopropoxy)cyclohexyl)-4,4-dimethyl-5-oxo-2-thioxoimidazolidin-1-yl)-3-(trifluoromethyl)picolinonitrile as a light yellow solid. (ESI) m z 535.1 $[M+1]^+$; $^1$H NMR (400 MHz, $CDCl_3$) δ 8.98 (d, J=2.0 Hz, 1H), 8.24 (d, J=2.0 Hz, 1H), 3.76-3.65 (m, 1H), 3.62 (t, J=5.6 Hz, 2H), 3.53 (t, J=6.4 Hz, 2H), 3.40-3.29 (m, 1H), 2.89 (s, 2H), 2.30-2.18 (m, 2H), 2.16-2.05 (m, 2H), 1.83 (d, J=12.4 Hz, 2H), 1.63 (s, 6H), 1.45-1.24 (m, 2H).

2-((2R,6S)-4-(tert-Butoxycarbonyl)-2,6-dimethylpiperazin-1-yl)acetic acid. To a solution of tert-butyl (3R,5S)-4-(2-methoxy-2-oxoethyl)-3,5-dimethylpiperazine-1-carboxylate (2.27 g, 7.93 mmol, 1 equiv.) in THE (20 mL) was added lithium hydroxide (208.8 mg, 8.7 mmol, 1.1 equiv.) in water (5 mL), and the reaction solution was stirred at room temperature. After 18 h the reaction solution was concentrated under vacuum, and azeotroped three times with chloroform to remove residual water to provide crude 2-((2R, 6S)-4-(tert-butoxycarbonyl)-2,6-dimethylpiperazin-1-yl) acetic acid (2.19 g, 7.8 mmol, 99% yield) as an off-white glassy-solid. The material was carried forward without further purification. MS (ESI) m/z 273.2 $[M+1]^+$.

tert-Butyl (3R,5S)-4-(2-((6-(2,6-dioxopiperidin-3-yl) pyridin-3-yl)amino)-2-oxoethyl)-3,5-dimethylpiperazine-1-carboxylate. To a solution of 3-(5-aminopyridin-2-yl)piperidine-2,6-dione hydrochloride (1.6 g, 7.8 mmol) and 2-((2R, 6S)-4-(tert-butoxycarbonyl)-2,6-dimethylpiperazin-1-yl) acetic acid (2.3 g, 8.6 mmol) in pyridine (20 mL) was added 1-(3-dimethylaminopropyl)-3-ethylcarbodiimide hydrochloride (2.990 g, 15.59 mmol). The mixture was stirred at 50° C. After 12 h the reaction solution was concentrated and the crude material purified by silica gel column chromatography (2% methanol in dichloromethane) to give tert-butyl (3R,5S)-4-(2-((6-(2,6-dioxopiperidin-3-yl)pyridin-3-yl) amino)-2-oxoethyl)-3,5-dimethylpiperazine-1-carboxylate (1.7 g, 3.7 mmol, 47% yield) as a yellow solid. $^1$H NMR (400 MHz, DMSO-$d_6$) δ 10.83 (s, 1H), 9.87 (s, 1H), 8.69 (d, J=2.4 Hz, 1H), 8.04 (dd, J=8.4, 2.4 Hz, 1H), 7.32 (d, J=8.4 Hz, 1H), 3.98 (dd, J=9.6, 5.4 Hz, 1H), 3.73 (s, 2H), 3.17 (d, J=5.4 Hz, 2H), 2.72-2.52 (m, 6H), 2.29-2.18 (m, 1H), 2.15-2.05 (m, 1H), 1.40 (s, 9H), 1.02 (d, J=5.6 Hz, 6H).

2-((2R,6S)-2,6-dimethylpiperazin-1-yl)-N-(6-(2,6-dioxopiperidin-3-yl)pyridin-3-yl)acetamide hydrobromide. To a solution of (3R,5S)-tert-butyl 4-(2-((6-(2,6-dioxopiperidin-3-yl)pyridin-3-yl)amino)-2-oxoethyl)-3,5-dimethylpiperazine-1-carboxylate (0.100 g, 0.218 mmol) in dichloromethane (5 mL) was added 30% hydrogen bromide in acetic acid (0.1 mL, 1.09 mmol). The mixture was stirred at 25° C. After 1 h the reaction solution was concentrated to give 2-((2R,6S)-2,6-dimethylpiperazin-1-yl)-N-(6-(2,6-dioxopiperidin-3-yl)pyridin-3-yl)acetamide hydrobromide (0.095 g, 0.215 mmol, 99% yield) as a yellow solid that was carried forward without further purification. $^1$H NMR (400 MHz, DMSO-$d_6$) δ 10.97 (s, 2H), 9.25 (s, 2H), 8.89 (s, 1H), 8.19 (s, 1H), 7.56 (d, J=8.0 Hz, 1H), 4.14 (dd, J=10.4, 5.2 Hz, 3H), 3.74 (s, 2H), 3.57-3.38 (m, 2H), 3.13 (s, 2H), 2.72-2.62 (m, 1H), 2.56 (d, J=4.8 Hz, 1H), 2.36-2.26 (m, 1H), 2.13 (dd, J=13.2, 5.2 Hz, 1H), 1.28 (d, J=5.2 Hz, 6H).

2-((2R,6S)-4-(3-((trans-4-(3-(6-Cyano-5-(trifluoromethyl)pyridin-3-yl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide hydrochloride. To a solution of 2-((2R,6S)-2,6-dimethylpiperazin-1-yl)-N-(6-(2,6-dioxopiperidin-3-yl)pyridin-3-yl)acetamide hydrobromide (0.080 g, 0.220 mmol, 1 equiv.) and 5-(3-(trans-4-(3-bromopropoxy)cyclohexyl)-4,4-dimethyl-5-oxo-2-thioxoimidazolidin-1-yl)-3-(trifluoromethyl)picolinonitrile (0.142 g, 0.270 mmol, 1.2 equiv.) in N,N-dimethylformamide (2 mL, 0.1 M) was added N,N-diisopropylethylamine (0.19 mL, 1.110 mmol, 5 equiv.) and sodium iodide (0.003 g, 0.0200 mmol, 0.1 equiv.). The mixture was stirred at 60° C. After 12 h the reaction solution was diluted and purified by standard methods to give 2-((2R, 6S)-4-(3-((trans-4-(3-(6-cyano-5-(trifluoromethyl)pyridin-3-yl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide hydrochloride (55 mg, 0.066 mmol, 30% yield) as a yellow solid. MS (ESI) m/z 812.3 $[M+1]^+$; $^1$H NMR (400 MHz, DMSO-$d_6$) δ 12.50-11.30 (m, 2H), 11.00 (s, 1H), 9.14 (d, J=2.0 Hz, 1H), 8.98 (s, 1H), 8.74 (d, J=2.0 Hz, 1H), 8.35 (d, J=6.4 Hz, 1H), 7.66 (d, J=8.4 Hz, 1H), 4.40-3.95 (m, 5H), 3.95-3.65 (m, 3H), 3.51 (t, J=5.4 Hz, 2H), 3.27 (d, J=3.6 Hz, 3H), 3.11 (s, 2H), 2.83 (d, J=11.6 Hz, 2H), 2.73-2.64 (m, 1H), 2.60-2.54 (m, 1H), 2.43-2.32 (m, 1H), 2.18-1.96 (m, 5H), 1.79-1.66 (m, 2H), 1.57 (s, 6H), 1.42-1.28 (m, 8H).

Example 5: 2-((2R,6S)-4-(3-((trans-4-(3-(4-Cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide hydrochloride

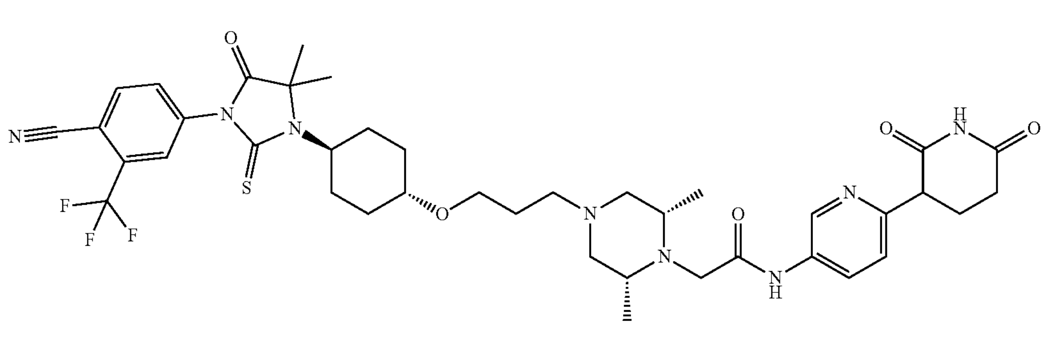 [SMILES: C[C@@H]1CN(CCCO[C@H]2CC[C@H](N3C(=S)N(c4ccc(C#N)c(C(F)(F)F)c4)C(=O)C3(C)C)CC2)C[C@H](C)N1CC(=O)Nc1ccc(C2CCC(=O)NC2=O)nc1]

4-(4,4-Dimethyl-5-oxo-3-(trans-4-(3-((tetrahydro-2H-pyran-2-yl)oxy)propoxy)cyclohexyl)-2-thioxoimidazolidin-1-yl)-2-(trifluoromethyl)benzonitrile. To a solution of methyl 2-methyl-2-((trans-4-(3-((tetrahydro-2H-pyran-2-yl)oxy)propoxy)cyclohexyl)amino)propanoate (5.0 g, 14.0 mmol, 1 equiv.) and 4-isothiocyanato-2-(trifluoromethyl)benzonitrile (6.4 g, 28.0 mmol, 2 equiv.) in ethyl acetate (50 mL) was added N,N-diisopropylethylamine (4.6 mL, 28.0 mmol, 2 equiv.) and the reaction solution was stirred at 90° C. After 12 h the reaction solution was concentrated and purified by silica gel column chromatography (10-50% ethyl acetate in petroleum ether) to give 4-(4,4-dimethyl-5-oxo-3-(trans-4-(3-((tetrahydro-2H-pyran-2-yl)oxy)propoxy)cyclohexyl)-2-thioxoimidazolidin-1-yl)-2-(trifluoromethyl)benzonitrile (6.5 g, 11.7 mmol, 84% yield) as a brown oil. MS (ESI) m/z 554.4 $[M+1]^+$; $^1$H NMR (400 MHz, $CDCl_3$) δ 7.95 (d, J=8.4 Hz, 1H), 7.84 (d, J=2.0 Hz, 1H), 7.74-7.71 (m, 1H), 4.60-4.58 (m, 1H), 3.84-3.82 (m, 2H), 3.71-3.61 (m, 1H), 3.60-3.52 (m, 2H), 3.50-3.49 (m, 2H), 3.47-3.32 (m, 1H), 2.22-2.20 (m, 2H), 2.19 (d, J=12.0 Hz, 2H), 1.88-1.87 (m, 6H), 1.85-1.84 (m, 2H), 1.60 (s, 6H), 1.56-1.55 (m, 2H), 1.54-1.35 (m, 2H).

4-(3-(trans-4-(3-Hydroxypropoxy)cyclohexyl)-4,4-dimethyl-5-oxo-2-thioxoimidazolidin-1-yl)-2-(trifluoromethyl)benzonitrile. To a solution of 4-(4,4-dimethyl-5-oxo-3-(trans-4-(3-((tetrahydro-2H-pyran-2-yl)oxy)propoxy)cyclohexyl)-2-thioxoimidazolidin-1-yl)-2-(trifluoromethyl)benzonitrile (6.5 g, 11.7 mmol) in methanol (50 mL) was added 1 M aqueous hydrochloric acid (5.0 mL, 5 mmol) and the reaction solution was stirred at room temperature. After 2 h the reaction solution was diluted with saturated aqueous sodium bicarbonate (30 mL) and extracted with ethyl acetate (2×50 mL). The combined organic layers were washed with brine, dried over anhydrous sodium sulfate and concentrated to give 4-(3-(trans-4-(3-hydroxypropoxy)cyclohexyl)-4,4-dimethyl-5-oxo-2-thioxoimidazolidin-1-yl)-2-(trifluoromethyl)benzonitrile (5.0 g, 10.7 mmol, 91% yield) as a brown oil. MS (ESI) m/z 470.2 $[M+1]^+$.

4-(3-(trans-4-(3-Bromopropoxy)cyclohexyl)-4,4-dimethyl-5-oxo-2-thioxoimidazolidin-1-yl)-2-(trifluoromethyl)benzonitrile. To a solution of give 4-(3-(trans-4-(3-hydroxypropoxy)cyclohexyl)-4,4-dimethyl-5-oxo-2-thioxoimidazolidin-1-yl)-2-(trifluoromethyl)benzonitrile (5.0 g, 10.7 mmol, 1 equiv.) in dichloromethane (50 mL) and N,N-dimethylformamide (5 mL) was added thionyl bromide (1.7 mL, 21.3 mmol, 4 equiv.) at 0° C. and the reaction solution was gradually warmed to room temperature. After 12 h the reaction solution was diluted with saturated aqueous sodium bicarbonate (50 mL) and extracted with ethyl acetate (2×50 mL). The combined organic layers were washed with brine, dried over anhydrous sodium sulfate and concentrated. The resulting crude material was purified by silica gel column chromatography to give 4-(3-(trans-4-(3-bromopropoxy)cyclohexyl)-4,4-dimethyl-5-oxo-2-thioxoimidazolidin-1-yl)-2-(trifluoromethyl)benzonitrile (5.0 g, 9.4 mmol, 88% yield) as a light yellow oil. MS (ESI) m/z 534.1 $[M+1]^+$; $^1$H NMR (400 MHz, $CDCl_3$) δ7.95 (d, J=8.4 Hz, 1H), 7.84 (d, J=2.0 Hz, 1H), 7.74-7.71 (m, 1H), 3.71-3.61 (m, 1H), 3.60-3.53 (m, 2H), 3.52 (t, J=6.4 Hz, 2H), 3.35-3.32 (m, 1H), 2.21 (d, J=12.0 Hz, 2H), 2.19-2.05 (m, 2H), 1.83 (d, J=12.0 Hz, 2H), 1.65 (s, 2H), 1.60 (s, 6H), 1.35-1.32 (m, 2H).

2-((2R,6S)-4-(3-((trans-4-(3-(4-Cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide hydrochloride. To a solution of 2-((2R,6S)-2,6-dimethylpiperazin-1-yl)-N-(6-(2,6-dioxopiperidin-3-yl)pyridin-3-yl)acetamide hydrobromide (0.100 g, 0.278 mmol, 1 equiv.) and 4-(3-(trans-4-(3-bromopropoxy)cyclohexyl)-4,4-dimethyl-5-oxo-2-thioxoimidazolidin-1-yl)-2-(trifluoromethyl)benzonitrile (0.178 g, 0.330 mmol, 1.2 equiv.) in N,N-dimethylformamide (2 mL, 0.14 M) was added N,N-diisopropylethylamine (0.24 mL, 1.390 mmol, 5 equiv.) and sodium iodide (0.004 g, 0.030 mmol, 0.1 equiv.). The reaction solution was stirred at 60° C. After 12 h water (20 mL) was added and the solution was extracted with ethyl acetate (3×20 mL). The combined organic layers were washed with brine (20 mL), dried over anhydrous sodium sulfate, filtered and concentrated. The crude material was purified by standard methods to afford 2-((2R,6S)-4-(3-((trans-4-(3-(4-cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide hydrochloride (53.62 mg, 0.0644 mmol, 23% yield) as a yellow solid. MS (ESI) m/z 811.3 $[M+1]^+$; $^1$H NMR (400 MHz, DMSO-$d_6$) δ 12.20-11.10 (m, 2H), 10.97 (s, 1H), 8.94 (s, 1H), 8.35 (d, J=8.4 Hz, 1H), 8.27 (s, 1H), 8.20 (d, J=1.6 Hz, 1H), 7.98 (dd, J=8.4, 1.6 Hz, 1H), 7.59 (d, J=8.4 Hz, 1H), 4.23-3.62 (m, 8H), 3.52 (t, J=5.6 Hz, 2H), 3.32-3.06 (m, 5H), 2.83 (d, J=12.0 Hz, 2H), 2.73-2.63 (m, 1H), 2.61-2.54 (m, 1H), 2.40-2.28 (m, 1H), 2.18-2.05 (m, 3H), 1.99 (dd, J=9.2, 5.2 Hz, 2H), 1.73 (d, J=10.4 Hz, 2H), 1.56 (s, 6H), 1.32 (s, 8H).

Example 6: 2-((2R,6S)-4-(2-((trans-4-(3-(5-Chloro-6-cyanopyridin-3-yl)-5,5-dimethyl-4-oxo-2-thioxoimidazolidin-1-yl)cyclohexyl)oxy)ethyl)-2,6-dimethylpiperazin-1-yl)-N-(6-(2,6-dioxopiperidin-3-yl)pyridin-3-yl)acetamide hydrochloride

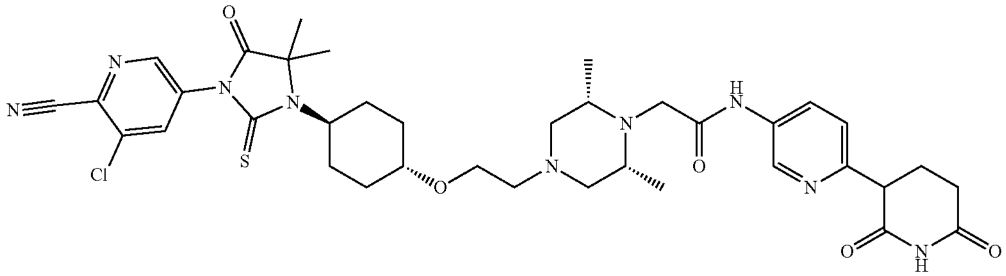 [SMILES: C[C@@H]1CN(CCO[C@H]2CC[C@H](N3C(=S)N(c4cnc(C#N)c(Cl)c4)C(=O)C3(C)C)CC2)C[C@H](C)N1CC(=O)Nc1ccc(C2CCC(=O)NC2=O)nc1]

3-Chloro-5-isothiocyanato-pyridine-2-carbonitrile. To a solution of 5-amino-3-chloro-pyridine-2-carbonitrile (10.00 g, 65.12 mmol, 1 equiv.) in toluene (20 mL) was added thiophosgene (5.96 mL, 78.14 mmol, 1.2 equiv.). The mixture was stirred at 110° C. After 16 h the reaction solution was concentrated and purified by silica gel chromatography (20-50% ethyl acetate in petroleum ether) to give 3-chloro-5-isothiocyanato-pyridine-2-carbonitrile (8.000 g, 40.89 mmol, 63% yield) as a red solid. MS (ESI) m/z 196.2 $[M+1]^+$.

3-Chloro-5-(4,4-dimethyl-5-oxo-3-(trans-4-(2-((tetrahydro-2H-pyran-2-yl)oxy)ethoxy)cyclohexyl)-2-thioxoimidazolidin-1-yl)picolinonitrile. A mixture of methyl 3-chloro-5-isothiocyanato-pyridine-2-carbonitrile (4.000 g, 20.45 mmol, 1 equiv.) and methyl 2-methyl-2-((trans-4-(2-((tetrahydro-2H-pyran-2-yl)oxy)ethoxy)cyclohexyl)amino)propanoate (7.720 g, 22.49 mmol, 1.1 equiv.) in ethyl acetate (100 mL, 0.2 M) was added triethylamine (5.7 mL, 40.89 mmol, 2 equiv.). The reaction solution was stirred at 90° C. After 6 hours the reaction solution was concentrated and purified by silica gel column chromatography (10-50% ethyl acetate in petroleum ether) to give 3-chloro-5-(4,4-dimethyl-5-oxo-3-(trans-4-(2-((tetrahydro-2H-pyran-2-yl)oxy)ethoxy)cyclohexyl)-2-thioxoimidazolidin-1-yl)picolinonitrile (4.000 g, 7.89 mmol, 39% yield) as a yellow solid. MS (ESI) m/z 507.2 $[M+1]^+$; $^1$H NMR (400 MHz, DMSO-$d_6$) δ 8.92-8.72 (m, 1H), 8.62-8.31 (m, 1H), 4.68-4.50 (m, 1H), 3.91-3.63 (m, 4H), 3.62-3.52 (m, 3H), 3.50-3.39 (m, 3H), 2.91-2.73 (m, 3H), 2.10-2.03 (m, 2H), 1.75-1.68 (m, 3H), 1.55 (s, 6H), 1.50-1.43 (m, 4H).

3-Chloro-5-(3-(trans-4-(2-hydroxyethoxy)cyclohexyl)-4,4-dimethyl-5-oxo-2-thioxoimidazolidin-1-yl)picolinonitrile. To a solution of 3-chloro-5-(4,4-dimethyl-5-oxo-3-(trans-4-(2-((tetrahydro-2H-pyran-2-yl)oxy)ethoxy)cyclohexyl)-2-thioxoimidazolidin-1-yl)picolinonitrile (4.000 g, 7.89 mmol, 1 equiv.) in methanol (30 mL, 0.27 M) was added 2 M aqueous hydrochloride acid (3 mL, 15.78 mmol, 2 equiv.). The reaction solution was stirred at 25° C. After 2 h the pH of the mixture was adjusted to 8 by addition of saturated sodium carbonate. The aqueous phase was extracted with ethyl acetate (250 mL). The combined organic layers were washed with brine (80 mL), dried over anhydrous sodium sulfate, filtered and concentrated under reduced pressure. The crude material was purified by silica gel chromatography (33-100% ethyl acetate in petroleum ether) to give 3-chloro-5-(3-(trans-4-(2-hydroxyethoxy)cyclohexyl)-4,4-dimethyl-5-oxo-2-thioxoimidazolidin-1-yl)picolinonitrile (2.400 g, 0.01 mmol, 69% yield) as a yellow solid. MS (ESI) m/z 423.3 $[M+1]^+$; $^1$H NMR (400 MHz, $CDCl_3$) δ 7.59 (s, 1H), 7.43-7.33 (m, 2H), 7.15 (br d, J=7.0 Hz, 1H), 6.57 (br s, 1H), 4.40 (t, J=6.7 Hz, 2H), 2.98 (s, 3H), 2.70-2.55 (m, 2H), 1.53 (s, 5H), 1.54-1.51 (m, 1H), 1.54-1.51 (m, 1H), 1.54-1.51 (m, 1H), 1.54-1.51 (m, 1H).

5-(3-(trans-4-(2-Bromoethoxy)cyclohexyl)-4,4-dimethyl-5-oxo-2-thioxoimidazolidin-1-yl)-3-chloropicolinonitrile. To a solution of 3-chloro-5-(3-(trans-4-(2-hydroxyethoxy)cyclohexyl)-4,4-dimethyl-5-oxo-2-thioxoimidazolidin-1-yl)picolinonitrile (2.150 g, 5.08 mmol, 1 equiv.) in dichloromethane (5 mL, 1 M) and N,N-dimethylformamide (0.50 mL) was added thionyl bromide (0.65 mL, 10.17 mmol, 2 equiv.) at 0° C. The mixture was stirred at 25° C. for 16 h. The pH of the mixture was adjusted to 8 by saturated sodium carbonate. The organic layer was separated, and the aqueous layer was extracted with ethyl acetate (3×150 mL). The combined organic layers were washed with brine (50 mL), dried over anhydrous sodium sulfate, filtered and concentrated under reduced pressure. The crude material was purified by silica gel chromatography (50-100% ethyl acetate in petroleum ether) to give 5-(3-(trans-4-(2-bromoethoxy)cyclohexyl)-4,4-dimethyl-5-oxo-2-thioxoimidazolidin-1-yl)-3-chloropicolinonitrile (2.3 g, 4.73 mmol, 93% yield) as a red solid. MS (ESI) m/z 485.1 $[M+1]^+$; H NMR (400 MHz, DMSO-$d_6$) δ 8.90-8.72 (m, 1H), 8.60-8.44 (m, 1H), 3.93-3.81 (m, 1H), 3.79-3.72 (m, 2H), 3.61-3.53 (m, 2H), 3.34 (br s, 1H), 2.90-2.74 (m, 2H), 2.12-2.02 (m, 2H), 1.76-1.67 (m, 2H), 1.59-1.52 (m, 6H), 1.44-1.28 (m, 2H).

2-((2R,6S)-4-(2-((trans-4-(3-(5-Chloro-6-cyanopyridin-3-yl)-5,5-dimethyl-4-oxo-2-thioxoimidazolidin-1-yl)cyclohexyl)oxy)ethyl)-2,6-dimethylpiperazin-1-yl)-N-(6-(2,6-dioxopiperidin-3-yl)pyridin-3-yl)acetamide. To a solution of 5-(3-(trans-4-(2-bromoethoxy)cyclohexyl)-4,4-dimethyl-5-oxo-2-thioxoimidazolidin-1-yl)-3-chloropicolinonitrile (0.120 g, 0.250 mmol, 1 equiv.) and 2-((2S,6R)-2,6-dimethylpiperazin-1-yl)-N-(6-(2,6-dioxopiperidin-3-yl)pyridin-3-yl)acetamide (0.163 g, 0.370 mmol, 1.5 equiv.) in N,N-dimethylformamide (4 mL, 0.07 M) was added N,N-diisopropylethylamine (0.22 mL, 1.23 mmol, 5 equiv.) in one portion under nitrogen. The mixture was stirred at 50° C. After 12 h the reaction solution was diluted with water (80 mL) and extracted with ethyl acetate (4×30 mL). The combined organic layers were washed with brine (50 mL), dried over anhydrous sodium sulfate, filtered and concentrated. The crude material was purified by standard methods to give 2-((2R,6S)-4-(2-((trans-4-(3-(5-chloro-6-cyanopyridin-3-yl)-5,5-dimethyl-4-oxo-2-thioxoimidazolidin-1-yl)cyclohexyl)oxy)ethyl)-2,6-dimethylpiperazin-1-yl)-N-(6-(2,6-dioxopiperidin-3-yl)pyridin-3-yl)acetamide hydrochloride (0.087 g, 0.109 mmol, 44% yield) as a yellow solid. MS (ESI) m/z 764.3 $[M+1]^+$; $^1$H NMR (400 MHz, DMSO-$d_6$) δ 11.97-11.09 (m, 1H), 10.96 (s, 1H), 8.91 (br s, 1H), 8.82 (d, J=2.0 Hz, 1H), 8.53 (d, J=1.8 Hz, 1H), 8.23 (br s, 1H), 7.61-7.52 (m, 1H), 7.56 (br d, J=8.8 Hz, 1H), 4.16 (br dd, J=4.6, 10.3 Hz, 4H), 3.86 (br s, 4H), 3.63 (br s, 2H), 3.42-3.18 (m, 5H), 2.93-2.79 (m, 2H), 2.78-2.61 (m, 2H), 2.57 (br d, J=4.8 Hz, 1H), 2.39-2.27 (m, 1H), 2.18-2.07 (m, 3H), 1.71 (br d, J=10.1 Hz, 2H), 1.55 (s, 6H), 1.46-1.22 (m, 8H).

Example 7: 2-((2R,6S)-4-(3-((trans-4-(3-(3-Chloro-4-cyanophenyl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide hydrochloride

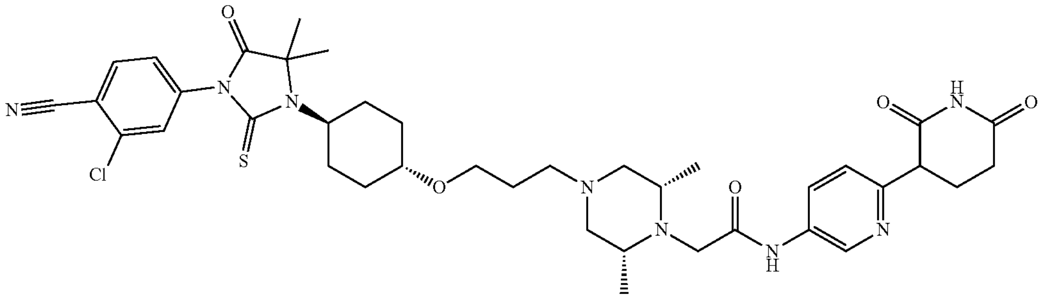 [SMILES: C[C@@H]1CN(CCCO[C@H]2CC[C@H](N3C(=S)N(c4ccc(C#N)c(Cl)c4)C(=O)C3(C)C)CC2)C[C@H](C)N1CC(=O)Nc1ccc(C2CCC(=O)NC2=O)nc1]

2-Chloro-4-(4,4-dimethyl-5-oxo-3-(trans-4-(3-((tetrahydro-2H-pyran-2-yl)oxy)propoxy)cyclohexyl)-2-thioxoimidazolidin-1-yl)benzonitrile. To a solution of methyl 2-methyl-2-((trans-4-(3-((tetrahydro-2H-pyran-2-yl)oxy)propoxy)cyclohexyl)amino)propanoate (10.0 g, 28.0 mmol, 1 equiv.) in ethyl acetate (100 mL, 0.28 M) was added 2-chloro-4-isothiocyanatobenzonitrile (10.9 g, 56.0 mmol, 2 equiv.) and triethylamine (7.8 mL, 56.0 mmol, 2 equiv.) and the reaction solution was stirred at 80° C. After 8 h the reaction solution was diluted with water (100 mL) and extracted with ethyl acetate (3×40 mL). The combined organic layers were washed brine (40 mL), dried over anhydrous sodium sulfate and concentrated. The crude material was purified by silica gel column chromatography (9-20% ethyl acetate in petroleum ether) to give 2-chloro-4-(4,4-dimethyl-5-oxo-3-(trans-4-(3-((tetrahydro-2H-pyran-2-yl)oxy)propoxy)cyclohexyl)-2-thioxoimidazolidin-1-yl)benzonitrile (8.50 g, 16.3 mmol, 58% yield) as a red oil. MS (ESI) m/z542.2 [M+23]+.

4-(3-(trans-4-(3-Hydroxypropoxy)cyclohexyl)-4,4-dimethyl-5-oxo-2-thioxoimidazolidin-1-yl)-2-(trifluoromethyl) benzonitrile. To a solution of 2-chloro-4-(4,4-dimethyl-5-oxo-3-(trans-4-(3-((tetrahydro-2H-pyran-2-yl)oxy)propoxy) cyclohexyl)-2-thioxoimidazolidin-1-yl)benzonitrile (6.80 g, 13.1 mmol) in methanol (50 mL) was added 1 M hydrochloric acid (5 mL, 13.07 mmol) and the reaction solution was stirred at 25° C. After 2 h the reaction solution was diluted with saturated aqueous sodium bicarbonate (100 mL) and extracted with ethyl acetate (3×50 mL). the combined organic layers were washed with brine, dried over anhydrous sodium sulfate and concentrated. The resulting crude material was purified by silica gel column chromatography (20-70% ethyl acetate in petroleum ether) to give 4-(3-(trans-4-(3-hydroxypropoxy)cyclohexyl)-4,4-dimethyl-5-oxo-2-thioxoimidazolidin-1-yl)-2-(trifluoromethyl)benzonitrile (5.60 g, 12.8 mmol, 98% yield) as a yellow solid. $^1$H NMR (400 MHz, DMSO-$d_6$) δ 8.12 (d, J=8.4 Hz, 1H), 7.92 (d, J=1.6 Hz, 1H), 7.61 (dd, J=2.0, 8.4 Hz, 1H), 3.89-3.76 (m, 1H), 3.48-3.42 (m, 4H), 3.24-3.16 (m, 1H), 2.79 (d, J=11.2 Hz, 2H), 2.04 (d, J=10.8 Hz, 2H), 1.70 (d, J=10.8 Hz, 2H), 1.65-1.59 (m, 2H), 1.53 (s, 6H), 1.34-1.25 (m, 2H).

4-(3-(trans-4-(3-Bromopropoxy)cyclohexyl)-4,4-dimethyl-5-oxo-2-thioxoimidazolidin-1-yl)-2-chlorobenzonitrile. To a solution of 4-(3-(trans-4-(3-hydroxypropoxy)cyclohexyl)-4,4-dimethyl-5-oxo-2-thioxoimidazolidin-1-yl)-2-(trifluoromethyl)benzonitrile (5.8 g, 13.3 mmol) in dichloromethane (50 mL) and N,N-dimethylformamide (5 mL) was added thionyl bromide (2.1 mL, 26.6 mmol, 2 equiv.) at 0° C. After 8 h the reaction solution was diluted with saturated aqueous sodium bicarbonate (100 mL) and extracted with ethyl acetate (3×40 mL). The combined organic layers were washed with brine, dried over anhydrous sodium sulfate and concentrated. The crude material was purified by silica gel column chromatography (0-35% ethyl acetate in petroleum ether) to give 4-(3-(trans-4-(3-bromopropoxy)cyclohexyl)-4,4-dimethyl-5-oxo-2-thioxoimidazolidin-1-yl)-2-chlorobenzonitrile (4.8 g, 9.6 mmol, 72% yield) as a yellow solid. $^1$H NMR (400 MHz, DMSO-$d_6$) δ 8.14-8.11 (m, 1H), 7.93 (d, J=1.6 Hz, 1H), 7.61 (dd, J=1.6, 8.0 Hz, 1H), 3.84 (s, 1H), 3.58-3.51 (m, 4H), 3.27-3.21 (m, 1H), 2.81 (d, J=11.6 Hz, 2H), 2.06 (m, 2H), 1.71 (d, J=11.6 Hz, 2H), 1.53 (s, 6H), 1.33 (d, J=13.2 Hz, 2H).

2-((2R,6S)-4-(3-((trans-4-(3-(3-Chloro-4-cyanophenyl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide hydrochloride. A mixture of 4-(3-((trans-4-(3-bromopropoxy)cyclohexyl)-4,4-dimethyl-5-oxo-2-thioxoimidazolidin-1-yl)-2-chlorobenzonitrile (150.0 mg, 0.300 mmol, 1 equiv.), 2-((2R,6S)-2,6-dimethylpiperazin-1-yl)-N-(6-(2,6-dioxopiperidin-3-yl) pyridin-3-yl)acetamide (162.1 mg, 0.450 mmol, 1.5 equiv.) N,N-diisopropylethylamine (194.3 mg, 1.5 mmol, 5 equiv.) in N,N-dimethylformamide (4 mL, 0.08 M) was heated to 50° C. After 12 h the reaction solution was diluted with DMSO (1 mL) and purified by standard methods to give 2-((2R,6S)-4-(3-((trans-4-(3-(3-chloro-4-cyanophenyl)-5,5-dimethyl-4-oxo-2-thioxoimidazolidin-1-yl)cyclohexyl)oxy) propyl)-2,6-dimethylpiperazin-1-yl)-N-(6-(2,6-dioxopiperidin-3-yl)pyridin-3-yl)acetamide hydrochloride (98 mg, 0.12 mmol, 41% yield) as a yellow solid. MS (ESI) m/z 777.3 $[M+1]^+$; $^1$H NMR (400 MHz, DMSO-$d_6$) δ 11.80-11.10 (m, 1H), 10.96 (s, 1H), 8.92 (s, 1H), 8.25 (d, J=8.4 Hz, 1H), 8.13 (d, J=7.6 Hz, 1H), 7.93 (s, 1H), 7.59 (d, J=8.4 Hz, 2H), 4.23-3.62 (m, 8H), 3.52 (t, J=5.6 Hz, 2H), 3.32-3.06 (m, 5H), 2.83 (d, J=12.0 Hz, 2H), 2.73-2.63 (m, 1H), 2.61-2.54 (m, 1H), 2.40-2.28 (m, 1H), 2.18-2.05 (m, 3H), 1.99 (dd, J=9.2, 5.2 Hz, 2H), 1.73 (d, J=10.4 Hz, 2H), 1.53 (s, 6H), 1.31 (s, 8H).

Example 8: 2-((2R,6S)-4-(3-(trans-4-(3-(6-Cyano-5-(trifluoromethyl)pyridin-3-yl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide hydrochloride

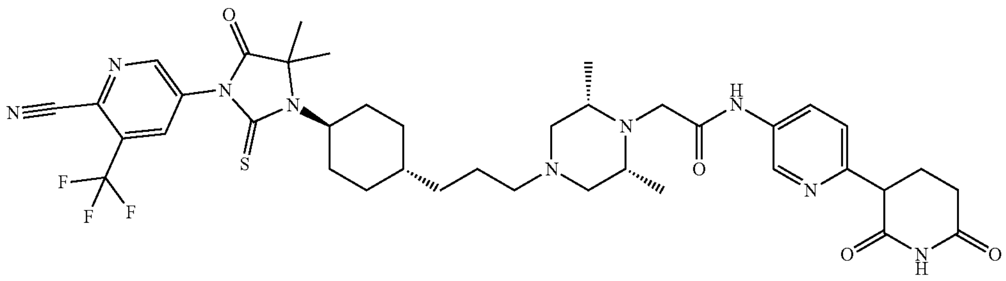 [SMILES: C[C@@H]1CN(CCC[C@H]2CC[C@H](N3C(=S)N(c4cnc(C#N)c(C(F)(F)F)c4)C(=O)C3(C)C)CC2)C[C@H](C)N1CC(=O)Nc1ccc(C2CCC(=O)NC2=O)nc1]

5-(3-(trans-4-(3-Hydroxypropyl)cyclohexyl)-4,4-dimethyl-5-oxo-2-thioxoimidazolidin-1-yl)-3-(trifluoromethyl) picolinonitrile. To a solution of methyl 2-((trans-4-(3-hydroxypropyl)cyclohexyl)amino)-2-methylpropanoate (1.47 g, 5.71 mmol, 1 equiv.) and 5-isothiocyanato-3-(trifluoromethyl)picolinonitrile (1.44 g, 6.28 mmol, 1.1 equiv.) in ethyl acetate (15 mL, 0.38 M) was added N,N-diisopropylethylamine(2.21 g, 17.13 mmol, 3 equiv.) and the reaction solution was stirred 80° C. After 16 h the reaction solution was concentrated under reduced pressure and the crude material was purified by standard methods to afford 5-(3-(trans-4-(3-hydroxypropyl)cyclohexyl)-4,4-dimethyl-5-oxo-2-thioxoimidazolidin-1-yl)-3-(trifluoromethyl)picolinonitrile (1.80 g, 3.96 mmol, 69% yield) as brown solid. MS (ESI) m/z 455.0 $[M+1]^+$; $^1$H NMR (400 MHz, $CDCl_3$) δ 8.99 (d, J=2.0 Hz, 1H), 8.25 (d, J=2.0 Hz, 1H), 3.80-3.72 (m, 1H), 3.65 (t, J=6.4 Hz, 2H), 2.72-2.70 (m, 2H), 1.97-1.94 (m, 2H), 1.85-1.82 (m, 2H), 1.63 (s, 6H), 1.58-1.54 (m, 1H), 1.42-1.29 (m, 4H), 1.12-1.02 (m, 2H).

5-(3-(trans-4-(3-Bromopropyl)cyclohexyl)-4,4-dimethyl-5-oxo-2-thioxoimidazolidin-1-yl)-3-(trifluoromethyl)picolinonitrile. To a solution of 5-(3-(trans-4-(3-hydroxypropyl) cyclohexyl)-4,4-dimethyl-5-oxo-2-thioxoimidazolidin-1-yl)-3-(trifluoromethyl)picolinonitrile (1.80 g, 3.96 mmol, 1 equiv.) in dichloromethane (18 mL, 0.22 M) and N,N-dimethylfromamide (1.8 mL) was added thionyl bromide (1.650 g, 7.92 mmol, 2 equiv.) slowly at 0° C. The reaction solution was stirred at 0° C. After 12 h the reaction solution was diluted with water (30 mL) and extracted with dichloromethane (2×25 mL). The combined organic layers were dried over anhydrous sodium sulfate and concentrated. The crude residue was purified by silica gel column chromatography (5-80% ethyl acetate in hexanes) to give 5-(3-(trans-4-(3-bromopropyl)cyclohexyl)-4,4-dimethyl-5-oxo-2-thioxoimidazolidin-1-yl)-3-(trifluoromethyl)picolinonitrile (1.75 g, 3.38 mmol, 85% yield) as brown solid. MS (ESI) m/z 516.9 $[M+1]^+$; $^1$H NMR (400 MHz, $CDCl_3$) δ 8.99 (d, J=2.0 Hz, 1H), 8.25 (d, J=2.0 Hz, 1H), 3.80-3.71 (m, 1H), 3.42 (t, J=6.8 Hz, 2H), 2.74-2.72 (m, 2H), 1.96-1.79 (m, 6H), 1.63 (s, 6H), 1.40-1.33 (m, 3H), 1.13-1.04 (m, 2H).

2-((2R,6S)-4-(3-(trans-4-(3-(6-Cyano-5-(trifluoromethyl) pyridin-3-yl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide hydrochloride. To a solution of 5-(3-(trans-4-(3-bromopropyl)cyclohexyl)-4,4-dimethyl-5-oxo-2-thioxoimidazolidin-1-yl)-3-(trifluoromethyl)picolinonitrile (0.100 g, 0.190 mmol, 1 equiv.) and 2-((2S,6R)-2,6-dimethylpiperazin-1-yl)-N-(6-(2,6-dioxopiperidin-3-yl)pyridin-3-yl)acetamide hydrobromide (0.128 g, 0.290 mmol, 1.5 equiv.) in N,N-dimethylformamide (2 mL, 0.1 M) was added N,N-diisopropylethylamine (0.17 mL, 0.970 mmol, 5 equiv.) The reaction solution was stirred at 50° C. After 12 h the reaction solution was concentrated and the crude material was purified by standard methods to provide 2-((2R,6S)-4-(3-(trans-4-(3-(6-cyano-5-(trifluoromethyl)pyridin-3-yl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl) pyridin-3-yl)acetamide hydrochloride (0.075 g, 0.089 mmol, 47% yield) as yellow solid. MS (ESI) m/z 796.3 $[M+1]^+$; $^1$H NMR (400 MHz, DMSO-$d_6$) δ 11.43 (s, 1H), 10.94 (s, 1H), 9.16 (s, 1H), 8.89 (s, 1H), 8.75-8.73 (m, 1H), 8.21 (s, 1H), 7.55-7.53 (m, 1H), 4.18-4.16 (m, 1H), 3.64 (m, 1H), 3.13-3.04 (m, 5H), 2.79-2.67 (m, 6H), 2.37-2.30 (m, 4H), 2.17-2.12 (m, 2H), 1.83-1.75 (m, 6H), 1.58 (s, 6H), 1.29-1.10 (m, 10H).

Example 9: 3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1(2H)-yl)pyridin-3-yl) propanamide

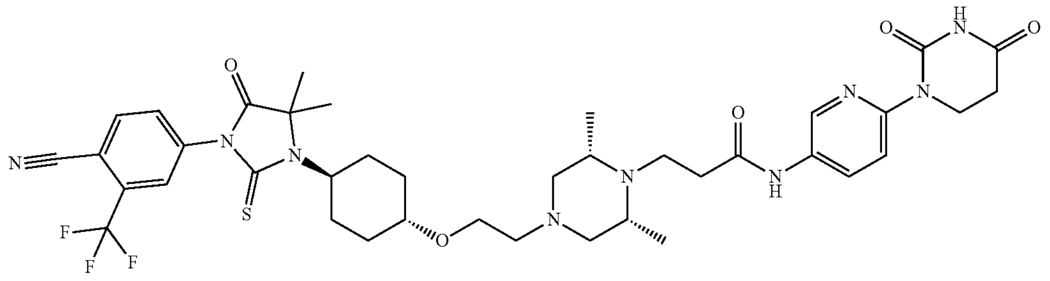 [SMILES: C[C@@H]1CN(CCO[C@H]2CC[C@H](N3C(=S)N(c4ccc(C#N)c(C(F)(F)F)c4)C(=O)C3(C)C)CC2)C[C@H](C)N1CCC(=O)Nc1ccc(N2CCC(=O)NC2=O)nc1]

- tert-Butyl (3R,5S)-4-(3-ethoxy-3-oxopropyl)-3,5-dimethylpiperazine-1-carboxylate. tert-Butyl (3S,5R)-3,5-dimethylpiperazine-1-carboxylate (5. g, 23.33 mmol, 1 equiv.) was combined with lithium perchlorate (10.02 g, 93.33 mmol, 4 equiv.) and ethyl acrylate (26.7 mL, 233.32 mmol, 10 equiv.) and the reaction solution was heated to 30° C. for 18 h. The solution was concentrated and purified by silica gel column chromatography (1-5% MeOH in dichloromethane) to provide tert-butyl (3R,5S)-4-(3-ethoxy-3-oxopropyl)-3,5-dimethylpiperazine-1-carboxylate (3.43 g, 11.43 mmol, 49% yield). MS (ESI) m/z 301.2 $[M+1]^+$.

Ethyl 3-((2R,6S)-2,6-dimethylpiperazin-1-yl)propanoate. To a 30 ml vial containing tert-butyl (3R,5S)-4-(3-methoxy-3-oxopropyl)-3,5-dimethylpiperazine-1-carboxylate (680. mg, 2.16 mmol) was added dichloromethane (1 mL) followed by 4 M hydrochloric acid in 1,4-dioxane (13.52 mL, 54.07 mmol, 25 equiv.). The reaction solution was stirred at room temperature. After 15 min the reaction solution was concentrated to give a yellow solid. The material was taken up in ethyl acetate and washed with sodium bicarbonate. The organic layer was separated and the aqueous layers were extracted with 3×25 ml ethyl acetate. The organic layers were combined, dried over anhydrous magnesium sulfate and concentrated to provide ethyl 3-((2R,6S)-2,6-dimethylpiperazin-1-yl)propanoate (380 mg, 1.78 mmol, 82% yield) as a yellow oil. MS (ESI) m/z 215.2 $[M+1]^+$.

Ethyl 3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl) propanoate. To a 20 ml vial containing 4-(3-(trans-4-(2-bromoethoxy)cyclohexyl)-4,4-dimethyl-5-oxo-2-thioxoimidazolidin-1-yl)-2-(trifluoromethyl)benzonitrile (290 mg, 0.56 mmol) and ethyl 3-((2R,6S)-2,6-dimethylpiperazin-1-yl)propanoate (120 mg, 0.56 mmol, 1 equiv.) was added N,N-dimethylformamide (1.1666 mL, 0.48 M) and N,N-diisopropylethylamine (0.59 mL, 3.36 mmol, 6 equiv.). The reaction solution was heated to 50° C. with stirring. After 14 the reaction solution was diluted with 100 ml ethyl acetate and washed with saturated aqueous sodium bicarbonate (100 mL) followed by brine (100 mL). The organic layer was dried over magnesium sulfate and concentrated to give a yellow oil. The crude material was purified by column chromatography (1-8% MeOH in DCM with 0.2% triethylamine) to provide methyl 3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)propanoate as a clear, colorless oil. MS (ESI) m/z=652.4 $[M+1]^+$. $^1H$ NMR (400 MHz, $CDCl_3$) δ 7.94 (d, J=8.2 Hz, 1H), 7.83 (s, 1H), 7.71 (dd, J=2.1, 8.3 Hz, 1H), 4.12 (q, J=7.1 Hz, 2H), 3.60 (t, J=6.2 Hz, 2H), 3.38-3.25 (m, 1H), 3.20-3.11 (m, 2H), 2.95-2.81 (m, 2H), 2.78 (br d, J=10.6 Hz, 2H), 2.71-2.59 (m, 2H), 2.52 (t, J=6.2 Hz, 2H), 2.44-2.35 (m, 2H), 2.23-2.17 (m, 2H), 1.92 (t, J=10.7 Hz, 2H), 1.86-1.76 (m, 2H), 1.60-1.59 (m, 6H), 1.41-1.29 (m, 2H), 1.26 (t, J=7.1 Hz, 3H), 1.11-1.06 (m, 6H)

3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)propenamide. 3-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)propanoic acid (75.0 mg, 0.12 mmol, 1.0 equiv.), 1-(5-aminopyridin-2-yl)dihydropyrimidine-2,4(1H,3H)-dione (32.2 mg, 0.16 mmol, 1.2 equiv.), N,N-diisopropylethylamine (0.06 mL, 0.38 mmol, 3.0 equiv.) were combined in DMF (0.5 mL) and stirred for 5 min. HATU (94.1 mg, 0.24 mmol, 2.0 equiv.) was added in one portion and the reaction was stirred at room temperature. After 18 h the reaction solution was diluted with brine (50 mL) and extracted with ethyl acetate (3×50 mL). The combined organic layers were dried over anhydrous magnesium sulfate, and concentrated. The resulting crude material was purified by standard methods to give 3-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1(2H)-yl)pyridin-3-yl)propenamide(21.7 mg, 0.02 mmol, 20% yield). MS (ESI) m/z 812.0 $[M+1]^+$; $^1H$ NMR (400 MHz, $CD_3OD$) δ 8.70 (d, J=2.32 Hz, 1H), 8.48 (br s, 1H), 8.08-8.16 (m, m 2H), 7.87 (dd, J=8.25, 1.65 Hz, 1H), 7.39 (d, J=8.56 Hz, 1H), 4.03 (dd, J=10.03, 5.26 Hz, 1H), 3.86 (br s, 1H), 3.64-3.80 (m, 2H), 3.36-3.44 (m, 1H), 3.05-3.31 (m, 3H), 2.89-3.05 (m, 4H), 2.79 (br t, J=5.26 Hz, 2H), 2.53-2.75 (m, 4H), 2.30-2.50 (m, 1H), 2.14-2.30 (m, 5H), 1.85 (br d, J=12.10 Hz, 2H), 1.61 (s, 6H), 1.19-1.46 (m, 8H).

Example 10: 2-((2R,6S)-4-(3-(trans-4-(3-(3-Chloro-4-cyanophenyl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide hydrochloride

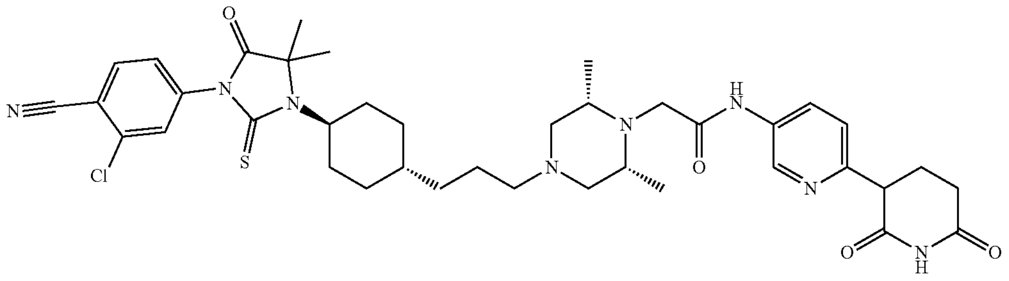 [SMILES: C[C@@H]1CN(CCC[C@H]2CC[C@H](N3C(=S)N(c4ccc(C#N)c(Cl)c4)C(=O)C3(C)C)CC2)C[C@H](C)N1CC(=O)Nc1ccc(C2CCC(=O)NC2=O)nc1]

3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)propanoic acid. To a 2-dram vial containing methyl 3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)propanoate (289. mg, 0.4400 mmol) was added 1,4-Dioxane (1.478 mL) followed by a solution of lithium hydroxide (15.93 mg, 0.6700 mmol) in 0.2 ml water. The reaction solution was stirred at room temperature for 2 hours. The solution was concentrated to provide 3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl) propanoic acid (263 mg, 0.4217 mmol, 95% yield) as a glassy oil that was carried forward without further purification. MS (ESI) m/z 624.3 $[M+1]^+$.

3-((2R,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1(2H)-yl)pyridin-3-yl)

2-Chloro-4-(3-(trans-4-(3-hydroxypropyl)cyclohexyl)-4,4-dimethyl-5-oxo-2-thioxoimidazolidin-1-yl)benzonitrile. To a solution of methyl 2-((trans-4-(3-hydroxypropyl)cyclohexyl)amino)-2-methylpropanoate (1.31 g, 5.1 mmol, 1 equiv.) and 2-chloro-4-isothiocyanatobenzonitrile (1.08 g, 5.57 mmol, 1.1 equiv.) in ethyl acetate (25 mL) was added N,N-diisopropylethylamine (2.51 mL, 15.18 mmol, 3 equiv.) and the reaction mixture was stirred at 80° C. After 18 h the reaction solution was concentrated and purified by column chromatography (15-50% ethyl acetate in petroleum ether) to afford 2-chloro-4-(3-(trans-4-(3-hydroxypropyl)cyclohexyl)-4,4-dimethyl-5-oxo-2-thioxoimidazolidin-1-yl) benzonitrile (1.26 g, 3.01 mmol, 59% yield) as a brown oil. MS (ESI) m/z 420.1 $[M+1]^+$.

4-(3-(trans-4-(3-Bromopropyl)cyclohexyl)-4,4-dimethyl-5-oxo-2-thioxoimidazolidin-1-yl)-2-chlorobenzonitrile. To a solution of 2-chloro-4-(3-(trans-4-(3-hydroxypropyl)cyclohexyl)-4,4-dimethyl-5-oxo-2-thioxoimidazolidin-1-yl)benzonitrile (1.26 g, 3.01 mmol) in N,N-dimethylformamide (0.30 mL) and dichloromethane (3 mL) was added thionyl bromide (1.88 g, 9.03 mmol, 3 equiv.) slowly at 0° C. After 12 h the reaction solution was concentrated under reduced pressure and purified by silica gel column chromatography (15-30% ethyl acetate in petroleum ether) to give 4-(3-(trans-4-(3-bromopropyl)cyclohexyl)-4,4-dimethyl-5-oxo-2-thioxoimidazolidin-1-yl)-2-chlorobenzonitrile (1.21 g, 2.50 mmol, 83% yield) as yellow solid. $^1$H NMR (400 MHz, $CDCl_3$) δ 7.79 (d, J=8.4 Hz, 1H), 7.58 (d, J=2.0 Hz, 1H), 7.42 (dd, J=8.4, 2.0 Hz, 1H), 3.87 (m, 1H), 3.43 (t, J=6.8 Hz, 2H), 2.70 (s, 2H), 1.94-1.82 (m, 6H), 1.59 (s, 6H), 1.39-1.36 (m, 3H), 1.12-1.03 (m, 2H).

2-((2R,6S)-4-(3-(trans-4-(3-(3-Chloro-4-cyanophenyl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide hydrochloride. To a solution of 4-(3-(trans-4-(3-bromopropyl)cyclohexyl)-4,4-dimethyl-5-oxo-2-thioxoimidazolidin-1-yl)-2-chlorobenzonitrile (0.120 g, 0.250 mmol, 1 equiv.) and 2-((2R,6S)-2,6-dimethylpiperazin-1-yl)-N-(6-(2,6-dioxopiperidin-3-yl)pyridin-3-yl)acetamide hydrobromide (0.107 g, 0.300 mmol, 1.2 equiv.) in N,N-dimethylformamide (2 mL, 0.125 M) was added N,N-diisopropylethylamine (0.13 mL, 0.750 mmol, 3 equiv.). The mixture was stirred at 60° C. After 12 h the reaction solution was diluted with DMSO (1 mL) and purified by standard methods to provide 2-((2S,6R)-4-(3-(trans-4-(3-(3-chloro-4-cyanophenyl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide hydrochloride (74.7 mg, 0.096 mmol, 38% yield) as a yellow solid. MS (ESI) m/z 761.3 $[M+1]^+$; $^1$H NMR (400 MHz, DMSO-$d_6$) δ 12.1-11.1 (m, 2H), 10.96 (s, 1H), 8.93 (s, 1H), 8.27 (d, J=6.4 Hz, 1H), 8.14 (d, J=8.4 Hz, 1H), 7.93 (d, J=2.0 Hz, 1H), 7.66-7.54 (m, 2H), 4.18 (dd, J=10.4, 5.2 Hz, 1H), 4.03 (s, 3H), 3.92-3.58 (m, 4H), 3.19 (s, 2H), 3.05 (s, 2H), 2.83-2.62 (m, 3H), 2.60-2.53 (m, 1H), 2.40-2.28 (m, 1H), 2.19-2.10 (m, 1H), 1.89-1.68 (m, 6H), 1.54 (s, 6H), 1.33 (d, J=4.8 Hz, 6H), 1.26-1.17 (m, 3H), 1.09 (q, J=11.2 Hz, 2H).

Example 11: 2-((2S,6R)-4-(3-(trans-4-(3-(5-Chloro-6-cyanopyridin-3-yl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide hydrochloride

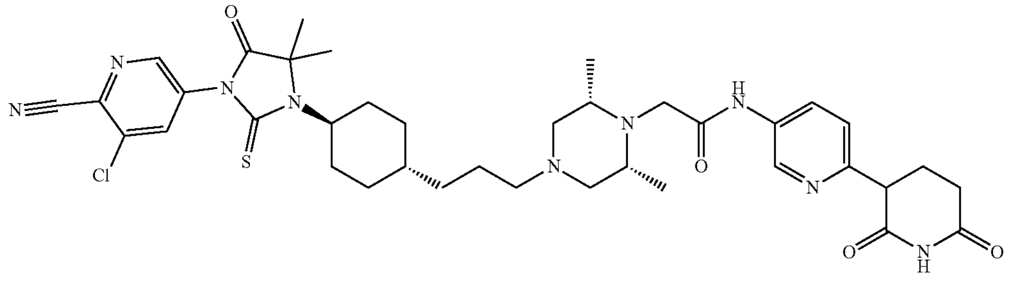

3-Chloro-5-(3-(trans-4-(3-hydroxypropyl)cyclohexyl)-4,4-dimethyl-5-oxo-2-thioxoimidazolidin-1-yl)picolinonitrile. A mixture of methyl 3-chloro-5-isothiocyanato-pyridine-2-carbonitrile (1.600 g, 8.18 mmol, 1 equiv.) and methyl 2-((trans-4-(3-hydroxypropyl)cyclohexyl)amino)-2-methylpropanoate (2.320 g, 9 mmol, 1.1 equiv.) in ethyl acetate (100 mL) was added triethylamine (2.28 mL, 16.36 mmol, 2 equiv.) and the reaction solution was stirred at 90° C. After 6 h the reaction solution was concentrated and purified by silica gel column chromatography (10-100% ethyl acetate in petroleum ether) to give 3-chloro-5-(3-(trans-4-(3-hydroxypropyl)cyclohexyl)-4,4-dimethyl-5-oxo-2-thioxoimidazolidin-1-yl)picolinonitrile (2.000 g, 4.75 mmol, 58% yield) as a yellow solid. MS (ESI) m/z 421.2 $[M+1]^+$; $^1$H NMR (400 MHz, $CDCl_3$) δ 8.67-8.50 (m, 1H), 7.98-7.83 (m, 1H), 3.80-3.48 (m, 4H), 2.75-2.52 (m, 2H), 1.93-1.60 (m, 6H), 1.51-1.28 (m, 3H), 1.27-1.15 (m, 5H), 1.06-0.89 (m, 3H).

5-(3-(trans-4-(3-Bromopropyl)cyclohexyl)-4,4-dimethyl-5-oxo-2-thioxoimidazolidin-1-yl)-3-chloropicolinonitrile. To a solution of 3-chloro-5-(3-(trans-4-(3-hydroxypropyl)cyclohexyl)-4,4-dimethyl-5-oxo-2-thioxoimidazolidin-1-yl)picolinonitrile (2.000 g, 4.75 mmol, 1 equiv.) in dichloromethane (5 mL, 0.1 M) and N,N-dimethylformamide (0.50 mL) was added thionyl bromide (0.61 mL, 9.5 mmol, 2 equiv.) at 0° C. The reaction solution was stirred at 25° C. After 16 h the pH of the reaction solution was adjusted to 8 by addition of saturated sodium carbonate. The aqueous phase was extracted with ethyl acetate (100 mL×2). The combined organic layers were washed with brine (25 mL), dried over anhydrous sodium sulfate, filtered and concentrated. The crude material was purified by silica gel column chromatography (50-100% ethyl acetate in petroleum ether) to give 5-(3-(trans-4-(3-bromopropyl)cyclohexyl)-4,4-dimethyl-5-oxo-2-thioxoimidazolidin-1-yl)-3-chloropicolinonitrile (1.600 g, 3.31 mmol, 70% yield) as a red solid. MS (ESI) m/z 483.1 $[M+1]^+$; $^1$H NMR (400 MHz, $CDCl_3$) δ 8.73-8.50 (m, 1H), 7.98-7.82 (m, 1H), 3.78-3.65 (m, 1H), 3.37-3.29 (m, 2H), 2.77-2.49 (m, 2H), 1.93-1.80 (m, 4H), 1.57-1.52 (m, 6H), 1.30 (br t, J=5.6 Hz, 3H), 1.08-0.97 (m, 2H).

2-((2S,6R)-4-(3-(trans-4-(3-(5-Chloro-6-cyanopyridin-3-yl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide hydrochloride. To a solution of 2-((2R,6S)-2,6-dimethylpiperazin-1-yl)-N-(6-(2,6-dioxopiperidin-3-yl)pyridin-3-yl)acetamide (0.150 g, 0.420 mmol, 1 equiv.) and 5-(3-(trans-4-(3-bromopropyl)cyclohexyl)-4,4-dimethyl-5-oxo-2-thioxoimidazolidin-1-yl)-3-chloropicolinonitrile (0.242 g, 0.500 mmol, 1.2 equiv.) in N,N-dimethylformamide (2 mL) was added N,N-diisopropylethylamine (0.36 mL, 2.090 mmol, 5 equiv.). The mixture was stirred at 50° C. After 12 h water was added (20 mL) and the solution was extracted with ethyl acetate (3×20 mL). The combined organic layers were washed with brine (20 mL), dried over anhydrous sodium sulfate, filtered and concentrated. The crude material was purified by standard methods to give 2-((2S,6R)-4-(3-(trans-4-(3-(5-chloro-6- cyanopyridin-3-yl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide hydrochloride (0.125 g, 0.160 mmol, 38% yield) as a yellow solid. MS (ESI) m/z 762.3 $[M+1]^+$; $^1H$ NMR (400 MHz, DMSO-$d_6$) δ 12.55-11.20 (m, 2H), 11.00 (s, 1H), 8.97 (s, 1H), 8.82 (d, J=2.0 Hz, 1H), 8.53 (d, J=2.0 Hz, 1H), 8.33 (d, J=6.8 Hz, 1H), 7.66 (d, J=8.4 Hz, 1H), 4.36-4.03 (m, 5H), 3.90-3.65 (m, 3H), 3.36-3.16 (s, 2H), 3.14-2.95 (m, 2H), 2.80-2.64 (m, 3H), 2.61-2.54 (m, 1H), 2.43-2.30 (m, 1H), 2.19-2.10 (m, 1H), 1.87-1.68 (m, 6H), 1.55 (s, 6H), 1.36 (d, J=5.4 Hz, 6H), 1.27-1.17 (m, 3H), 1.15-1.04 (m, 2H).

Example 12: 2-((2R,6S)-4-(3-((trans-4-(3-(4-Cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(6-(2,4-dioxotetrahydropyrimidin-1(2H)-yl)pyridin-3-yl) acetamide hydrochloride 2-((2R,6S)-2,6-Dimethylpiperazin-1-yl)-N-(6-(2,4-dioxotetrahydropyrimidin-1(2H)-yl)pyridin-3-yl)acetamide hydrobromide. To a solution of tert-butyl (3R,5S)-4-(2-((6-(2,4-dioxotetrahydropyrimidin-1(2H)-yl)pyridin-3-yl)oxy)-2-oxoethyl)-3,5-dimethylpiperazine-1-carboxylate (0.300 g, 0.650 mmol, 1 equiv.) in dichloromethane (20 mL) was added 30% hydrobromic acid in acetic acid (1.5 mL, 0.650 mmol, 1 equiv.) and the reaction solution was stirred at 10° C. After 12 h the reaction solution was concentrated to give crude 2-((2R,6S)-2,6-dimethylpiperazin-1-yl)-N-(6-(2,4-dioxotetrahydropyrimidin-1(2H)-yl)pyridin-3-yl)acetamide-hydrobromide (0.250 g, crude) as a red solid, which was carried forward without further purification. MS (ESI) m/z 383.3 $[M+Na]^+$.

2-((2R,6S)-4-(3-((trans-4-(3-(4-Cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(6-(2,4-dioxotetrahydropyrimidin-1(2H)-yl)pyridin-3-yl) acetamide hydrochloride. To a solution of 4-(3-(trans-4-(3-

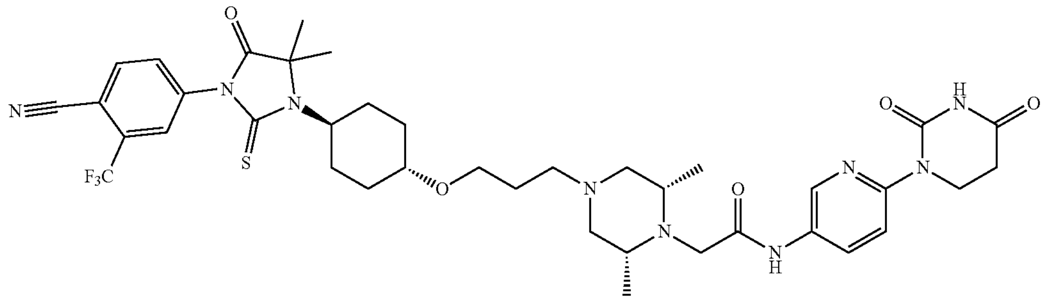 [SMILES: C[C@@H]1CN(CCCO[C@H]2CC[C@H](N3C(=S)N(c4ccc(C#N)c(C(F)(F)F)c4)C(=O)C3(C)C)CC2)C[C@H](C)N1CC(=O)Nc1ccc(N2CCC(=O)NC2=O)nc1]

tert-Butyl (3R,5S)-4-(2-((6-(2,4-dioxotetrahydropyrimidin-1(2H)-yl)pyridin-3-yl)amino)-2-oxoethyl)-3,5-dimethylpiperazine-1-carboxylate. To a solution of 1-(5-aminopyridin-2-yl)dihydropyrimidine-2,4(1H,3H)-dione (0.200 g, 0.970 mmol, 1 equiv.) and 2-((2S,6R)-4-(tert-butoxycarbonyl)-2,6-dimethylpiperazin-1-yl)acetic acid (0.264 g, 0.970 mmol, 1 equiv.) in N,N-dimethylacetamide (5 mL) was added HATU (0.369 g, 0.970 mmol, 1 equiv.) and N,N-diisopropylethylamine (0.51 mL, 2.910 mmol, 3 equiv.) and the reaction solution was stirred at room temperature. After 12 h the reaction solution was diluted with DMSO and purified by semi-preparative reverse phase HPLC (4-34% acetonitrile+0.225% formic acid in water, over 11 min). The collected fraction was concentrated to remove most of the acetonitrile and the aqueous phase was lyophilized to give tert-butyl (3R,5S)-4-(2-((6-(2,4-dioxotetrahydropyrimidin-1(2H)-yl)pyridin-3-yl)amino)-2-oxoethyl)-3,5-dimethylpiperazine-1-carboxylate (0.350 g, 0.760 mmol, 78% yield) as a light yellow solid. MS (ESI) m/z 461.2 $[M+1]^+$; $^1H$ NMR (400 MHz, DMSO-$d_6$) δ 11.03 (s, 1H), 10.52 (s, 1H), 9.49 (br s, 1H), 8.71-8.63 (m, 1H), 8.08-7.94 (m, 1H), 7.80-7.70 (m, 1H), 4.38-4.24 (m, 2H), 4.02 (br t, J=6.6 Hz, 3H), 4.11-3.98 (m, 1H), 3.64 (br s, 2H), 3.15 (br s, 1H), 2.69 (t, J=6.6 Hz, 2H), 1.42 (s, 9H), 1.33 (br d, J=6.3 Hz, 5H), 1.26 (br s, 2H).

bromopropoxy)cyclohexyl)-4,4-dimethyl-5-oxo-2-thioxoimidazolidin-1-yl)-2-(trifluoromethyl)benzonitrile (0.150. g, 0.280 mmol, 1 equiv.) and 2-((2R,6S)-2,6-dimethylpiperazin-1-yl)-N-(6-(2,4-dioxotetrahydropyrimidin-1(2H)-yl)pyridin-3-yl)acetamidehydrobromide (0.249 g, 0.560 mmol, 2 equiv.) in N,N-dimethylformamide (5 mL) was added N,N-diisopropylethylamine (0.49 mL, 2.820 mmol, 10 equiv.) and the reaction solution was stirred at 50° C. After 12 h the reaction solution was diluted with water (80 mL) and extracted with ethyl acetate (4×30 mL). the combined organic layers were washed with brine (40 mL), dried over anhydrous sodium sulfate and concentrated. The resulting crude material was purified by standard methods to give 2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1(2H)-yl)pyridin-3-yl)acetamide hydrochloride (0.080 g, 0.096 mmol, 34% yield) as a yellow solid. MS (ESI) m/z 812.5 $[M+1]^+$; $^1H$ NMR (400 MHz, DMSO-$d_6$) δ 12.18-11.33 (m, 1H), 11.31-10.65 (m, 1H), 11.08 (br s, 1H), 10.52 (s, 1H), 8.69 (d, J=2.0 Hz, 1H), 8.34 (d, J=8.3 Hz, 1H), 8.19 (s, 1H), 8.04 (dd, J=2.5, 9.0 Hz, 1H), 7.97 (dd, J=1.6, 8.4 Hz, 1H), 7.73 (d, J=9.0 Hz, 1H), 4.01 (br t, J=6.4 Hz, 1H), 3.72 (br s, 5H), 3.51 (br t, J=5.6 Hz, 2H), 3.36-3.00 (m, 6H), 2.96-2.74 (m, 3H), 2.74-2.64 (m, 3H), 2.15-1.85 (m, 4H), 1.83-1.64 (m, 3H), 1.55 (s, 6H), 1.39-1.25 (m, 8H).

Example 13:2-((R)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)-N-(6-(2,6-dioxopiperidin-3-yl)pyridin-3-yl)acetamide hydrochloride

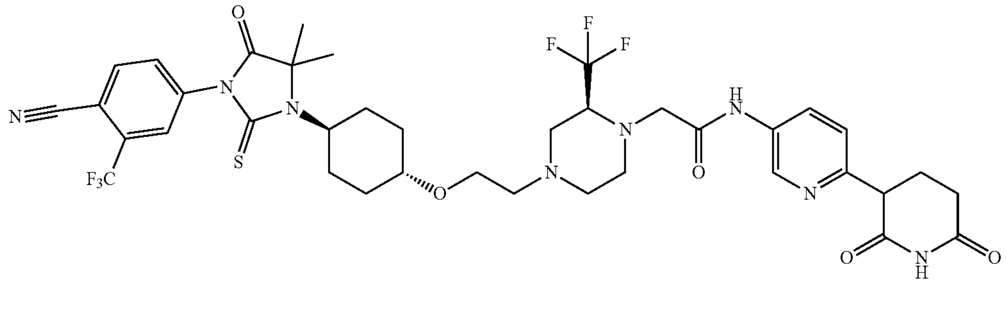 [SMILES: CC1(C)C(=O)N(c2ccc(C#N)c(C(F)(F)F)c2)C(=S)N1[C@H]1CC[C@H](OCCN2CCN(CC(=O)Nc3ccc(C4CCC(=O)NC4=O)nc3)[C@H](C(F)(F)F)C2)CC1]

tert-Butyl (R)-4-(2-methoxy-2-oxoethyl)-3-(trifluoromethyl)piperazine-1-carboxylate. To a 40 ml vial was added tert-butyl (R)-3-(trifluoromethyl)piperazine-1-carboxylate (0.5 g, 1.97 mmol), N,N-diisopropylethylamine (0.69 mL, 3.93 mmol, 2 equiv.), methyl bromoacetate (1.09 mL, 11.8 mmol, 6 equiv.) and THE (20 mL, 0.1 M). The reaction solution was stirred at room temperature. After 18 the solution was diluted with 100 ml ethyl acetate and 100 ml water. The organic layer was removed and the aqueous layer was extracted with 2×50 ml ethyl acetate. Then combined organic layers were dried over magnesium sulfate and concentrated. The crude material was purified by silica gel column chromatography (1-50% ethyl acetate in hexanes) to provide tert-butyl (R)-4-(2-methoxy-2-oxoethyl)-3-(trifluoromethyl)piperazine-1-carboxylate (0.557 g, 1.71 mmol, 88% yield) as a yellow oil. MS (ESI) m/z 227 $[M-99]^+$.

Methyl (R)-2-(2-(trifluoromethyl)piperazin-1-yl)acetate. tert-Butyl (R)-3-(trifluoromethyl)piperazine-1-carboxylate (250 mg, 0.7 mmol), and trifluoroacetic acid (0.58 mL, 7.6 mmol, 10 equiv.) were combined in dichloromethane (7.6 mL, 1 M) and stirred at room temperature in a screw capped scintillation vial. After 1 h, the solution was concentrated methyl (R)-2-(2-(trifluoromethyl)piperazin-1-yl)acetate (255 mg, 0.75 mmol, 98% yield) as a yellow oil that was carried forward without further purification. MS (ESI) m/z 227 $[M+1]^+$.

Methyl 2-((R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl) acetate. To a 1-dram vial containing 4-(3-(trans-4-(2-bromoethoxy)cyclohexyl)-4,4-dimethyl-5-oxo-2-thioxoimidazolidin-1-yl)-2-(trifluoromethyl)benzonitrile (0.5 g, 0.96 mmol, 1 equiv.), methyl (R)-2-(2-(trifluoromethyl)piperazin-1-yl)acetate (0.33 g, 0.96 mmol, 1 equiv.) and sodium iodide (2.7 mg, 0.02 mmol, 0.1 equiv.) was added acetonitrile (5 mL) followed by N,N-diisopropylethylamine (0.8 mL, 4.82 mmol, 5 equiv.). The reaction vial was heated with stirring to 60° C. After 16 h the reaction solution was diluted with ethyl acetate (100 mL), washed with saturated aqueous sodium chloride (100 mL), dried over anhydrous sodium sulfate and concentrated. The crude material was purified by silica gel column chromatography (0-100% ethyl acetate in hexane) to afford methyl 2-((R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)acetate (0.6 g, 0.89 mmol, 91% yield). MS (ESI) m/z 664.2 $[M+1]^+$.

2-((R)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)acetic acid. To a chilled solution of methyl 2-((R)-4-(2-((trans-4-(3-(4-cyano-3-(trifluoromnethyl)phenyl)-5,5-dimethyl-4-oxo-2-thioxoimidazolidin-1-yl)cyclohexyl)oxy)ethyl)-2-(trifluoromethyl)piperazin-1-yl)acetate (0.6 g, 0.9 mmol, 1 equiv.) in a mixture of tetrahydrofuran/methanol/water (3:1:1, 5 mL), lithium hydroxide monohydrate (0.58 g, 1.3 mmol, 1.5 equiv.) was added in one portion at 0° C. The resulting solution was stirred at room temperature. After 3 h the reaction solution was diluted with water (20 mL) and extracted with 10% methanol in dichloromethane (4×50 mL). The organic layer was dried over anhydrous magnesium sulfate, filtered and concentrated to give the 2-((R)-4-(2-((trans-4-(3-(4-cyano-3-(trifluoromethyl)phenyl)-5,5-dimethyl-4-oxo-2-thioxoimidazolidin-1-yl)cyclohexyl)oxy) ethyl) 2-(trifluoromethyl)piperazin-1-yl)acetic acid(0.33 g, 0.46 mmol, 51% yield), which was carried forward without further purification. MS (ESI) m/z 650.2 $[M+1]^+$.

2-((R)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)-N-(6-(2,6-dioxopiperidin-3-yl)pyridin-3-yl)acetamide hydrochloride. To a 2 dram vial containing 2-((R)-4-(2-((trans-4-(3-(4-cyano-3-(trifluoromethyl)phenyl)-5,5-dimethyl-4-oxo-2-thioxoimidazolidin-1-yl)cyclohexyl)oxy) ethyl)-2-(trifluoromethyl)piperazin-1-yl)acetic acid (0.12 g, 0.19 mmol, 1 equiv.) and 3-(5-aminopyridin-2-yl)piperidine-2,6-dione (0.05 g, 0.22 mmol, 1.2 equiv.) was added acetonitrile (1.5 mL) and N,N-dimethylforamide (1.5 mL). the reaction solution was stirred until all solids were dissolved. 1-Methylimidazole (0.07 mL, 0.84 mmol, 5 equiv.) was added followed by N-(chloro(dimethylamino)methylene)-N-methylmethanaminium hexafluorophosphate (0.12 g, 0.41 mmol, 2.2 equiv.) and the reaction solution was stirred at room temperature. After 1 h the reaction solution was diluted with dimethylsulfoxide to a total volume of 3 ml, filtered, and purified by standard methods to give 2-((R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)-N-(6-(2,6-dioxopiperidin-3-yl)pyridin-3-yl)acetamide hydrochloride (0.05 g, 0.05 mmol, 27% yield). MS (ESI) m/z 837.2 $[M+1]^+$; $^1H$ NMR (400 MHz, DMSO-$d_6$) δ 10.81-10.95 (m, 1H), 10.48-10.70 (m, 1H), 8.73-8.94 (m, 1H), 8.24-8.33 (m, 1H), 8.08-8.19 (m, 2H), 7.82-7.95 (m, 1H), 7.45-7.60 (m, 1H), 4.32 (br dd, J=3.18, 2.08 Hz, 4H), 3.78-3.86 (m, 3H), 3.67 (br d, J=9.05 Hz, 3H), 3.46 (br d, J=9.66 Hz, 1H), 3.24-3.39 (m, 4H), 3.12 (br s, 2H), 2.70-2.87 (m, 2H), 2.54-2.67 (m, 1H), 2.21-2.32 (m, 1H), 1.96-2.12 (m, 3H), 1.59-1.76 (m, 2H), 1.41-1.53 (m, 6H), 1.22-1.36 (m, 2H).

Example 14: 2-((2R,4r,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide hydrochloride

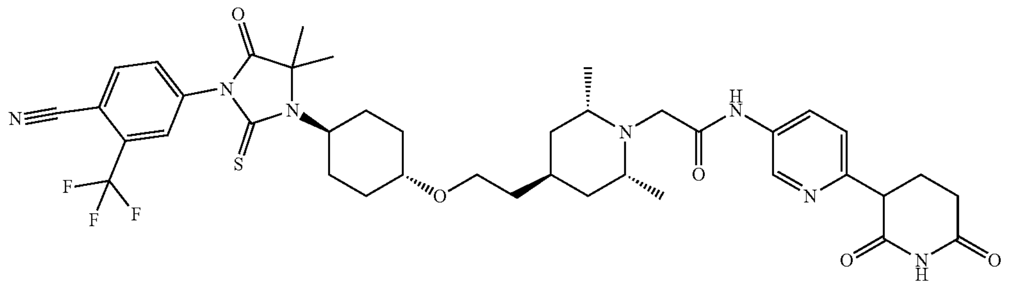 [SMILES: C[C@@H]1C[C@@H](CCO[C@H]2CC[C@H](N3C(=S)N(c4ccc(C#N)c(C(F)(F)F)c4)C(=O)C3(C)C)CC2)C[C@H](C)N1CC(=O)Nc1ccc(C2CCC(=O)NC2=O)nc1]

(2S,6R)-1-Benzyl-2,6-dimethylpiperidin-4-one. To a solution of 3-oxopentanedioic acid (100.0 g, 684.5 mmol, 1 equiv.) in water (200 mL) was added acetaldehyde (150.8 g, 1368.9 mmol, 2 equiv.) at 20° C. The reaction was stirred at 20° C. for 20 min and then cooled to 0° C. and phenylmethanamine (74.61 mL, 684.5 mmol, 1 equiv.) was added dropwise. The reaction solution was allowed to warm to room temperature and stirred for 48 h. The reaction solution was extracted with ethyl acetate 3000 mL (1000 mL×3) and the combined organic layers were washed with brine 500 mL. The organic layers were dried with anhydrous sodium sulfate, filtrated and concentrated. The crude material was purified by silica gel column chromatography to give (2S,6R)-1-benzyl-2,6-dimethylpiperidin-4-one (27.70 g, 127.5 mmol, 19% yield) as a yellow oil. $^1H$ NMR (400 MHz, $CDCl_3$) δ 7.42 (d, J=7.2 Hz, 2H), 7.37-7.29 (m, 2H), 7.27-7.20 (m, 1H), 3.86 (s, 2H), 3.17-3.09 (qd, J=6.4, 13.2 Hz, 2H), 2.42-2.28 (m, 4H), 1.16 (d, J=6.4 Hz, 6H).

Ethyl 2-((2R,6S)-1-benzyl-2,6-dimethylpiperidin-4-ylidene)acetate. To a solution of sodium hydride (8.283 g, 207.1 mmol, 1.5 equiv.) in THE (50 mL) was added ethyl 2-(diethoxyphosphoryl)acetate (40.23 g, 179.5 mmol, 1.3 equiv.) in THE (100 mL) dropwise at 0° C. The mixture was stirred at 0° C. for 30 min. (2S,6R)-1-benzyl-2,6-dimethylpiperidin-4-one (30.00 g, 138.1 mmol, 1 equiv.) in THF (200 mL) was added to above solution dropwise and the reaction solution was warmed to room temperature. After 12 h the reaction solution was neutralized by addition of ammonium chloride saturated solution and poured into ice-water (200 mL). The aqueous phase was extracted with ethyl acetate (3×500 mL). The combined organic layers were washed with brine (300 mL), dried with anhydrous sodium sulfate, filtered and concentrated. The crude material was purified by flash silica gel chromatography (2.0% ethyl acetate in petroleum ether) (petroleum ether: ethyl acetate=3:1, Rf: 0.65) and then re-purified by semi-preparative reverse phase HPLC (55-85% acetonitrile+0.05% ammonium hydroxide in water, over 20 min). The collected fraction was concentrated, and the aqueous phase was extracted with ethyl acetate (3×500 mL). The combined organic layers were washed with brine (300 mL), dried with anhydrous sodium sulfate, filtered and concentrated to give ethyl 2-((2R,6S)-1-benzyl-2,6-dimethylpiperidin-4-ylidene) acetate (11.7 g, 40.7 mmol, 30% yield) as a yellow oil. MS (ESI) m/z 288.2 $[M+1]^+$; $^1H$ NMR (400 MHz, $CDCl_3$) δ 7.45-7.35 (m, 2H), 7.30 (t, J=7.6 Hz, 2H), 7.26-7.16 (m, 1H), 5.63 (s, 1H), 4.15 (q, J=7.2 Hz, 2H), 3.82 (s, 2H), 3.57 (dd, J=2.8, 14.0 Hz, 1H), 2.84-2.62 (m, 2H), 2.29-2.08 (m, 3H), 1.33-1.23 (m, 3H), 1.14 (dd, J=6.4, 16.4 Hz, 6H).

tert-Butyl (2S,6R)-4-(2-ethoxy-2-oxoethyl)-2,6-dimethylpiperidine-1-carboxylate. To a solution of ethyl 2-((2R,6S)-1-benzyl-2,6-dimethylpiperidin-4-ylidene)acetate (5.300 g, 18.44 mmol, 1 equiv.) and di-tert-butyl dicarbonate (6.037 g, 27.66 mmol, 1.5 equiv.) in THE (80 mL, 0.23 M) was added 10% Palladium on carbon (1.500 g, 1.84 mmol, 10 mol %) under nitrogen. The reaction mixture was stirred at room temperature for 12 hours under hydrogen (50 psi). The reaction mixture was filtered and concentrated to give a residue which was purified by flash silica gel chromatography (1% ethyl acetate in petroleum ether, petroleum ether: ethyl acetate=5:1) to give tert-butyl (2S,6R)-4-(2-ethoxy-2-oxoethyl)-2,6-dimethylpiperidine-1-carboxylate(2.630 g, 8.784 mmol, 48% yield) as a yellow oil. $^1H$ NMR (400 MHz, $CDCl_3$) δ 4.26 (s, 1H), 4.21 (m, 1H), 4.17-4.10 (m, 2H), 2.26-2.18 (m, 2H), 2.13-2.05 (m, 1H), 1.99-1.84 (m, 1H), 1.66-1.55 (m, 1H), 1.47 (s, 9H), 1.36-1.29 (m, 1H), 1.29-1.25 (m, 3H), 1.24-1.19 (m, 6H), 1.15-1.02 (m, 2H).

tert-Butyl (2S,6R)-4-(2-hydroxyethyl)-2,6-dimethylpiperidine-1-carboxylate. To a solution of lithium aluminumhydride (0.500 g, 13.18 mmol, 1.5 equiv.) in THE (10 mL) was added a solution of tert-butyl (2S,6R)-4-(2-ethoxy-2-oxoethyl)-2,6-dimethylpiperidine-1-carboxylate(2.630 g, 8.780 mmol, 1 equiv.) in THE (40 mL) at 0° C. The reaction solution was slowly warmed to room temperature over 1 h. The reaction solution was quenched by addition water 0.5 mL, 15% sodium hydroxide solution (1 mL) and water 1.5 mL. The slurry was stirred for 0.5 h, filtered and concentrated in vacuo. The crude material was diluted with water 100 mL and extracted with ethyl acetate 100 mL×3. The combined organic layers were washed with brine 100 mL, dried over anhydrous sodium sulfate, filtered and concentrated. The residue was purified by silica gel column chromatography (20% ethyl acetate in petroleum ether) to provide tert-butyl (2S,6R)-4-(2-hydroxyethyl)-2,6-dimethylpiperidine-1-carboxylate (2.180 g, 8.470 mmol, 96% yield) as a yellow solid. $^1$H NMR (400 MHz, $CDCl_3$) δ 4.40-4.25 (m, 1H), 4.24-4.07 (m, 1H), 3.77-3.65 (m, 2H), 2.12-2.03 (m, 1H), 1.68-1.56 (m, 2H), 1.55-1.49 (m, 2H), 1.49-1.42 (m, 9H), 1.33-1.26 (m, 1H), 1.25-1.17 (m, 6H), 1.05 (m, 1H).

tert-Butyl (2S,6R)-4-(2-bromoethyl)-2,6-dimethylpiperidine-1-carboxylate. To a solution of tert-butyl (2S,6R)-4-(2-hydroxyethyl)-2,6-dimethylpiperidine-1-carboxylate (2.180 g, 8.470 mmol, 1 equiv.) and triphenylphosphine (3.332 g, 12.71 mmol, 1.5 equiv.) in dichloromethane (40 mL, 0.21 M). To the reaction solution was added carbon tetrabromide (4.214 g, 12.71 mmol, 1.5 equiv.) at 0° C. The reaction mixture was allowed to slowly warm to room temperature. After 2 h the reaction solution was poured into saturated sodium bicarbonate solution (100 mL) and the aqueous phase was extracted with dichloromethane (3×100 mL). The combined organic layers were washed with brine (100 mL), dried over anhydrous sodium sulfate, filtered and concentrated. The crude material was purified by silica gel chromatography (1% ethyl acetate in petroleum ether) to provide tert-butyl (2S,6R)-4-(2-bromoethyl)-2,6-dimethylpiperidine-1-carboxylate (2.160 g, 6.744 mmol, 80% yield) as a clear, colorless oil. $_1$H NMR (400 MHz, $CDCl_3$) δ 4.45-4.27 (m, 1H), 4.26-4.06 (m, 1H), 3.51-3.29 (m, 2H), 2.18-1.96 (m, 2H), 1.89-1.75 (m, 2H), 1.73-1.53 (m, 2H), 1.48-1.39 (m, 9H), 1.33-1.25 (m, 1H), 1.24-1.19 (m, 6H), 1.13-0.97 (m, 1H).

tert-Butyl (2R,6S)-4-(2-((trans-4-(dibenzylamino)cyclohexyl)oxy)ethyl)-2,6-dimethylpiperidine-1-carboxylate. To a solution of trans-4-(dibenzylamino)cyclohexanol (12.18 g, 41.22 mmol, 2 equiv.) and tert-butyl (2S,6R)-4-(2-bromoethyl)-2,6-dimethylpiperidine-1-carboxylate (6.600 g, 20.61 mmol, 1 equiv.) in xylene (120 mL, 0.17 M) was added potassium hydroxide (5.318 g, 94.80 mmol, 4.6 equiv.) and tetrabutylammonium bromide (1.328 g, 4.120 mmol, 0.2 equiv.). The reaction was stirred at 30° C. After 24 h the reaction solution was diluted with water (200 mL) and extracted with ethyl acetate (3×250 mL). The combined organic layers were washed with brine (150 mL), dried over anhydrous sodium sulfate, filtered and concentrated. The crude material was purified by flash silica gel column chromatography (2.5-3% ethyl acetate in petroleum ether) to provide tert-butyl (2R,6S)-4-(2-((trans-4-(dibenzylamino)cyclohexyl)oxy)ethyl)-2,6-dimethylpiperidine-1-carboxylate (2.800 g, 5.236 mmol, 25% yield) as a yellow oil. $^1$H NMR (400 MHz, $CDCl_3$) δ 7.42-7.33 (m, 4H), 7.33-7.27 (m, 4H), 7.24-7.17 (m, 2H), 4.36-4.23 (m, 2H), 4.22-4.15 (m, 1H), 3.62 (s, 4H), 3.48 (t, J=6.4 Hz, 1H), 3.45-3.37 (m, 1H), 3.19-3.06 (m, 1H), 2.53 (m, 1H), 2.09-2.04 (m, 3H), 2.01-1.86 (m, 3H), 1.63-1.59 (m, 1H), 1.57-1.51 (m, 2H), 1.47-1.46 (m, 9H), 1.43-1.33 (m, 2H), 1.28-1.24 (m, 2H), 1.21 (s, 2H), 1.17 (d, J=7.0 Hz, 6H), 1.14-1.08 (m, 1H), 1.07-0.92 (m, 1H).

tert-Butyl (2R,6S)-4-(2-((trans-4-aminocyclohexyl)oxy)ethyl)-2,6-dimethylpiperidine-1-carboxylate. To a solution of tert-butyl (2R,6S)-4-(2-((trans-4-(dibenzylamino)cyclohexyl)oxy)ethyl)-2,6-dimethylpiperidine-1-carboxylate (2.800 g, 5.240 mmol, 1 equiv.) in methanol (60 mL) was added palladium on carbon (2.000 g) under nitrogen. The reaction was stirred at room temperature for 12 hours under hydrogen (15 psi). The reaction mixture was filtered and concentrated to give tert-butyl (2R,6S)-4-(2-((trans-4-aminocyclohexyl)oxy)ethyl)-2,6-dimethylpiperidine-1-carboxylate (1.837 g, 5.180 mmol, 98% yield) yellow oil which was carried forward without further purification. $^1$H NMR (400 MHz, DMSO-$d_6$) δ 4.23-4.08 (m, 2H), 4.08-3.93 (m, 1H), 3.50-3.40 (m, 2H), 3.40-3.33 (m, 1H), 3.18-3.04 (m, 1H), 2.55-2.51 (m, 2H), 2.49 (br s, 1H), 2.05-1.83 (m, 4H), 1.82-1.68 (m, 2H), 1.67-1.47 (m, 2H), 1.46-1.32 (m, 16H), 1.29-1.15 (m, 2H), 1.15-1.07 (m, 9H), 1.07-0.87 (m, 3H).

tert-Butyl (2S,6R)-4-(2-((trans-4-((1-methoxy-2-methyl-1-oxopropan-2-yl)amino)cyclohexyl)oxy)ethyl)-2,6-dimethylpiperidine-1-carboxylate. To a solution of tert-butyl (2R,6S)-4-(2-((trans-4-aminocyclohexyl)oxy)ethyl)-2,6-dimethylpiperidine-1-carboxylate (1.837 g, 5.180 mmol, 1 equiv.) in acetonitrile (10 mL, 0.5 M) was added potassium iodide (0.086 g, 0.520 mmol, 10 mol %), potassium carbonate (2.148 g, 15.54 mmol, 3 equiv.) and methyl 2-bromo-2-methylpropanoate (3.75 mL, 25.91 mmol, 5 equiv.). The reaction was stirred at 110° C. After 48 h the reaction solution was filtered and concentrated to give tert-butyl (2S,6R)-4-(2-((trans-4-((1-methoxy-2-methyl-1-oxopropan-2-yl)amino)cyclohexyl)oxy)ethyl)-2,6-dimethylpiperidine-1-carboxylate (2.400 g, 5.279 mmol, crude) as a yellow oil which was carried forward without further purification. MS (ESI) m/z 455.5 $[M+1]^+$.

tert-Butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate and tert-butyl (2R,4r,6S)-4-(2-(((1r,4R)-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate. To a solution of tert-butyl (2S,6R)-4-(2-((trans-4-((1-methoxy-2-methyl-1-oxopropan-2-yl)amino)cyclohexyl)oxy)ethyl)-2,6-dimethylpiperidine-1-carboxylate (2.160 g, 4.750 mmol, 1 equiv.) and 4-isothiocyanato-2-(trifluoromethyl)benzonitrile (1.084 g, 4.750 mmol, 1 equiv.) in ethyl acetate (10 mL, 0.47 M) was added N,N-diisoproplyethylamine (1.660 mL, 9.500 mmol, 2 equiv.). The reaction was stirred at 90° C. After 12 h the reaction solution was diluted with water (50 mL) and extracted with ethyl acetate (3×50 mL). The combined organic layers were washed with brine (50 mL), dried over anhydrous sodium sulfate, filtered and concentrated. The crude material was purified by flash silica gel column chromatography to afford the mixture of diastereomers, which were separated by SFC (DAICEL CHIRAL PAK IG: 250 mm*30 mm. 10 um, 20% methanol+0.1% $NH_3$·H2O) to give tert-butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate (1.060 g, 1.629 mmol, 34% yield) and tert-butyl (2R,4r,6S)-4-(2-((trans-4-(3-(4-cyano-3-

(trifluoromethyl)phenyl)-5,5-dimethyl-4-oxo-2-thioxoimidazolidin-1-yl)cyclohexyl)oxy)ethyl)-2,6-dimethylpiperidine-1-carboxylate (0.360 g, 0.553 mmol, 12% yield). tert-butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate: $^1$H NMR (400 MHz, $CDCl_3$) δ 7.95 (d, J=8.0 Hz, 1H), 7.85 (d, J=2.0 Hz, 1H), 7.72 (dd, J=2.0, 8.0 Hz, 1H), 4.38-4.22 (m, 2H), 3.72-3.59 (m, 1H), 3.54 (t, J=6.4 Hz, 2H), 3.37-3.24 (m, 1H), 3.03-2.75 (m, 2H), 2.21 (br d, J=12.4 Hz, 2H), 2.03-1.90 (m, 1H), 1.89-1.77 (m, 2H), 1.61 (s, 6H), 1.58 (m, 2H), 1.54-1.48 (m, 2H), 1.47 (s, 9H), 1.40-1.26 (m, 4H), 1.19 (d, J=7.2 Hz, 6H). tert-Butyl (2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate: $^1$H NMR (400 MHz, $CDCl_3$) δ 7.95 (d, J=8.4 Hz, 1H), 7.85 (d, J=2.0 Hz, 1H), 7.72 (dd, J=2.0, 8.4 Hz, 1H), 4.28-4.10 (m, 2H), 3.76-3.58 (m, 1H), 3.49 (t, J=6.0 Hz, 2H), 3.30 (m, 1H), 3.03-2.76 (m, 2H), 2.19 (br d, J=12.0 Hz, 2H), 2.12-1.98 (m, 2H), 1.89-1.76 (m, 2H), 1.61 (s, 6H), 1.52 (br t, J=6.4 Hz, 2H), 1.47 (s, 9H), 1.40-1.25 (m, 3H), 1.22 (d, J=6.8 Hz, 6H), 1.03 (m, 2H).

4-(3-(trans-4-(2-((2R,4s,6S)-2,6-Dimethylpiperidin-4-yl)ethoxy)cyclohexyl)-4,4-dimethyl-5-oxo-2-thioxoimidazolidin-1-yl)-2-(trifluoromethyl)benzonitrile. To a solution of tert-butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate (1.060 g, 1.630 mmol, 1 equiv.) in dichloromethane (5 mL) was added 4 M hydrochloric acid in 1,4-dioxane (20 mL, 80.00 mmol), and the reaction solution was stirred at room temperature. After 2 h the reaction solution was concentrated. The resulting yellow solid was taken up in saturated aqueous sodium bicarbonate (50 mL) and extracted with ethyl acetate (3×100 mL). The combined organic layers were washed with brine (50 mL), dried over anhydrous sodium sulfate and concentrated to provide 4-(3-(trans-4-(2-((2R,4s,6S)-2,6-dimethylpiperidin-4-yl)ethoxy)cyclohexyl)-4,4-dimethyl-5-oxo-2-thioxoimidazolidin-1-yl)-2-(trifluoromethyl)benzonitrile (0.920 g, 1.67 mmol, 99% yield) as a yellow solid which was carried forward without further purification. MS (ESI) m/z 551.4 $[M+1]^+$; $^1$H NMR (400 MHz, $CDCl_3$) δ 7.95 (d, J=8.0 Hz, 1H), 7.84 (d, J=2.0 Hz, 1H), 7.72 (dd, J=2.0, 8.0 Hz, 1H), 3.74-3.59 (m, 1H), 3.51 (t, J=6.8 Hz, 2H), 3.31 (m, 1H), 2.92 (m, 4H), 2.20 (br d, J=12.0 Hz, 2H), 2.02-1.92 (m, 1H), 1.82 (br d, J=12.0 Hz, 2H), 1.70 (q, J=6.8 Hz, 2H), 1.64-1.56 (s, 6H), 1.51 (br d, J=12.8 Hz, 2H), 1.40-1.27 (m, 4H), 1.09 (br d, J=6.0 Hz, 6H).

Benzyl 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetate. To a mixture of 4-(3-(trans-4-(2-((2R,4s,6S)-2,6-dimethylpiperidin-4-yl)ethoxy)cyclohexyl)-4,4-dimethyl-5-oxo-2-thioxoimidazolidin-1-yl)-2-(trifluoromethyl)benzonitrile (0.080 g, 0.150 mmol, 1 equiv.) and benzyl 2-bromoacetate (0.040 g, 0.170 mmol, 1.2 equiv.) in acetonitrile (0.5 mL, 0.3 M) was added N,N-diisopropylethylamine (0.08 mL, 0.440 mmol, 3 equiv.) and the reaction solution was stirred at room temperature. After 12 h the reaction solution was filtered and concentrated, and the crude material purified by preparatory TLC (dichloromethane:methanol=10:1, Rf=0.7) to afford benzyl 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetate (0.092 g, 0.132 mmol, 91% yield) as a yellow solid. MS (ESI) m/z 699.2 $[M+1]^+$; $^1$H NMR (400 MHz, DMSO-$d_6$) δ 8.33 (d, J=8.0 Hz, 1H), 8.19 (s, 1H), 7.96 (d, J=8.0 Hz, 1H), 7.36-7.34 (m, 5H), 5.10 (s, 2H), 3.53 (s, 2H), 3.43-3.40 (m, 2H), 3.17-3.16 (m, 4H), 2.92 (s, 2H), 2.85-2.75 (m, 2H), 2.05-2.02 (m, 2H), 1.72-1.69 (m, 3H), 1.56 (s, 6H), 1.45-1.35 (m, 2H), 1.30-1.25 (m, 4H), 0.95 (d, J=6.0 Hz, 6H).

2-((2R,4s,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetic acid. To a mixture of benzyl 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetate (0.082 g, 0.1200 mmol, 1 equiv.) in THF (1 mL) was added lithium hydroxide (0.011 g, 0.4700 mmol, 4 equiv.). The reaction solution was stirred at 25° C. for 3 h. Hydrochloric acid (1M) was added to the reaction solution and its pH was adjusted to 5-6. The mixture was concentrated in vacuum and purified by semi-preparative reverse phase HPLC (30%-60% acetonitrile in water+0.225% formic acid, 10 min) to afford 2-((2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetic acid (0.042 g, 0.069 mmol, 59% yield) as a yellow liquid. MS (ESI) m/z 609.4 $[M+1]^+$.

2-((2R,4r,6S)-4-(2-((trans-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide hydrochloride. To a solution of 3-(5-aminopyridin-2-yl)piperidine-2,6-dione (0.040 g, 0.195 mmol, 1 equiv.) and 2-((2S,4s,6R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetic acid (0.119 g, 0.195 mmol, 1 equiv.) in pyridine (1 mL) was added 1-(3-dimethylaminopropyl)-3-ethylcarbodiimide hydrochloride (0.075 g, 0.390 mmol, 21 equiv.). The reaction solution was stirred at 50° C. After 12 h the reaction solution was diluted with water and extracted with ethyl acetate (3×10 mL). The combined organic layers were washed with brine (20 mL), dried over anhydrous sodium sulfate, filtered and concentrated. The crude material was purified by standard methods to give 2-((2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide hydrochloride (50.38 mg, 0.063 mmol, 32% yield) as a white solid. MS(ESI) m z796.3 $[M+1]^+$; $^1$H NMR (400 MHz, DMSO-$d_6$) δ 12.11-11.51 (m, 1H), 10.91 (d, J=3.2 Hz, 1H), 10.36-9.09 (m, 1H), 8.85 (dd, J=8.0, 2.4 Hz, 1H), 8.33 (d, J=8.4 Hz, 1H), 8.20-8.12 (m, 2H), 7.98-7.95 (m, 1H), 7.51 (d, J=8.4 Hz, 1H), 4.33-4.26 (m, 2H), 4.15-4.08 (m, 1H), 3.82 (s, 2H), 3.60 (s, 1H), 3.48 (t, J=6.0 Hz, 2H), 3.28-3.17 (m, 1H), 2.82 (d, J=10.4 Hz, 2H), 2.70-2.60 (m, 1H), 2.58-2.52 (m, 1H), 2.34-2.26 (m, 1H), 2.17-1.92 (m, 6H), 1.73-1.61 (m, 6H), 1.54 (s, 6H), 1.35 (d, J=6.4 Hz, 4H), 1.33-1.25 (m, 2H), 1.21 (d, J=6.4 Hz, 2H).

Example 15: 2-((2R,6S)-4-(4-((trans)-4-(3-(4-Cyano-3-(trifluoromethyl)phenyl)-5,5-dimethyl-4-oxo-2-thioxoimidazolidin-1-yl)cyclohexyl)butyl)-2,6-dimethylpiperazin-1-yl)-N-(6-(2,4-dioxotetrahydropyrimidin-1(2H)-yl)pyridin-3-yl)acetamide

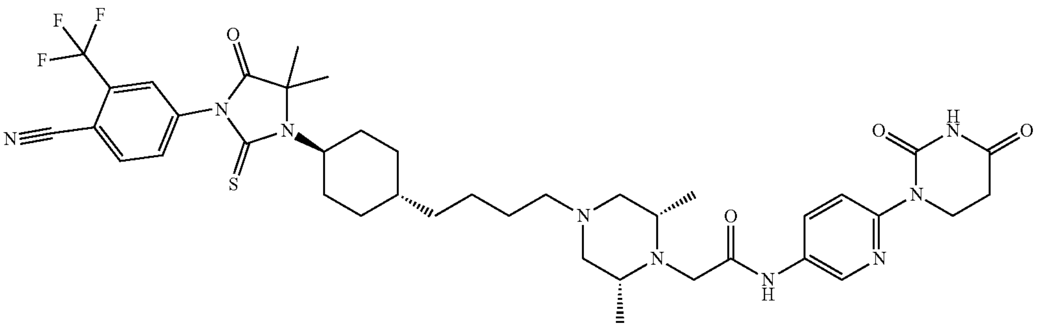 [SMILES: C[C@@H]1CN(CCCC[C@H]2CC[C@H](N3C(=S)N(c4ccc(C#N)c(C(F)(F)F)c4)C(=O)C3(C)C)CC2)C[C@H](C)N1CC(=O)Nc1ccc(N2CCC(=O)NC2=O)nc1]

tert-Butyl (trans-4-(2-(methoxy(methyl)amino)-2-oxoethyl)cyclohexyl)carbamate. To a solution of 2-(trans-4-((tert-butoxycarbonyl)amino)cyclohexyl)acetic acid (2.000 g, 7.770 mmol, 1 equiv.) and N, O-dimethyihydroxylamine hydrochloride (0.830 g, 8.550 mmol, 1.1 equiv.) in N,N-dimethylformamide (20 mL, 0.38 M) was added N,N-diisopropylethylamine (6.94 mL, 38.86 mmol) and HATU (4.430 g, 11.66 mmol, 5 equiv.) and the reaction solution was stirred at room temperature. After 12 h the reaction solution was diluted with water (100 mL) and extracted with ethyl acetate (2×60 mL). The combined organic layers were washed with brine (50 mL), dried over anhydrous sodium sulfate and concentrated. The resulting crude material was purified by silica gel column chromatography (0-30% ethyl acetate in petroleum ether) to give tert-butyl (trans-4-(2-(methoxy(methyl)amino)-2-oxoethyl)cyclohexyl)carbamate (2.200 g, 7.323 mmol, 94% yield) as a white solid. $^1$H NMR (400 MHz, $CDCl_3$) δ 4.41 (s, 1H), 3.66 (s, 3H), 3.37 (s, 1H), 3.17 (s, 3H), 2.31-2.29 (d, J=6.4 Hz, 2H), 2.04-1.97 (m, 2H), 1.85-1.79 (m, 3H), 1.43 (s, 9H), 1.18-1.02 (m, 4H).

tert-Butyl (trans-4-(2-oxoethyl)cyclohexyl)carbamate. To a solution of tert-butyl (trans-4-(2-(methoxy(methyl)amino)-2-oxoethyl)cyclohexyl)carbamate (2.2 g, 7.320 mmol, 1 equiv.) in dichloromethane (10 mL) was added sodium a solution of 70% bis(2-methoxyethoxy)aluminum hydride in toluene (4.08 mL, 14.65 mmol, 2 equiv.) at 0° C. After stirring for 2 h the reaction solution was diluted with water (20 mL) and saturated aqueous ammonium chloride (10 mL). The solution was extracted with dichloromethane (3×30 mL), the combined organic layers were dried over anhydrous sodium sulfate and concentrated. The resulting crude oil was purified by silica gel column chromatography (0-25% ethyl acetate in petroleum ether) to afford tert-butyl (trans-4-(2-oxoethyl)cyclohexyl)carbamate (1.450 g, 6.008 mmol, 82% yield) as a white solid. $^1$H NMR (400 MHz, $CDCl_3$) δ 9.65-9.64 (t, J=2.0 Hz, 1H), 6.69-6.64 (m, 1H), 3.19-3.13 (m, 1H), 2.55-2.52 (m, 1H), 2.29-2.27 (m, 2H), 1.75-1.64 (m, 5H), 1.36 (s, 9H), 1.17-1.08 (m, 2H), 1.06-0.83 (m, 2H).

Ethyl (E)-4-(trans-4-((tert-butoxycarbonyl)amino)cyclohexyl)but-2-enoate. To a solution of tert-butyl (trans-4-(2-oxoethyl)cyclohexyl)carbamate (1.450 g, 6.010 mmol, 1 equiv.) in toluene (10 mL, 0.6 M) was added ethyl 2-(triphenylphosphoranylidene)acetate (2.300 g, 6.610 mmol, 1.1 equiv.) and the reaction mixture was stirred at 80° C. After 12 h the reaction solution was concentrated and the resulting crude material was purified by silica gel column chromatography (0-20% ethyl acetate in hexanes) to give ethyl (E)-4-(trans-4-((tert-butoxycarbonyl)amino)cyclohexyl)but-2-enoate (0.890 g, 2.858 mmol, 48% yield) as a white solid. $^1$H NMR (400 MHz, $CDCl_3$) δ 6.95-6.88 (m, 1H), 5.82-5.78 (m, 1H), 4.36 (s, 1H), 4.24-4.14 (m, 2H), 3.37 (s, 1H), 2.12-2.08 (m, 2H), 2.05-1.99 (m, 2H), 1.79-1.76 (m, 2H), 1.46-1.36 (m, 10H), 1.31-1.27 (t, J=7.2 Hz, 3H), 1.13-0.99 (m, 4H).

tert-Butyl (trans-4-(4-hydroxybutyl)cyclohexyl)carbamate. To a solution of sodium borohydride (0.811 g, 21.43 mmol, 7.5 equiv.) in ethanol (16 mL) and THE (16 mL) was added anhydrous lithium chloride (0.900 g, 21.43 mmol, 7.5 equiv.) at 0° C. and the solution was stirred for 10 min. To the reaction solution was added a solution of ethyl (E)-4-(trans-4-((tert-butoxycarbonyl)amino)cyclohexyl)but-2-enoate (0.890. g, 2.860 mmol, 1 equiv.) in THE (8 mL) and the reaction solution was stirred at 15° C. After 12 h the reaction solution was quenched by slow addition of 1 M aqueous hydrochloric acid (10 mL) and the solution was extracted with ethyl acetate (3×20 mL). The combined organic layers were dried over anhydrous sodium sulfate, concentrated, and purified by silica gel column chromatography (0-25% ethyl acetate in hexanes) to give tert-butyl (trans-4-(4-hydroxybutyl)cyclohexyl)carbamate (0.750 g, 2.763 mmol, 96% yield) as a white solid. $^1$H NMR (400 MHz, $CDCl_3$) δ 4.37 (s, 1H), 3.66-3.62 (t, J=6.8 Hz, 2H), 3.36 (s, 1H), 2.00-1.98 (m, 2H), 1.78-1.75 (m, 2H), 1.58-1.51 (m, 2H), 1.44 (s, 9H), 1.40-1.32 (m, 2H), 1.28-1.14 (m, 4H), 1.08-0.94 (m, 4H).

4-(trans-4-Aminocyclohexyl)butan-1-ol. To a solution of tert-butyl (trans-4-(4-hydroxybutyl)cyclohexyl)carbamate (0.750. g, 2.760 mmol, 1 equiv.) in dichloromethane (2 mL) was added 4 M hydrochloric acid in 1,4-dioxane (4 mL, 16 mmol, 5.8 equiv.) and the reaction solution was stirred at room temperature. After 12 h the reaction solution was concentrated to remove organic solvents and then diluted with saturated sodium bicarbonate (30 mL) and extracted with ethyl acetate (2×30 mL). The combined organic layers were washed with brine (30 mL), dried over anhydrous sodium sulfated and concentrated to give 4-(trans-4-aminocyclohexyl)butan-1-ol (0.410 g, 2.394 mmol, 87% yield) as a white solid which was carried forward without further purification. $^1$H NMR (400 MHz, $CDCl_3$) δ 3.62-3.59 (t, J=6.4 Hz, 2H), 2.61-2.54 (m, 1H), 1.85-1.81 (m, 2H), 1.75-1.72 (m, 2H), 1.56-1.49 (m, 4H), 1.39-1.31 (m, 2H), 1.25-1.12 (m, 3H), 1.10-1.00 (m, 2H), 0.97-0.87 (m, 2H).

Methyl 2-((trans-4-(4-hydroxybutyl)cyclohexyl)amino)-2-methylpropanoate. To a solution of methyl 2-bromo-2-methylpropanoate (1.733 g, 9.570 mmol, 4 equiv.) and 4-(trans-4-aminocyclohexyl)butan-1-ol (0.410. g, 2.390 mmol, 1 equiv.) in acetonitrile (3 mL) was added potassium carbonate (0.993 g, 7.180 mmol, 3 equiv.) and sodium iodide (0.072 g, 0.480 mmol, 0.2 equiv.) and the reaction solution was stirred at 80° C. After 12 h the reaction solution was diluted with ethyl acetate, filtered and concentrated to provide crude methyl 2-((trans-4-(4-hydroxybutyl)cyclohexyl)amino)-2-methylpropanoate (1.000 g, crude) as a brown oil. MS (ESI) m/z 272.3 $[M+1]^+$.

4-(3-(trans-4-(4-Hydroxybutyl)cyclohexyl)-4,4-dimethyl-5-oxo-2-thioxoimidazolidin-1-yl)-2-(trifluoromethyl)benzonitrile. To a solution of methyl 2-((trans-4-(4-hydroxybutyl)cyclohexyl)amino)-2-methylpropanoate (1.000. g, 2.320 mmol, 1 equiv.) and 4-isothiocyanato-2-(trifluoromethyl)benzonitrile (0.556 g, 2.440 mmol, 1.1 equiv.) in ethyl acetate (12 mL) was added N,N-diisopropylethylamine (1.15 mL, 6.960 mmol, 3 equiv.) and the reaction mixture was stirred for at 80° C. After 3 h the reaction solution was diluted with ethyl acetate (20 mL) and concentrated. The resulting crude oil was purified by silica gel column chromatography (0-35% ethyl acetate in petroleum ether) to give 4-(3-(trans-4-(4-hydroxybutyl)cyclohexyl)-4,4-dimethyl-5-oxo-2-thioxoimidazolidin-1-yl)-2-(trifluoromethyl)benzonitrile (0.360 g, 0.736 mmol, 32% yield) as a brown solid. MS (ESI) m/z 468.1 $[M+1]^+$.

4-(3-(trans-4-(4-Bromobutyl)cyclohexyl)-4,4-dimethyl-5-oxo-2-thioxoimidazolidin-1-yl)-2-(trifluoromethyl)benzonitrile. To a solution of 4-(3-(trans-4-(4-hydroxybutyl)cyclohexyl)-4,4-dimethyl-5-oxo-2-thioxoimidazolidin-1-yl)-2-(trifluoromethyl)benzonitrile (0.360. g, 0.770 mmol, 1 equiv.) in dichloromethane (3 mL) was added N,N-dimethylformamide (0.30 mL) and thionyl bromide (0.400 g, 1.920 mmol, 2.5 equiv.) and the reaction solution was stirred at 15° C. After 12 h the reaction solution was concentrated and purified by silica gel column chromatography (0-20% ethyl acetate in petroleum ether) to give 4-(3-(trans-4-(4-bromobutyl)cyclohexyl)-4,4-dimethyl-5-oxo-2-thioxoimidazolidin-1-yl)-2-(trifluoromethyl)benzonitrile (0.280 g, 0.517 mmol, 67% yield) as a brown solid. MS (ESI) m/z 530.0 $[M+1]^+$; $^1$H NMR (400 MHz, $CDCl_3$) δ 7.96-7.94 (d, J=8.4 Hz, 1H), 7.86-7.85 (d, J=1.6 Hz, 1H), 7.75-7.72 (d, J=8.4, 1.6 Hz, 1H), 3.85 (s, 1H), 3.45-3.41 (t, J=6.8 Hz, 2H), 2.69 (s, 2H), 1.95-1.92 (m, 2H), 1.88-1.83 (m, 4H), 1.61 (s, 6H), 1.50-1.44 (m, 2H), 1.36-1.34 (m, 1H), 1.27-1.25 (m, 2H), 1.11-1.01 (m, 2H).

(3S,5R)-tert-. Butyl 4-(2-((6-(2,4-dioxotetrahydropyrimidin-1(2H)-yl)pyridin-3-yl)amino)-2-oxoethyl)-3,5-dimethylpiperazine-1-carboxylate. To a solution of 1-(5-aminopyridin-2-yl)dihydropyrimidine-2,4(1H,3H)-dione (0.200 g, 0.970 mmol) and 2-((2S,6R)-4-(tert-butoxycarbonyl)-2,6-dimethylpiperazin-1-yl)acetic acid (0.264 g, 0.970 mmol) in DMF (5 mL) was added HATU (0.369 g, 0.970 mmol) and N,N-diisopropylethylamine (0.51 mL, 2.910 mmol) in one portion under nitrogen and the reaction solution was stirred at room temperature. After 12 h the reaction solution was diluted with water (80 mL) and extracted with ethyl acetate (4×30 mL). The combined organic layers were washed with brine (50 mL), dried over anhydrous sodium sulfate and concentrated. The resulting crude material was purified by standard methods to provide (3S,5R)-tert-. Butyl 4-(2-((6-(2,4-dioxotetrahydropyrimidin-1(2H)-yl)pyridin-3-yl)amino)-2-oxoethyl)-3,5-dimethylpiperazine-1-carboxylate (0.400 g, 0.859 mmol, 89% yield) as a light yellow soli. MS (ESI) m/z 461.3 $[M+1]^+$.

2-((2S,6R)-2,6-Dimethylpiperazin-1-yl)-N-(6-(2,4-dioxotetrahydropyrimidin-1(2H)-yl)pyridin-3-yl)acetamide hydrobromide. To a solution of (3S,5R)-tert-butyl 4-(2-((6-(2,4-dioxotetrahydropyrimidin-1(2H)-yl)pyridin-3-yl)amino)-2-oxoethyl)-3,5-dimethylpiperazine-1-carboxylate (0.300 g, 0.650 mmol) in dichloromethane (20 mL) was added 30% hydrogen bromide in acetic acid (1.5 mL, 0.650 mmol) in one portion and the reaction solution was stirred at 10° C. After 12 h the reaction solution was concentrated to provide crude 2-((2S,6R)-2,6-dimethylpiperazin-1-yl)-N-(6-(2,4-dioxotetrahydropyrimidin-1(2H)-yl)pyridin-3-yl)acetamide hydrobromide (0.300 g, 0.680 mmol) as a light pink solid, which was carried forward without further purification.

2-((2R,6S)-4-(4-((trans)-4-(3-(4-Cyano-3-(trifluoromethyl)phenyl)-5,5-dimethyl-4-oxo-2-thioxoimidazolidin-1-yl)cyclohexyl)butyl)-2,6-dimethylpiperazin-1-yl)-N-(6-(2,4-dioxotetrahydropyrimidin-1(2H)-yl)pyridin-3-yl)acetamide hydrochloride. To a solution of 4-(3-((trans)-4-(4-bromobutyl)cyclohexyl)-4,4-dimethyl-5-oxo-2-thioxoimidazolidin-1-yl)-2-(trifluoromethyl)benzonitrile (0.080 g, 0.150 mmol) and 2-((2S,6R)-2,6-dimethylpiperazin-1-yl)-N-(6-(2,4-dioxotetrahydropyrimidin-1(2H)-yl)pyridin-3-yl)acetamide (0.100 g, 0.230 mmol) in DMF (5 mL) was added N,N-diisopropylethylamine (0.13 mL, 0.750 mmol) in one portion under nitrogen and the reaction solution was stirred at 50° C. After 12 h the reaction solution was diluted with water (80 mL) and extracted with ethyl acetate (4×30 mL). The combined organic layers were washed with brine (50 mL), dried over anhydrous sodium sulfate and concentrated. The resulting crude material was purified by standard methods to provide 2-((2R,6S)-4-(4-((trans)-4-(3-(4-cyano-3-(trifluoromethyl)phenyl)-5,5-dimethyl-4-oxo-2-thioxoimidazolidin-1-yl)cyclohexyl)butyl)-2,6-dimethylpiperazin-1-yl)-N-(6-(2,4-dioxotetrahydropyrimidin-1(2H)-yl)pyridin-3-yl)acetamide hydrochloride (0.074 g, 0.091 mmol, 60% yield) as a yellow solid. MS (ESI) m/z 810.6 $[M+1]^+$; $^1$H NMR (400 MHz, DMSO-$d_6$) δ 11.79-10.85 (m, 1H), 10.52 (s, 1H), 8.68 (d, J=2.4 Hz, 1H), 8.34 (d, J=8.4 Hz, 1H), 8.19 (s, 1H), 8.04 (dd, J=2.8, 8.8 Hz, 1H), 7.97 (br d, J=8.4 Hz, 1H), 7.73 (d, J=8.8 Hz, 1H), 4.01 (br t, J=6.4 Hz, 3H), 3.83 (br s, 1H), 3.67 (br s, 2H), 3.35-2.94 (m, 4H), 2.81-2.64 (m, 4H), 1.82 (br d, J=11.2 Hz, 2H), 1.78-1.64 (m, 5H), 1.55 (s, 6H), 1.32 (br s, 9H), 1.23 (br s, 4H), 1.07 (br d, J=12.4 Hz, 2H).

Example 16: 2-((2R,6S)-4-(4-((trans)-4-(3-(4-Cyano-3-(trifluoromethyl)phenyl)-5,5-dimethyl-4-oxo-2-thioxoimidazolidin-1-yl)cyclohexyl)butyl)-2,6-dimethylpiperazin-1-yl)-N-(6-(2,6-dioxopiperidin-3-yl)pyridin-3-yl)acetamide

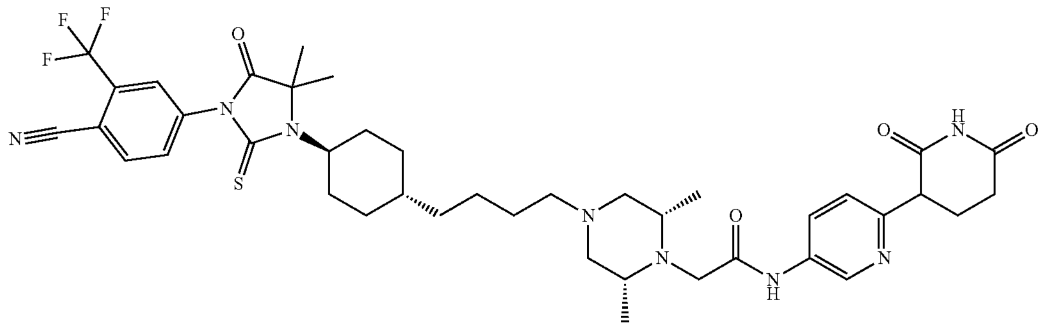

2-((2R,6S)-4-(4-((trans)-4-(3-(4-Cyano-3-(trifluoromethyl)phenyl)-5,5-dimethyl-4-oxo-2-thioxoimidazolidin-1-yl)cyclohexyl)butyl)-2,6-dimethylpiperazin-1-yl)-N-(6-(2,6-dioxopiperidin-3-yl)pyridin-3-yl)acetamide hydrochloride. To a solution of 4-(3-((trans)-4-(4-bromobutyl)cyclohexyl)-4,4-dimethyl-5-oxo-2-thioxoimidazolidin-1-yl)-2-(trifluoromethyl)benzonitrile (0.100 g, 0.190 mmol) and 2-((2S,6R)-2,6-dimethylpiperazin-1-yl)-N-(6-(2,6-dioxopiperidin-3-yl)pyridin-3-yl)acetamide (0.081 g, 0.230 mmol) in DMF (3 mL) was added N,N-diisopropylethylamine (0.16 mL, 0.940 mmol) and the reaction solution was stirred at 50° C. After 12 h the reaction solution was concentrated and purified by standard methods to provide 2-((2R,6S)-4-(4-((trans)-4-(3-(4-cyano-3-(trifluoromethyl)phenyl)-5,5-dimethyl-4-oxo-2-thioxoimidazolidin-1-yl)cyclohexyl)butyl)-2,6-dimethylpiperazin-1-yl)-N-(6-(2,6-dioxopiperidin-3-yl)pyridin-3-yl)acetamide hydrochloride (69.03 mg, 0.084 mmol, 45% yield) as a yellow solid. MS (ESI) m/z 809.3 $[M+1]^+$; $^1H$ NMR (400 MHz, DMSO-$d_6$) δ 12.16-11.31 (m, 2H), 10.97 (s, 1H), 8.94 (s, 1H), 8.32 (m, 2H), 8.19 (d, J=1.2 Hz, 1H), 8.00-7.94 (m, 1H), 7.61 (d, J=8.8 Hz, 1H), 4.20 (dd, J=10.8, 4.8 Hz, 2H), 4.06 (s, 2H), 3.88-3.63 (m, 3H), 3.22 (s, 2H), 3.05 (s, 2H), 2.82-2.51 (m, 4H), 2.41-2.29 (m, 1H), 2.18-2.10 (m, 1H), 1.81 (d, J=12.0 Hz, 2H), 1.72 (d, J=9.2 Hz, 4H), 1.54 (s, 6H), 1.34 (d, J=5.6 Hz, 8H), 1.22 (s, 4H), 1.14-1.00 (m, 2H).

Example 17: 2-((2R,4r,6S)-4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide

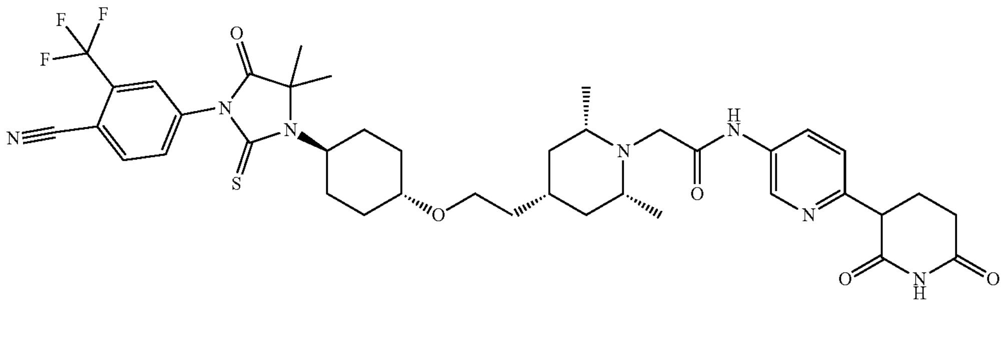 [SMILES: C[C@@H]1C[C@H](CCO[C@H]2CC[C@H](N3C(=S)N(c4ccc(C#N)c(C(F)(F)F)c4)C(=O)C3(C)C)CC2)C[C@H](C)N1CC(=O)Nc1ccc(C2CCC(=O)NC2=O)nc1]

(2S,6R)-1-Benzyl-2,6-dimethylpiperidin-4-one. To a solution of 3-oxopentanedioic acid (100.0 g, 684.5 mmol, 1 equiv.) in water (200 mL) was added acetaldehyde (150.8 g, 1368.9 mmol, 2 equiv.) at 20° C. The reaction was stirred at 20° C. for 20 min and then cooled to 0° C. and phenylmethanamine (74.61 mL, 684.5 mmol, 1 equiv.) was added dropwise. The reaction solution was allowed to warm to room temperature and stirred for 48 h. The reaction solution was extracted with ethyl acetate 3000 mL (1000 mL×3) and the combined organic layers were washed with brine 500 mL. The organic layers were dried with anhydrous sodium sulfate, filtrated and concentrated. The crude material was purified by silica gel column chromatography to give (2S,6R)-1-benzyl-2,6-dimethylpiperidin-4-one(27.70 g, 127.5 mmol, 19% yield) as a yellow oil. $^1$H NMR (400 MHz, $CDCl_3$-d) δ7.42 (d, J=7.2 Hz, 2H), 7.37-7.29 (m, 2H), 7.27-7.20 (m, 1H), 3.86 (s, 2H), 3.17-3.09 (qd, J=6.4, 13.2 Hz, 2H), 2.42-2.28 (m, 4H), 1.16 (d, J=6.4 Hz, 6H).

Ethyl 2-((2R,6S)-1-benzyl-2,6-dimethylpiperidin-4-ylidene)acetate. To a solution of sodium hydride (8.283 g, 207.1 mmol, 1.5 equiv.) in THE (50 mL) was added ethyl 2-(diethoxyphosphoryl)acetate (40.23 g, 179.5 mmol, 1.3 equiv.) in THE (100 mL) dropwise at 0° C. The mixture was stirred at 0° C. for 30 min. (2S,6R)-1-benzyl-2,6-dimethylpiperidin-4-one (30.00 g, 138.1 mmol, 1 equiv.) in THF (200 mL) was added to above solution dropwise and the reaction solution was warmed to room temperature. After 12 h the reaction solution was neutralized by addition of ammonium chloride saturated solution and poured into ice-water (200 mL). The aqueous phase was extracted with ethyl acetate (500 mL×3). The combined organic layers were washed with brine (300 mL), dried with anhydrous sodium sulfate, filtered and concentrated. The crude material was purified by flash silica gel chromatography (2.0% ethyl acetate in petroleum ether) (petroleum ether: ethyl acetate=3:1, Rf: 0.65) and then re-purified by semi-preparative reverse phase HPLC (55-85% acetonitrile+0.05% ammonium hydroxide in water, over 20 min). The collected fraction was concentrated and the aqueous phase was extracted with ethyl acetate (500 mL×3). The combined organic phase was washed with brine (300 mL), dried with anhydrous sodium sulfate, filtered and concentrated to give ethyl 2-((2R,6S)-1-benzyl-2,6-dimethylpiperidin-4-ylidene)acetate (11.7 g, 40.7 mmol, 30% yield) as a yellow oil. MS (ESI) m/z 288.2 $[M+1]^+$; $^1$H NMR (400 MHz, $CDCl_3$-d) δ 7.45-7.35 (m, 2H), 7.30 (t, J=7.6 Hz, 2H), 7.26-7.16 (m, 1H), 5.63 (s, 1H), 4.15 (q, J=7.2 Hz, 2H), 3.82 (s, 2H), 3.57 (dd, J=2.8, 14.0 Hz, 1H), 2.84-2.62 (m, 2H), 2.29-2.08 (m, 3H), 1.33-1.23 (m, 3H), 1.14 (dd, J=6.4, 16.4 Hz, 6H).

tert-Butyl (2S,6R)-4-(2-ethoxy-2-oxoethyl)-2,6-dimethylpiperidine-1-carboxylate. To a solution of ethyl 2-((2R,6S)-1-benzyl-2,6-dimethylpiperidin-4-ylidene)acetate (5.300 g, 18.44 mmol, 1 equiv.) and di-tert-butyl dicarbonate (6.037 g, 27.66 mmol, 1.5 equiv.) in THE (80 mL, 0.23 M) was added 10% Pd/C (1.500 g, 1.84 mmol, 10 mol %) under nitrogen. The reaction mixture was stirred at room temperature for 12 hours under hydrogen (50 psi). The reaction mixture was filtered and concentrated to give a residue which was purified by flash silica gel chromatography (1% ethyl acetate in petroleum ether, petroleum ether: ethyl acetate=5:1) to give tert-butyl (2S,6R)-4-(2-ethoxy-2-oxoethyl)-2,6-dimethylpiperidine-1-carboxylate(2.630 g, 8.784 mmol, 48% yield) as a yellow oil. $^1$H NMR (400 MHz, $CDCl_3$-d) δ 4.26 (s, 1H), 4.21 (m, 1H), 4.17-4.10 (m, 2H), 2.26-2.18 (m, 2H), 2.13-2.05 (m, 1H), 1.99-1.84 (m, 1H), 1.66-1.55 (m, 1H), 1.47 (s, 9H), 1.36-1.29 (m, 1H), 1.29-1.25 (m, 3H), 1.24-1.19 (m, 6H), 1.15-1.02 (m, 2H).

tert-Butyl (2S,6R)-4-(2-hydroxyethyl)-2,6-dimethylpiperidine-1-carboxylate. To a solution of lithium aluminumhydride (0.500 g, 13.18 mmol, 1.5 equiv.) in THE (10 mL) was added a solution of tert-butyl (2S,6R)-4-(2-ethoxy-2-oxoethyl)-2,6-dimethylpiperidine-1-carboxylate(2.630 g, 8.780 mmol, 1 equiv.) in THE (40 mL) at 0° C. The reaction solution was slowly warmed to room temperature over 1 h. The reaction solution was quenched by addition water 0.5 mL, 15% sodium hydroxide solution (1 mL) and water 1.5 mL. The slurry was stirred for 0.5 h, filtered and concentrated in vacuo. The crude material was diluted with water 100 mL and extracted with ethyl acetate 100 mL×3. The combined organic layers were washed with brine 100 mL, dried over anhydrous sodium sulfate, filtered and concentrated. The residue was purified by silica gel chromatography (20% ethyl acetate in petroleum ether) to provide tert-butyl (2S,6R)-4-(2-hydroxyethyl)-2,6-dimethylpiperidine-1-carboxylate (2.180 g, 8.470 mmol, 96% yield) as a yellow solid. $^1$H NMR (400 MHz, $CDCl_3$-d) δ 4.40-4.25 (m, 1H), 4.24-4.07 (m, 1H), 3.77-3.65 (m, 2H), 2.12-2.03 (m, 1H), 1.68-1.56 (m, 2H), 1.55-1.49 (m, 2H), 1.49-1.42 (m, 9H), 1.33-1.26 (m, 1H), 1.25-1.17 (m, 6H), 1.05 (m, 1H).

tert-Butyl (2S,6R)-4-(2-bromoethyl)-2,6-dimethylpiperidine-1-carboxylate. To a solution of tert-butyl (2S,6R)-4-(2-hydroxyethyl)-2,6-dimethylpiperidine-1-carboxylate (2.180 g, 8.470 mmol, 1 equiv.) and triphenylphosphine (3.332 g, 12.71 mmol, 1.5 equiv.) in dichloromethane (40 mL, 0.21 M). To the reaction solution was added carbon tetrabromide (4.214 g, 12.71 mmol, 1.5 equiv.) at 0° C. The reaction mixture was allowed to slowly warm to room temperature. After 2 h the reaction solution was poured into saturated sodium bicarbonate solution (100 mL) and the aqueous phase was extracted with dichloromethane (100 mL×3). The combined organic layers were washed with brine (100 mL), dried over anhydrous sodium sulfate, filtered and concentrated. The crude material was purified by silica gel chromatography (1% ethyl acetate in petroleum ether) to provide tert-Butyl (2S,6R)-4-(2-bromoethyl)-2,6-dimethylpiperidine-1-carboxylate (2.160 g, 6.744 mmol, 80% yield) as a clear, colorless oil. $^1$H NMR (400 MHz, $CDCl_3$-d) δ 4.45-4.27 (m, 1H), 4.26-4.06 (m, 1H), 3.51-3.29 (m, 2H), 2.18-1.96 (m, 2H), 1.89-1.75 (m, 2H), 1.73-1.53 (m, 2H), 1.48-1.39 (m, 9H), 1.33-1.25 (m, 1H), 1.24-1.19 (m, 6H), 1.13-0.97 (m, 1H).

tert-Butyl (2R,6S)-4-(2-((trans-4-(dibenzylamino)cyclohexyl)oxy)ethyl)-2,6-dimethylpiperidine-1-carboxylate. To a solution of trans-4-(dibenzylamino)cyclohexanol (12.18 g, 41.22 mmol, 2 equiv.) and tert-Butyl (2S,6R)-4-(2-bromoethyl)-2,6-dimethylpiperidine-1-carboxylate (6.600 g, 20.61 mmol, 1 equiv.) in xylene (120 mL, 0.17 M) was added potassium hydroxide (5.318 g, 94.80 mmol, 4.6 equiv.) and tetrabutylammonium bromide (1.328 g, 4.120 mmol, 0.2 equiv.). The reaction was stirred at 30° C. After 24 h the reaction solution was diluted with water (200 mL) and extracted with ethyl acetate (250 mL×3). The combined organic layers were washed with brine (150 mL), dried with anhydrous sodium sulfate, filtered and concentrated. The crude material was purified by flash silica gel chromatography (2.5-3% ethyl acetate in petroleum ether) to provide tert-butyl (2R,6S)-4-(2-((trans-4-(dibenzylamino)cyclohexyl)oxy)ethyl)-2,6-dimethylpiperidine-1-carboxylate (2.800 g, 5.236 mmol, 25% yield) as a yellow oil. $^1$H NMR (400 MHz, $CDCl_3$-d) δ 7.42-7.33 (m, 4H), 7.33-7.27 (m, 4H), 7.24-7.17 (m, 2H), 4.36-4.23 (m, 2H), 4.22-4.15 (m, 1H), 3.62 (s, 4H), 3.48 (t, J=6.4 Hz, 1H), 3.45-3.37 (m, 1H), 3.19-3.06 (m, 1H), 2.53 (m, 1H), 2.09-2.04 (m, 3H), 2.01-1.86 (m, 3H), 1.63-1.59 (m, 1H), 1.57-1.51 (m, 2H), 1.47-

1.46 (m, 9H), 1.43-1.33 (m, 2H), 1.28-1.24 (m, 2H), 1.21 (s, 2H), 1.17 (d, J=7.0 Hz, 6H), 1.14-1.08 (m, 1H), 1.07-0.92 (m, 1H).

tert-Butyl (2R,6S)-4-(2-((trans-4-aminocyclohexyl)oxy)ethyl)-2,6-dimethylpiperidine-1-carboxylate. To a solution of tert-butyl (2R,6S)-4-(2-((trans-4-(dibenzylamino)cyclohexyl)oxy)ethyl)-2,6-dimethylpiperidine-1-carboxylate (2.800 g, 5.240 mmol, 1 equiv.) in Methanol (60 mL) was added Pd/C (2.000 g) under nitrogen. The reaction was stirred at room temperature for 12 hours under hydrogen (15 psi). The reaction mixture was filtered and concentrated to give tert-Butyl (2R,6S)-4-(2-((trans-4-aminocyclohexyl)oxy)ethyl)-2,6-dimethylpiperidine-1-carboxylate (1.837 g, 5.180 mmol, 98% yield) yellow oil which was carried forward without further purification. $^1$H NMR (400 MHz, DMSO-$d_6$) δ 4.23-4.08 (m, 2H), 4.08-3.93 (m, 1H), 3.50-3.40 (m, 2H), 3.40-3.33 (m, 1H), 3.18-3.04 (m, 1H), 2.55-2.51 (m, 2H), 2.49 (br s, 1H), 2.05-1.83 (m, 4H), 1.82-1.68 (m, 2H), 1.67-1.47 (m, 2H), 1.46-1.32 (m, 16H), 1.29-1.15 (m, 2H), 1.15-1.07 (m, 9H), 1.07-0.87 (m, 3H).

tert-Butyl (2S,6R)-4-(2-((trans-4-((1-methoxy-2-methyl-1-oxopropan-2-yl)amino)cyclohexyl)oxy)ethyl)-2,6-dimethylpiperidine-1-carboxylate. To a solution of tert-Butyl (2R,6S)-4-(2-((trans-4-aminocyclohexyl)oxy)ethyl)-2,6-dimethylpiperidine-1-carboxylate (1.837 g, 5.180 mmol, 1 equiv.) in acetonitrile (10 mL, 0.5 M) was added potassium iodide (0.086 g, 0.520 mmol, 10 mol %), potassium carbonate (2.148 g, 15.54 mmol, 3 equiv.) and methyl 2-bromo-2-methylpropanoate (3.75 mL, 25.91 mmol, 5 equiv.). The reaction was stirred at 110° C. After 48 h the reaction solution was filtered and concentrated to give tert-butyl (2S,6R)-4-(2-((trans-4-((1-methoxy-2-methyl-1-oxopropan-2-yl)amino)cyclohexyl)oxy)ethyl)-2,6-dimethylpiperidine-1-carboxylate (2.400 g, 5.279 mmol, crude) as a yellow oil which was carried forward without further purification. MS (ESI) m/z 455.5 $[M+1]^+$.

tert-Butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate and tert-butyl (2R,4r,6S)-4-(2-(((1r,4R)-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate. To a solution of tert-butyl (2S,6R)-4-(2-((trans-4-((1-methoxy-2-methyl-1-oxopropan-2-yl)amino)cyclohexyl)oxy)ethyl)-2,6-dimethylpiperidine-1-carboxylate (2.160 g, 4.750 mmol, 1 equiv.) and 4-isothiocyanato-2-(trifluoromethyl)benzonitrile (1.084 g, 4.750 mmol, 1 equiv.) in ethyl acetate (10 mL, 0.47 M) was added N,N-diisoproplyethylamine (1.660 mL, 9.500 mmol, 2 equiv.). The reaction was stirred at 90° C. After 12 h the reaction solution was diluted with water (50 mL) and extracted with ethyl acetate (50 mL×3). The combined organic layers were washed with brine (50 mL), dried with anhydrous sodium sulfate, filtered and concentrated. The crude material was purified by flash silica gel chromatography to afford the mixture of diastereomers, which were separated by SFC (DAICEL CHIRAL PAK IG: 250 mm*30 mm. 10 um, 20% methanol+0.1% $NH_3$·H2O) to give tert-butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate (1.060 g, 1.629 mmol, 34% yield) and tert-butyl (2R,4r,6S)-4-(2-(((1r,4R)-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate (0.360 g, 0.553 mmol, 12% yield). tert-Butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate: $^1$H NMR (400 MHz, $CDCl_3$-d) δ 7.95 (d, J=8.0 Hz, 1H), 7.85 (d, J=2.0 Hz, 1H), 7.72 (dd, J=2.0, 8.0 Hz, 1H), 4.38-4.22 (m, 2H), 3.72-3.59 (m, 1H), 3.54 (t, J=6.4 Hz, 2H), 3.37-3.24 (m, 1H), 3.03-2.75 (m, 2H), 2.21 (br d, J=12.4 Hz, 2H), 2.03-1.90 (m, 1H), 1.89-1.77 (m, 2H), 1.61 (s, 6H), 1.58 (m, 2H), 1.54-1.48 (m, 2H), 1.47 (s, 9H), 1.40-1.26 (m, 4H), 1.19 (d, J=7.2 Hz, 6H). tert-Butyl (2R,4r,6S)-4-(2-(((1r,4R)-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate: $^1$H NMR (400 MHz, $CDCl_3$-d) δ 7.95 (d, J=8.4 Hz, 1H), 7.85 (d, J=2.0 Hz, 1H), 7.72 (dd, J=2.0, 8.4 Hz, 1H), 4.28-4.10 (m, 2H), 3.76-3.58 (m, 1H), 3.49 (t, J=6.0 Hz, 2H), 3.30 (m, 1H), 3.03-2.76 (m, 2H), 2.19 (br d, J=12.0 Hz, 2H), 2.12-1.98 (m, 2H), 1.89-1.76 (m, 2H), 1.61 (s, 6H), 1.52 (br t, J=6.4 Hz, 2H), 1.47 (s, 9H), 1.40-1.25 (m, 3H), 1.22 (d, J=6.8 Hz, 6H), 1.03 (m, 2H).

4-(3-(trans-4-(2-((2R,4s,6S)-2,6-Dimethylpiperidin-4-yl)ethoxy)cyclohexyl)-4,4-dimethyl-5-oxo-2-thioxoimidazolidin-1-yl)-2-(trifluoromethyl)benzonitrile. To a solution of tert-butyl (2R,4s,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidine-1-carboxylate (1.060 g, 1.630 mmol, 1 equiv.) in dichloromethane (5 mL) was added 4 M HCl in 1,4-dioxane (20 mL, 80.00 mmol). The reaction was stirred at room temperature. After 2 h the reaction solution was concentrated. The resulting yellow solid was taken up in saturated aqueous sodium bicarbonate (50 mL) and extracted with ethyl acetate (100 mL×3). The combined organic layers were washed with brine (50 mL), dried over anhydrous sodium sulfate and concentrated to provide 4-(3-(trans-4-(2-((2R,4s,6S)-2,6-dimethylpiperidin-4-yl)ethoxy)cyclohexyl)-4,4-dimethyl-5-oxo-2-thioxoimidazolidin-1-yl)-2-(trifluoromethyl)benzonitrile (0.920 g, 1.67 mmol, 99% yield) as a yellow solid which was carried forward without further purification. MS (ESI) m/z 551.4 $[M+1]^+$; $^1$H NMR (400 MHz, $CDCl_3$-d) δ 7.95 (d, J=8.0 Hz, 1H), 7.84 (d, J=2.0 Hz, 1H), 7.72 (dd, J=2.0, 8.0 Hz, 1H), 3.74-3.59 (m, 1H), 3.51 (t, J=6.8 Hz, 2H), 3.31 (m, 1H), 2.92 (m, 4H), 2.20 (br d, J=12.0 Hz, 2H), 2.02-1.92 (m, 1H), 1.82 (br d, J=12.0 Hz, 2H), 1.70 (q, J=6.8 Hz, 2H), 1.64-1.56 (s, 6H), 1.51 (br d, J=12.8 Hz, 2H), 1.40-1.27 (m, 4H), 1.09 (br d, J=6.0 Hz, 6H).

2-((2R,4r,6S)-4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide hydrochloride. To a solution of 3-(5-aminopyridin-2-yl)piperidine-2,6-dione (0.019 g, 0.093 mmol) and 2-((2S,4r,6R)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)acetic acid (0.056 g, 0.093 mmol) in pyridine (1 mL) was added 1-(3-dimethylaminopropyl)-3-ethylcarbodiimide hydrochloride (0.035 g, 0.185 mmol) and the reaction solution was stirred at 50° C. After 12 h the reaction solution was diluted with water (10 mL) and extracted with ethyl acetate (3×10 mL). The combined organic layers were washed with brine (20 mL), dried over anhydrous sodium sulfate and concentrated. The resulting crude material was purified by standard methods to provide 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide hydrochloride (6.340 mg, 0.008 mmol, 8.6% yield) as a white solid. MS(ESI) m/z 796.3 $[M+1]^+$; $^1H$ NMR (400 MHz, DMSO-$d_6$) δ 11.70-11.22 (m, 1H), 10.96-10.84 (m, 1H), 10.09-9.08 (m, 1H), 8.82-8.67 (m, 1H), 8.33 (d, J=8.4 Hz, 1H), 8.19 (s, 1H), 8.09-7.90 (m, 2H), 7.75-7.39 (m, 1H), 4.28 (s, 1H), 4.18 (s, 1H), 4.04 (dd, J=10.0, 5.2 Hz, 2H), 3.64 (s, 1H), 3.55-3.42 (m, 3H), 3.23 (d, J=4.4 Hz, 1H), 2.81 (d, J=10.0 Hz, 2H), 2.61 (dd, J=10.8, 5.6 Hz, 2H), 2.32-2.20 (m, 1H), 2.16-2.04 (m, 3H), 1.90-1.67 (m, 6H), 1.55 (d, J=1.2 Hz, 6H), 1.46-1.29 (m, 7H), 1.24-1.11 (m, 4H).

Example 18: 2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide

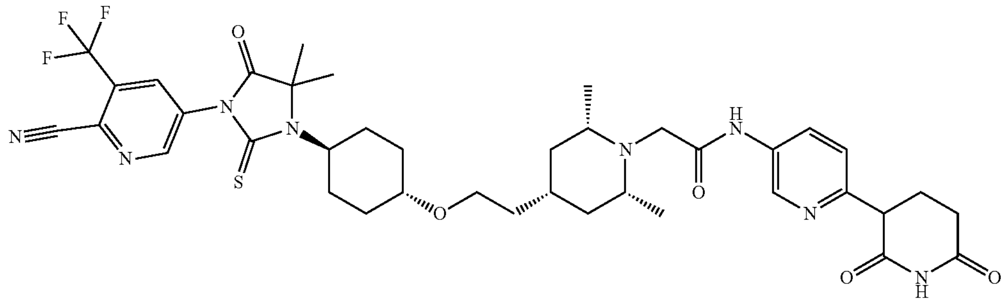 [SMILES: C[C@@H]1C[C@H](CCO[C@H]2CC[C@H](N3C(=S)N(c4cnc(C#N)c(C(F)(F)F)c4)C(=O)C3(C)C)CC2)C[C@H](C)N1CC(=O)Nc1ccc(C2CCC(=O)NC2=O)nc1]

2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide hydrochloride. To a solution of 2-((2S,4r,6R)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetic acid (0.100 g, 0.164 mmol) and 3-(5-aminopyridin-2-yl)piperidine-2,6-dione (0.050 g, 0.246 mmol) in pyridine (2 mL) was added 1-(3-dimethylaminopropyl)-3-ethylcarbodiimide hydrochloride (0.063 g, 0.328 mmol) and the reaction solution was stirred at 50° C. After 12 h the reaction solution was diluted with water (20 mL) and extracted with ethyl acetate (2×20 mL)>the combined organic layers were washed with brine (20 mL), dried over anhydrous sodium sulfate and concentrated. The resulting crude material was purified by standard methods to provide 2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide hydrochloride (59.62 mg, 0.074 mmol, 45.0% yield as an off-white solid. MS (ESI) m/z 797.3 $[M+1]^+$; $^1H$ NMR (400 MHz, DMSO-$d_6$) δ 11.96-11.34 (m, 1H), 10.89 (s, 1H), 10.22-9.04 (m, 2H), 8.81 (dd, J=8.0, 2.4 Hz, 1H), 8.74 (d, J=2.0 Hz, 1H), 8.09 (dd, J=8.8, 2.4 Hz, 1H), 7.46 (d, J=8.8 Hz, 1H), 4.33-4.18 (m, 2H), 4.10-4.04 (m, 1H), 3.86 (s, 1H), 3.46 (q, J=6.0 Hz, 4H), 3.29-3.17 (m, 1H), 2.92-2.74 (m, 2H), 2.70-2.54 (m, 2H), 2.31-2.22 (m, 1H), 2.16-2.01 (m, 3H), 1.87 (d, J=13.6 Hz, 1H), 1.81-1.67 (m, 4H), 1.56 (d, J=2.0 Hz, 6H), 1.52-1.26 (m, 8H), 1.24-1.12 (m, 4H).

Example 19: 2-((2R,4s,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide

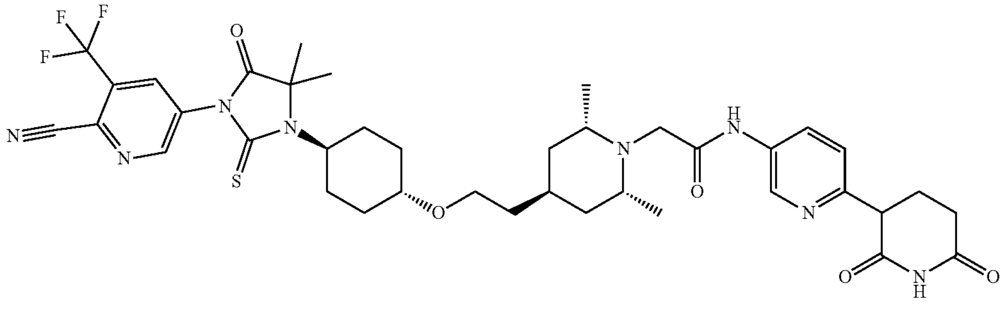 [SMILES: C[C@@H]1C[C@@H](CCO[C@H]2CC[C@H](N3C(=S)N(c4cnc(C#N)c(C(F)(F)F)c4)C(=O)C3(C)C)CC2)C[C@H](C)N1CC(=O)Nc1ccc(C2CCC(=O)NC2=O)nc1]

2-((2R,4s,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide hydrochloride. To a solution of 2-((2S,4s,6R)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)acetic acid (0.100 g, 0.164 mmol) and 3-(5-aminopyridin-2-yl)piperidine-2,6-dione (0.050 g, 0.246 mmol) in pyridine (2 mL) was added 1-(3-dimethylaminopropyl)-3-ethylcarbodiimide hydrochloride (0.063 g, 0.328 mmol) and the reaction solution was stirred at 50° C. After 12 h the reaction solution was diluted with water (20 mL) and extracted with ethyl acetate (2×20 mL). The combined organic layers were washed with brine (20 mL), dried over anhydrous sodium sulfate and concentrated. The resulting crude material was purified by standard methods to provide 2-((2R,4s,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide hydrochloride as a yellow solid. MS (ESI) m/z 797.3 $[M+1]^+$; $^1H$ NMR (400 MHz, DMSO-$d_6$) δ 12.24-11.67 (m, 1H), 10.94 (d, J=5.6 Hz, 1H), 10.45-9.05 (m, 2H), 8.89 (d, J=2.0 Hz, 1H), 8.74 (d, J=2.0 Hz, 1H), 8.26-8.15 (m, 1H), 7.57 (dd, J=8.4, 6.0 Hz, 1H), 4.36-4.25 (m, 2H), 4.20-4.13 (m, 1H), 3.84-3.82 (m, 1H), 3.60 (s, 1H), 3.48 (t, J=6.0 Hz, 2H), 3.22 (t, J=10.0 Hz, 1H), 2.82 (d, J=11.6 Hz, 2H), 2.71-2.61 (m, 1H), 2.60-2.51 (m, 2H), 2.40-2.26 (m, 1H), 2.18-2.10 (m, 1H), 2.09-1.92 (m, 4H), 1.78-1.59 (m, 7H), 1.56 (s, 6H), 1.40-1.15 (m, 8H).

Example 20: 2-((2R,4r,6S)-4-(3-((trans)-4-(3-(4-Cyano-3-(trifluoromethyl)phenyl)-5,5-dimethyl-4-oxo-2-thioxoimidazolidin-1-yl)cyclohexyl)propoxy)-2,6-dimethylpiperidin-1-yl)-N-(6-(2,6-dioxopiperidin-3-yl)pyridin-3-yl)acetamide

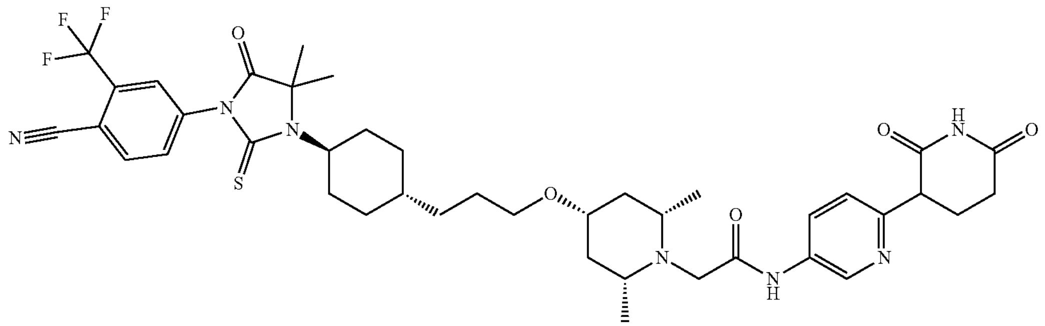 [SMILES: C[C@@H]1C[C@H](OCCC[C@H]2CC[C@H](N3C(=S)N(c4ccc(C#N)c(C(F)(F)F)c4)C(=O)C3(C)C)CC2)C[C@H](C)N1CC(=O)Nc1ccc(C2CCC(=O)NC2=O)nc1]

(2R,4r,6S)-tert-Butyl 4-(3-((trans)-4-(dibenzylamino)cyclohexyl)propoxy)-2,6-dimethylpiperidine-1-carboxylate. To a solution of (2S,4r,6R)-tert-butyl 4-hydroxy-2,6-dimethylpiperidine-1-carboxylate (3.000 g, 13.08 mmol) and (trans)-N,N-dibenzyl-4-(3-bromopropyl)cyclohexanamine (6.290 g, 15.70 mmol) in xylenes (45 mL) was added tetrabutylammonium bromide (0.840 g, 2.620 mmol) and potassium hydroxide (3.5 mL, 65.41 mmol), and the reaction solution was stirred at 30° C. After 12 h the reaction solution was diluted withy water (100 mL) and extracted with ethyl acetate (3×100 mL). The combined organic layers were washed with brine, dried over sodium sulfate and concentrated. The resulting crude material was purified by standard methods to provide (2R,4r,6S)-tert-butyl 4-(3-((trans)-4-(dibenzylamino)cyclohexyl)propoxy)-2,6-dimethylpiperidine-1-carboxylate (5.300 g, 9.657 mmol, 74% yield) as a white solid. $^1H$ NMR (400 MHz, DMSO-$d_6$) δ 7.34-7.26 (m, 8H), 7.21-7.16 (m, 2H), 4.15-4.02 (m, 2H), 3.57-3.52 (m, 5H), 2.39-2.31 (m, 1H), 1.81 (d, J=11.6 Hz, 2H), 1.76-1.68 (m, 6H), 1.53-1.26 (m, 15H), 1.23 (d, J=7.2 Hz, 6H), 1.16-1.11 (m, 3H), 0.77-0.66 (m, 2H).

(2R,4r,6S)-tert-Butyl 4-(3-((trans)-4-aminocyclohexyl)propoxy)-2,6-dimethylpiperidine-1-carboxylate. To a solution of (2R,4r,6S)-tert-butyl 4-(3-((trans)-4-(dibenzylamino)cyclohexyl)propoxy)-2,6-dimethylpiperidine-1-carboxylate (5.300 g, 9.657 mmol) in methanol (100 mL) and ammonium hydroxide (2 mL) was added 10% palladium on activated carbon (3.000 g, 28.19 mmol) under nitrogen atmosphere. The suspension was degassed under vacuum and purged with hydrogen for three times. The mixture was stirred at 25° C. for 12 h under hydrogen (15 Psi). The reaction mixture was filtered through a pad of celite and the filtrate was concentrated invacuo to give crude (2R,4r,6S)-tert-butyl 4-(3-((trans)-4-aminocyclohexyl)propoxy)-2,6-dimethylpiperidine-1-carboxylate (3.000 g, 8.140 mmol, 84% yield) which was carried forward without further purification. $^1H$ NMR (400 MHz, DMSO-$d_6$) δ 4.17-4.03 (m, 2H), 3.56 (q, J=4.0 Hz, 1H), 3.35 (s, 2H), 2.47-2.39 (m, 1H), 1.77-1.60 (m, 8H), 1.52-1.44 (m, 2H), 1.39 (s, 9H), 1.27-1.12 (m, 9H), 1.01-0.79 (m, 4H).

(2R,4r,6S)-tert-Butyl 4-(3-((trans)-4-((1-methoxy-2-methyl-1-oxopropan-2-yl)amino)cyclohexyl)propoxy)-2,6-dimethylpiperidine-1-carboxylate. To a solution of (2R,4r,6S)-tert-butyl 4-(3-((trans)-4-aminocyclohexyl)propoxy)-2,6-dimethylpiperidine-1-carboxylate (1.500 g, 4.070 mmol) and methyl 2-bromo-2-methylpropanoate (3.680 g, 20.35 mmol) in acetonitrile (5 mL) was added sodium iodide (0.060 g, 0.410 mmol) and potassium carbonate (1.690 g, 12.21 mmol). The mixture was stirred at 110° C. After 12 h the reaction solution was filtered and concentrated to provide crude 2R,4r,6S)-tert-butyl 4-(3-((1r,4R)-4-((1-methoxy-2-methyl-1-oxopropan-2-yl)amino)cyclohexyl)propoxy)-2,6-dimethylpiperidine-1-carboxylate (1.900 g, 4.054 mmol, 99.6% yield) which was carried forward without further purification. MS (ESI) m/z 469.4 $[M+1]^+$.

(2R,4r,6S)-tert-Butyl 4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidine-1-carboxylate. To a solution of (2R,4r,6S)-tert-butyl 4-(3-((trans)-4-((1-methoxy-2-methyl-1-oxopropan-2-yl)amino) cyclohexyl)propoxy)-2,6-dimethylpiperidine-1-carboxylate (1.900 g, 4.050 mmol) and 4-isothiocyanato-2-(trifluoromethyl)benzonitrile (0.930 g, 4.050 mmol) in ethyl acetate (10 mL) was added N,N-diisopropylethylamine (2.11 mL, 12.16 mmol) and the reaction solution was stirred at 90° C. after 12 h the reaction solution was filtered and concentrated and purified by standard methods to provide (2R,4r,6S)-tert-butyl 4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidine-1-carboxylate (2.400 g, 3.610 mmol, 89% yield) as a yellow oil. $^1$H NMR (400 MHz, DMSO-$d_6$) δ 8.33 (d, J=8.0 Hz, 1H), 8.19 (d, J=1.6 Hz, 1H), 7.97 (dd, J=1.6, 8.4 Hz, 1H), 4.14-4.06 (m, 2H), 3.90-3.74 (m, 1H), 3.59-3.54 (m, 1H), 3.40-3.37 (m, 2H), 2.80-2.63 (m, 2H), 1.80 (d, J=12.0 Hz, 2H), 1.75-1.70 (m, 6H), 1.56-1.47 (m, 8H), 1.39 (s, 9H), 1.27-1.23 (m, 9H), 1.18-1.16 (m, 2H).

4-(3-((trans)-4-(3-(((2R,4r,6S)-2,6-Dimethylpiperidin-4-yl)oxy)propyl)cyclohexyl)-4,4-dimethyl-5-oxo-2-thioxoimidazolidin-1-yl)-2-(trifluoromethyl)benzonitrile hydrobromide. To a solution of (2R,4r,6S)-tert-butyl 4-(3-((trasn)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidine-1-carboxylate (2.400 g, 3.610 mmol) in dichloromethane (20 mL) was added 33% hydrogen bromide in acetic acid (20 mL, 3.610 mmol), and the reaction solution was stirred at room temperature. After 12 h the reaction solution was concentrated to provide crude 4-(3-((trans)-4-(3-(((2R,4r,6S)-2,6-dimethylpiperidin-4-yl)oxy) propyl)cyclohexyl)-4,4-dimethyl-5-oxo-2-thioxoimidazolidin-1-yl)-2-(trifluoromethyl)benzonitrile hydrobromide (2.000 g, 3.542 mmol, 98% yield), which was carried forward without further purification. MS (ESI) m/z 565.3 $[M+1]^+$.

Benzyl 2-((2R,4r,6S)-4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl) acetate. To a solution of 4-(3-((trans)-4-(3-(((2R,4r,6S)-2,6-dimethylpiperidin-4-yl)oxy)propyl)cyclohexyl)-4,4-dimethyl-5-oxo-2-thioxoimidazolidin-1-yl)-2-(trifluoromethyl)benzonitrile and benzyl 2-bromoacetate (1.220 g, 5.310 mmol) in acetonitrile (20 mL) was added N,N-diisopropylethylamine (3.080 mL, 17.71 mmol) and the reaction solution was stirred at room temperature. After 12 h the reaction solution was concentrated and purified by standard methods to provide benzyl 2-((2R,4r,6S)-4-(3-((trans)-4-(3-(4-cyano-3-(trifluoromethyl)phenyl)-5,5-dimethyl-4-oxo-2-thioxoimidazolidin-1-yl)cyclohexyl) propoxy)-2,6-dimethylpiperidin-1-yl)acetate (0.800 g, 1.122 mmol, 32% yield) as a yellow oil. $^1$H NMR (400 MHz, DMSO-$d_6$) δ 8.33 (d, J=8.4 Hz, 1H), 8.20 (d, J=2.0 Hz, 1H), 7.97 (dd, J=1.6, 8.4 Hz, 1H), 7.38-7.32 (m, 5H), 5.09 (s, 2H), 3.83 (s, 1H), 3.53 (s, 2H), 3.23-3.15 (m, 1H), 2.79-2.66 (m, 4H), 1.88-1.77 (m, 4H), 1.71 (d, J=10.4 Hz, 2H), 1.54 (s, 6H), 1.50-1.42 (m, 3H), 1.23-1.15 (m, 4H), 1.06-0.95 (m, 10H).

2-((2R,4r,6S)-4-(3-((trans)-4-(3-(4-Cyano-3-(trifluoromethyl)phenyl)-5,5-dimethyl-4-oxo-2-thioxoimidazolidin-1-yl)cyclohexyl)propoxy)-2,6-dimethylpiperidin-1-yl)acetic acid. To a solution of benzyl 2-((2R,4r,6S)-4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)acetate (0.800 g, 1.120 mmol) in THE (3 mL), methanol (3 mL), water (3 mL) was added lithium hydroxide (0.135 g, 5.610 mmol) and the mixture was stirred at room temperature. After 12 h the reaction solution was adjusted to pH=7 by addition of aqueous HCl and concentrated to provide crude 2-((2R,4r,6S)-4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)acetic acid (1.000 g, 1.606 mmol) as a yellow oil, which was carried forward without further purification. $^1$H NMR (400 MHz, DMSO-$d_6$) δ 8.34 (d, J=8.4 Hz, 1H), 8.19 (d, J=1.6 Hz, 1H), 7.97 (dd, J=1.6, 8.4 Hz, 1H), 3.83 (s, 1H), 3.36 (s, 3H), 3.18 (s, 4H), 2.67 (d, J=2.0 Hz, 2H), 1.88 (d, J=12.4 Hz, 2H), 1.81-1.78 (m, 2H), 1.70 (d, J=11.6 Hz, 2H), 1.54 (s, 6H), 1.48 (d, J=7.2 Hz, 2H), 1.18 (s, 3H), 1.09 (d, J=6.4 Hz, 10H).

2-((2R,4r,6S)-4-(3-((trans)-4-(3-(4-Cyano-3-(trifluoromethyl)phenyl)-5,5-dimethyl-4-oxo-2-thioxoimidazolidin-1-yl)cyclohexyl)propoxy)-2,6-dimethylpiperidin-1-yl)-N-(6-(2,6-dioxopiperidin-3-yl)pyridin-3-yl)acetamide hydrochloride. To a solution of 2-((2R,4r,6S)-4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)acetic acid (0.100 g, 0.161 mmol) and 3-(5-aminopyridin-2-yl)piperidine-2,6-dione (0.049 g, 0.241 mmol) in pyridine (2 mL) was added 1-(3-dimethylaminopropyl)-3-ethylcarbodiimide hydrochloride (0.062 g, 0.321 mmol) and the reaction solution was stirred at 50° C. After 12 h the reaction solution was diluted with water (10 mL) and extracted with ethyl acetate (3×10 mL). The combined organic layers were washed with brine (10 mL), dried over anhydrous sodium sulfate and concentrated. The resulting crude material was purified by standard methods to provide 2-((2R,4r,6S)-4-(3-((trans)-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)-N-(6-(2,6-dioxopiperidin-3-yl)pyridin-3-yl)acetamide hydrochloride (47 mg, 0.055 mmol, 34% yield) as a yellow solid. MS (ESI) m/z 810.3 $[M+1]^+$; $^1$H NMR (400 MHz, DMSO-$d_6$) δ 11.81-11.33 (m, 1H), 10.89 (s, 1H), 10.34-9.14 (m, 1H), 8.80 (dd, J=2.4, 10.0 Hz, 1H), 8.33 (d, J=8.4 Hz, 1H), 8.19 (d, J=1.6 Hz, 1H), 8.1-8.05 (m, 1H), 7.97 (dd, J=1.6, 8.4 Hz, 1H), 7.46 (d, J=8.4 Hz, 1H), 4.30-4.22 (m, 2H), 4.07 (dd, J=5.2, 10.0 Hz, 1H), 3.83 (s, 2H), 3.41 (q, J=6.4 Hz, 2H), 2.75-2.59 (m, 3H), 2.55 (d, J=4.8 Hz, 1H), 2.30-2.22 (m, 1H), 2.18-2.05 (m, 3H), 1.81 (d, J=11.6 Hz, 2H), 1.74-1.63 (m, 3H), 1.54 (s, 9H), 1.40-1.30 (m, 4H), 1.23 (d, J=6.4 Hz, 7H), 1.07 (d, J=12.4 Hz, 2H).

Example 21: 2-((R)-4-(3-((trans)-4-(3-(6-Cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(6-(2,6-dioxopiperidin-3-yl)pyridin-3-yl)acetamide

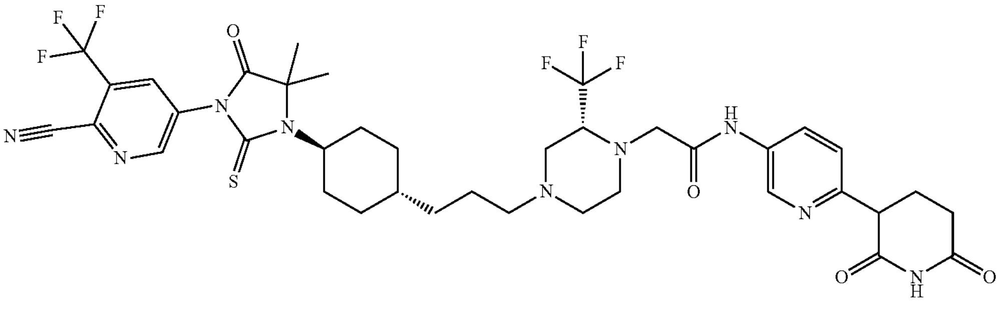 [SMILES: CC1(C)C(=O)N(c2cnc(C#N)c(C(F)(F)F)c2)C(=S)N1[C@H]1CC[C@H](CCCN2CCN(CC(=O)Nc3ccc(C4CCC(=O)NC4=O)nc3)[C@@H](C(F)(F)F)C2)CC1]

2-((R)-4-(3-((trans)-4-(3-(6-Cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(6-(2,6-dioxopiperidin-3-yl)pyridin-3-yl)acetamide hydrochloride. To a mixture of 5-(3-((trans)-4-(3-bromopropyl)cyclohexyl)-4,4-dimethyl-5-oxo-2-thioxoimidazolidin-1-yl)-3-(trifluoromethyl)picolinonitrile (0.075 g, 0.150 mmol) in DMF (1 mL) was added N-(6-(2,6-dioxopiperidin-3-yl)pyridin-3-yl)-2-((R)-2-(trifluoromethyl)piperazin-1-yl) acetamide (0.070 g, 0.150 mmol) and N,N-diisopropylethylamine (0.038 g, 0.290 mmol) and the reaction solution was stirred at 50° C. After 8 h the reaction solution was diluted with water (50 mL) and extracted with ethyl acetate (3×30 mL). The combined organic layers were washed with brine (50 mL), dried over anhydrous sodium sulfate and concentrated. The resulting crude material was purified by standard methods to provide 2-((R)-4-(3-((trans)-4-(3-(6-cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(6-(2,6-dioxopiperidin-3-yl)pyridin-3-yl)acetamide hydrochloride (0.057 g, 0.065 mmol, 45% yield) as a yellow solid. MS (ESI) m/z 836.4 $[M+H]^+$; $^1H$ NMR (400 MHz, DMSO-$d_6$) δ 10.90 (s, 1H), 10.82-10.64 (m, 1H), 10.45-10.30 (m, 1H), 9.15 (d, J=1.6 Hz, 1H), 8.83-8.74 (m, 2H), 8.09 (d, J=8.8 Hz, 1H), 7.44 (d, J=8.8 Hz, 1H), 4.42-4.32 (m, 1H), 4.09-4.04 (q, J=4.4 Hz, 1H), 3.92-3.78 (m, 2H), 3.74-3.63 (m, 4H), 3.20-3.05 (m, 5H), 2.83-2.72 (m, 2H), 2.65-2.60 (m, 1H), 2.31-2.22 (m, 1H), 2.16-2.09 (m, 1H), 1.85 (d, J=12.4 Hz, 2H), 1.78-1.69 (m, 4H), 1.57 (s, 6H), 1.33-1.16 (m, 4H), 1.14-1.04 (m, 2H).

Example 22: 2-((R)-4-(3-((trans)-4-(3-(4-Cyano-3-(trifluoromethyl)phenyl)-5,5-dimethyl-4-oxo-2-thioxoimidazolidin-1-yl)cyclohexyl)propyl)-2-(trifluoromethyl)piperazin-1-yl)-N-(6-(2,6-dioxopiperidin-3-yl)pyridin-3-yl)acetamide

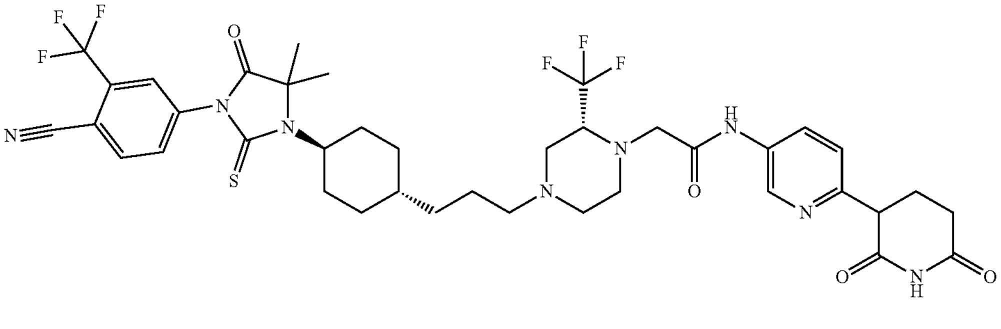 [SMILES: CC1(C)C(=O)N(c2ccc(C#N)c(C(F)(F)F)c2)C(=S)N1[C@H]1CC[C@H](CCCN2CCN(CC(=O)Nc3ccc(C4CCC(=O)NC4=O)nc3)[C@@H](C(F)(F)F)C2)CC1]

2-((R)-4-(3-((trans)-4-(3-(4-Cyano-3-(trifluoromethyl)phenyl)-5,5-dimethyl-4-oxo-2-thioxoimidazolidin-1-yl)cyclohexyl)propyl)-2-(trifluoromethyl)piperazin-1-yl)-N-(6-(2,6-dioxopiperidin-3-yl)pyridin-3-yl)acetamide hydrochloride. To a mixture of 4-(3-((trans)-4-(3-bromopropyl)cyclohexyl)-4,4-dimethyl-5-oxo-2-thioxoimidazolidin-1-yl)-2-(trifluoromethyl)benzonitrile (0.086 g, 0.170 mmol) in DMF (1 mL) was added N-(6-(2,6-dioxopiperidin-3-yl)pyridin-3-yl)-2-((S)-2-(trifluoromethyl)piperazin-1-yl)acetamide (0.080 g, 0.170 mmol) and N,N-diisopropylethylamine (0.043 g, 0.330 mmol) and the reaction solution was stirred at 50° C. After 8 h the reaction solution was diluted with water (50 mL) and extracted with ethyl acetate (3×30 mL). The combined organic layers were washed with brine (50 mL), dried over anhydrous sodium sulfate and concentrated. The resulting crude material was purified by standard methods to provide 2-((R)-4-(3-((trans)-4-(3-(4-Cyano-3-(trifluoromethyl)phenyl)-5,5-dimethyl-4-oxo-2-thioxoimidazolidin-1-yl)cyclohexyl)propyl)-2-(trifluoromethyl)piperazin-1-yl)-N-(6-(2,6-dioxopiperidin-3-yl)pyridin-3-yl) acetamide hydrochloride (0.069 g, 0.081 mmol, 49% yield) as a yellow solid. MS (ESI) m/z 835.2 $[M+1]^+$; $^1H$ NMR (400 MHz, DMSO-$d_6$) δ 11.22-11.07 (m, 1H), 10.97 (s, 1H), 10.67 (s, 1H), 9.00-8.84 (m, 1H), 8.35 (d, J=8.4 Hz, 1H), 8.29-8.16 (m, 2H), 7.98 (dd, J=1.6, 8.0 Hz, 1H), 7.56 (d, J=8.8 Hz, 1H), 4.43-4.35 (m, 1H), 4.17 (dd, J=4.8, 10.4 Hz, 1H), 3.89-3.81 (m, 1H), 3.75-3.62 (m, 3H), 3.56-3.51 (m, 1H), 3.21-3.04 (m, 5H), 2.88-2.70 (m, 2H), 2.70-2.62 (m, 1H), 2.61-2.53 (m, 1H), 2.36-2.28 (m, 1H), 2.17-2.10 (m, 1H), 1.87-1.72 (m, 6H), 1.56 (s, 6H), 1.34-1.15 (m, 4H), 1.13-1.04 (m, 2H).

Example 23: 2-((R)-4-(3-(((trans)-4-(3-(6-Cyano-5-(trifluoromethyl)pyridin-3-yl)-5,5-dimethyl-4-oxo-2-thioxoimidazolidin-1-yl)cyclohexyl)oxy)propyl)-2-(trifluoromethyl)piperazin-1-yl)-N-(6-(2,6-dioxopiperidin-3-yl)pyridin-3-yl)acetamide

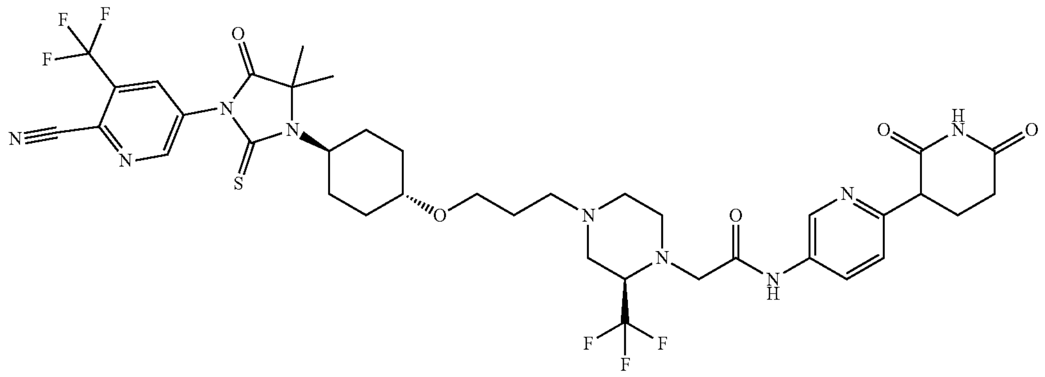 [SMILES: CC1(C)C(=O)N(c2cnc(C#N)c(C(F)(F)F)c2)C(=S)N1[C@H]1CC[C@H](OCCCN2CCN(CC(=O)Nc3ccc(C4CCC(=O)NC4=O)nc3)[C@@H](C(F)(F)F)C2)CC1]

2-((R)-4-(3-(((trans)-4-(3-(6-Cyano-5-(trifluoromethyl)pyridin-3-yl)-5,5-dimethyl-4-oxo-2-thioxoimidazolidin-1-yl)cyclohexyl)oxy)propyl)-2-(trifluoromethyl)piperazin-1-yl)-N-(6-(2,6-dioxopiperidin-3-yl)pyridin-3-yl)acetamide hydrochloride. To a solution of 4-(3-((trans)-4-(4-bromobutyl)cyclohexyl)-4,4-dimethyl-5-oxo-2-thioxoimidazolidin-1-yl)-2-(trifluoromethyl)benzonitrile (0.131 g, 0.250 mmol) in DMF (2 mL) was added 2-((2R,6S)-2,6-dimethylpiperazin-1-yl)-N-(5-(2,6-dioxopiperidin-3-yl)pyridin-2-yl)acetamide (0.090 g, 0.250 mmol) and N-ethyl-N-isopropylpropan-2-amine (0.040 mL, 0.250 mmol)) and the reaction solution was stirred at 50° C. After 8 h the reaction solution was diluted with water (50 mL) and extracted with ethyl acetate (3x30 mL). The combined organic layers were washed with brine (50 mL), dried over anhydrous sodium sulfate and concentrated. The resulting crude material was purified by standard methods to provide 2-((R)-4-(3-(((trans)-4-(3-(6-cyano-5-(trifluoromethyl)pyridin-3-yl)-5,5-dimethyl-4-oxo-2-thioxoimidazolidin-1-yl)cyclohexyl)oxy)propyl)-2-(trifluoromethyl)piperazin-1-yl)-N-(6-(2,6-dioxopiperidin-3-yl)pyridin-3-yl)acetamide hydrochloride as an off-white solid. MS (ESI) m/z 852.1 $[M+1]^+$; $^1$HNMR (400 MHz, DMSO-$d_6$) δ 10.89 (d, J=12 Hz, 1H), 10.53-10.18 (m, 1H), 9.15 (d, J=1.6 Hz, 1H), 8.91-8.49 (m, 2H), 8.37-7.89 (m, 1H), 7.56-7.19 (m, 1H), 4.54-4.29 (m, 1H), 4.17-3.95 (m, 2H), 3.84 (s, 2H), 3.51 (d, J=6.0 Hz, 4H), 3.34-3.06 (m, 7H), 2.92-2.772 (m, 2H), 2.64-2.53 (m, 2H), 2.30-2.9 (m, 1H), 2.19-2.02 (m, 4H), 2.02-1.90 (m, 2H), 1.75-1.67 (m, 2H), 1.57 (s, 6H), 1.45-1.21 (m, 2H).

Example 24: 2-((R)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2-(trifluoromethyl)piperazin-1-yl)-N-(6-(2,6-dioxopiperidin-3-yl)pyridin-3-yl)acetamide

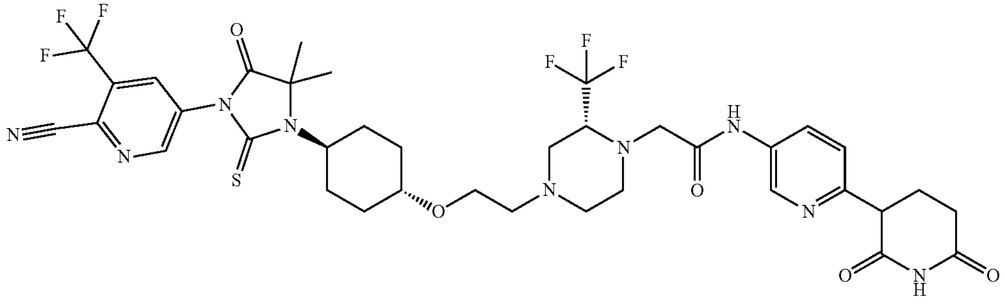 [SMILES: CC1(C)C(=O)N(c2cnc(C#N)c(C(F)(F)F)c2)C(=S)N1[C@H]1CC[C@H](OCCN2CCN(CC(=O)Nc3ccc(C4CCC(=O)NC4=O)nc3)[C@@H](C(F)(F)F)C2)CC1]

5-(4,4-Dimethyl-5-oxo-3-(trans-4-(2-((tetrahydro-2H-pyran-2-yl)oxy)ethoxy)cyclohexyl)-2-thioxoimidazolidin-1-yl)-3-(trifluoromethyl)picolinonitrile. Methyl 2-methyl-2-((trans-4-(2-((tetrahydro-2H-pyran-2-yl)oxy)ethoxy)

cyclohexyl)amino)propanoate (6.70 g, 19.51 mmol, 1 equiv.), 5-isothiocyanato-3-(trifluoromethyl)picolinonitrile (8.94 g, 39.0 mmol, 2 equiv.), and N,N-diisopropylethylamine (6.8 mL, 39.0 mmol, 2 equiv.) were combined in ethyl acetate (56 mL, 0.35 M) and heated to 90° C. in a sealed tube for 16 h. The reaction was diluted with ethyl acetate (100 mL) and washed with water (100 mL), and brine (100 mL), dried over anhydrous magnesium sulfate and concentrated. The crude material was purified by silica gel column chromatography (10%-100% ethyl acetate in hexanes) to afford 5-(4,4-dimethyl-5-oxo-3-(trans-4-(2-((tetrahydro-2H-pyran-2-yl)oxy)ethoxy)cyclohexyl)-2-thioxoimidazolidin-1-yl)-3-(trifluoromethyl)picolinonitrile (3.5 g, 6.4743 mmol, 33% yield) as a brown solid. MS (ESI) m/z 541.3 $[M+1]^+$.

5-(3-(trans-4-(2-Hydroxyethoxy)cyclohexyl)-4,4-dimethyl-5-oxo-2-thioxoimidazolidin-1-yl)-3-(trifluoromethyl)picolinonitrile. To a solution of 5-(4,4-dimethyl-5-oxo-3-(trans-4-(2-((tetrahydro-2H-pyran-2-yl)oxy)ethoxy)cyclohexyl)-2-thioxoimidazolidin-1-yl)-3-(trifluoromethyl)picolinonitrile (3.50 g, 6.47 mmol, 1 equiv.) in dichloromethane (30 mL) was added 4 M hydrochloric acid (16.2 mL, 64.7 mmol, 10 equiv.) and the reaction solution was stirred at room temperature. After 3 h the reaction solution was concentrated to provide 5-(3-(trans-4-(2-hydroxyethoxy)cyclohexyl)-4,4-dimethyl-5-oxo-2-thioxoimidazolidin-1-yl)-3-(trifluoromethyl)picolinonitrile (3.20 g, 6.4 mmol, 99% yield) as a reddish oil. The crude material was carried forward without further purification. MS (ESI) m/z 457.0 $[M+1]^+$.

5-(3-(trans-4-(2-Bromoethoxy)cyclohexyl)-4,4-dimethyl-5-oxo-2-thioxoimidazolidin-1-yl)-3-(trifluoromethyl)picolinonitrile. A solution of 5-(3-(trans-4-(2-hydroxyethoxy)cyclohexyl)-4,4-dimethyl-5-oxo-2-thioxoimidazolidin-1-yl)-3-(trifluoromethyl)picolinonitrile (3.20 g, 6.49 mmol) in dichloromethane (30 mL) and N,N-dimethylformamide (5 mL) was added thionyl bromide (1.26 mL, 16.2 mmol, 2.5 equiv.) and the reaction solution was stirred at room temperature. After 2 h the reaction solution was concentrated and the crude material was purified by silica gel column chromatography (5%-80% ethyl acetate in hexanes) to give 5-(3-(trans-4-(2-bromoethoxy)cyclohexyl)-4,4-dimethyl-5-oxo-2-thioxoimidazolidin-1-yl)-3-(trifluoromethyl)picolinonitrile (2.00 g, 3.85 mmol, 59% yield) as a reddish brown oil. MS (ESI) m/z 519.8 $[M+1]^+$.

2-((R)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-2-(trifluoromethyl)piperazin-1-yl)-N-(6-(2,6-dioxopiperidin-3-yl)pyridin-3-yl)acetamide hydrochloride. To a solution of 5-(3-((trans)-4-(2-bromoethoxy)cyclohexyl)-4,4-dimethyl-5-oxo-2-thioxoimidazolidin-1-yl)-3-(trifluoromethyl)picolinonitrile (0.130 g, 0.250 mmol) in DMF (2 mL) was added N-(6-(2,6-dioxopiperidin-3-yl)pyridin-3-yl)-2-((S)-2-(trifluoromethyl)piperazin-1-yl)acetamide (0.120 g, 0.250 mmol) and N-ethyl-N-isopropylpropan-2-amine (0.161 g, 1.250 mmol) and the reaction solution was stirred at 50° C. After 8 h the reaction solution was diluted with water (50 mL) and extracted with ethyl acetate (3×30 mL). The combined organic layers were washed with brine (50 mL), dried over anhydrous sodium sulfate and concentrated. The resulting crude material was purified by standard methods to provide 2-((R)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-2-(trifluoromethyl)piperazin-1-yl)-N-(6-(2,6-dioxopiperidin-3-yl)pyridin-3-yl)acetamide hydrochloride (51.4 mg, 0.058 mmol, 24% yield) as an off-white solid. MS (ESI) m/z 838.1 $[M+1]^+$; $^1$HNMR (400 MHz, DMSO-$d_6$) δ 11.18-10.72 (m, 2H), 10.62-10.17 (m, 1H), 9.15 (d, J=1.6 Hz, 1H), 8.96-8.48 (m, 2H), 8.34-7.90 (m, 1H), 7.64-7.28 (m, 1H), 4.46-4.32 (m, 1H), 4.16-4.02 (m, 2H), 3.90-3.85 (m, 5H), 3.57-3.47 (m, 2H), 3.44-3.28 (m, 4H), 3.26-3.07 (m, 3H), 2.95-2.75 (m, 2H), 2.62 (dd, J=5.6 Hz, 1H), 2.32-2.20 (m, 1H), 2.19-1.97 (m, 3H), 1.81-1.63 (m, 2H), 1.57 (s, 6H), 1.50-1.26 (m, 2H).

Example 25: 2-((R)-4-(3-(((trans)-4-(3-(4-Cyano-3-(trifluoromethyl)phenyl)-5,5-dimethyl-4-oxo-2-thioxoimidazolidin-1-yl)cyclohexyl)oxy)propyl)-2-(trifluoromethyl)piperazin-1-yl)-N-(6-(2,6-dioxopiperidin-3-yl)pyridin-3-yl)acetamide

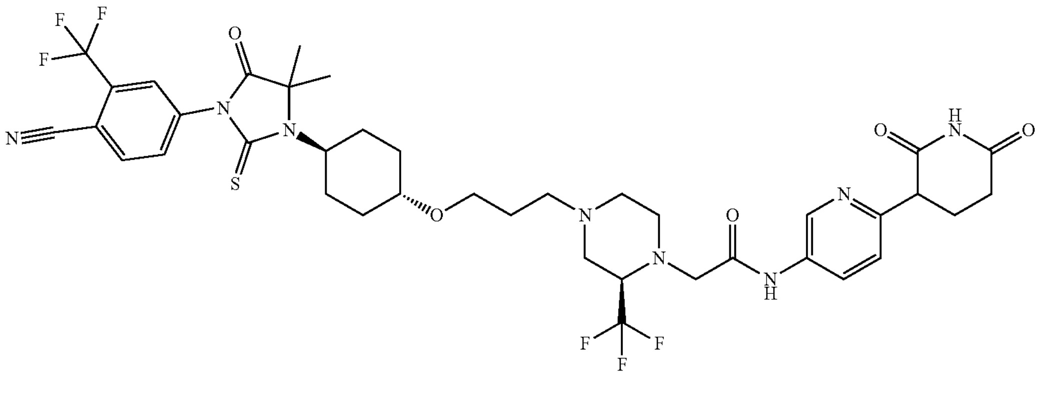 [SMILES: CC1(C)C(=O)N(c2ccc(C#N)c(C(F)(F)F)c2)C(=S)N1[C@H]1CC[C@H](OCCCN2CCN(CC(=O)Nc3ccc(C4CCC(=O)NC4=O)nc3)[C@@H](C(F)(F)F)C2)CC1]

(3R)-tert-Butyl 4-(2-((6-(2,6-dioxopiperidin-3-yl)pyridin-3-yl)amino)-2-oxoethyl)-3-(trifluoromethyl)piperazine-1-carboxylate. To a mixture of 3-(5-aminopyridin-2-yl)piperidine-2,6-dione (0.473 g, 2.310 mmol) in pyridine (5 mL) was added (R)-2-(4-(tert-butoxycarbonyl)-2-(trifluoromethyl)piperazin-1-yl)acetic acid (0.600 g, 1.920 mmol) and 1-(3-dimethylaminopropyl)-3-ethylcarbodiimide (0.749 g, 3.910 mmol) and the reaction solution was stirred at 50° C. After 8 h the reaction solution was diluted with water (50 mL) and extracted with ethyl acetate (3×30 mL). The combined organic layers were washed with brine (50 mL), dried over anhydrous sodium sulfate and concentrated. The resulting crude material was purified by standard methods to provide (3R)-tert-butyl 4-(2-((6-(2,6-dioxopiperidin-3-yl)pyridin-3-yl)amino)-2-oxoethyl)-3-(trifluoromethyl)piperazine-1-carboxylate (0.620 g, 1.241 mmol, 65% yield) as a white solid. MS (ESI) m/z 500.0 $[M+1]^+$; $^1$H NMR (400

MHz, DMSO-$d_6$) δ 10.83 (s, 1H), 9.96 (s, 1H), 8.66 (d, J=2.4 Hz, 1H), 8.02 (dd, J=2.4, 8.4 Hz, 1H), 7.32 (d, J=8.4 Hz, 1H), 4.08-4.00 (m, 2H), 3.73 (d, J=16.4 Hz, 2H), 3.54-3.41 (m, 2H), 2.84 (s, 2H), 2.67-2.57 (m, 1H), 2.55-2.52 (m, 1H), 2.22 (m, 1H), 2.14-2.07 (m, 1H), 1.39 (s, 9H), 1.24-1.14 (m, 2H).

N-(6-(2,6-Dioxopiperidin-3-yl)pyridin-3-yl)-2-((R)-2-(trifluoromethyl)piperazin-1-yl)acetamide hydrobromide. To a mixture of (3R)-tert-butyl 4-(2-((6-(2,6-dioxopiperidin-3-yl)pyridin-3-yl)amino)-2-oxoethyl)-3-(trifluoromethyl) piperazine-1-carboxylate (0.062 g, 1.240 mmol) in dichloromethane (10 mL) was added 30% hydrogen bromide in acetic acid (1.0 mL, 1.240 mmol) and the reaction solution was stirred at room temperature. After 8 h the reaction solution was concentrated to provide crude N-(6-(2,6-Dioxopiperidin-3-yl)pyridin-3-yl)-2-((R)-2-(trifluoromethyl) piperazin-1-yl)acetamide hydrobromide (0.590 g, 1.228 mmol, 99% yield), which was carried forward without further purification. $^1$H NMR (400 MHz, DMSO-$d_6$) δ 11.27-11.01 (m, 1H), 10.44-10.28 (m, 1H), 8.29 (d, J=7.6 Hz, 1H), 8.17-8.08 (m, 1H), 7.65 (d, J=8.4 Hz, 1H), 4.23-4.10 (m, 2H), 3.80-3.74 (m, 1H), 3.69-3.64 (m, 1H), 3.56 (s, 1H), 3.29 (s, 2H), 3.16-3.06 (m, 4H), 2.68-2.58 (m, 2H), 2.41-2.25 (m, 1H), 1.90 (s, 7H).

2-((R)-4-(3-(((trans)-4-(3-(4-Cyano-3-(trifluoromethyl) phenyl)-5,5-dimethyl-4-oxo-2-thioxoimidazolidin-1-yl)cyclohexyl)oxy)propyl)-2-(trifluoromethyl)piperazin-1-yl)-N-(6-(2,6-dioxopiperidin-3-yl)pyridin-3-yl)acetamide hydrochloride. To a mixture of 4-(3-((trans)-4-(3-bromopropoxy)cyclohexyl)-4,4-dimethyl-5-oxo-2-thioxoimidazolidin-1-yl)-2-(trifluoromethyl)benzonitrile (0.089 g, 0.170 mmol) in DMF (1 mL) was added N-(6-(2,6-dioxopiperidin-3-yl)pyridin-3-yl)-2-((R)-2-(trifluoromethyl)piperazin-1-yl)acetamide (0.080 g, 0.170 mmol) and N,N-diisopropylethylamine (0.043 g, 0.330 mmol) and the reaction solution was stirred at 50° C. After 8 h the reaction solution was diluted with water (50 mL) and extracted with ethyl acetate (3×30 mL). The combined organic layers were washed with brine (50 mL), dried over anhydrous sodium sulfate and concentrated. The resulting crude material was purified by standard methods to provide 2-((R)-4-(3-(((trans)-4-(3-(4-cyano-3-(trifluoromethyl)phenyl)-5,5-dimethyl-4-oxo-2-thioxoimidazolidin-1-yl)cyclohexyl)oxy)propyl)-2-(trifluoromethyl)piperazin-1-yl)-N-(6-(2,6-dioxopiperidin-3-yl)pyridin-3-yl)acetamide hydrochloride (0.063 g, 0.070 mmol, 42% yield) as a yellow solid. MS (ESI) m/z 851.2 $[M+1]^+$; $^1$H NMR (400 MHz, DMSO-$d_6$) δ 10.94-10.86 (m, 1H), 10.85-10.72 (m, 1H), 10.49-10.31 (m, 1H), 8.89-8.71 (m, 1H), 8.35 (d, J=8.4 Hz, 1H), 8.20 (s, 1H), 8.18-8.05 (m, 1H), 8.01-7.96 (m, 1H), 7.46 (d, J=8.4 Hz, 1H), 3.92-3.80 (m, 2H), 3.73-3.63 (m, 3H), 3.52 (m, 4H), 3.31-3.09 (m, 6H), 2.89-2.78 (m, 2H), 2.66-2.61 (m, 1H), 2.56 (m, 2H), 2.32-2.23 (m, 1H), 2.15-2.05 (m, 3H), 2.02-1.91 (m, 2H), 1.77-1.70 (m, 2H), 1.56 (s, 6H), 1.38-1.28 (m, 2H).

Example 26: 2-((2R,4r,6S)-4-(3-((trans)-4-(3-(6-Cyano-5-(trifluoromethyl)pyridin-3-yl)-5,5-dimethyl-4-oxo-2-thioxoimidazolidin-1-yl)cyclohexyl) propoxy)-2,6-dimethylpiperidin-1-yl)-N-(6-(2,6-dioxopiperidin-3-yl)pyridin-3-yl)acetamide

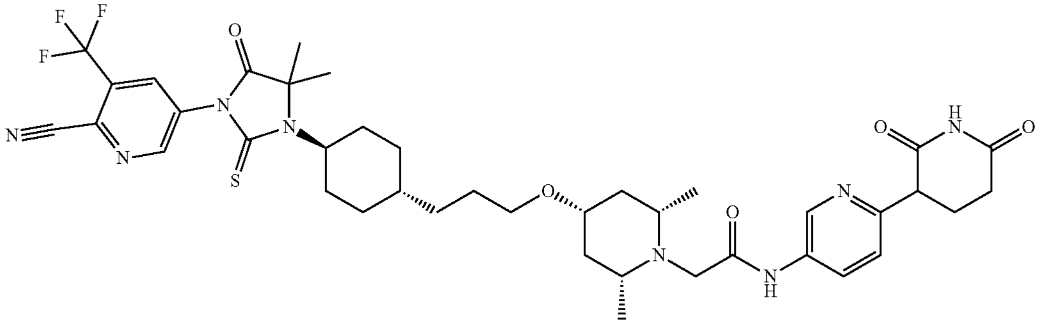 [SMILES: C[C@@H]1C[C@H](OCCC[C@H]2CC[C@H](N3C(=S)N(c4cnc(C#N)c(C(F)(F)F)c4)C(=O)C3(C)C)CC2)C[C@H](C)N1CC(=O)Nc1ccc(C2CCC(=O)NC2=O)nc1]

(2R,4r,6S)-tert-Butyl 4-(3-((trans)-4-(3-(6-Cyano-5-(trifluoromethyl)pyridin-3-yl)-5,5-dimethyl-4-oxo-2-thioxoimidazolidin-1-yl)cyclohexyl)propoxy)-2,6-dimethylpiperidine-1-carboxylate. To a solution of (2R,4r,6S)-tert-butyl 4-(3-((trans)-4-((1-methoxy-2-methyl-1-oxopropan-2-yl) amino)cyclohexyl)propoxy)-2,6-dimethylpiperidine-1-carboxylate (1.900 g, 4.054 mmol) and 5-isothiocyanato-3-(trifluoromethyl)picolinonitrile (0.929 g, 4.054 mmol) in ethyl acetate (10 mL) was added N,N-diisopropylethylamine (2.11 mL, 12.16 mmol) and the reaction solution was stirred at 90° C. After 12 h the reaction solution was concentrated and purified by silica gel column chromatography to provide (2R,4r,6S)-tert-butyl 4-(3-((trans)-4-(3-(6-Cyano-5-(trifluoromethyl)pyridin-3-yl)-5,5-dimethyl-4-oxo-2-thioxoimidazolidin-1-yl)cyclohexyl)propoxy)-2,6-dimethylpiperidine-1-carboxylate (2.500 g, 3.755 mmol, 92% yield) as a yellow oil. $^1$H NMR (400 MHz, DMSO-$d_6$) δ 9.14 (d, J=2.0 Hz, 1H), 8.74 (d, J=2.0 Hz, 1H), 4.15-4.06 (m, 2H), 3.83 (s, 1H), 3.60-3.55 (m, 1H), 3.40-3.37 (m, 2H), 2.84-2.63 (m, 2H), 1.80 (d, J=13.2 Hz, 2H), 1.76-1.65 (m, 6H), 1.57-1.45 (m, 8H), 1.39 (s, 9H), 1.26 (d, J=7.2 Hz, 9H), 1.11-1.02 (m, 2H).

5-(3-((trans)-4-(3-(((2R,4r,6S)-2,6-Dimethylpiperidin-4-yl)oxy)propyl)cyclohexyl)-4,4-dimethyl-5-oxo-2-thioxoimidazolidin-1-yl)-3-(trifluoromethyl)picolinonitrile. To a solution of (2R,4r,6S)-tert-butyl 4-(3-((trans)-4-(3-(6-cyano-5-(trifluoromethyl)pyridin-3-yl)-5,5-dimethyl-4-oxo-2-thioxoimidazolidin-1-yl)cyclohexyl)propoxy)-2,6-dimethylpiperidine-1-carboxylate (2.500 g, 3.755 mmol) in dichloromethane (20 mL) was added 33% hydrogen bromide in acetic acid (20 mL, 3.755 mmol). The mixture was stirred at 25° C. for 12 h. The pH of the reaction mixture was adjust to 7 by addition of saturated sodium bicarbonate solution. The mixture was extracted with ethyl acetate (50 mL×3). The combined organic phase was washed with brine (50 mL), dried over anhydrous sodium sulfate, filtered and concentrated in vacuo. The resulting crude material was purified by standard methods to provide 5-(3-((trans)-4-(3-(((2R,4r,6S)-2,6-dimethylpiperidin-4-yl)oxy)propyl)cyclohexyl)-4,4-dimethyl-5-oxo-2-thioxoimidazolidin-1-yl)-3-

(trifluoromethyl)picolinonitrile (0.550 g, 0.972 mmol, 26% yield) as a light-yellow solid. ₁H NMR (400 MHz, DMSO-$d_6$) δ 9.15 (d, J=2.0 Hz, 1H), 8.74 (d, J=2.0 Hz, 1H), 8.34 (s, 1H), 3.84 (s, 1H), 3.41-3.34 (m, 3H), 2.87 (dd, J=6.0, 10.0 Hz, 2H), 2.72 (d, J=10.4 Hz, 2H), 1.99 (d, J=11.6 Hz, 2H), 1.81 (d, J=12.0 Hz, 2H), 1.71 (d, J=10.4 Hz, 2H), 1.56 (s, 6H), 1.52-1.45 (m, 2H), 1.21 (d, J=7.2 Hz, 3H), 1.12 (d, J=6.4 Hz, 6H), 1.07-0.97 (m, 4H).

Benzyl 2-((2R,4r,6S)-4-(3-((trans)-4-(3-(6-cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)acetate. To a solution of 5-(3-((trans)-4-(3-(((2R,4r,6S)-2,6-dimethylpiperidin-4-yl)oxy)propyl)cyclohexyl)-4,4-dimethyl-5-oxo-2-thioxoimidazolidin-1-yl)-3-(trifluoromethyl)picolinonitrile (0.100 g, 0.177 mmol) in acetonitrile (2 mL) was added N,N-diisopropylethylamine (0.15 mL, 0.880 mmol) and the reaction solution was stirred at room temperature. After 12 h the reaction solution was concentrated and purified by silica gel column chromatography to provide benzyl 2-((2R,4r,6S)-4-(3-((trans)-4-(3-(6-cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)acetate (0.110 g, 0.154 mmol, 87% yield as a yellow oil. $^1$H NMR (400 MHz, DMSO-$d_6$) δ 9.15 (d, J=2.0 Hz, 1H), 8.74 (d, J=2.0 Hz, 1H), 7.40-7.30 (m, 5H), 5.09 (s, 2H), 3.84 (s, 1H), 3.53 (s, 2H), 3.38-3.34 (m, 2H), 3.23-3.14 (m, 1H), 2.80-2.65 (m, 4H), 1.88-1.77 (m, 4H), 1.71 (d, J=9.6 Hz, 2H), 1.56 (s, 6H), 1.50-1.43 (m, 2H), 1.22-1.17 (m, 3H), 1.12-1.04 (m, 2H), 1.02 (d, J=6.4 Hz, 6H), 0.99-0.92 (m, 2H).

2-((2R,4r,6S)-4-(3-((trans)-4-(3-(6-Cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl) acetic acid. To a solution of benzyl 2-((2R,4r,6S)-4-(3-((trans)-4-(3-(6-cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)acetate (0.090 g, 0.126 mmol) in THE (1 mL), water (0.2 mL) was added lithium hydroxide (0.015 g, 0.630 mmol) and the reaction solution was stirred at room temperature. After 12 h the reaction solution was adjusted to pH 7 by addition of 1 M aqueous hydrochloric acid and extracted with dichloromethane (3×10 mL). the combined organic layers were washed with brine, dried over anhydrous sodium sulfate and concentrated to provide crude 2-((2R,4r,6S)-4-(3-((trans)-4-(3-(6-Cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)acetic acid (0.100 g, 0.160 mmol) as a yellow oil which was carried forward without further purification.

2-((2R,4r,6S)-4-(3-((trans)-4-(3-(6-Cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)-N-(6-(2,6-dioxopiperidin-3-yl)pyridin-3-yl)acetamide hydrochloride. To a solution of 2-((2R,4r,6S)-4-(3-((trans)-4-(3-(6-Cyano-5-(trifluoromethyl)pyridin-3-yl)-5,5-dimethyl-4-oxo-2-thioxoimidazolidin-1-yl)cyclohexyl) propoxy)-2,6-dimethylpiperidin-1-yl)acetic acid (0.100 g, 0.160 mmol) and 3-(5-aminopyridin-2-yl)piperidine-2,6-dione (0.049 g, 0.240 mmol) in pyridine (2 mL) was added 1-(3-dimethylaminopropyl)-3-ethylcarbodiimide hydrochloride (0.061 g, 0.321 mmol) and the reaction solution was stirred at 50° C. After 8 h the reaction solution was diluted with water (50 mL) and extracted with ethyl acetate (3×30 mL). The combined organic layers were washed with brine (50 mL), dried over anhydrous sodium sulfate and concentrated. The resulting crude material was purified by standard methods to provide 2-((2R,4r,6S)-4-(3-((trans)-4-(3-(6-cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)-N-(6-(2,6-dioxopiperidin-3-yl)pyridin-3-yl)acetamide hydrochloride (44.04 mg, 0.053 mmol, 33% yield) as a yellow solid. MS (ESI) m/z 811.2 $[M+1]^+$; $^1$H NMR (400 MHz, DMSO-$d_6$) δ 11.89-11.35 (m, 1H), 10.90 (s, 1H), 10.36-9.22 (m, 1H), 9.15 (d, J=2.0 Hz, 1H), 8.81 (dd, J=2.4, 10.8 Hz, 1H), 8.75 (d, J=2.0 Hz, 1H), 8.09 (td, J=3.2, 8.4 Hz, 1H), 7.47 (d, J=8.4 Hz, 1H), 4.31-4.23 (m, 2H), 4.08 (dd, J=5.2, 10.0 Hz, 1H), 3.57-3.50 (m, 2H), 3.41 (q, J=6.0 Hz, 2H), 2.79-2.59 (m, 3H), 2.55 (d, J=4.8 Hz, 1H), 2.30-2.22 (m, 1H), 2.18-2.05 (m, 3H), 1.81 (d, J=11.6 Hz, 2H), 1.75-1.63 (m, 3H), 1.61-1.44 (m, 9H), 1.40-1.31 (m, 4H), 1.23 (d, J=6.4 Hz, 7H), 1.08 (d, J=11.6 Hz, 2H).

Example 27: 2-((2R,4r,6S)-4-(2-((trans)-4-(3-(4-Cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)-N-(6-(2,6-dioxopiperidin-3-yl)pyridin-3-yl)acetamide

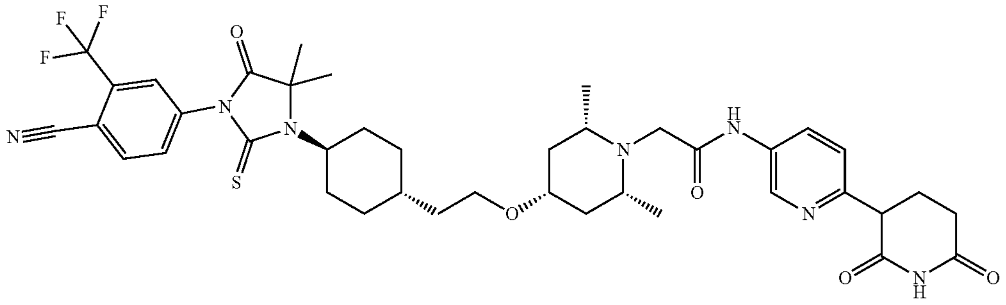 [SMILES: C[C@@H]1C[C@H](OCC[C@H]2CC[C@H](N3C(=S)N(c4ccc(C#N)c(C(F)(F)F)c4)C(=O)C3(C)C)CC2)C[C@H](C)N1CC(=O)Nc1ccc(C2CCC(=O)NC2=O)nc1]

(2R,4r,6S)-tert-Butyl 4-(2-((trans)-4-(dibenzylamino)cyclohexyl)ethoxy)-2,6-dimethylpiperidine-1-carboxylate. To a solution of (trans)-N,N-dibenzyl-4-(2-bromoethyl)cyclohexanamine (5.660 g, 14.65 mmol) and (2S,4r,6R)-tert-butyl 4-hydroxy-2,6-dimethylpiperidine-1-carboxylate (2.800 g, 12.21 mmol) in o-Xylene (60 mL) was added potassium hydroxide (3.080 g, 54.95 mmol) and tetra-n-butylammonium bromide (0.790 g, 2.440 mmol) and the reaction mixture was stirred at 15° C. After 12 h the reaction solution was concentrated and purified by standard methods to provide (2R,4r,6S)-tert-butyl 4-(2-((trans)-4-(dibenzylamino) cyclohexyl)ethoxy)-2,6-dimethylpiperidine-1-carboxylate (3.500 g, 6.545 mmol, 53.6% yield) as a white solid. $^1$H NMR (400 MHz, $CDCl_3$) δ 7.43-7.36 (m, 5H), 7.30-7.26 (m, 4H), 7.22-7.18 (m, 1H), 4.28-4.20 (m, 2H), 3.63 (s, 3H), 3.56-3.52 (m, 1H), 3.42-3.39 (m, 2H), 2.50-2.44 (m, 1H), 1.97-1.87 (m, 4H), 1.80-1.77 (m, 2H), 1.72-1.66 (m, 2H), 1.62-1.55 (m, 2H), 1.47 (s, 9H), 1.44-1.38 (m, 4H), 1.32-1.30 (m, 6H), 0.90-0.82 (m, 2H).

(2R,4r,6S)-tert-Butyl 4-(2-((trans)-4-aminocyclohexyl)ethoxy)-2,6-dimethylpiperidine-1-carboxylate. To a solution of (2R,4r,6S)-tert-butyl 4-(2-((trans)-4-(dibenzylamino)cyclohexyl)ethoxy)-2,6-dimethylpiperidine-1-carboxylate (3.500 g, 6.540 mmol) in Methanol (40 mL) was added ammonium hydroxide (0.23 g, 6.54 mmol) and palladium on activated carbon (0.350 g, 0.330 mmol), the reaction mixture was stirred for 12 hours at 20 C under molecular hydrogen atmosphere (15 Psi). The reaction mixture was poured into methanol (50 mL) and filtered, the filter liquor was concentrated under reduced pressure to afford (2R,4r,6S)-tert-Butyl 4-(2-((trans)-4-aminocyclohexyl)ethoxy)-2,6-dimethylpiperidine-1-carboxylate (2.000 g, 5.640 mmol, 86% yield) as colorless oil. $^1$H NMR (400 MHz, DMSO-$d_6$) δ 4.12-4.08 (m, 2H), 3.57-3.55 (m, 1H), 3.41-3.38 (m, 5H), 2.45-2.39 (m, 1H), 1.73-1.65 (m, 8H), 1.39-1.35 (m, 11H), 1.25 (d, J=6.8 Hz, 6H), 0.98-0.84 (m, 4H).

(2R,4r,6S)-tert-Butyl 4-(2-((trans)-4-((1-methoxy-2-methyl-1-oxopropan-2-yl)amino)cyclohexyl)ethoxy)-2,6-dimethylpiperidine-1-carboxylate. To a solution of (2R,4r,6S)-tert-Butyl 4-(2-((trans)-4-aminocyclohexyl)ethoxy)-2,6-dimethylpiperidine-1-carboxylate (1.900 g, 5.360 mmol) and methyl 2-bromo-2-methylpropanoate (3.880 g, 21.44 mmol) in acetonitrile (6 mL) was added potassium carbonate (2.220 g, 16.08 mmol) and sodium iodide (0.080 g, 0.540 mmol) and the reaction solution was stirred at 110° C. After 15 h the reaction solution was diluted with ethyl acetate (15 mL), filtered and concentrated to provide crude (2R,4r,6S)-tert-butyl 4-(2-((trans)-4-((1-methoxy-2-methyl-1-oxopropan-2-yl)amino)cyclohexyl)ethoxy)-2,6-dimethylpiperidine-1-carboxylate (4.8 g), which was carried forward without further purification.

(2R,4r,6S)-tert-Butyl 4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidine-1-carboxylate. To a solution of (2R,4r,6S)-tert-butyl 4-(2-((trans)-4-((1-methoxy-2-methyl-1-oxopropan-2-yl)amino)cyclohexyl)ethoxy)-2,6-dimethylpiperidine-1-carboxylate (2.400 g, 2.640 mmol) and 4-isothiocyanato-2-(trifluoromethyl)benzonitrile (1.200 g, 5.280 mmol) in ethyl acetate (1 mL) was added N-ethyl-N-isopropylpropan-2-amine (1.38 mL, 7.920 mmol) and the reaction mixture was stirred at 80° C. After 12 h the reaction solution was concentrated and purified by standard methods to provide (2R,4r,6S)-tert-butyl 4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidine-1-carboxylate (1.150 g, 1.767 mmol, 67% yield) as a brown oil. MS (ESI) m/z 551.2 $[M+1]^+$; $^1$H NMR (400 MHz, $CDCl_3$) δ 7.97-7.95 (d, J=8.0 Hz, 1H), 7.87 (d, J=1.6 Hz, 1H), 7.76-7.73 (dd, J=8.0, 1.6 Hz, 1H), 4.29-4.25 (m, 2H), 3.87 (s, 1H), 3.61-3.56 (m, 1H), 3.49-3.46 (t, J=6.0 Hz, 2H), 2.69 (s, 2H), 1.98-1.91 (m, 4H), 1.88-1.85 (m, 2H), 1.75-1.69 (m, 2H), 1.63 (s, 6H), 1.54-1.51 (m, 3H), 1.49 (s. 9H), 1.35-1.34 (d, J=6.8 Hz, 6H), 1.18-1.07 (m, 2H).

4-(3-((trans)-4-(2-(((2R,4r,6S)-2,6-Dimethylpiperidin-4-yl)oxy)ethyl)cyclohexyl)-4,4-dimethyl-5-oxo-2-thioxoimidazolidin-1-yl)-2-(trifluoromethyl)benzonitrile. To a solution of (2R,4r,6S)-tert-butyl 4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidine-1-carboxylate (1.150 g, 1.770 mmol) in dichloromethane (15 mL) was added 2,2,2-trifluoroacetic acid (5. mL, 65.34 mmol) and the reaction mixture was stirred at room temperature. After 2 h the reaction solution was concentrated, and the resulting material was taken up in saturated aqueous sodium bicarbonate solution and extracted with ethyl acetate (4×50 mL). the combined organic layers were washed with brine (50 mL), dried over anhydrous sodium sulfate and concentrated to provide 4-(3-((trans)-4-(2-(((2R,4r,6S)-2,6-dimethylpiperidin-4-yl)oxy)ethyl)cyclohexyl)-4,4-dimethyl-5-oxo-2-thioxoimidazolidin-1-yl)-2-(trifluoromethyl)benzonitrile (0.870 g, 1.580 mmol, 90% yield) as a white solid. $^1$H NMR (400 MHz, $CDCl_3$) δ 7.96-7.95 (d, J=8.0 Hz, 1H), 7.86 (d, J=1.6 Hz, 1H), 7.75-7.72 (dd, J=8.0, 1.6 Hz, 1H), 3.86 (s, 1H), 3.52-3.49 (m, 2H), 3.35-3.27 (m, 1H), 2.75-2.59 (m, 4H), 2.02-1.92 (m, 4H), 1.86-1.83 (m, 2H), 1.61 (s, 6H), 1.52-1.49 (m, 3H), 1.16-1.14 (d, J=6.4 Hz, 6H), 1.10-0.96 (m, 4H).

Benzyl 2-((2R,4r,6S)-4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetate. To a solution of 4-(3-((trans)-4-(2-(((2R,4r,6S)-2,6-dimethylpiperidin-4-yl)oxy)ethyl)cyclohexyl)-4,4-dimethyl-5-oxo-2-thioxoimidazolidin-1-yl)-2-(trifluoromethyl)benzonitrile (0.870. g, 1.580 mmol) in acetonitrile (9 mL) was added benzyl 2-bromoacetate (0.723 g, 3.160 mmol) and N-ethyl-N-isopropylpropan-2-amine (0.83 mL, 4.740 mmol) and the reaction solution was stirred at room temperature. After 12 h the reaction solution was concentrated and purified by standard methods to provide benzyl 2-((2R,4r,6S)-4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetate (1.100 g, 1.574 mmol) as a brown solid. MS (ESI) m/z 699.3 $[M+1]^+$.

2-((2R,4r,6S)-4-(2-((trans)-4-(3-(4-Cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetic acid. To a solution of benzyl 2-((2R,4r,6S)-4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetate (1.100 g, 1.570 mmol) in THE (12 mL) and water (1.5 mL) was added lithium hydroxide (0.189 g, 7.870 mmol) and the reaction solution was stirred at 50° C. After 12 h the reaction solution was concentrated and extracted with 10:1 DCM/methanol (3×30 mL). the combined organic layers were dried over sodium sulfate and concentrated to provide 2-((2R,4r,6S)-4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetic acid (0.900 g, 1.478 mmol, 93% yield) as a brown solid that was carried forward without further purification. MS (ESI) m/z 609.3 $[M+1]^+$; $^1$H NMR (400 MHz, DMSO-$d_6$) δ 8.34-8.32 (d, J=8.0 Hz, 1H), 8.19 (d, J=1.6 Hz, 1H), 7.98-7.96 (dd, J=8.0, 1.6 Hz, 1H), 3.79 (s, 2H), 3.16 (s, 2H), 2.72-2.67 (m, 2H), 2.03-2.00 (m, 2H), 1.81-1.70 (m, 4H), 1.54 (s, 6H), 1.45-1.38 (m, 5H), 1.27-1.19 (m, 7H), 1.15-1.01 (m, 3H), 0.87-0.80 (m, 2H).

2-((2R,4r,6S)-4-(2-((trans)-4-(3-(4-Cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)-N-(6-(2,6-dioxopiperidin-3-yl)pyridin-3-yl)acetamide hydrochloride. To a solution of 2-((2R,4r,6S)-4-(2-((trans)-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)acetic acid (0.100 g, 0.164 mmol) and 3-(5-aminopyridin-2-yl)piperidine-2,6-dione (0.051 g, 0.246 mmol) in pyridine (2 mL) was added 1-(3-dimethylaminopropyl)-3-ethylcarbodiimide hydrochloride (0.063 g, 0.329 mmol) and the reaction solution was stirred at 50° C. After 8 h the reaction solution was diluted with water (50 mL) and extracted with ethyl acetate (3×30 mL). The combined organic layers were washed with brine (50 mL), dried over anhydrous sodium sulfate and concentrated. The resulting crude material was purified by standard methods to provide 2-((2R,4r,6S)-4-(2-((trans)-4-(3-(4-Cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)-N-(6-(2,6-dioxopiperidin-3-yl)pyridin-3-yl)acetamide hydrochloride (62.09 mg, 0.076 mmol, 46% yield) as a yellow solid. MS (ESI) m/z 796.2 $[M+1]^+$; WXW-418-541140-004, $^1H$ NMR (400 MHz, DMSO-$d_6$) δ 11.88-11.38 (m, 1H), 10.89 (s, 1H), 10.45-9.18 (m, 1H), 8.81 (dd, J=2.4, 10.0 Hz, 1H), 8.34 (d, J=8.4 Hz, 1H), 8.19 (d, J=1.2 Hz, 1H), 8.12-8.06 (m, 1H), 7.97 (dd, J=1.6, 8.4 Hz, 1H), 7.46 (d, J=8.8 Hz, 1H), 4.28 (s, 2H), 4.07 (dd, J=5.2, 10.0 Hz, 1H), 3.84 (s, 1H), 3.68 (s, 1H), 3.54-3.44 (m, 3H), 2.76-2.59 (m, 3H), 2.57-2.52 (m, 1H), 2.30-2.23 (m, 1H), 2.19-2.07 (m, 3H), 1.81 (d, J=12.8 Hz, 2H), 1.75-1.66 (m, 3H), 1.55 (s, 6H), 1.45-1.29 (m, 8H), 1.23 (d, J=6.4 Hz, 3H), 1.16-1.04 (m, 2H).

Example 28: 2-((2R,4r,6S)-4-(2-((trans)-4-(3-(6-Cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)-N-(6-(2,6-dioxopiperidin-3-yl)pyridin-3-yl)acetamide clohexyl)ethoxy)-2,6-dimethylpiperidine-1-carboxylate (3.500 g, 6.540 mmol) in Methanol (40 mL) was added ammonium hydroxide (0.23 g, 6.54 mmol) and palladium on activated carbon (0.350 g, 0.330 mmol), the reaction mixture was stirred for 12 hours at 20 C under molecular hydrogen atmosphere (15 Psi). The reaction mixture was poured into methanol (50 mL) and filtered, the filter liquor was concentrated under reduced pressure to afford (2R,4r,6S)-tert-Butyl 4-(2-((trans)-4-aminocyclohexyl)ethoxy)-2,6-dimethylpiperidine-1-carboxylate (2.000 g, 5.640 mmol, 86% yield) as colorless oil. $^1H$ NMR (400 MHz, DMSO-$d_6$) δ 4.12-4.08 (m, 2H), 3.57-3.55 (m, 1H), 3.41-3.38 (m, 5H), 2.45-2.39 (m, 1H), 1.73-1.65 (m, 8H), 1.39-1.35 (m, 11H), 1.25 (d, J=6.8 Hz, 6H), 0.98-0.84 (m, 4H).

(2R,4r,6S)-tert-Butyl 4-(2-((trans)-4-((1-methoxy-2-methyl-1-oxopropan-2-yl)amino)cyclohexyl)ethoxy)-2,6-dimethylpiperidine-1-carboxylate. To a solution of (2R,4r,6S)-tert-Butyl 4-(2-((trans)-4-aminocyclohexyl)ethoxy)-2,6-dimethylpiperidine-1-carboxylate (1.900 g, 5.360 mmol) and methyl 2-bromo-2-methylpropanoate (3.880 g, 21.44 mmol) in acetonitrile (6 mL) was added potassium carbonate (2.220 g, 16.08 mmol) and sodium iodide (0.080 g, 0.540 mmol) and the reaction solution was stirred at 110° C. After 15 h the reaction solution was diluted with ethyl acetate (15 mL), filtered and concentrated to provide crude (2R,4r,6S)-tert-butyl 4-(2-((trans)-4-((1-methoxy-2-methyl-1-oxopropan-2-yl)amino)cyclohexyl)ethoxy)-2,6-dimethylpiperidine-1-carboxylate (4.8 g), which was carried forward without further purification.

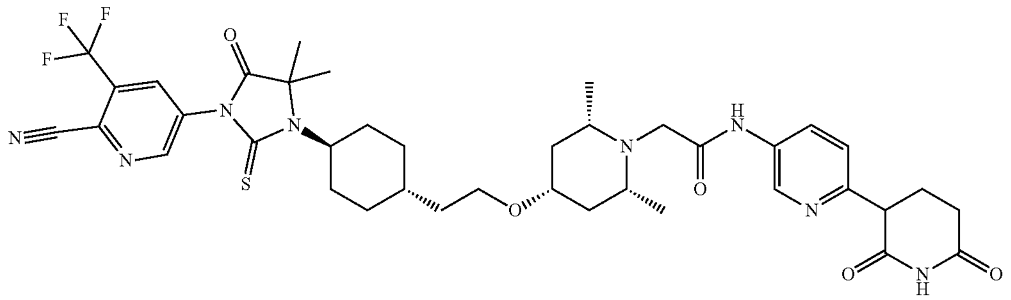 [SMILES: C[C@@H]1C[C@H](OCC[C@H]2CC[C@H](N3C(=S)N(c4cnc(C#N)c(C(F)(F)F)c4)C(=O)C3(C)C)CC2)C[C@H](C)N1CC(=O)Nc1ccc(C2CCC(=O)NC2=O)nc1]

(2R,4r,6S)-tert-Butyl 4-(2-((trans)-4-(dibenzylamino)cyclohexyl)ethoxy)-2,6-dimethylpiperidine-1-carboxylate. To a solution of (trans)-N,N-dibenzyl-4-(2-bromoethyl)cyclohexanamine (5.660 g, 14.65 mmol) and (2S,4r,6R)-tert-butyl 4-hydroxy-2,6-dimethylpiperidine-1-carboxylate (2.800 g, 12.21 mmol) in o-Xylene (60 mL) was added potassium hydroxide (3.080 g, 54.95 mmol) and tetra-n-butylammonium bromide (0.790 g, 2.440 mmol) and the reaction mixture was stirred at 15° C. After 12 h the reaction solution was concentrated and purified by standard methods to provide (2R,4r,6S)-tert-butyl 4-(2-((trans)-4-(dibenzylamino)cyclohexyl)ethoxy)-2,6-dimethylpiperidine-1-carboxylate (3.500 g, 6.545 mmol, 53.6% yield) as a white solid. $^1H$ NMR (400 MHz, $CDCl_3$) δ 7.43-7.36 (m, 5H), 7.30-7.26 (m, 4H), 7.22-7.18 (m, 1H), 4.28-4.20 (m, 2H), 3.63 (s, 3H), 3.56-3.52 (m, 1H), 3.42-3.39 (m, 2H), 2.50-2.44 (m, 1H), 1.97-1.87 (m, 4H), 1.80-1.77 (m, 2H), 1.72-1.66 (m, 2H), 1.62-1.55 (m, 2H), 1.47 (s, 9H), 1.44-1.38 (m, 4H), 1.32-1.30 (m, 6H), 0.90-0.82 (m, 2H).

(2R,4r,6S)-tert-Butyl 4-(2-((trans)-4-aminocyclohexyl)ethoxy)-2,6-dimethylpiperidine-1-carboxylate. To a solution of (2R,4r,6S)-tert-butyl 4-(2-((trans)-4-(dibenzylamino)cy- (2R,4r,6S)-tert-Butyl 4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidine-1-carboxylate. To a solution of (2R,4r,6S)-tert-butyl 4-(2-((trans)-4-((1-methoxy-2-methyl-1-oxopropan-2-yl)amino)cyclohexyl)ethoxy)-2,6-dimethylpiperidine-1-carboxylate (2.400 g, 2.64 mmol, 50%) and 5-isothiocyanato-3-(trifluoromethyl)picolinonitrile (0.730 g, 3.170 mmol) in ethyl acetate (15 mL) was added N-ethyl-N-isopropylpropan-2-amine (1.38 mL, 7.920 mmol) and the reaction mixture was stirred for at 80° C. After 3 h the reaction solution was concentrated and purified by standard methods to provide (2R,4r,6S)-tert-butyl 4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidine-1-carboxylate (1.200 g, 1.841 mmol, 70% yield) as a brown oil. MS (ESI) m/z 552.2$[M-99]^+$; $^1H$ NMR (400 MHz, DMSO-$d_6$) δ 8.98 (d, J=2.0 Hz, 1H), 8.25 (d, J=2.0 Hz, 1H), 4.29-4.21 (m, 2H), 3.82 (m, 1H), 3.59-3.54 (m, 1H), 3.48-3.45 (t, J=6.4 Hz, 2H), 2.68-2.59 (m, 2H), 1.97-1.89 (m, 4H), 1.85-1.82 (m, 2H), 1.73-1.67 (m, 2H), 1.63 (s, 6H), 1.54-1.49 (m, 3H), 1.47 (s, 9H), 1.34-1.32 (d, J=7.2 Hz, 6H), 1.14-1.05 (m, 2H).

5-(3-((trans)-4-(2-(((2R,4r,6S)-2,6-Dimethylpiperidin-4-yl)oxy)ethyl)cyclohexyl)-4,4-dimethyl-5-oxo-2-thioxoimidazolidin-1-yl)-3-(trifluoromethyl)picolinonitrile. To a solution of (2R,4r,6S)-tert-butyl 4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidine-1-carboxylate (1.200 g, 1.840 mmol) in dichloromethane (15 mL) was added trifluoroacetic acid (5. mL) and the reaction mixture was stirred for 2 hours at 15° C. The reaction mixture was concentrated under reduced pressure to afford a residue. Water (30 mL) was added and the pH adjust to 7-8 by saturated solution of sodium bicarbonate, extracted with ethyl acetate (50 mL×4), organic phase was concentrated under reduce pressure to afford 5-(3-((trans)-4-(2-(((2R,4r,6S)-2,6-dimethylpiperidin-4-yl)oxy)ethyl)cyclohexyl)-4,4-dimethyl-5-oxo-2-thioxoimidazolidin-1-yl)-3-(trifluoromethyl)picolinonitrile (1.010 g, 1.831 mmol, 99% yield) as brown solid. $^1$H NMR (400 MHz, DMSO-$d_6$) δ 8.98 (d, J=2.0 Hz, 1H), 8.25 (d, J=2.0 Hz, 1H), 3.85 (m, 1H), 3.51-3.49 (m, 2H), 3.36-3.28 (m, 1H), 2.78-2.59 (m, 4H), 2.03-1.92 (m, 5H), 1.86 (m, 2H), 1.63 (s, 6H), 1.54-1.50 (m, 3H), 1.17-1.16 (d, J=6.4 Hz, 6H), 1.10-1.00 (m, 4H).

tert-Butyl 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetate. To a solution of 5-(3-((trans)-4-(2-(((2R,4r,6S)-2,6-dimethylpiperidin-4-yl)oxy)ethyl)cyclohexyl)-4,4-dimethyl-5-oxo-2-thioxoimidazolidin-1-yl)-3-(trifluoromethyl)picolinonitrile (0.650 g, 1.180 mmol) in acetonitrile (12 mL) was added tert-butyl 2-bromoacetate (0.253 g, 1.300 mmol) and N-ethyl-N-isopropylpropan-2-amine (0.62 mL, 3.530 mmol) and the reaction mixture was stirred at room temperature. After 12 h the reaction solution was concentrated and purified by standard methods to provide tert-butyl 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetate (0.600 g, 0.901 mmol, 77% yield) as a brown oil. MS (ESI) m/z 666.3 [M+1]$^+$.

2-((2R,4r,6S)-4-(2-((trans)-4-(3-(6-Cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetic acid. To a solution of tert-butyl 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetate (0.600. g, 0.900 mmol) in dichloromethane (6 mL) was added trifluoroacetic acid (2.0 mL) and the reaction mixture was stirred at room temperature. After 12 h the reaction solution was concentrated and purified by standard methods to provide 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetic acid (0.820 mmol) as a brown solid. MS (ESI) m/z 610.3 [M+1]$^+$.

2-((2R,4r,6S)-4-(2-((trans)-4-(3-(6-Cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)-N-(6-(2,6-dioxopiperidin-3-yl)pyridin-3-yl)acetamide. To a solution of 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)acetic acid (0.120 g, 0.197 mmol) and 3-(5-aminopyridin-2-yl)piperidine-2,6-dione (0.061 g, 0.295 mmol) in pyridine (2 mL) was added 1-(3-dimethylaminopropyl)-3-ethylcarbodiimide hydrochloride (0.075 g, 0.394 mmol) and the reaction solution was stirred at 50° C. After 12 h the reaction solution was diluted with water (50 mL) and extracted with ethyl acetate (3×30 mL). The combined organic layers were washed with brine (50 mL), dried over anhydrous sodium sulfate and concentrated. The resulting crude material was purified by standard methods to provide 2-((2R,4r,6S)-4-(2-((trans)-4-(3-(6-cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)-N-(6-(2,6-dioxopiperidin-3-yl)pyridin-3-yl)acetamide (78.7 mg, 0.098 mmol, 50% yield) as a white solid. MS (ESI) m/z 797.3 [M+1]$^+$; $^1$H NMR (400 MHz, DMSO-$d_6$) δ 10.82 (s, 1H), 9.86 (s, 1H), 9.15 (d, J=2.0 Hz, 1H), 8.73 (dd, J=2.0, 11.2 Hz, 2H), 8.06 (dd, J=2.4, 8.4 Hz, 1H), 7.31 (d, J=8.4 Hz, 1H), 3.97 (dd, J=5.2, 9.6 Hz, 1H), 3.84 (s, 1H), 3.49-3.41 (m, 2H), 3.30-3.25 (m, 1H), 3.23 (s, 2H), 2.75-2.62 (m, 4H), 2.62-2.52 (m, 2H), 2.28-2.18 (m, 1H), 2.14-2.06 (m, 1H), 1.83 (t, J=11.2 Hz, 4H), 1.72 (d, J=10.4 Hz, 2H), 1.56 (s, 6H), 1.42-1.35 (m, 3H), 1.24-1.10 (m, 4H), 1.06 (d, J=6.4 Hz, 6H).

Example 29: 2-((2R,4r,6S)-4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)-N-(6-(2,6-dioxopiperidin-3-yl)pyridin-3-yl)acetamide

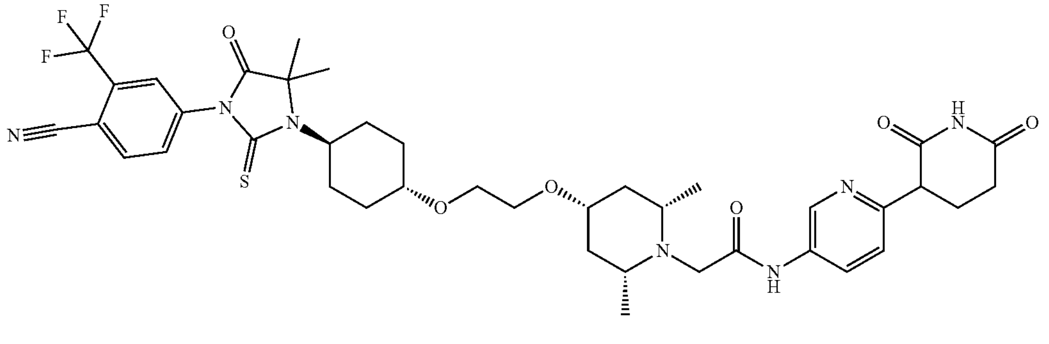 [SMILES: C[C@@H]1C[C@H](OCCO[C@H]2CC[C@H](N3C(=S)N(c4ccc(C#N)c(C(F)(F)F)c4)C(=O)C3(C)C)CC2)C[C@H](C)N1CC(=O)Nc1ccc(C2CCC(=O)NC2=O)nc1]

(2R,4r,6S)-tert-Butyl 4-(2-(((trans)-4-(dibenzylamino)cyclohexyl)oxy)ethoxy)-2,6-dimethylpiperidine-1-carboxylate. To a solution of (2R,4r,6S)-tert-butyl 4-hydroxy-2,6-dimethylpiperidine-1-carboxylate (1.400 g, 6.110 mmol) and (trans)-N,N-dibenzyl-4-(2-bromoethoxy)cyclohexanamine (3.680 g, 9.157 mmol) in xylenes (30 mL) was added tetrabutylammonium bromide (0.394 g, 1.221 mmol) and potassium hydroxide (1.713 g, 30.53 mmol) and the reaction solution was stirred at room temperature. After 12 h the reaction solution was diluted with water (50 mL) and extracted with ethyl acetate (3×50 mL). the combined organic layers were washed with brine (50 mL), dried over anhydrous sodium sulfate and concentrated. The resulting crude material was purified by standard methods to provide (2R,4r,6S)-tert-butyl 4-(2-(((trans)-4-(dibenzylamino)cyclohexyl)oxy)ethoxy)-2,6-dimethylpiperidine-1-carboxylate (2.600 g, 4.721 mmol, 77% yield) as a white solid. $^1$H NMR (400 MHz, DMSO-$d_6$) δ 7.41-7.24 (m, 8H), 7.23-7.13 (m, 2H), 4.18-4.01 (m, 2H), 3.63-3.52 (m, 5H), 3.47 (dd, J=2.8, 9.2 Hz, 4H), 3.19 (t, J=10.8 Hz, 1H), 2.39 (t, J=11.6 Hz, 1H), 1.98 (d, J=10.2 Hz, 2H), 1.85-1.66 (m, 6H), 1.39 (s, 11H), 1.24 (d, J=7.2 Hz, 6H), 1.01-0.88 (m, 2H).

(2R,4r,6S)-tert-Butyl 4-(2-(((trans)-4-aminocyclohexyl)oxy)ethoxy)-2,6-dimethylpiperidine-1-carboxylate. To a solution of (2R,4r,6S)-tert-butyl 4-(2-(((trans)-4-(dibenzylamino)cyclohexyl)oxy)ethoxy)-2,6-dimethylpiperidine-1-carboxylate (0.600 g, 1.089 mmol) in methanol (5 mL) and THE (5 mL) was added 10% palladium on activated carbon (0.115 g, 1.089 mmol) under nitrogen atmosphere. The suspension was degassed under vacuum and purged with hydrogen for three times. The mixture was stirred at 25° C. for 12 h under hydrogen (15 Psi). The reaction mixture was filtered through a pad of celite and the filtrate was concentrated invacuo to give crude (2R,4r,6S)-tert-butyl 4-(2-(((trans)-4-aminocyclohexyl)oxy)ethoxy)-2,6-dimethylpiperidine-1-carboxylate (0.400 g, 1.080 mmol) as a colorless oil, which was carried forward without further purification. MS (ESI) m/z 371.3 [M+1]$^+$.

(2R,4r,6S)-tert-Butyl 4-(2-(((trans)-4-((1-methoxy-2-methyl-1-oxopropan-2-yl)amino)cyclohexyl)oxy)ethoxy)-2,6-dimethylpiperidine-1-carboxylate. To a solution of (2R,4r,6S)-tert-butyl 4-(2-(((trans)-4-aminocyclohexyl)oxy)ethoxy)-2,6-dimethylpiperidine-1-carboxylate (0.400 g, 1.080 mmol) and methyl 2-bromo-2-methylpropanoate (0.977 g, 5.400 mmol) in acetonitrile (1 mL) was added potassium carbonate (0.448 g, 3.239 mmol) and sodium iodide (0.016 g, 0.108 mmol) and the reaction solution was stirred at 110° C. After 12 h the reaction solution was filtered and concentrated to provide crude (2R,4r,6S)-tert-butyl 4-(2-(((trans)-4-((1-methoxy-2-methyl-1-oxopropan-2-yl)amino)cyclohexyl)oxy)ethoxy)-2,6-dimethylpiperidine-1-carboxylate (0.500 g, 1.062 mmol), which was carried forward without further purification. MS (ESI) m/z 471.4 [M+1]$^+$.

(2R,4r,6S)-tert-Butyl 4-(2-(((trans)-4-(dibenzylamino)cyclohexyl)oxy)ethoxy)-2,6-dimethylpiperidine-1-carboxylate. To a solution of (2R,4r,6S)-tert-butyl 4-(2-(((trans)-4-((1-methoxy-2-methyl-1-oxopropan-2-yl)amino)cyclohexyl)oxy)ethoxy)-2,6-dimethylpiperidine-1-carboxylate (0.500 g, 1.062 mmol) and 4-isothiocyanato-2-(trifluoromethyl)benzonitrile (0.242 g, 1.062 mmol) in ethyl acetate (5 mL) was added N,N-diisopropylethylamine (0.55 mL, 3.19 mmol) and the reaction solution was stirred at 90° C. After 12 h the reaction solution was concentrated and purified by silica gel column chromatography to provide (2R,4r,6S)-tert-butyl 4-(2-(((trans)-4-(dibenzylamino)cyclohexyl)oxy)ethoxy)-2,6-dimethylpiperidine-1-carboxylate (0.470 g, 0.705 mmol, 66% yield) as a yellow oil. $^1$H NMR (400 MHz, DMSO-$d_6$) δ 8.33 (d, J=8.0 Hz, 1H), 8.19 (d, J=1.6 Hz, 1H), 7.97 (dd, J=1.6, 8.0 Hz, 1H), 3.82 (s, 1H), 3.62-3.60 (m, 2H), 3.57-3.54 (m, 2H), 3.31-3.25 (m, 1H), 2.81 (d, J=12.8 Hz, 2H), 2.04 (d, J=10.8 Hz, 2H), 1.89 (d, J=11.2 Hz, 2H), 1.75-1.72 (m, 5H), 1.54 (s, 6H), 1.39 (s, 9H), 1.26 (s, 6H), 1.20-1.15 (m, 4H).

4-(3-((trans)-4-(2-(((2R,4r,6S)-2,6-Dimethylpiperidin-4-yl)oxy)ethoxy)cyclohexyl)-4,4-dimethyl-5-oxo-2-thioxoimidazolidin-1-yl)-2-(trifluoromethyl)benzonitrile. To a solution of (2R,4r,6S)-tert-butyl 4-(2-(((trans)-4-(dibenzylamino)cyclohexyl)oxy)ethoxy)-2,6-dimethylpiperidine-1-carboxylate (0.470 g, 0.705 mmol) in dichloromethane (5 mL) was added trifluoroacetic acid (2.0 mL, 25.78 mmol). The mixture was stirred at 25° C. for 2 h. The reaction mixture was concentrated invacuo to give crude 4-(3-((trans)-4-(2-(((2R,4r,6S)-2,6-dimethylpiperidin-4-yl)oxy)ethoxy)cyclohexyl)-4,4-dimethyl-5-oxo-2-thioxoimidazolidin-1-yl)-2-(trifluoromethyl)benzonitrile (0.400 g, 0.706 mmol), which was carried forward without further purification.

tert-Butyl 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetate. To a solution of 4-(3-((trans)-4-(2-(((2R,4r,6S)-2,6-dimethylpiperidin-4-yl)oxy)ethoxy)cyclohexyl)-4,4-dimethyl-5-oxo-2-thioxoimidazolidin-1-yl)-2-(trifluoromethyl)benzonitrile (0.400 g, 0.706 mmol) and tert-butyl 2-bromoacetate (0.206 g, 1.059 mmol) in acetonitrile (5 mL) was added N,N-dimethylformamide (0.61 mL, 3.530 mmol) and the reaction solution was stirred at room temperature. After 12 h the reaction solution was concentrated and purified by standard methods to provide tert-butyl 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetate (0.150 g, 0.220 mmol, 31% yield) as a yellow oil. $^1$H NMR (400 MHz, DMSO-$d_6$) δ 8.33 (d, J=8.4 Hz, 1H), 8.19 (d, J=1.6 Hz, 1H), 7.97 (dd, J=1.6, 8.4 Hz, 1H), 3.83 (s, 1H), 3.49 (s, 4H), 3.29-3.22 (m, 2H), 2.83-2.71 (m, 4H), 2.04 (d, J=10.8 Hz, 2H), 1.88 (dd, J=4.0, 11.6 Hz, 2H), 1.70 (d, J=10.4 Hz, 2H), 1.54 (s, 6H), 1.40 (s, 9H), 1.36-1.25 (m, 2H), 1.06-0.92 (m, 10H).

2-((2R,4r,6S)-4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetic acid. To a solution of tert-butyl 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetate (0.150 g, 0.220 mmol) in dichloromethane (5 mL) was added trifluoroacetic acid (1.0 mL, 12.89 mmol) and the reaction solution was stirred at room temperature. After 12 h the reaction solution was concentrated to provide crude 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetic acid (0.150 g, 0.240 mmol), which was carried forward without further purification.

2-((2R,4r,6S)-4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)-N-(6-(2,6-dioxopiperidin-3-yl)pyridin-3-yl)acetamide hydrochloride. To a solution of 2-((2R,4r,6S)-4-(2-(((trans)-4-(3-(4-cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)acetic acid (0.050 g, 0.080 mmol) and 3-(5-aminopyridin-2-yl)piperidine-2,6-dione (0.049 g, 0.240 mmol) in pyridine (1 mL) was added 1-(3-dimethylaminopropyl)-3-ethylcarbodiimide hydrochloride (0.092 g, 0.480 mmol). and the reaction solution was stirred at 50° C. After 12 h the reaction solution was diluted with water (50 mL) and extracted with ethyl acetate (3×30 mL). The combined organic layers were washed with brine (50 mL), dried over anhydrous sodium sulfate and concentrated. The resulting crude material was purified by standard methods to provide 2-((2R,4r,6S)-4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)-N-(6-(2,6-dioxopiperidin-3-yl)pyridin-3-yl)acetamide hydrochloride (73 mg, 0.089 mmol, 40% yield) as a yellow solid. MS (ESI) m/z 812.3 $[M+1]^+$; $^1H$ NMR (400 MHz, DMSO-$d_6$) δ 12.22-11.69 (m, 1H), 10.96 (d, J=4.0 Hz, 1H), 10.68-9.20 (m, 1H), 8.95-8.84 (m, 1H), 8.33 (d, J=8.0 Hz, 1H), 8.23-8.16 (m, 2H), 7.97 (dd, J=1.6, 8.4 Hz, 1H), 7.58 (dd, J=4.4, 8.4 Hz, 1H), 4.31 (s, 2H), 4.21-4.12 (m, 1H), 3.71 (s, 2H), 3.53 (d, J=4.8 Hz, 6H), 3.26 (t, J=10.8 Hz, 1H), 2.80 (d, J=11.6 Hz, 2H), 2.72-2.61 (m, 1H), 2.59-2.52 (m, 1H), 2.39-2.27 (m, 1H), 2.20-2.01 (m, 5H), 1.78-1.65 (m, 3H), 1.54 (s, 6H), 1.41-1.28 (m, 6H), 1.24 (d, J=6.4 Hz, 3H).

Example 30: 2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)-N-(6-(2,6-dioxopiperidin-3-yl)pyridin-3-yl)acetamide hydrogen for three times. The mixture was stirred at 25° C. for 12 h under hydrogen (15 Psi). The reaction mixture was filtered through a pad of celite and the filtrate was concentrated invacuo to give crude (2R,4r,6S)-tert-butyl 4-(2-(((trans)-4-aminocyclohexyl)oxy)ethoxy)-2,6-dimethylpiperidine-1-carboxylate (0.400 g, 1.080 mmol) as a colorless oil, which was carried forward without further purification. MS (ESI) m/z 371.3 $[M+1]^+$.

(2R,4r,6S)-tert-Butyl 4-(2-(((trans)-4-((1-methoxy-2-methyl-1-oxopropan-2-yl)amino)cyclohexyl)oxy)ethoxy)-2,6-dimethylpiperidine-1-carboxylate. To a solution of (2R,4r,6S)-tert-butyl 4-(2-(((trans)-4-aminocyclohexyl)oxy)ethoxy)-2,6-dimethylpiperidine-1-carboxylate (0.400 g, 1.080 mmol) and methyl 2-bromo-2-methylpropanoate (0.977 g, 5.400 mmol) in acetonitrile (1 mL) was added potassium carbonate (0.448 g, 3.239 mmol) and sodium iodide (0.016 g, 0.108 mmol) and the reaction solution was stirred at 110° C. After 12 h the reaction solution was filtered and concentrated to provide crude (2R,4r,6S)-tert-butyl 4-(2-(((trans)-4-((1-methoxy-2-methyl-1-oxopropan-2-yl)

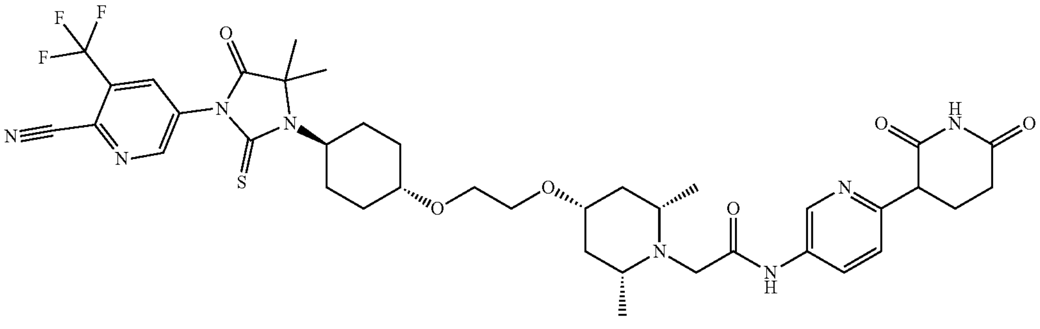 [SMILES: C[C@@H]1C[C@H](OCCO[C@H]2CC[C@H](N3C(=S)N(c4cnc(C#N)c(C(F)(F)F)c4)C(=O)C3(C)C)CC2)C[C@H](C)N1CC(=O)Nc1ccc(C2CCC(=O)NC2=O)nc1]

(2R,4r,6S)-tert-Butyl 4-(2-(((trans)-4-(dibenzylamino)cyclohexyl)oxy)ethoxy)-2,6-dimethylpiperidine-1-carboxylate. To a solution of (2R,4r,6S)-tert-butyl 4-hydroxy-2,6-dimethylpiperidine-1-carboxylate (1.400 g, 6.110 mmol) and (trans)-N,N-dibenzyl-4-(2-bromoethoxy)cyclohexanamine (3.680 g, 9.157 mmol) in xylenes (30 mL) was added tetrabutylammonium bromide (0.394 g, 1.221 mmol) and potassium hydroxide (1.713 g, 30.53 mmol) and the reaction solution was stirred at room temperature. After 12 h the reaction solution was diluted with water (50 mL) and extracted with ethyl acetate (3×50 mL). the combined organic layers were washed with brine (50 mL), dried over anhydrous sodium sulfate and concentrated. The resulting crude material was purified by standard methods to provide (2R,4r,6S)-tert-butyl 4-(2-(((trans)-4-(dibenzylamino)cyclohexyl)oxy)ethoxy)-2,6-dimethylpiperidine-1-carboxylate (2.600 g, 4.721 mmol, 77% yield) as a white solid. $^1H$ NMR (400 MHz, DMSO-$d_6$) δ 7.41-7.24 (m, 8H), 7.23-7.13 (m, 2H), 4.18-4.01 (m, 2H), 3.63-3.52 (m, 5H), 3.47 (dd, J=2.8, 9.2 Hz, 4H), 3.19 (t, J=10.8 Hz, 1H), 2.39 (t, J=11.6 Hz, 1H), 1.98 (d, J=10.2 Hz, 2H), 1.85-1.66 (m, 6H), 1.39 (s, 11H), 1.24 (d, J=7.2 Hz, 6H), 1.01-0.88 (m, 2H).

(2R,4r,6S)-tert-Butyl 4-(2-(((trans)-4-aminocyclohexyl)oxy)ethoxy)-2,6-dimethylpiperidine-1-carboxylate. To a solution of (2R,4r,6S)-tert-butyl 4-(2-(((trans)-4-(dibenzylamino)cyclohexyl)oxy)ethoxy)-2,6-dimethylpiperidine-1-carboxylate (0.600 g, 1.089 mmol) in methanol (5 mL) and THE (5 mL) was added 10% palladium on activated carbon (0.115 g, 1.089 mmol) under nitrogen atmosphere. The suspension was degassed under vacuum and purged with amino)cyclohexyl)oxy)ethoxy)-2,6-dimethylpiperidine-1-carboxylate (0.500 g, 1.062 mmol), which was carried forward without further purification. MS (ESI) m/z 471.4 $[M+1]^+$.

(2R,4r,6S)-tert-Butyl 4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidine-1-carboxylate. To a solution of (2R,4r,6S)-tert-butyl 4-(2-(((trans)-4-((1-methoxy-2-methyl-1-oxopropan-2-yl)amino)cyclohexyl)oxy)ethoxy)-2,6-dimethylpiperidine-1-carboxylate (0.300 g, 0.637 mmol) and 5-isothiocyanato-3-(trifluoromethyl)picolinonitrile (0.146 g, 0.637 mmol) in ethyl acetate (5 mL) was added N,N-diisopropylethylamine (0.33 mL, 1.910 mmol). The mixture was stirred at 90° C. for 12 h. The reaction mixture was concentrated invacuo to give the crude product. The residue was purified by flash silica gel chromatography (0~27% ethyl acetate in petroleum ether) to provide (2R,4r,6S)-tert-butyl 4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidine-1-carboxylate (0.340 g, 0.509 mmol, 80% yield) as a yellow oil. $^1H$ NMR (400 MHz, DMSO-$d_6$) δ 9.14 (d, J=2.0 Hz, 1H), 8.74 (d, J=2.0 Hz, 1H), 3.83 (s, 1H), 3.63 (t, J=4.0 Hz, 1H), 3.57-3.53 (m, 3H), 3.32-3.25 (m, 1H), 2.82 (d, J=11.2 Hz, 2H), 2.04 (d, J=10.8 Hz, 2H), 1.76-1.66 (m, 7H), 1.55 (s, 6H), 1.39 (s, 9H), 1.34-1.23 (m, 10H).

5-(3-((trans)-4-(2-(((2R,4r,6S)-2,6-Dimethylpiperidin-4-yl)oxy)ethoxy)cyclohexyl)-4,4-dimethyl-5-oxo-2-thioxoimidazolidin-1-yl)-3-(trifluoromethyl)picolinonitrile. To a solution of (2R,4r,6S)-tert-butyl 4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidine-1-carboxylate (0.340 g, 0.509 mmol) in dichloromethane (5 mL) was added trifluoroacetic acid (2.0 mL, 25.78 mmol). The mixture was stirred at 25° C. for 2 h. The reaction mixture was concentrated invacuo to give crude 5-(3-((trans)-4-(2-(((2R,4r,6S)-2,6-dimethylpiperidin-4-yl)oxy)ethoxy)cyclohexyl)-4,4-dimethyl-5-oxo-2-thioxoimidazolidin-1-yl)-3-(trifluoromethyl)picolinonitrile (0.290 g, 0.511 mmol) which was carried forward without further purification. MS (ESI) m/z 568.3 $[M+1]^+$.

tert-Butyl 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetate. To a solution of 5-(3-((trans)-4-(2-(((2R,4r,6S)-2,6-dimethylpiperidin-4-yl)oxy)ethoxy)cyclohexyl)-4,4-dimethyl-5-oxo-2-thioxoimidazolidin-1-yl)-3-(trifluoromethyl)picolinonitrile (0.290 g, 0.511 mmol) and tert-butyl 2-bromoacetate (0.149 g, 0.766 mmol) in acetonitrile (5 mL) was added N,N-dimethylformamide (0.44 mL, 2.55 mmol) and the reaction solution was stirred at room temperature. After 12 h the reaction solution was concentrated and purified by silica gel column chromatography to provide tert-butyl 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetate (0.270 g, 0.396 mmol, 78% yield) as a yellow oil. $^1$H NMR (400 MHz, DMSO-$d_6$) δ 9.14 (d, J=2.0 Hz, 1H), 8.74 (d, J=2.0 Hz, 1H), 3.84 (s, 1H), 3.49 (s, 4H), 3.34 (s, 2H), 3.29-3.23 (m, 2H), 2.88-2.70 (m, 4H), 2.04 (d, J=10.4 Hz, 2H), 1.88 (d, J=12.0 Hz, 2H), 1.70 (d, J=11.2 Hz, 2H), 1.56 (s, 6H), 1.40 (s, 9H), 1.32 (d, J=12.8 Hz, 2H), 1.08-0.91 (m, 8H).

2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)-N-(6-(2,6-dioxopiperidin-3-yl)pyridin-3-yl)acetamide hydrochloride. To a solution of 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetic acid (0.120 g, 0.192 mmol) and 3-(5-aminopyridin-2-yl)piperidine-2,6-dione (0.118 g, 0.575 mmol) in pyridine (1 mL) was added 1-(3-dimethylaminopropyl)-3-ethylcarbodiimide hydrochloride (0.221 g, 1.151 mmol) and the reaction solution was stirred at 50° C. After 8 h the reaction solution was diluted with water (50 mL) and extracted with ethyl acetate (3×30 mL). The combined organic layers were washed with brine (50 mL), dried over anhydrous sodium sulfate and concentrated. The resulting crude material was purified by standard methods to provide 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)-N-(6-(2,6-dioxopiperidin-3-yl)pyridin-3-yl)acetamide hydrochloride (61.17 mg, 0.075 mmol, 39% yield) as a yellow solid. MS (ESI) m/z 813.3 $[M+1]^+$; $^1$H NMR (400 MHz, DMSO-$d_6$) δ 12.04-11.36 (m, 1H), 10.91 (s, 1H), 10.47-9.20 (m, 1H), 9.14 (d, J=2.0 Hz, 1H), 8.84 (dd, J=2.4, 8.0 Hz, 1H), 8.74 (d, J=2.0 Hz, 1H), 8.12 (td, J=2.4, 8.8 Hz, 1H), 7.50 (d, J=8.8 Hz, 1H), 4.29 (s, 2H), 4.14-4.07 (m, 1H), 3.85 (s, 1H), 3.68-3.65 (m, 1H), 3.53 (d, J=4.8 Hz, 6H), 3.26 (t, J=10.8 Hz, 1H), 2.81 (d, J=12.0 Hz, 2H), 2.70-2.60 (m, 1H), 2.58-2.52 (m, 1H), 2.35-2.23 (m, 1H), 2.20-2.02 (m, 5H), 1.76-1.63 (m, 3H), 1.56 (s, 6H), 1.41-1.29 (m, 6H), 1.24 (d, J=6.4 Hz, 3H).

Example 31: 2-(4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)-N-(6-(2,6-dioxopiperidin-3-yl)pyridin-3-yl)acetamide

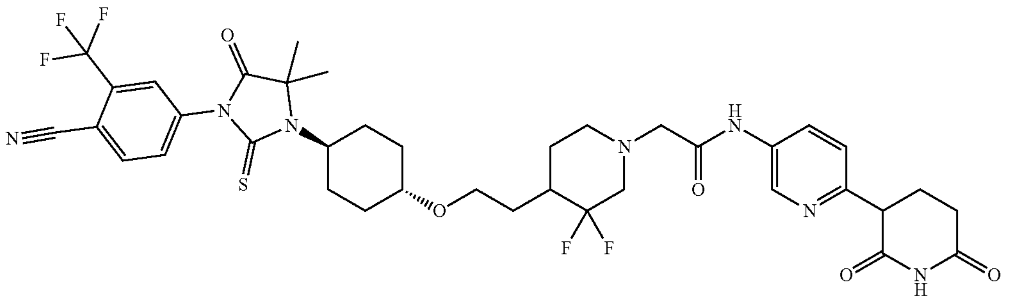 [SMILES: CC1(C)C(=O)N(c2ccc(C#N)c(C(F)(F)F)c2)C(=S)N1[C@H]1CC[C@H](OCCC2CCN(CC(=O)Nc3ccc(C4CCC(=O)NC4=O)nc3)CC2(F)F)CC1]

tert-Butyl 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetic acid. To a solution of tert-butyl 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetate (0.270 g, 0.396 mmol) in dichloromethane (5 mL) was added trifluoroacetic acid (1.0 mL, 12.89 mmol) and the reaction solution was stirred at room temperature. After 12 h the reaction solution was concentrated to provide crude 2-((2R,4r,6S)-4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)acetic acid (0.250 g, 0.400 mmol), which was carried forward without further purification. MS (ESI) m/z 626.3 $[M+1]^+$.

2-((2R,4r,6S)-4-(2-(((trans)-4-(3-(6-Cyano-5-(trifluoromethyl)pyridin-3-yl)-5,5-dimethyl-4-oxo-2-thioxoimidazolitert-butyl 4-(2-(((1r,4r)-4-(dibenzylamino)cyclohexyl)oxy)ethyl)-3,3-difluoropiperidine-1-carboxylate. To a solution of tert-butyl 3,3-difluoro-4-(2-((methylsulfonyl)oxy)ethyl)piperidine-1-carboxylate (1.81 g, 5.27 mmol) in xylenes (30 mL) was added (1r,4r)-4-(dibenzylamino)cyclohexan-1-ol (3.11 g, 10.54 mmol), tetrabutylammonium bromide (0.340 g, 1.054 mmol), and potassium hydroxide (1.479 g, 26.4 mmol). The reaction mixture was heated to 30° C. for 24 h. The reaction mixture was partitioned between water and ethyl acetate. The organic layer was removed and the aqueous layer was extracted with ethyl acetate twice more. The combined organic layer was washed with brine, dried over sodium sulfate, and filtered. The filtrate was taken and volatile organics were removed under reduced pressure to give a light yellow solid. The solid was taken up in ethyl acetate and purified on a silica gel column using 0-75% ethyl acetate in hexanes over 2000 mL. Fractions containing desired product were combined and volatile organics were removed under reduced pressure to give tert-butyl 4-(2-(((1r,4r)-4-(dibenzylamino)cyclohexyl)oxy)ethyl)-3,3-difluoropiperidine-1-carboxylate (1.79 g, 3.30 mmol, 63% yield) as a colorless oil. MS (ESI) m/z 543.2 $[M+1]^+$.

tert-Butyl 4-(2-(((1r,4r)-4-aminocyclohexyl)oxy)ethyl)-3,3-difluoropiperidine-1-carboxylate. To a solution of tert-butyl 4-(2-(((1r,4r)-4-(dibenzylamino)cyclohexyl)oxy)ethyl)-3,3-difluoropiperidine-1-carboxylate (2.65 g, 4.88 mmol) in Methanol (50 ml) was added palladium on carbon (500 mg, 4.70 mmol). Air in the flask was evacuated and replaced with hydrogen (3×, 15 psi, balloon). The reaction mixture was stirred at ambient temperature for 18 h. The reaction was filtered through celite. The filter cake was washed with more methanol. The filtrate was taken and volatile organics were removed under reduced pressure to give tert-butyl 4-(2-(((1r,4r)-4-aminocyclohexyl)oxy)ethyl)-3,3-difluoropiperidine-1-carboxylate (1.72 g, 4.75 mmol, 97% yield) as a light yellow oil. MS (ESI) m/z 363.2 $[M+1]^+$.

tert-Butyl 3,3-difluoro-4-(2-(((1r,4r)-4-((1-methoxy-2-methyl-1-oxopropan-2-yl)amino)cyclohexyl)oxy)ethyl)piperidine-1-carboxylate. To a solution of tert-butyl 4-(2-(((1r,4r)-4-aminocyclohexyl)oxy)ethyl)-3,3-difluoropiperidine-1-carboxylate (1.72 g, 4.75 mmol) in acetonitrile (20 ml) was added methyl 2-bromo-2-methylpropanoate (1.718 g, 9.49 mmol), potassium iodide (0.079 g, 0.475 mmol), and potassium carbonate (1.312 g, 9.49 mmol). The reaction mixture was stirred at 110° C. for 20 h. The reaction mixture was partitioned between water and ethyl acetate. The organic layer was removed and the aqueous layer was extracted with ethyl acetate twice more. The combined organic layer was washed with brine, dried over sodium sulfate, and filtered. The filtrate was taken and volatile organics were removed under reduced pressure to give tert-butyl 3,3-difluoro-4-(2-(((1r,4r)-4-((1-methoxy-2-methyl-1-oxopropan-2-yl)amino)cyclohexyl)oxy)ethyl)piperidine-1-carboxylate (2.20 g, 4.76 mmol) as a yellow oil, which was carried forward without further purification. MS (ESI) m/z 463.2 $[M+1]^+$.

tert-Butyl-4-(2-(((1r,4r)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidine-1-carboxylate. To a solution of tert-butyl 3,3-difluoro-4-(2-(((1r,4r)-4-((1-methoxy-2-methyl-1-oxopropan-2-yl)amino)cyclohexyl)oxy)ethyl)piperidine-1-carboxylate (0.730 g, 1.578 mmol) in ethyl acetate (7 mL) was added 4-isothiocyanato-2-(trifluoromethyl)benzonitrile (0.360 g, 1.578 mmol) and diisopropylethylamine (0.827 mL, 4.73 mmol). The reaction vial was sealed and stirred at 90° C. for 18 h. The reaction mixture was partitioned between water and ethyl acetate. 5 mL of brine were added to reduce emulsion. The organic layer was removed and the aqueous layer was extracted with ethyl acetate twice more. The combined organic layer was washed with brine, dried over sodium sulfate, and filtered. The filtrate was taken and volatile organics were removed under reduced pressure to give a foamy dark orange semi-solid. The solid was taken up in ethyl acetate and purified on a silica gel column using 0-100% ethyl acetate in hexanes over 1000 mL. Fractions containing desired product were combined and volatile organics were removed under reduced pressure to give tert-butyl 4-(2-(((1r,4r)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidine-1-carboxylate (396 mg, 0.601 mmol, 38% yield) as a foamy orange semi-solid. MS (ESI) m/z 559.2 $[M-99]^+$.

4-(3-((1r,4r)-4-(2-(3,3-difluoropiperidin-4-yl)ethoxy)cyclohexyl)-4,4-dimethyl-5-oxo-2-thioxoimidazolidin-1-yl)-2-(trifluoromethyl)benzonitrile hydrochloride. To a solution of 4-(3-((1r,4r)-4-(2-(3,3-difluoropiperidin-4-yl)ethoxy)cyclohexyl)-4,4-dimethyl-5-oxo-2-thioxoimidazolidin-1-yl)-2-(trifluoromethyl)benzonitrile, HCl (395 mg, 0.664 mmol, 110% yield) in 1,4-Dioxane (3.0 ml) was added HCl (2.0 ml, 8.00 mmol) (4.0 M in dioxane). The reaction was stirred at ambient temperature for 90 min. Volatile organics were removed under reduced pressure to give 4-(3-((1r,4r)-4-(2-(3,3-difluoropiperidin-4-yl)ethoxy)cyclohexyl)-4,4-dimethyl-5-oxo-2-thioxoimidazolidin-1-yl)-2-(trifluoromethyl)benzonitrile hydrochloride (395 mg, 0.664 mmol) as a foamy orange semi-solid that was carried forward without further purification. MS (ESI) m/z 559.2 $[M+1]^+$.

tert-butyl 2-(4-(2-(((1r,4r)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)acetate. To a solution of 4-(3-((1r,4r)-4-(2-(3,3-difluoropiperidin-4-yl)ethoxy)cyclohexyl)-4,4-dimethyl-5-oxo-2-thioxoimidazolidin-1-yl)-2-(trifluoromethyl)benzonitrile, HCl (0.395 g, 0.664 mmol) in acetonitrile (7 mL) was added triethylamine (0.278 mL, 1.991 mmol) and tert-butyl 2-bromoacetate (0.825 mL, 5.59 mmol). The reaction vessel was sealed and stirred at 70° C. for 18 h. Volatile organics were removed under reduced pressure to give an orange solid. Solid was taken up in dichloromethane and purified on a silica gel column using 0-100% ethyl acetate in hexanes over 1200 mL. Fractions containing desired product were combined and volatile organics were removed under reduced pressure to give tert-butyl 2-(4-(2-(((1r,4r)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)acetate (277 mg, 0.412 mmol, 62.0% yield) as a foamy orange semi-solid. MS (ESI) m/z 673.2 $[M+1]^+$.

2-(4-(2-(((1r,4r)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)acetic acid. To a flask containing tert-butyl 2-(4-(2-(((1r,4r)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetate (0.277 g, 0.411 mmol) was added HCl (5.0 ml, 20.0 mmol) (4.0 M in dioxane). The reaction mixture was stirred at ambient temperature for 3 h. Volatile organics were removed under reduced pressure to give 2-(4-(2-(((1r,4r)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)acetic acid hydrochloride (307 mg, 0.470 mmol, 114% yield) as a light brown solid, which was carried forward without further purification. MS (ESI) m/z 617.2 $[M+1]^+$.

2-(4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)-N-(6-(2,6-dioxopiperidin-3-yl)pyridin-3-yl)acetamide hydrochloride. To a solution of 2-(4-(2-(((trans)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)acetic acid, hydrochloride (107 mg, 0.164 mmol) in N,N-dimethylformamide (1.5 mL) was added 3-(5-aminopyridin-2-yl)piperidine-2,6-dione (40.3 mg, 0.197 mmol), 1-methyl-1H-imidazole (0.052 mL, 0.655 mmol), and N-(chloro(dimethylamino)methylene)-N-methylmethanaminium hexafluorophosphate(V) (92 mg, 0.328 mmol) and the reaction solution was stirred at room temperature. After 18 h the reaction solution was diluted with DMSO (1 mL), filtered, and purified by standard methods to provide 2-(4-(2-(((trans)-4-(3-(4-cyano-3-(trifluoromethyl)phenyl)-5,5-dimethyl-4-oxo-2-thioxoimidazolidin-1-yl)cyclohexyl)oxy)ethyl)-3,3-difluoropiperidin-1-yl)-N-(6-(2,6-dioxopiperidin-3-yl)pyridin-3-yl)acetamide hydrochloride (60 mg, 0.071 mmol, 43% yield) as a white solid. MS (ESI) m/z 804.2 $[M+1]^+$; $^1$H NMR (DMSO-d6, 400 MHz) δ 11.56 (br s, 1H), 10.94 (br s, 1H), 8.87 (br s, 1H), 8.34 (br d, 1H, J=7.3 Hz), 8.1-8.3 (m, 2H), 7.9-8.1 (m, 1H), 7.55 (br d, 1H, J=7.8 Hz), 4.1-4.4 (m, 3H), 3.8-4.0 (m, 2H), 3.6-3.8 (m, 1H), 3.4-3.6 (m, 3H), 3.2-3.4 (m, 2H), 2.7-2.9 (m, 2H), 2.6-2.7 (m, 1H), 2.2-2.4 (m, 2H), 2.0-2.2 (m, 4H), 1.90 (br d, 1H, J=2.7 Hz), 1.6-1.8 (m, 3H), 1.4-1.6 (m, 6H), 1.2-1.4 (m, 2H).

Example 32: 2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)-N-(6-(2,6-dioxopiperidin-3-yl)pyridin-3-yl)acetamide mixture was stirred at ambient temperature for 18 h. The reaction was filtered through celite. The filter cake was washed with more methanol. The filtrate was taken and volatile organics were removed under reduced pressure to give tert-butyl 4-(2-(((trans)-4-aminocyclohexyl)oxy)ethyl)-3,3-difluoropiperidine-1-carboxylate (1.72 g, 4.75 mmol, 97% yield) as a light yellow oil. MS (ESI) m/z 363.2 $[M+1]^+$.

tert-Butyl 3,3-difluoro-4-(2-(((trans)-4-((1-methoxy-2-methyl-1-oxopropan-2-yl)amino)cyclohexyl)oxy)ethyl)piperidine-1-carboxylate. To a solution of tert-butyl 4-(2-(((trans)-4-aminocyclohexyl)oxy)ethyl)-3,3-difluoropiperidine-1-carboxylate (1.72 g, 4.75 mmol) in acetonitrile (20 ml) was added methyl 2-bromo-2-methylpropanoate (1.718 g, 9.49 mmol), potassium iodide (0.079 g, 0.475 mmol), and potassium carbonate (1.312 g, 9.49 mmol). The reaction mixture was stirred at 110° C. for 20 h. The reaction mixture was partitioned between water and ethyl acetate. The organic layer was removed and the aqueous layer was extracted with ethyl acetate twice more. The combined organic layer was washed with brine, dried

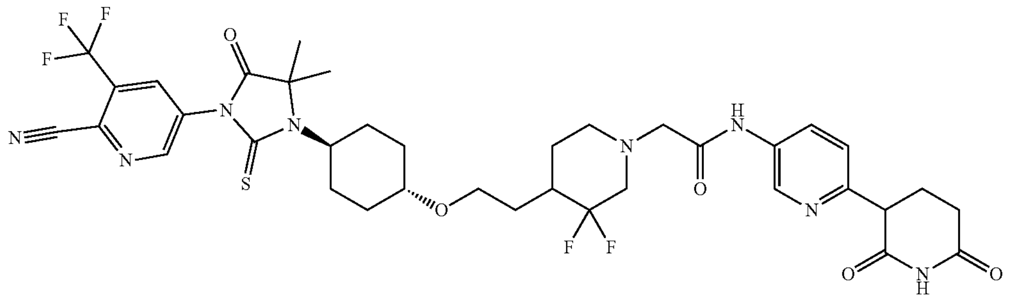 [SMILES: CC1(C)C(=O)N(c2cnc(C#N)c(C(F)(F)F)c2)C(=S)N1[C@H]1CC[C@H](OCCC2CCN(CC(=O)Nc3ccc(C4CCC(=O)NC4=O)nc3)CC2(F)F)CC1]

tert-Butyl 4-(2-(((trans)-4-(dibenzylamino)cyclohexyl)oxy)ethyl)-3,3-difluoropiperidine-1-carboxylate. To a solution of tert-butyl 3,3-difluoro-4-(2-((methyl sulfonyl)oxy)ethyl)piperidine-1l-carboxylate (1.81 g, 5.27 mmol) in xylenes (30 mL) was added (1r,4r)-4-(dibenzylamino)cyclohexan-1-ol (3.11 g, 10.54 mmol), tetrabutyl ammonium bromide (0.340 g, 1.054 mmol), and potassium hydroxide (1.479 g, 26.4 mmol). The reaction mixture was heated to 30° C. for 24 h. The reaction mixture was partitioned between water and ethyl acetate. The organic layer was removed and the aqueous layer was extracted with ethyl acetate twice more. The combined organic layer was washed with brine, dried over sodium sulfate, and filtered. The filtrate was taken and volatile organics were removed under reduced pressure to give a light yellow solid. The solid was taken up in ethyl acetate and purified on a silica gel column using 0-75% ethyl acetate in hexanes over 2000 mL. Fractions containing desired product were combined and volatile organics were removed under reduced pressure to give tert-butyl 4-(2-(((trans)-4-(dibenzylamino)cyclohexyl)oxy)ethyl)-3,3-difluoropiperidine-1-carboxylate (1.79 g, 3.30 mmol, 63% yield) as a colorless oil. MS (ESI) m/z 543.2 $[M+1]^+$.

tert-Butyl 4-(2-(((trans)-4-aminocyclohexyl)oxy)ethyl)-3,3-difluoropiperidine-1-carboxylate. To a solution of tert-butyl 4-(2-(((trans)-4-(dibenzylamino)cyclohexyl)oxy)ethyl)-3,3-difluoropiperidine-1-carboxylate (2.65 g, 4.88 mmol) in Methanol (50 ml) was added palladium on carbon (500 mg, 4.70 mmol). Air in the flask was evacuated and replaced with hydrogen (3×, 15 psi, balloon). The reaction over sodium sulfate, and filtered. The filtrate was taken and volatile organics were removed under reduced pressure to give tert-butyl 3,3-difluoro-4-(2-(((trans)-4-((1-methoxy-2-methyl-1-oxopropan-2-yl)amino)cyclohexyl)oxy)ethyl)piperidine-1-carboxylate (2.20 g, 4.76 mmol) as a yellow oil, which was carried forward without further purification. MS (ESI) m/z 463.2 $[M+1]^+$.

tert-Butyl 4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidine-1-carboxylate. To a solution of tert-butyl 3,3-difluoro-4-(2-(((trans)-4-((1-methoxy-2-methyl-1-oxopropan-2-yl)amino)cyclohexyl)oxy)ethyl)piperidine-1-carboxylate (1.47 g, 3.18 mmol) in ethyl acetate (14 mL) was added 5-isothiocyanato-3-(trifluoromethyl)picolinonitrile (0.728 g, 3.18 mmol) and diisopropylethylamine (1.665 mL, 9.53 mmol). The reaction vial was sealed and stirred at 90° C. for 18 h. The reaction mixture was partitioned between water and ethyl acetate. A few mL of brine were added to reduce emulsion. The organic layer was removed and the aqueous layer was extracted with ethyl acetate twice more. The combined organic layer was washed with brine, dried over sodium sulfate, and filtered. The filtrate was taken and volatile organics were removed under reduced pressure to give a foamy dark orange semi-solid. The solid was taken up in ethyl acetate and purified on a silica gel column using 0-100% ethyl acetate in hexanes over 1800 mL. Fractions containing desired product were combined and volatile organics were removed under reduced pressure to give tert-butyl 4-(2-(((trans)-4-(3-(6-cyano-5-(trifluoromethyl)pyridin-3-yl)-5,5-dimethyl-4-oxo- 2-thioxoimidazolidin-1-yl)cyclohexyl)oxy)ethyl)-3,3-difluoropiperidine-1-carboxylate (1.10 g, 1.667 mmol, 52% yield) as a foamy light orange semi-solid. MS (ESI) m/z 560.2 $[M-99]^+$.

5-(3-((trans)-4-(2-(3,3-Difluoropiperidin-4-yl)ethoxy)cyclohexyl)-4,4-dimethyl-5-oxo-2-thioxoimidazolidin-1-yl)-3-(trifluoromethyl)picolinonitrile hydrochloride. To a solution of tert-butyl 4-(2-(((1r,4r)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidine-1-carboxylate (1.10 g, 1.667 mmol) in 1,4-dioxane (5.0 ml) was added HCl (5.0 ml, 20.00 mmol) (4.0 M in dioxane). The reaction was stirred at ambient temperature for 90 min. Volatile organics were removed under reduced pressure to give 5-(3-((trans)-4-(2-(3,3-difluoropiperidin-4-yl)ethoxy)cyclohexyl)-4,4-dimethyl-5-oxo-2-thioxoimidazolidin-1-yl)-3-(trifluoromethyl)picolinonitrile hydrochloride (1.08 g, 1.812 mmol) as a foamy orange semi-solid that was carried forward without further purification. MS (ESI) m/z 560.2 $[M+1]^+$.

2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetate. To a solution of 5-(3-((trans)-4-(2-(3,3-difluoropiperidin-4-yl)ethoxy)cyclohexyl)-4,4-dimethyl-5-oxo-2-thioxoimidazolidin-1-yl)-3-(trifluoromethyl)picolinonitrile, HCl (1.08 g, 1.812 mmol) in acetonitrile (15 mL) was added triethylamine (0.758 mL, 5.44 mmol) and tert-butyl 2-bromoacetate (1.338 mL, 9.06 mmol). The reaction vessel was sealed and stirred at 70° C. for 18 h. Volatile organics were removed under reduced pressure to give an orange solid. Solid was taken up in dichloromethane and purified on a silica gel column using 0-100% ethyl acetate in hexanes over 2200 mL. Fractions containing desired product were combined and volatile organics were removed under reduced pressure to give tert-butyl 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetate (0.997 g, 1.480 mmol, 82% yield) as a foamy orange semi-solid. MS (ESI) m/z 674.2 $[M+1]^+$.

2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetic acid hydrochloride. To a flask containing tert-butyl 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetate (1.0 g, 1.484 mmol) was added HCl (10.0 ml, 40.0 mmol) (4.0 M in dioxane). The reaction mixture was stirred at ambient temperature for 3 h. Volatile organics were removed under reduced pressure to give 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetic acid hydrochloride (1.14 g, 1.743 mmol) as a light brown solid which was carried forward without further purification. MS (ESI) m/z 618.2 $[M+1]^+$.

2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)-N-(6-(2,6-dioxopiperidin-3-yl)pyridin-3-yl)acetamide hydrochloride. To a solution of 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)acetic acid, HCl (100 mg, 0.153 mmol) in Acetonitrile (1.0 mL) and DMF (1 mL) was added 3-(5-aminopyridin-2-yl)piperidine-2,6-dione (37.6 mg, 0.183 mmol), 1-methyl-1H-imidazole (0.049 mL, 0.612 mmol), and N-(chloro(dimethylamino)methylene)-N-methylmethanaminium hexafluorophosphate(V) (86 mg, 0.306 mmol) and the reaction solution was stirred at room temperature. After 18 h the reaction solution was diluted with DMSO (1 mL) and purified by standard methods to provide 2-(4-(2-(((trans)-4-(3-(6-cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)-N-(6-(2,6-dioxopiperidin-3-yl)pyridin-3-yl)acetamide hydrochloride. (12 mg, 0.014 mmol, 9% yield) as a white solid. MS (ESI) m/z 805.2 $[M+1]^+$; $^1H$ NMR (DMSO-d6, 400 MHz) δ 10.86 (s, 1H), 9.14 (d, 1H, J=2.0 Hz), 8.6-8.8 (m, 2H), 8.03 (dd, 1H, J=1.5, 8.4 Hz), 7.38 (d, 1H, J=8.4 Hz), 4.01 (br dd, 2H, J=5.2, 9.7 Hz), 3.8-3.9 (m, 2H), 3.4-3.6 (m, 3H), 3.2-3.3 (m, 2H), 2.7-2.9 (m, 3H), 2.6-2.7 (m, 1H), 2.2-2.3 (m, 2H), 1.8-2.2 (m, 7H), 1.7-1.8 (m, 2H), 1.5-1.6 (m, 7H), 1.2-1.5 (m, 3H).

Cell Based Assays

VCAP AR Degradation Assay. Test compounds were pre-dispensed into a Corning CellBind 96-well clear bottom plate (Cat #3300) using an acoustic dispenser to make a 10-point concentration series at 1:3 dilution for each compound. The final top concentration of each compound was 5 μM. DMSO at a final concentration of 0.1% was used as a control. VCaP cells cultured in DMEM with 8% fetal bovine serum (FBS) were seeded at 50K cells per well in a 200 μL volume into the compound plate and incubated at 37° C. in a $CO_2$ incubator for 24 h. The medium was carefully removed from the cells and the plate was placed on ice. One hundred μL of ice-cold 1× cell lysis buffer from Cell Signaling Technologies (Cat #9803) was added to each well of the cells and the plate was incubated at 4° C. on a shaker for 1 h. Fifteen μL of cell lysate was used for AR ELISA detection using a PathScan Total Sandwich AR ELISA kit (Cell Signaling Technology, Cat #12580). AR levels in compound-treated wells were normalized to that of DMSO control and expressed as percent of control (PoC) (y). A Four Parameter Logistic Model (Sigmoidal Dose-Response Model) was used to determine the compound's $DC_{50}$, and $EC_{50}$, using the following equation:

$$y=(A+((B-A)/(1+((C/x)^D))))$$

A=$Y_{Min}$ (lowest AR level normalized to DMSO control in response to compound treatment, as determined by curve fit)

B=$Y_{Max}$ (maximum AR level as determined by curve fit)

C=$EC_{50}$

D=Hill Slope x=compound concentration $EC_{50}$=the concentration of compound when y=($Y_{Max}$−$Y_{Min}$)/2

$DC_{50}$=the concentration of the compound when y=50% of DMSO control (50% AR degradation)

y=AR protein level normalized to DMSO control

The lowest measured AR level normalized to DMSO control in response to compound treatment, termed Y value, was used to characterize the compound-mediated AR degradation efficiency.

Each of the compounds in Table 1, was tested in the VCAP AR degradation assay, and was found to have activity therein. All of the compounds in Table 1 were shown to have an $DC_{50}$<1 μM and Y<50% of DMSO control.

Prostate Cancer Cell Proliferation Assay. VCAP or ENZR cells were plated at 10K cells per well in 96-well CellBind (Costar) plates using DMEM+8% FBS media. Cells were incubated overnight at 37° C. and test compound was serially diluted and added to the well. Following seven-day incubation, the assay media was removed by inversion and the plate was frozen overnight at −80° C. Plates were thawed at room temperature and 100 μL deionized water ($ddH_2O$) was added to each well. Plates were incubated at 37° C. in non-$CO_2$ incubator for 1 h and then frozen at −80° C. overnight. Plates were thawed to room temperature and 100-μL TNE buffer (NaCl, Tris, EDTA)+Hoescht dye (1.0 mg/ml, 1:400) was added to each well. Fluorescent signal was measured at 460 nm. All data were normalized as a percentage of the DMSO control. A Four Parameter Logistic Model (Sigmoidal Dose-Response Model) was used to determine the compound's $GI_{50}$ value, using the following equation:

$$y=(A+((B-A)/(1+((C/x)^\wedge D))))$$

A=$Y_{Min}$ (lowest cell viability in luminescence unit normalized to DMSO control in response to compound treatment determined by curve fit)

B=$Y_{Max}$ (maximum cell viability measured as luminescence unit normalized to DMSO control as determined by curve fit)

C=$EC_{50}$

D=Hill Slope $GI_{50}$=the concentration of the compound when Y=($Y_{Max}$+$Y_{t\,0}$)/2

$EC_{50}$=the concentration of compound when y=($Y_{Max}$−$Y_{Min}$)/2

$IC_{50}$=the concentration of the compound when Y=50% of DMSO control y=cell viability measured as luminescence unit and normalized as percentage of the DMSO control $t_0$=time when compound was added $Y_{t\,0}$=value of y at $t_0$ The compounds provided herein have been, or will be tested in the prostate cancer cell proliferation assay, and have shown, or will be shown, to have activity therein.

In Vivo Assays

AR Degradation Assay. In vivo AR degradation assays were performed in NSG mice bearing VCaP prostate cancer xenograft tumors. Male NSG mice were inoculated with VCaP cells in the flank region above the right leg. Following inoculation of the animals, the tumors were allowed to grow to approximately 500 $mm^3$ prior to randomization. The randomized animals were administered with test compounds formulated in 20% Labrasol, 80% 25 mM citrate buffer pH 3. The compounds were administered orally once daily for 3 days. After the last dose of compound administration, the plasma and tumors were collected and processed for AR degradation assays. Intratumoral AR levels were measured using western blot analysis. Statistical analysis was performed using a one-way analysis of variance (ANOVA).

The compounds provided herein have been, or will be tested in the in vivo AR degradation assay, and have shown, or will be shown, to have activity therein.

VCaP Prostate Cancer Xenograft model. The xenograft study was conducted with male NSG mice bearing VCaP prostate cancer xenograft tumors. Male NSG mice were inoculated subcutaneously with VCaP cells in the flank region above the right hind leg. Following inoculation of the animals, the tumors were allowed to grow to approximately 200 $mm^3$ prior to randomization. During randomization, the mice bearing VCaP tumors ranging between 75 and 250 $mm^3$ were pooled together and randomized into various treatment groups. Test compounds formulated in 20% Labrasol, 80% 25 mM citrate buffer pH 3 were administered in a dose volume of 5 mL/kg. The compounds were administered orally once daily for the duration of the study. Tumors were measured twice a week using calipers and tumor volumes were calculated using the formula $W^2 \times L/2$. Statistical analysis was performed using a one-way or two-way analysis of variance (ANOVA).

The compounds provided herein have been, or will be tested in the VCAP prostate cancer xenograft model and have shown, or will be shown, to be effective as treatments of prostate cancer in the models.

Activity Table

Each of the compounds in Table 1, was tested in one or more of the AR degradation assays shown above, for example, the VCAP AR Degradation Assay, and was found to have activity therein.

All of the compounds in Table 1 were shown to have a $DC_{50}$<10 μM and Y<70% of DMSO control, with some compounds having a $DC_{50}$ value D: $DC_{50}$≤0.005 μM, some a $DC_{50}$ value C: 0.005 μM<$DC_{50}$≤0.010 μM, some a $DC_{50}$ value B: 0.010 μM<$DC_{50}$≤0.1 μM, and others a $DC_{50}$ value A: 0.1 μM<$DC_{50}$≤10 μM.

Additionally the compounds were shown to have an AR degradation efficiency Y value<70% of DMSO control, with some compounds having 0<Y≤20% (shown as *), some compounds having 20%<Y≤30% (shown as ), and others having 30%<Y<70% (shown as *),

TABLE 1

| Cmpd No. | Cmpd Structure | Cmpd Name | MH+ Obs. | $DC_{50}$ | Y |
|---|---|---|---|---|---|
| 1 | 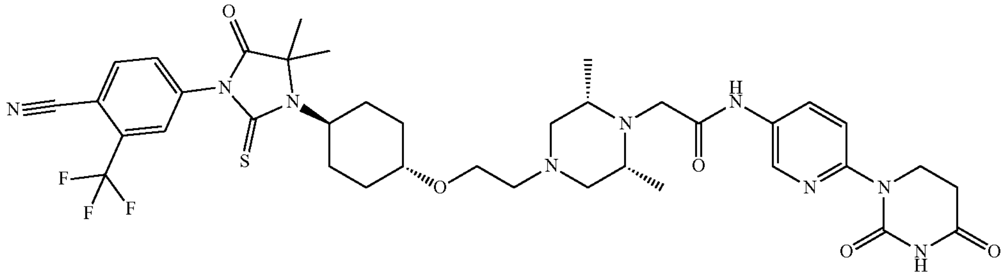 [SMILES: C[C@@H]1CN(CCO[C@H]2CC[C@H](N3C(=S)N(c4ccc(C#N)c(C(F)(F)F)c4)C(=O)C3(C)C)CC2)C[C@H](C)N1CC(=O)Nc1ccc(N2CCC(=O)NC2=O)nc1] | 2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1(2H)-yl)pyridin-3-yl)acetamide | 798.0 | A | *** |
| 2 | 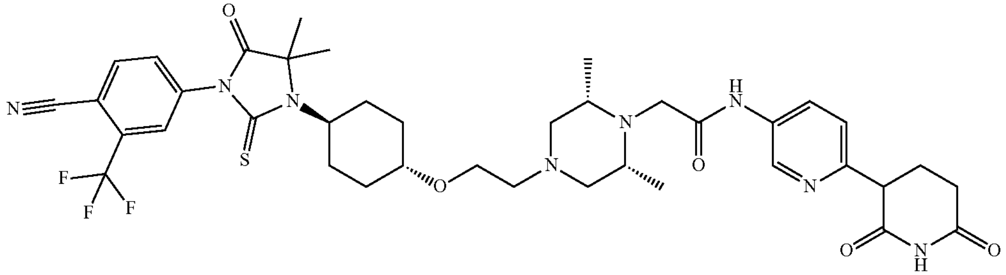 | 2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,6-dioxopiperidin-3-yl)pyridin-3-yl)acetamide | 797.0 | C | *** |
| 3 | 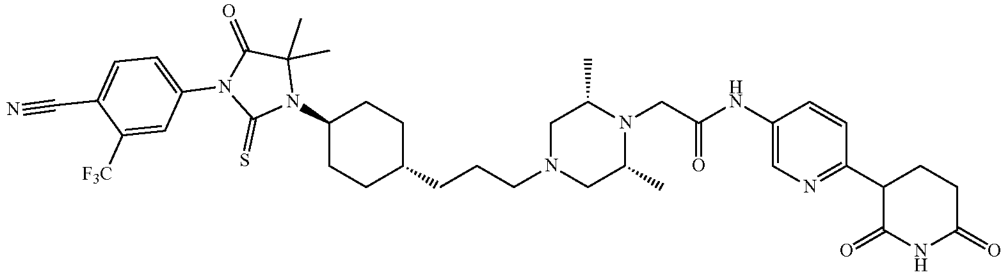 [SMILES: C[C@@H]1CN(CCC[C@H]2CC[C@H](N3C(=S)N(c4ccc(C#N)c(C(F)(F)F)c4)C(=O)C3(C)C)CC2)C[C@H](C)N1CC(=O)Nc1ccc(C2CCC(=O)NC2=O)nc1] | 2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide | 795.4 | C | *** |

TABLE 1-continued

| Cmpd No. | Cmpd Structure | Cmpd Name | MH+ Obs. | $DC_{50}$ | Y |
|---|---|---|---|---|---|
| 4 | 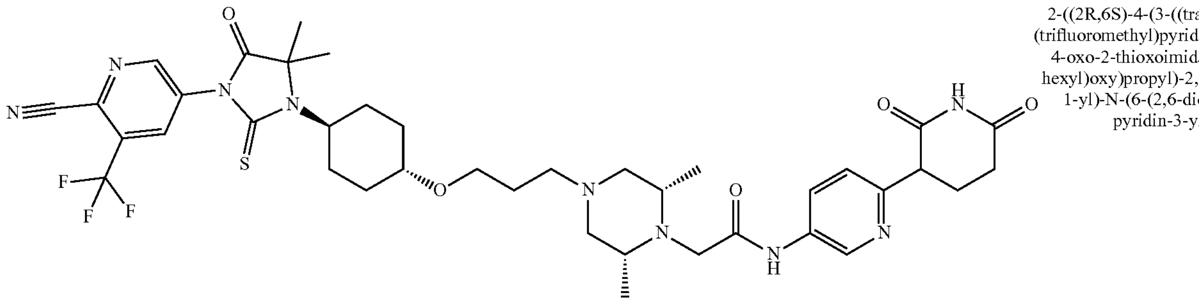 | 2-((2R,6S)-4-(3-((trans-4-(3-(6-cyano-5-(trifluoromethyl)pyridin-3-yl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide | 812.3 | D | ** |
| 5 | 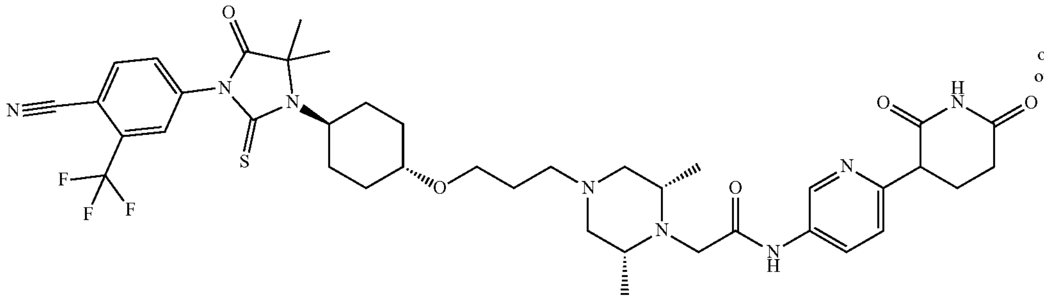 | 2-((2R,6S)-4-(3-((trans-4-(3-(4-cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide | 811.3 | D | ** |
| 6 | 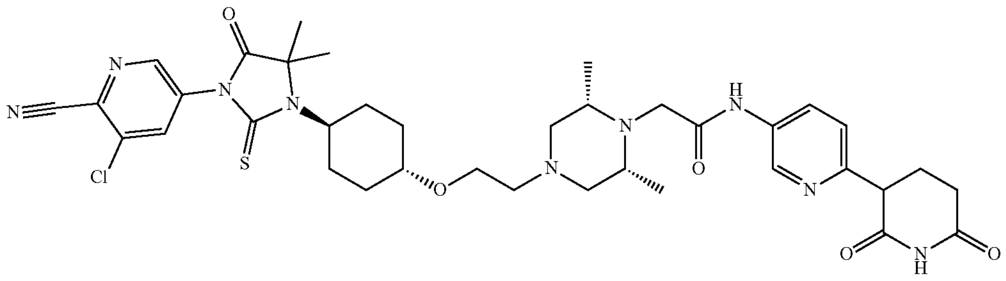 [SMILES: C[C@@H]1CN(CCO[C@H]2CC[C@H](N3C(=S)N(c4cnc(C#N)c(Cl)c4)C(=O)C3(C)C)CC2)C[C@H](C)N1CC(=O)Nc1ccc(C2CCC(=O)NC2=O)nc1] | 2-((2R,6S)-4-(2-((trans-4-(3-(5-chloro-6-cyanopyridin-3-yl)-5,5-dimethyl-4-oxo-2-thioxoimidazolidin-1-yl)cyclohexyl)oxy)ethyl)-2,6-dimethylpiperazin-1-yl)-N-(6-(2,6-dioxopiperidin-3-yl)pyridin-3-yl)acetamide | 764.3 | D | ** |

TABLE 1-continued

| Cmpd No. | Cmpd Structure | Cmpd Name | $MH^+$ Obs. | $DC_{50}$ | Y |
|---|---|---|---|---|---|
| 7 | 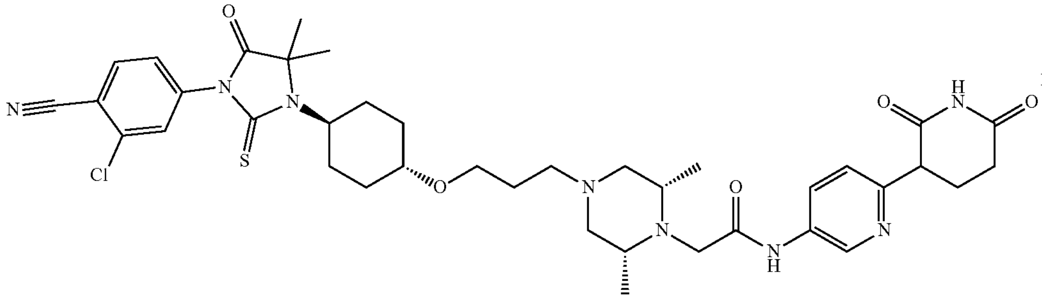 | 2-((2R,6S)-4-(3-((trans-4-(3-(3-chloro-4-cyanophenyl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide | 777.3 | D | * |
| 8 | 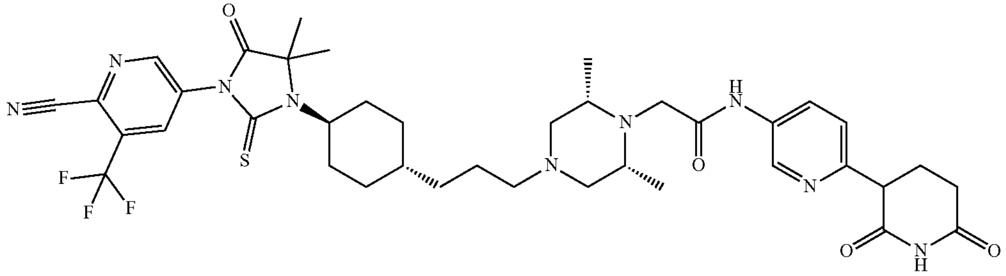 [SMILES: C[C@@H]1CN(CCC[C@H]2CC[C@H](N3C(=S)N(c4cnc(C#N)c(C(F)(F)F)c4)C(=O)C3(C)C)CC2)C[C@H](C)N1CC(=O)Nc1ccc(C2CCC(=O)NC2=O)nc1] | 2-((2R,6S)-4-(3-(trans-4-(3-(6-cyano-5-(trifluoromethyl)pyridin-3-yl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide | 796.3 | D | ** |
| 9 | 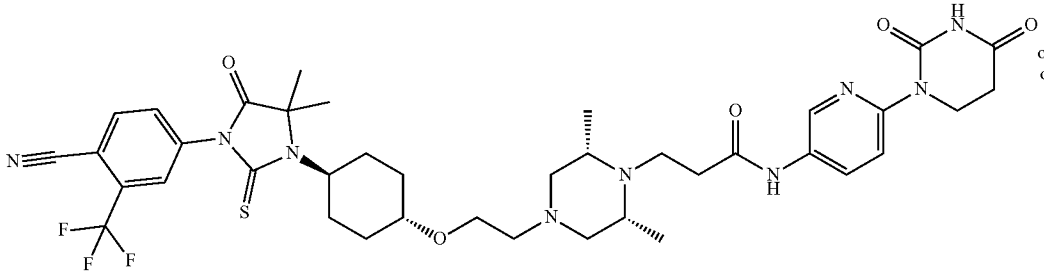 | 3-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1(2H)-yl)pyridin-3-yl)propenamide | 812.0 | B | *** |

TABLE 1-continued

| Cmpd No. | Cmpd Structure | Cmpd Name | MH+ Obs. | $DC_{50}$ | Y |
|---|---|---|---|---|---|
| 10 | 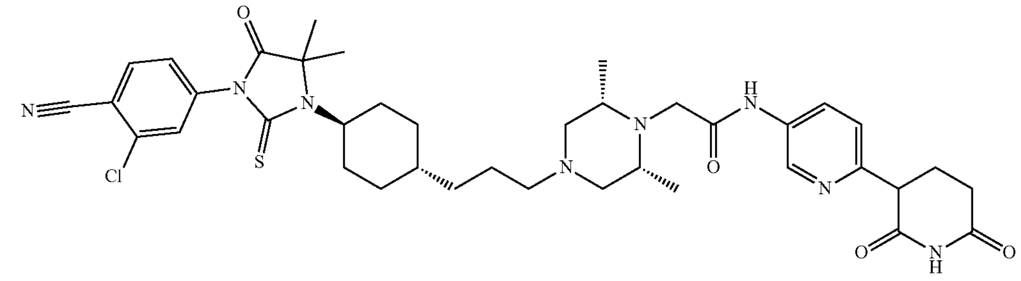 [SMILES: C[C@@H]1CN(CCC[C@H]2CC[C@H](N3C(=S)N(c4ccc(C#N)c(Cl)c4)C(=O)C3(C)C)CC2)C[C@H](C)N1CC(=O)Nc1ccc(C2CCC(=O)NC2=O)nc1] | 2-((2S,6R)-4-(3-(trans-4-(3-(3-chloro-4-cyanophenyl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide | 761.3 | B | *** |
| 11 | 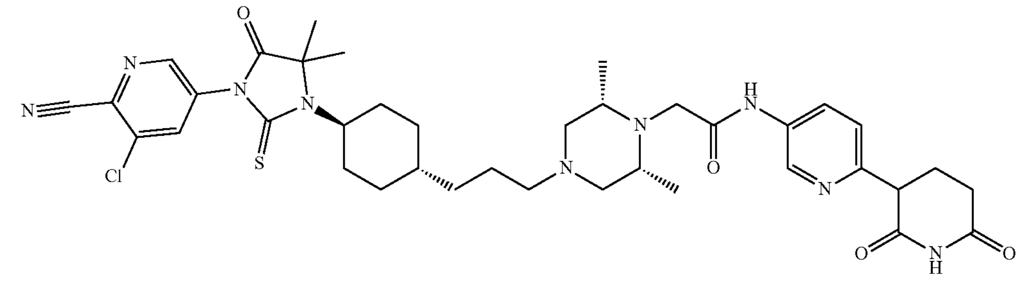 | 2-((2S,6R)-4-(3-(trans-4-(3-(5-chloro-6-cyanopyridin-3-yl)-5,5-dimethyl-4-oxo-2-thioxoimidazolidin-1-yl)cyclohexyl) propyl)-2,6-dimethylpiperazin-1-yl)-N-(6-(2,6-dioxopiperidin-3-yl)pyridin-3-yl)acetamide | 762.3 | D | ** |
| 12 | 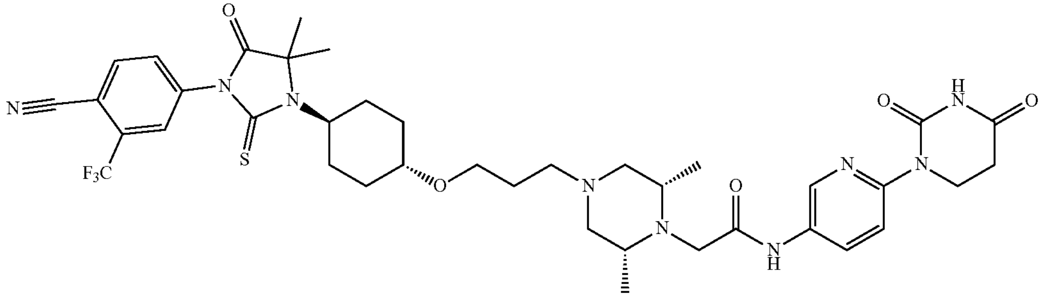 [SMILES: C[C@@H]1CN(CCCO[C@H]2CC[C@H](N3C(=S)N(c4ccc(C#N)c(C(F)(F)F)c4)C(=O)C3(C)C)CC2)C[C@H](C)N1CC(=O)Nc1ccc(N2CCC(=O)NC2=O)nc1] | 2-((2R,6S)-4-(2-((trans-4-(3-(4-cyano-3-(trifluoromethyl)phenyl)-5,5-dimethyl-4-oxo-2-thioxoimidazolidin-1-yl) cyclohexyl)oxy)ethyl)-2,6-dimethyl-piperazin-1-yl)-N-(6-(2,4-dioxotetra-hydropyrimidin-1(2H)-yl)pyridin-3-yl)acetamide | 812.5 | A | *** |

TABLE 1-continued

| Cmpd No. | Cmpd Structure | Cmpd Name | $MH^+$ Obs. | $DC_{50}$ | Y |
|---|---|---|---|---|---|
| 13 | 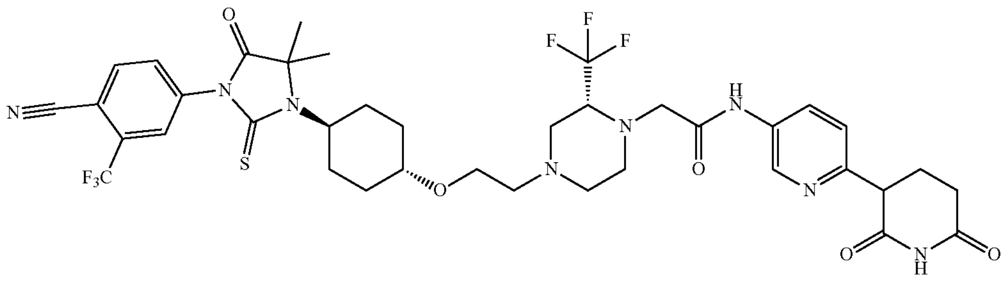 [SMILES: CC1(C)C(=O)N(c2ccc(C#N)c(C(F)(F)F)c2)C(=S)N1[C@H]1CC[C@H](OCCN2CCN(CC(=O)Nc3ccc(C4CCC(=O)NC4=O)nc3)[C@@H](C(F)(F)F)C2)CC1] | 2-((S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2-(trifluoromethyl)piperazin-1-yl)-N-(6-(2,6-dioxopiperidin-3-yl)pyridin-3-yl)acetamide | 837.2 | C | ** |
| 14 | 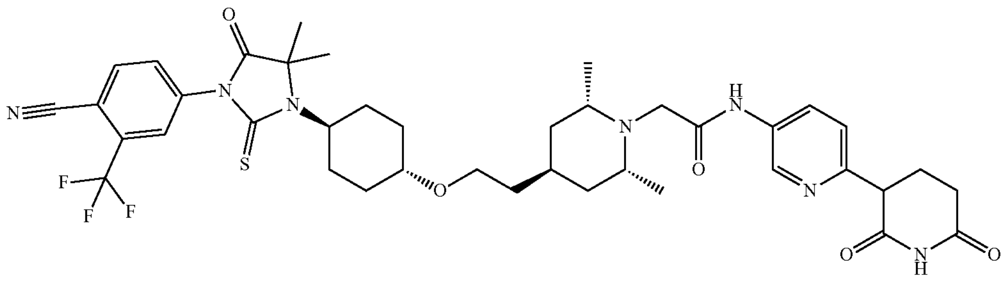 [SMILES: C[C@@H]1C[C@@H](CCO[C@H]2CC[C@H](N3C(=S)N(c4ccc(C#N)c(C(F)(F)F)c4)C(=O)C3(C)C)CC2)C[C@H](C)N1CC(=O)Nc1ccc(C2CCC(=O)NC2=O)nc1] | 2-((2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide | 796.3 | D | ** |
| 15 | 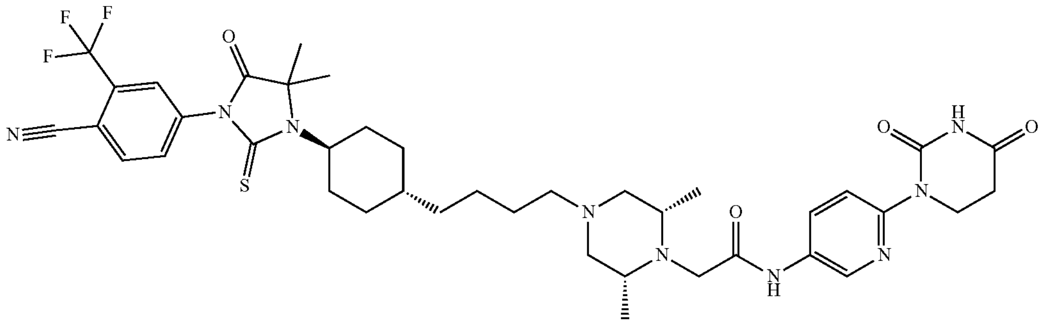 | 2-((2S,6R)-4-(4-(trans-4-(3-(4-cyano-3-(trifluoromethyl)phenyl)-5,5-dimethyl-4-oxo-2-thioxoimidazolidin-1-yl)cyclohexyl)butyl)-2,6-dimethylpiperazin-1-yl)-N-(6-(2,4-dioxotetrahydropyrimidin-1(2H)-yl)pyridin-3-yl)acetamide | 810.6 | A | *** |

TABLE 1-continued

| Cmpd No. | Cmpd Structure | Cmpd Name | MH+ Obs. | $DC_{50}$ | Y |
|---|---|---|---|---|---|
| 16 | 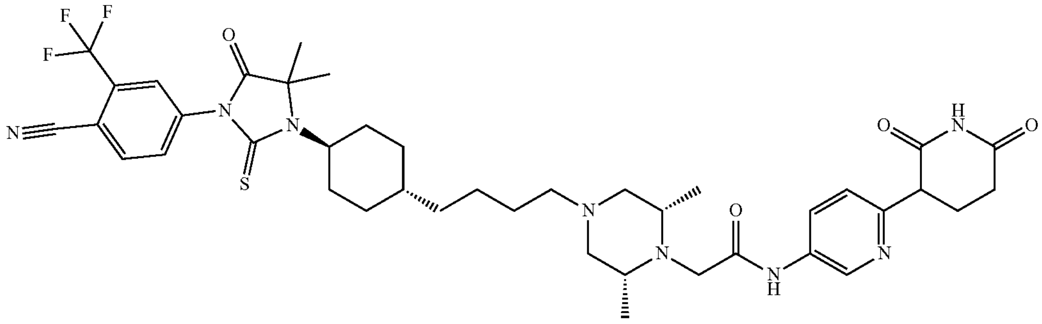 [SMILES: C[C@@H]1CN(CCCC[C@H]2CC[C@H](N3C(=S)N(c4ccc(C#N)c(C(F)(F)F)c4)C(=O)C3(C)C)CC2)C[C@H](C)N1CC(=O)Nc1ccc(C2CCC(=O)NC2=O)nc1] | 2-((2S,6R)-4-(4-(trans-4-(3-(4-cyano-3-(trifluoromethyl)phenyl)-5,5-dimethyl-4-oxo-2-thioxoimidazolidin-1-yl)cyclohexyl)butyl)-2,6-dimethyl-piperazin-1-yl)-N-(6-(2,6-dioxopiperidin-3-yl)pyridin-3-yl)acetamide | 809.3 | D | ** |
| 17 | 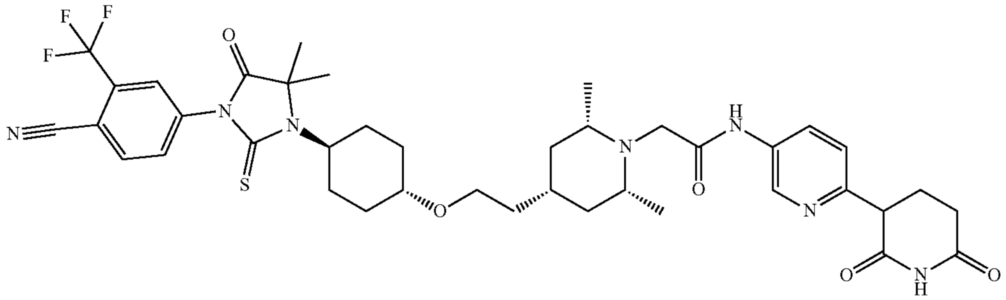 | 2-((2S,4r,6R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethyl-piperidin-1-yl)-N-(6-(2,6-dioxopiperidin-3-yl)pyridin-3-yl)acetamide | 796.3 | D | ** |
| 18 | 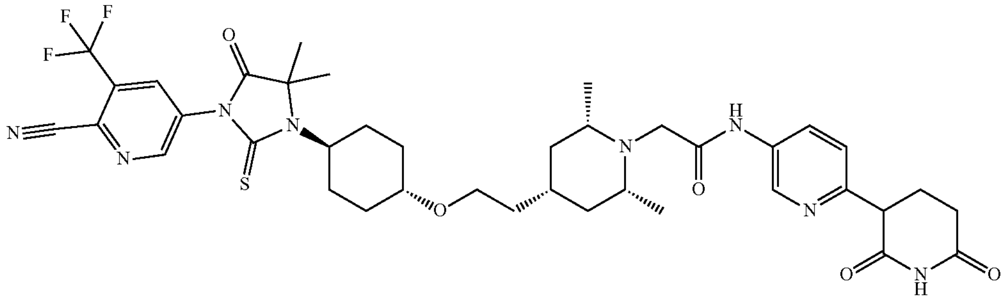 [SMILES: C[C@@H]1C[C@H](CCO[C@H]2CC[C@H](N3C(=S)N(c4cnc(C#N)c(C(F)(F)F)c4)C(=O)C3(C)C)CC2)C[C@H](C)N1CC(=O)Nc1ccc(C2CCC(=O)NC2=O)nc1] | 2-((2S,4r,6R)-4-(2-((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl) acetamide | 797.3 | D | * |

TABLE 1-continued

| Cmpd No. | Cmpd Structure | Cmpd Name | $MH^+$ Obs. | $DC_{50}$ | Y |
|---|---|---|---|---|---|
| 19 | 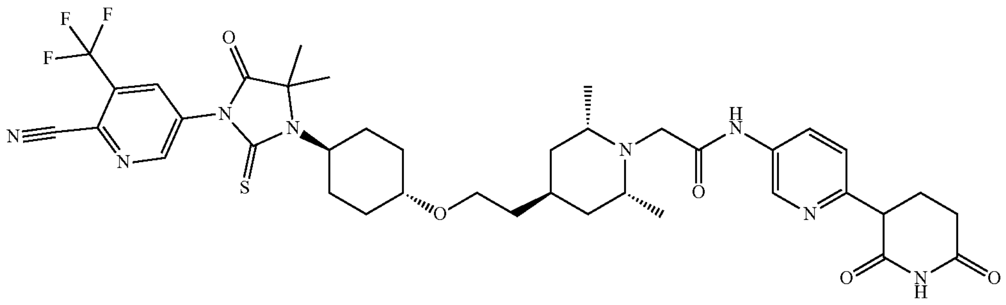 [SMILES: C[C@@H]1C[C@@H](CCO[C@H]2CC[C@H](N3C(=S)N(c4cnc(C#N)c(C(F)(F)F)c4)C(=O)C3(C)C)CC2)C[C@H](C)N1CC(=O)Nc1ccc(C2CCC(=O)NC2=O)nc1] | 2-((2S,4s,6R)-4-(2-((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl) acetamide | 797.3 | D | ** |
| 20 | 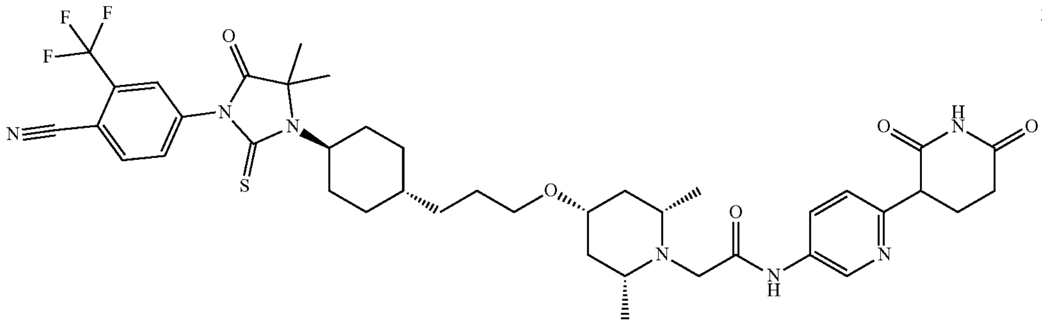 | 2-((2S,4r,6R)-4-(3-(trans-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)-N-(6-(2,6-dioxopiperidin-3-yl)pyridin-3-yl) acetamide | 810.3 | C | ** |
| 21 | 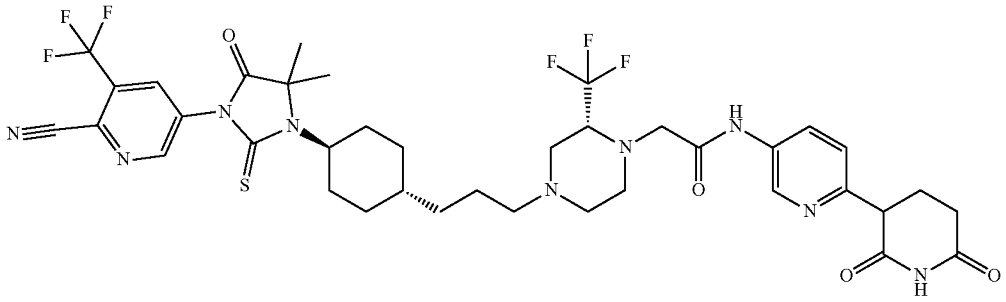 [SMILES: CC1(C)C(=O)N(c2cnc(C#N)c(C(F)(F)F)c2)C(=S)N1[C@H]1CC[C@H](CCCN2CCN(CC(=O)Nc3ccc(C4CCC(=O)NC4=O)nc3)[C@@H](C(F)(F)F)C2)CC1] | 2-((R)-4-(3-(trans-4-(3-(6-cyano-5-(trifluoromethyl)pyridin-3-yl)-5,5-dimethyl-4-oxo-2-thioxoimidazolidin-1-yl)cyclohexyl) propyl)-2-(trifluoromethyl) piperazin-1-yl)-N-(6-(2,6-dioxopiperidin-3-yl)pyridin-3-yl) acetamide | 836.4 | D | * |

TABLE 1-continued

| Cmpd No. | Cmpd Structure | Cmpd Name | MH+ Obs. | $DC_{50}$ | Y |
|---|---|---|---|---|---|
| 22 | 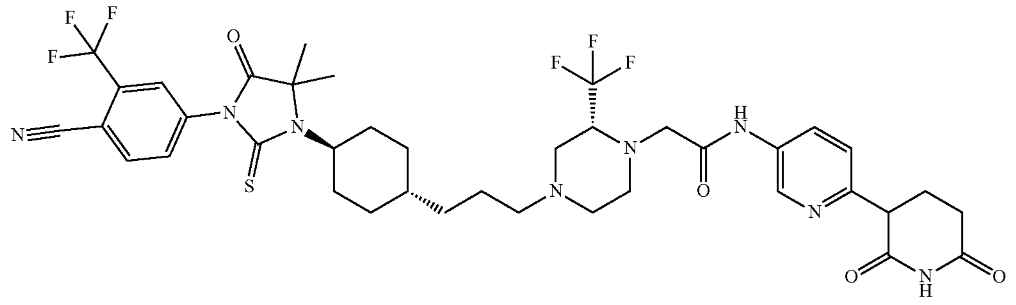 [SMILES: CC1(C)C(=O)N(c2ccc(C#N)c(C(F)(F)F)c2)C(=S)N1[C@H]1CC[C@H](CCCN2CCN(CC(=O)Nc3ccc(C4CCC(=O)NC4=O)nc3)[C@@H](C(F)(F)F)C2)CC1] | 2-((R)-4-(3-(trans-4-(3-(4-cyano-3-(trifluoromethyl)phenyl)-5,5-dimethyl-4-oxo-2-thioxoimidazolidin-1-yl)cyclohexyl)propyl)-2-(trifluoromethyl)piperazin-1-yl)-N-(6-(2,6-dioxopiperidin-3-yl)pyridin-3-yl)acetamide | 835.2 | B | ** |
| 23 | 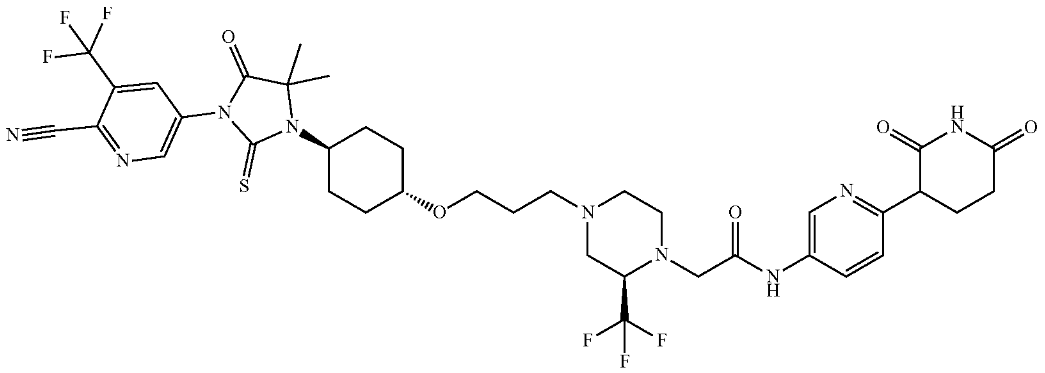 [SMILES: CC1(C)C(=O)N(c2cnc(C#N)c(C(F)(F)F)c2)C(=S)N1[C@H]1CC[C@H](OCCCN2CCN(CC(=O)Nc3ccc(C4CCC(=O)NC4=O)nc3)[C@@H](C(F)(F)F)C2)CC1] | 2-((R)-4-(3-((trans-4-(3-(6-cyano-5-(trifluoromethyl)pyridin-3-yl)-5,5-dimethyl-4-oxo-2-thioxoimidazolidin-1-yl)cyclohexyl)oxy)propyl)-2-(trifluoromethyl)piperazin-1-yl)-N-(6-(2,6-dioxopiperidin-3-yl)pyridin-3-yl)acetamide | 852.1 | D | * |
| 24 | 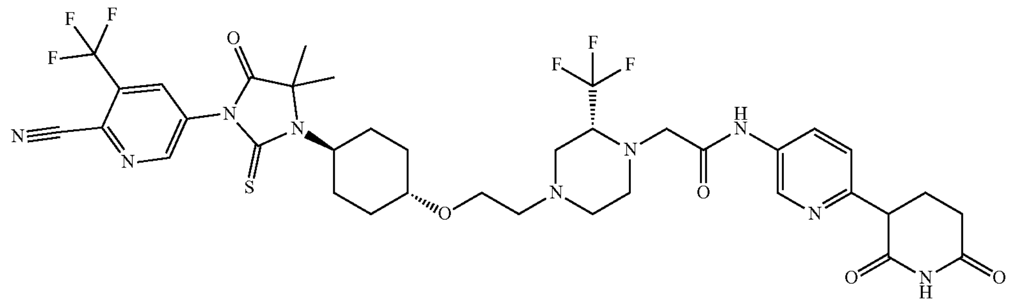 | 2-((R)-4-(2-((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2-(trifluoromethyl)piperazin-1-yl)-N-(6-(2,6-dioxopiperidin-3-yl)pyridin-3-yl)acetamide | 838.1 | D | ** |

TABLE 1-continued

| Cmpd No. | Cmpd Structure | Cmpd Name | MH+ Obs. | $DC_{50}$ | Y |
|---|---|---|---|---|---|
| 25 | 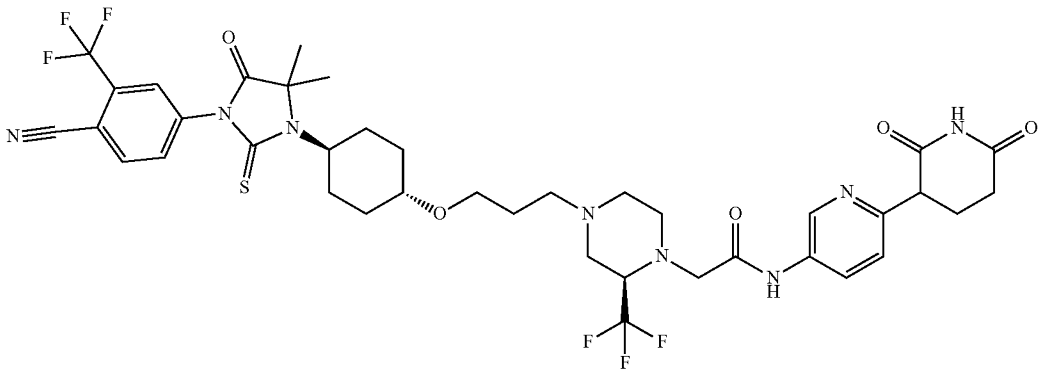 | 2-((R)-4-(3-((trans-4-(3-(4-cyano-3-(trifluoromethyl)phenyl)-5,5-dimethyl-4-oxo-2-thioxoimidazolidin-1-yl)cyclohexyl)oxy)propyl)-2-(trifluoromethyl)piperazin-1-yl)-N-(6-(2,6-dioxopiperidin-3-yl)pyridin-3-yl)acetamide | 851.2 | D | ** |
| 26 | 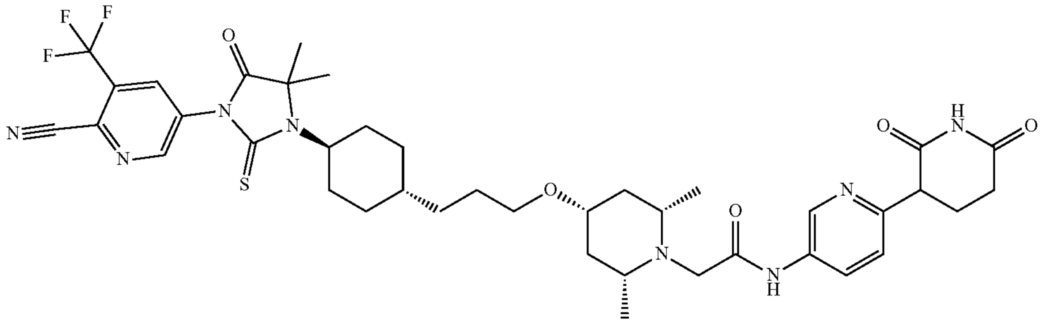 [SMILES: C[C@@H]1C[C@H](OCCC[C@H]2CC[C@H](N3C(=S)N(c4cnc(C#N)c(C(F)(F)F)c4)C(=O)C3(C)C)CC2)C[C@H](C)N1CC(=O)Nc1ccc(C2CCC(=O)NC2=O)nc1] | 2-((2S,4r,6R)-4-(3-(trans-4-(3-(6-cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)-N-(6-(2,6-dioxopiperidin-3-yl)pyridin-3-yl)acetamide | 811.2 | D | * |
| 27 | 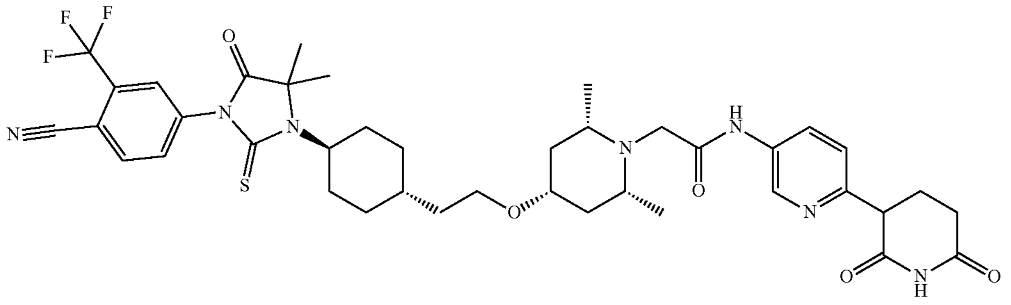 [SMILES: C[C@@H]1C[C@H](OCC[C@H]2CC[C@H](N3C(=S)N(c4ccc(C#N)c(C(F)(F)F)c4)C(=O)C3(C)C)CC2)C[C@H](C)N1CC(=O)Nc1ccc(C2CCC(=O)NC2=O)nc1] | 2-((2S,4r,6R)-4-(2-(trans-4-(3-(4-cyano-3-(trifluoromethyl)phenyl)-5,5-dimethyl-4-oxo-2-thioxoimidazolidin-1-yl)cyclohexyl)ethoxy)-2,6-dimethyl-piperidin-1-yl)-N-(6-(2,6-dioxopiperidin-3-yl)pyridin-3-yl)acetamide | 796.2 | C | ** |

TABLE 1-continued

| Cmpd No. | Cmpd Structure | Cmpd Name | MH+ Obs. | $DC_{50}$ | Y |
|---|---|---|---|---|---|
| 28 | 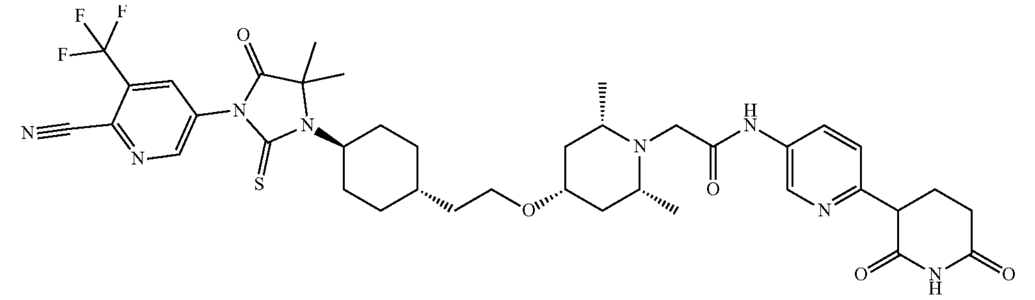 | 2-((2R,4r,6S)-4-(2-((trans)-4-(3-(6-Cyano-5-(trifluoromethyl)pyridin-3-yl)-5,5-dimethyl-4-oxo-2-thioxoimidazolidin-1-yl)cyclohexyl)ethoxy)-2,6-dimethyl-piperidin-1-yl)-N-(6-(2,6-dioxopiperidin-3-yl)pyridin-3-yl)acetamide | 797.3 | D | ** |
| 29 | 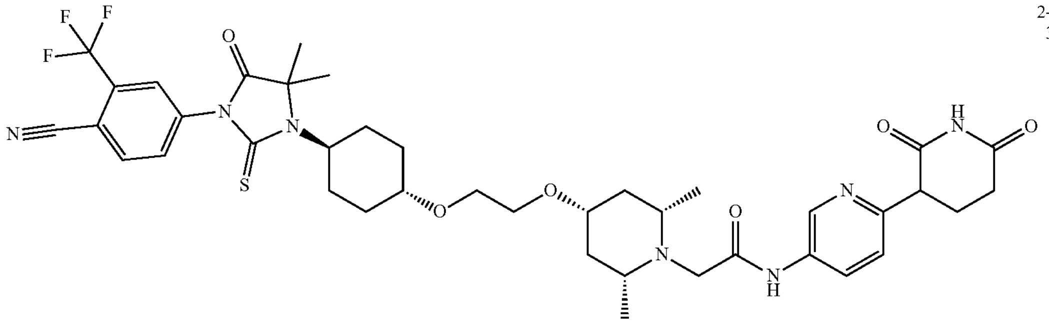 | 2-((2R,4r,6S)-4-(2-(((trans)-4-(3-(4-Cyano-3-(trifluoromethyl)phenyl)-5,5-dimethyl-4-oxo-2-thioxoimidazolidin-1-yl) cyclohexyl)oxy)ethoxy)-2,6-dimethylpiperidin-1-yl)-N-(6-(2,6-dioxopiperidin-3-yl)pyridin-3-yl) acetamide | 812.3 | D | ** |
| 30 | 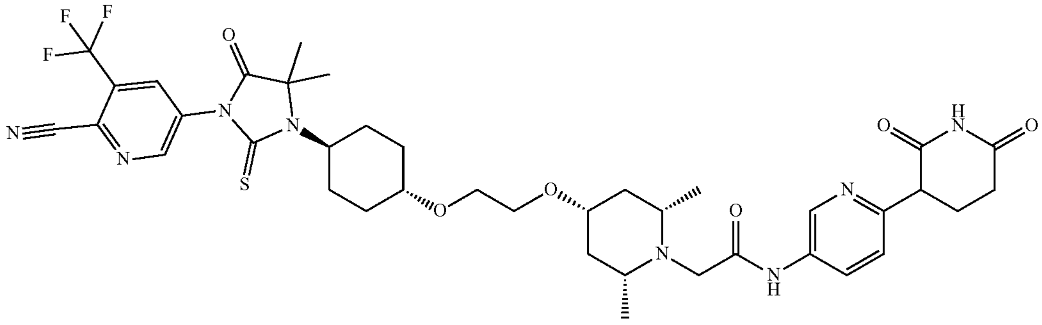 | 2-((2R,4r,6S)-4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)-N-(6-(2,6-dioxopiperidin-3-yl)pyridin-3-yl)acetamide | 813.3 | D | * |

TABLE 1-continued

| Cmpd No. | Cmpd Structure | Cmpd Name | MH+ Obs. | $DC_{50}$ | Y |
|---|---|---|---|---|---|
| 31 | 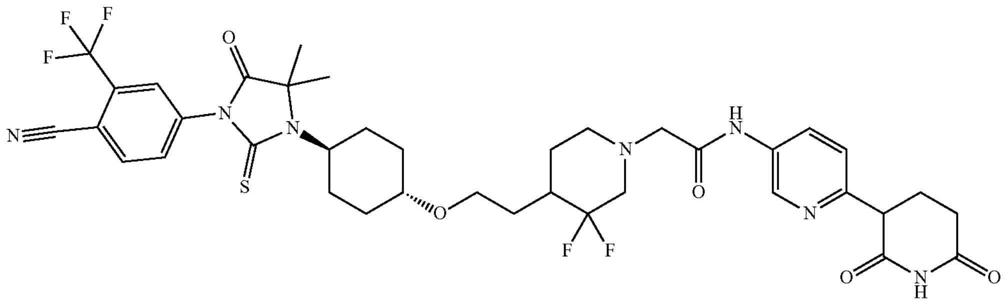 | 2-(4-(2-(((trans)-4-(3-(4-Cyano-3-(trifluoromethyl)phenyl)-5,5-dimethyl-4-oxo-2-thioxoimidazolidin-1-yl)cyclohexyl)oxy)ethyl)-3,3-difluoro-piperidin-1-yl)-N-(6-(2,6-dioxopiperidin-3-yl)pyridin-3-yl)acetamide | 804.2 | D | * |
| 32 | 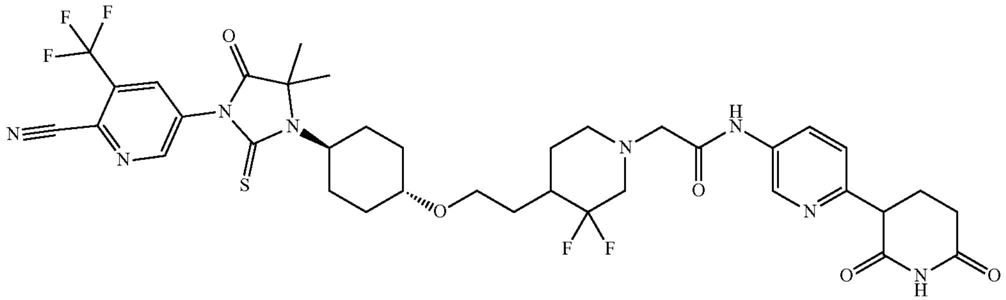 [SMILES: CC1(C)C(=O)N(c2cnc(C#N)c(C(F)(F)F)c2)C(=S)N1[C@H]1CC[C@H](OCCC2CCN(CC(=O)Nc3ccc(C4CCC(=O)NC4=O)nc3)CC2(F)F)CC1] | 2-(4-(2-(((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)-N-(6-(2,6-dioxopiperidin-3-yl)pyridin-3-yl)acetamide | 805.2 | D | * |

A number of references have been cited, the disclosures of which are incorporated herein by reference in their entirety.

What is claimed is:

1. A compound of formula I

I

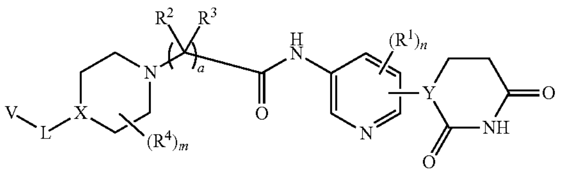

or a pharmaceutically acceptable salt thereof, wherein n is 0-3;

each $R^1$ is independently selected from halogen, CN, and $C_{1-3}$ alkyl;

a is 1 or 2;

$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;

m is 0-8;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;

Y is CH or N;

X is N or $CR^X$;

$R^X$ is hydrogen, halogen, —O($C_{1-6}$ alkyl) or —($C_{1-9}$ alkyl);

L is substituted or unsubstituted —O($C_{1-6}$ alkyl)-, —($C_{1-6}$ alkyl)O—, —O($C_{1-6}$ alkyl)O—, or —($C_{1-9}$ alkyl)-;

V is

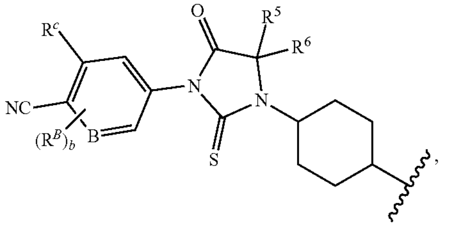

wherein

B is N, CH, or $CR^B$;

each $R^B$ is independently selected from halogen, and substituted or unsubstituted $C_{1-6}$ alkyl;

$R^C$ is halogen, $CF_3$ or $SF_5$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl; and b is 0-2.

2. The compound of claim 1, wherein n is 0.

3. The compound of claim 1, wherein a is 1, and $R^2$ and $R^3$ are both H.

4. The compound of claim 1, wherein each $R^4$ is substituted or unsubstituted methyl.

5. The compound of claim 1, wherein each $R^4$ is independently selected from methyl and $CF_3$.

6. The compound of claim 1, wherein L is —O($CH_2$)($CH_2$)—, —O($CH_2$)($CH_2$)($CH_2$)—, —O($CH_2$)($CH_2$)O—, —O($CH_2$)($CH_2$)($CH_2$)O—, —($CH_2$)($CH_2$)—, —($CH_2$)($CH_2$)($CH_2$)—, or —($CH_2$)($CH_2$)($CH_2$)($CH_2$)—.

7. The compound of claim 1, wherein B is CH.

8. The compound of claim 1, wherein B is N.

9. The compound of claim 1, wherein b is 0.

10. The compound of claim 1, wherein $R^C$ is $CF_3$, Cl or $SF_5$.

11. The compound of claim 1, wherein $R^5$ and $R^6$ are methyl.

12. The compound of claim 1, having formula II

II

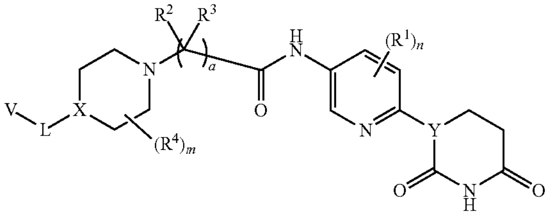

or a pharmaceutically acceptable salt thereof.

13. The compound of claim 1, having formula III

III

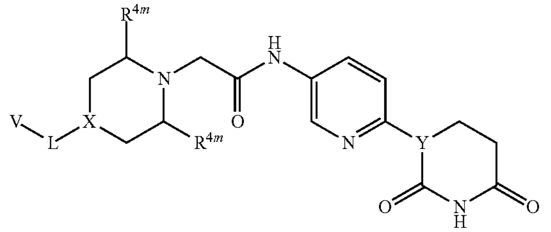

or a pharmaceutically acceptable salt thereof, wherein each $R^{4m}$ is independently hydrogen or substituted or unsubstituted methyl, wherein the substituents, when present are selected from 1 to 5 halo;

Y is CH or N;

L is substituted or unsubstituted —O($C_{1-3}$ alkyl)-, —O($C_{1-3}$ alkyl)O— or —($C_{1-4}$ alkyl)-;

n is 0;

V is

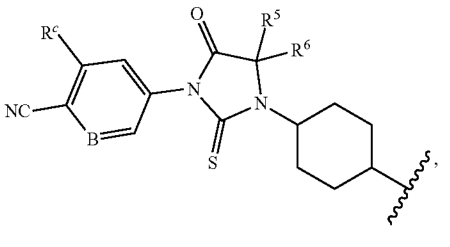

B is N or CH;

$R^C$ is halogen, $CF_3$ or $SF_5$; and $R^5$ and $R^6$ are $C_{1-3}$ alkyl.

14. The compound of claim 1, having formula IV

IV

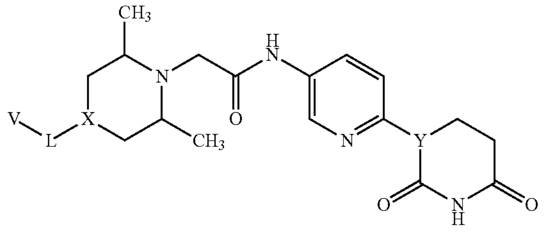

or a pharmaceutically acceptable salt thereof, wherein

Y is CH or N;

L is substituted or unsubstituted —O($C_{1-3}$ alkyl)-, —O($C_{1-3}$ alkyl)O— or —($C_{1-4}$ alkyl)-;

n is 0;

V is

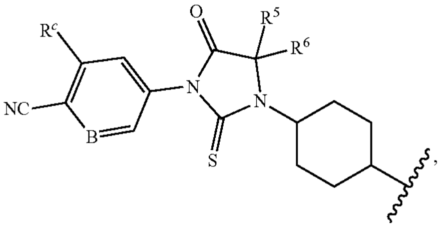

B is N or CH;

$R^C$ is halogen, $CF_3$ or $SF_5$; and $R^5$ and $R^6$ are $C_{1-3}$ alkyl.

15. The compound of claim 1, having formula V

V

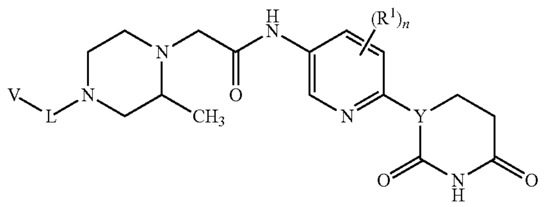

or a pharmaceutically acceptable salt thereof, wherein

Y is CH or N;

L is substituted or unsubstituted —O($C_{1-3}$ alkyl)-, —O($C_{1-3}$ alkyl)O— or —($C_{1-4}$ alkyl)-;

n is 0;

V is

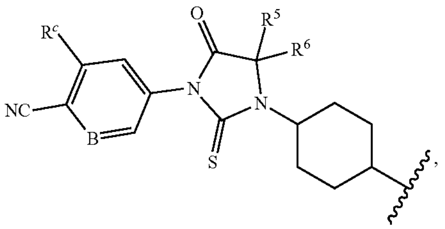

B is N or CH;

$R^C$ is halogen, $CF_3$ or $SF_5$; and $R^5$ and $R^6$ are $C_{1-3}$ alkyl.

16. The compound of claim 1, wherein the compound is selected from the group consisting of 2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1 (2H)-yl)pyridin-3-yl)acetamide;

2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,6-dioxopiperidin-3-yl)pyridin-3-yl)acetamide;

2-((2R,6S)-4-(3-(trans-4-(3-(4-cyano-3-(trifluoromethyl)phenyl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide;

2-((2R,6S)-4-(3-((trans-4-(3-(6-cyano-5-(trifluoromethyl)pyridin-3-yl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide;

2-((2R,6S)-4-(3-((trans-4-(3-(4-cyano-3-(trifluoromethyl)phenyl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide;

2-((2R,6S)-4-(2-((trans-4-(3-(5-chloro-6-cyanopyridin-3-yl)-5,5-dimethyl-4-oxo-2-thioxoimidazolidin-1-yl)cyclohexyl)oxy)ethyl)-2,6-dimethylpiperazin-1-yl)-N-(6-(2,6-dioxopiperidin-3-yl)pyridin-3-yl)acetamide;

2-((2R,6S)-4-(3-((trans-4-(3-(3-chloro-4-cyanophenyl)-5,5-dimethyl-4-oxo-2-thioxoimidazolidin-1-yl)cyclohexyl)oxy)propyl)-2,6-dimethylpiperazin-1-yl)-N-(6-(2,6-dioxopiperidin-3-yl)pyridin-3-yl)acetamide;

2-((2R,6S)-4-(3-(trans-4-(3-(6-cyano-5-(trifluoromethyl)pyridin-3-yl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide;

3-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1 (2H)-yl)pyridin-3-yl)propenamide;

2-((2S,6R)-4-(3-(trans-4-(3-(3-chloro-4-cyanophenyl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide;

2-((2S,6R)-4-(3-(trans-4-(3-(5-chloro-6-cyanopyridin-3-yl)-5,5-dimethyl-4-oxo-2-thioxoimidazolidin-1-yl)cyclohexyl)propyl)-2,6-dimethylpiperazin-1-yl)-N-(6-(2,6-dioxopiperidin-3-yl)pyridin-3-yl)acetamide;

2-((2R,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperazin-1-yl)-N-(6-(2,4-dioxotetrahydropyrimidin-1 (2H)-yl) pyridin-3-yl)acetamide;

2-((S)-4-(2-((trans-4-(3-(4-cyano-3-(trifluoromethyl)phenyl)-5,5-dimethyl-4-oxo-2-thioxoimidazolidin-1-yl) cyclohexyl)oxy)ethyl)-2-(trifluoromethyl)piperazin-1-yl)-N-(6-(2,6-dioxopiperidin-3-yl)pyridin-3-yl) acetamide;

2-((2R,4r,6S)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl) acetamide;

2-((2S,6R)-4-(4-(trans-4-(3-(4-cyano-3-(trifluoromethyl) phenyl)-5,5-dimethyl-4-oxo-2-thioxoimidazolidin-1-yl)cyclohexyl)butyl)-2,6-dimethylpiperazin-1-yl)-N-(6-(2,4-dioxotetrahydropyrimidin-1 (2H)-yl)pyridin-3-yl)acetamide;

2-((2S,6R)-4-(4-(trans-4-(3-(4-cyano-3-(trifluoromethyl) phenyl)-5,5-dimethyl-4-oxo-2-thioxoimidazolidin-1-yl)cyclohexyl)butyl)-2,6-dimethylpiperazin-1-yl)-N-(6-(2,6-dioxopiperidin-3-yl)pyridin-3-yl)acetamide;

2-((2S,4r,6R)-4-(2-((trans-4-(3-(4-cyano-3-(trifluoromethyl)phenyl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl) acetamide;

2-((2S,4r,6R)-4-(2-((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide;

2-((2S,4s,6R)-4-(2-((trans-4-(3-(6-cyano-5-(trifluoromethyl)pyridin-3-yl)-5,5-dimethyl-4-oxo-2-thioxoimidazolidin-1-yl)cyclohexyl)oxy)ethyl)-2,6-dimethylpiperidin-1-yl)-N-(6-(2,6-dioxopiperidin-3-yl)pyridin-3-yl)acetamide;

2-((2S,4r,6R)-4-(3-(trans-4-(3-(4-cyano-3-(trifluoromethyl)phenyl)-5,5-dimethyl-4-oxo-2-thioxoimidazolidin-1-yl)cyclohexyl)propoxy)-2,6-dimethylpiperidin-1-yl)-N-(6-(2,6-dioxopiperidin-3-yl)pyridin-3-yl) acetamide;

2-((R)-4-(3-(trans-4-(3-(6-cyano-5-(trifluoromethyl)pyridin-3-yl)-5,5-dimethyl-4-oxo-2-thioxoimidazolidin-1-yl)cyclohexyl)propyl)-2-(trifluoromethyl)piperazin-1-yl)-N-(6-(2,6-dioxopiperidin-3-yl)pyridin-3-yl) acetamide;

2-((R)-4-(3-(trans-4-(3-(4-cyano-3-(trifluoromethyl)phenyl)-5,5-dimethyl-4-oxo-2-thioxoimidazolidin-1-yl) cyclohexyl)propyl)-2-(trifluoromethyl)piperazin-1-yl)-N-(6-(2,6-dioxopiperidin-3-yl)pyridin-3-yl)acetamide;

2-((R)-4-(3-((trans-4-(3-(6-cyano-5-(trifluoromethyl) pyridin-3-yl)-5,5-dimethyl-4-oxo-2-thioxoimidazolidin-1-yl)cyclohexyl)oxy)propyl)-2-(trifluoromethyl) piperazin-1-yl)-N-(6-(2,6-dioxopiperidin-3-yl)pyridin-3-yl)acetamide;

2-((R)-4-(2-((trans-4-(3-(6-cyano-5-(trifluoromethyl) pyridin-3-yl)-5,5-dimethyl-4-oxo-2-thioxoimidazolidin-1-yl)cyclohexyl)oxy)ethyl)-2-(trifluoromethyl)piperazin-1-yl)-N-(6-(2,6-dioxopiperidin-3-yl)pyridin-3-yl)acetamide;

2-((R)-4-(3-((trans-4-(3-(4-cyano-3-(trifluoromethyl) phenyl)-5,5-dimethyl-4-oxo-2-thioxoimidazolidin-1-yl)cyclohexyl)oxy)propyl)-2-(trifluoromethyl)piperazin-1-yl)-N-(6-(2,6-dioxopiperidin-3-yl)pyridin-3-yl) acetamide;

2-((2S,4r,6R)-4-(3-(trans-4-(3-(6-cyano-5-(trifluoromethyl)pyridin-3-yl)-5,5-dimethyl-4-oxo-2-thioxoimidazolidin-1-yl)cyclohexyl)propoxy)-2,6-dimethylpiperidin-1-yl)-N-(6-(2,6-dioxopiperidin-3-yl)pyridin-3-yl) acetamide;

2-((2S,4r,6R)-4-(2-(trans-4-(3-(4-cyano-3-(trifluoromethyl)phenyl)-5,5-dimethyl-4-oxo-2-thioxoimidazolidin-1-yl)cyclohexyl)ethoxy)-2,6-dimethylpiperidin-1-yl)-N-(6-(2,6-dioxopiperidin-3-yl)pyridin-3-yl) acetamide;

2-((2R,4r,6S)-4-(2-((trans)-4-(3-(6-Cyano-5-(trifluoromethyl)pyridin-3-yl)-5,5-dimethyl-4-oxo-2-thioxoimidazolidin-1-yl)cyclohexyl)ethoxy)-2,6-dimethylpiperidin-1-yl)-N-(6-(2,6-dioxopiperidin-3-yl)pyridin-3-yl) acetamide;

2-((2R,4r,6S)-4-(2-((((trans)-4-(3-(4-Cyano-3-(trifluoromethyl)phenyl)-5,5-dimethyl-4-oxo-2-thioxoimidazolidin-1-yl)cyclohexyl)oxy)ethoxy)-2,6-dimethylpiperidin-1-yl)-N-(6-(2,6-dioxopiperidin-3-yl)pyridin-3-yl) acetamide;

2-((2R,4r,6S)-4-(2-((((trans)-4-(3-(6-Cyano-5-(trifluoromethyl)pyridin-3-yl)-5,5-dimethyl-4-oxo-2-thioxoimidazolidin-1-yl)cyclohexyl)oxy)ethoxy)-2,6-dimethylpiperidin-1-yl)-N-(6-(2,6-dioxopiperidin-3-yl)pyridin-3-yl)acetamide;

2-(4-(2-((((trans)-4-(3-(4-Cyano-3-(trifluoromethyl)phenyl)-5,5-dimethyl-4-oxo-2-thioxoimidazolidin-1-yl) cyclohexyl)oxy)ethyl)-3,3-difluoropiperidin-1-yl)-N-(6-(2,6-dioxopiperidin-3-yl)pyridin-3-yl)acetamide; and 2-(4-(2-((((trans)-4-(3-(6-Cyano-5-(trifluoromethyl)pyridin-3-yl)-5,5-dimethyl-4-oxo-2-thioxoimidazolidin-1-yl)cyclohexyl)oxy)ethyl)-3,3-difluoropiperidin-1-yl)-N-(6-(2,6-dioxopiperidin-3-yl)pyridin-3-yl)acetamide;

or a pharmaceutically acceptable salt thereof.

17. A pharmaceutical composition comprising an effective amount of a compound of claim 1, or a pharmaceutically acceptable salt thereof, and a pharmaceutically acceptable carrier, excipient or vehicle.

18. A method for the treatment of an androgen receptor mediated disease, the method comprising administering to a subject in need thereof an effective amount of a compound of claim 1, wherein the androgen mediated disease is prostate cancer.

19. A method for the treatment of an androgen receptor mediated disease, the method comprising administering to a subject in need thereof an effective amount of the pharmaceutical composition of claim 17, wherein the androgen mediated disease is prostate cancer.

20. The method of claim 18, wherein the prostate cancer is castration resistant prostate cancer (CRPC).

* * * * *